US008790645B2

(12) United States Patent
Kufer et al.

(10) Patent No.: US 8,790,645 B2
(45) Date of Patent: Jul. 29, 2014

(54) PHARMACEUTICAL COMPOSITION COMPRISING A BISPECIFIC ANTIBODY FOR EPCAM

(75) Inventors: Peter Kufer, Moosburg (DE); Meera Berry, Ulm (DE); Sonja Offner, Munich (DE); Klaus Brischwein, Munich (DE); Andreas Wolf, Planegg (DE); Tobias Raum, Munich (DE); Birgit Kohleisen, Munich (DE); Ulla Lenkkeri-Schütz, Eching (DE); Patrick Bauerle, Gauting (DE)

(73) Assignee: Amgen Research (Munich) GmbH, Munich (DE)

( * ) Notice: Subject to any disclaimer, the term of this patent is extended or adjusted under 35 U.S.C. 154(b) by 316 days.

(21) Appl. No.: 13/079,453

(22) Filed: Apr. 4, 2011

(65) Prior Publication Data

US 2011/0256137 A1 Oct. 20, 2011

Related U.S. Application Data

(63) Continuation of application No. 10/554,851, filed as application No. PCT/EP2004/005687 on May 26, 2004, now Pat. No. 7,919,089.

(30) Foreign Application Priority Data

May 31, 2003 (EP) .................................... 03012133
May 31, 2003 (EP) .................................... 03012134

(51) Int. Cl.
*A61K 39/395* (2006.01)
*C07K 16/00* (2006.01)
*C07K 16/30* (2006.01)
*C07K 16/28* (2006.01)

(52) U.S. Cl.
CPC ............. *C07K 16/30* (2013.01); *C07K 2317/31* (2013.01); *C07K 2317/622* (2013.01); *C07K 2319/00* (2013.01); *C07K 2317/92* (2013.01); *C07K 16/2809* (2013.01)
USPC .................. 424/136.1; 424/130.1; 424/133.1; 424/135.1; 424/144.1; 530/387.1; 530/387.3; 530/388.23

(58) Field of Classification Search
CPC .................. A61K 39/39558; A61K 2039/505; C07K 2317/92; C07K 16/30; C07K 716/2863
See application file for complete search history.

(56) References Cited

FOREIGN PATENT DOCUMENTS

| | | |
|---|---|---|
| DE | 19531348 | 2/1997 |
| WO | WO-99/25818 | 5/1999 |
| WO | WO-00/03016 | 1/2000 |
| WO | WO-00/06606 | 9/2001 |
| WO | WO-01/71005 | 9/2001 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Attwood (Science 290: 471-473, 2000).*
Skolnick et al. (Trends in Biotech. 18: 34-39, 2000).*
Flieger et al. (Cancer Immunol. Immunother. 2000, 49:441-448.*
ATTWOOD, Genomics. The Babel of bioinformatics. *Science*, 290: 471-3 (2000).
Balzar et al., The biology of the 17-1A antigen (Ep-CAM), *J. Mol. Med.*, 77: 699-712 (1999).
Barbas et al., Human autoantibody recognition of DNA. *Proc. Natl. Acad. Sci. USA*. 92: 2529-33 (1995).
Beiboer et al., Guided selection of a pan carcinoma specific antibody reveals similar binding characteristics yet structural divergence between the original murine antibody and its human equivalent. *J. Mol. Biol.* 296: 833-49 (2000).
Bendig, *Methods: A Companion to Methods in Enzymology*, 8: 83-93 (1995).
Chaubal et al. Ep-CAM—A marker for the detection of disseminated tumor cells in patients suffering from SCCHN, *Anticancer Res.* 19: 2237-42 (1999).
De Bree, et al., Clinical screening of monoclonal antibodies 323/A3, cSF-25 and K928 for suitability of targetting tumours in the upper aerodigestive and respiratory tract, *Nucl. Med. Commun.* 15: 613-27 (1994).
Flieger et al. A bispecific single-chain antibody directed against EpCAM/CD3 in combination with the cytokines interferon alpha and interleukin-2 efficiently retargets T and CD3+CD56+ natural-killer-like T lymphocytes to EpCAM-expressing tumor cells. *Cancer Immuno. Immunother.* 49: 441-8 (2000).
Gastl et al., Ep-CAM overexpression in breast cancer as a predictor of survival, *Lancet*, 356: Dec. 9, 2000.

(Continued)

*Primary Examiner* — Sharon Wen
(74) *Attorney, Agent, or Firm* — Marshall, Gerstein & Borun LLP

(57) ABSTRACT

The present invention provides a pharmaceutical composition comprising a bispecific single chain antibody construct. Said bispecific single chain antibody construct is characterized to comprise or consist of at least two domains, whereby one of said at least two domains specifically binds to human EpCAM and comprises at least one CDR-H3 region comprising the amino acid sequence NXID antigen and a second domain binds to human CD3 antigen. The invention further provides a process for the production of the pharmaceutical composition of the invention, a method for the prevention, treatment or amelioration of a tumorous disease and the use of the disclosed bispecific single chain antibody construct and corresponding means in the prevention, treatment or amelioration of a tumorous disease.

13 Claims, 72 Drawing Sheets

(56) References Cited

OTHER PUBLICATIONS

Figure 2C:
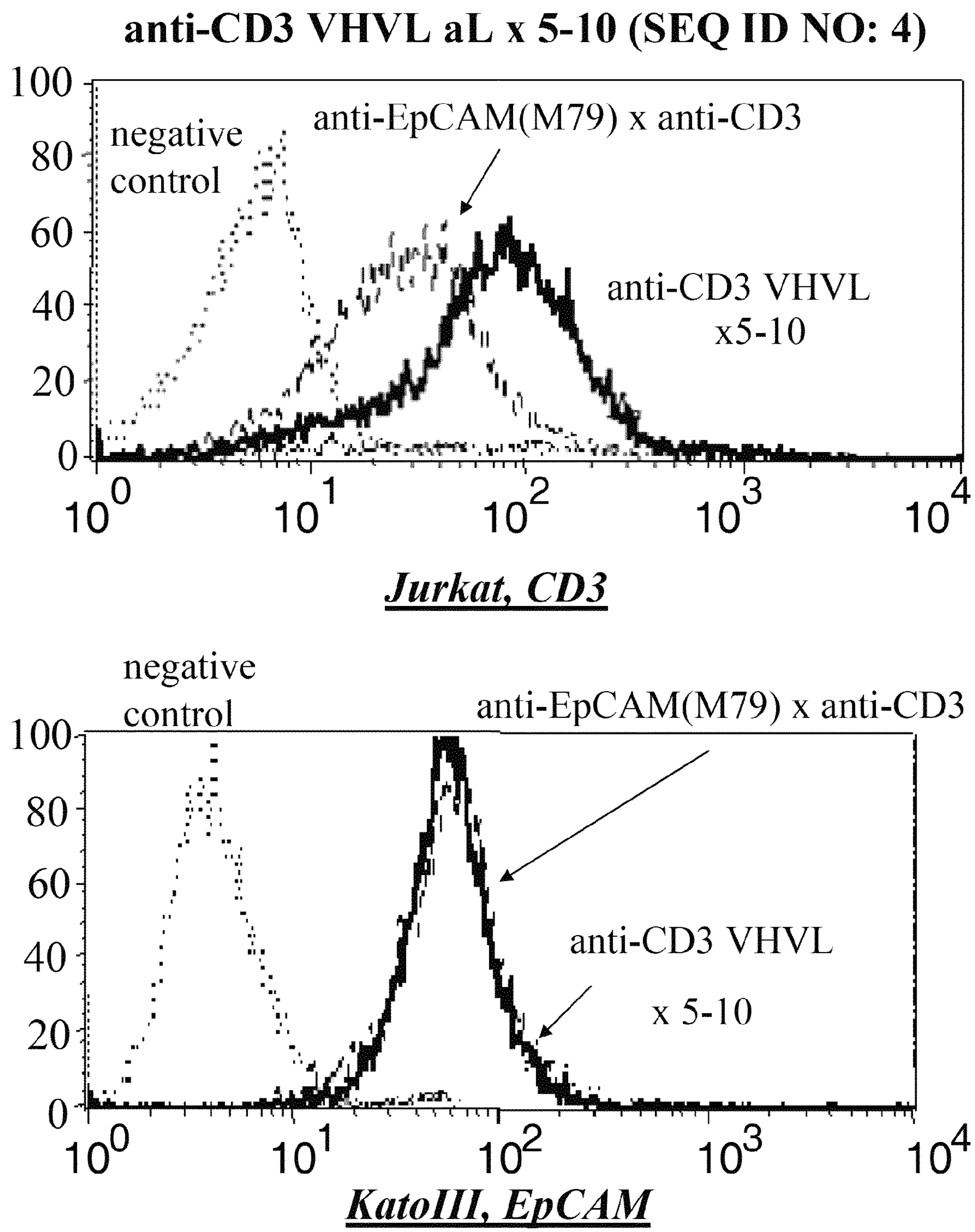
Figure 4A:
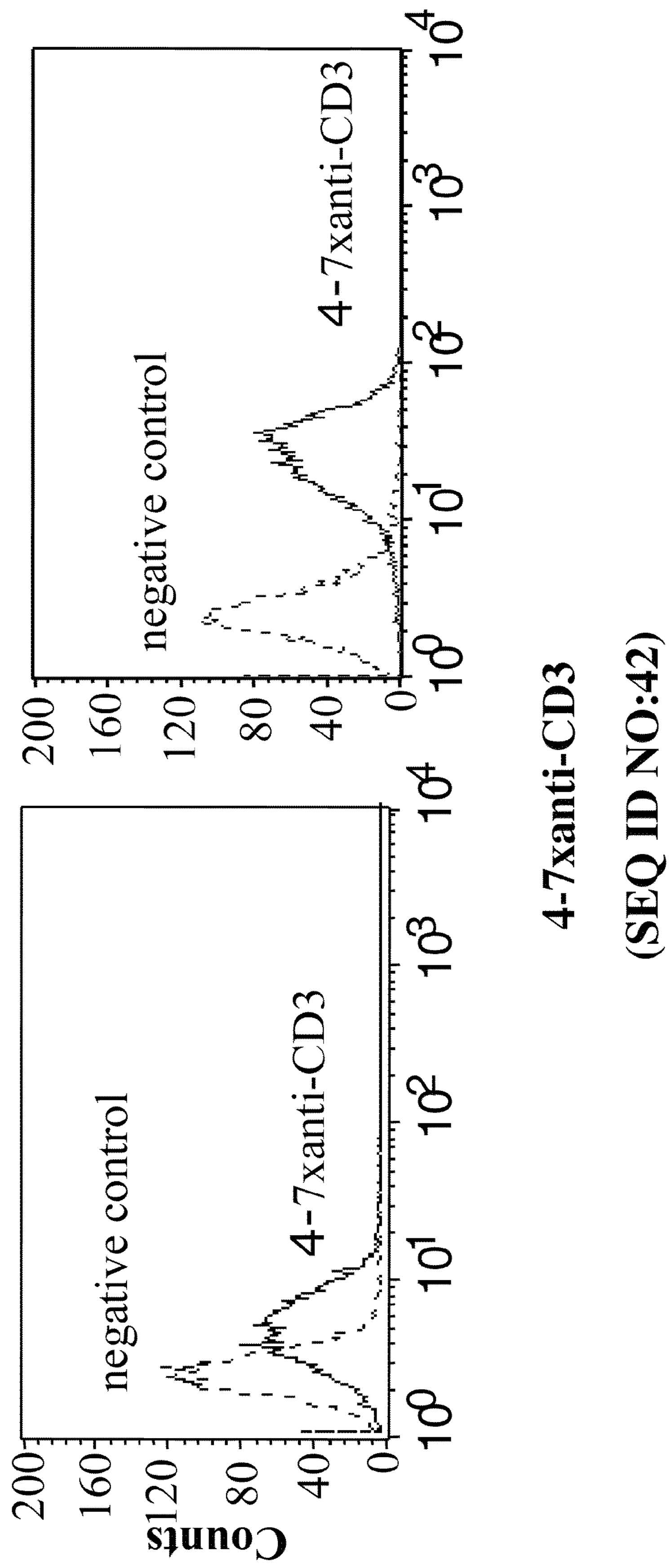
Figure 4B:
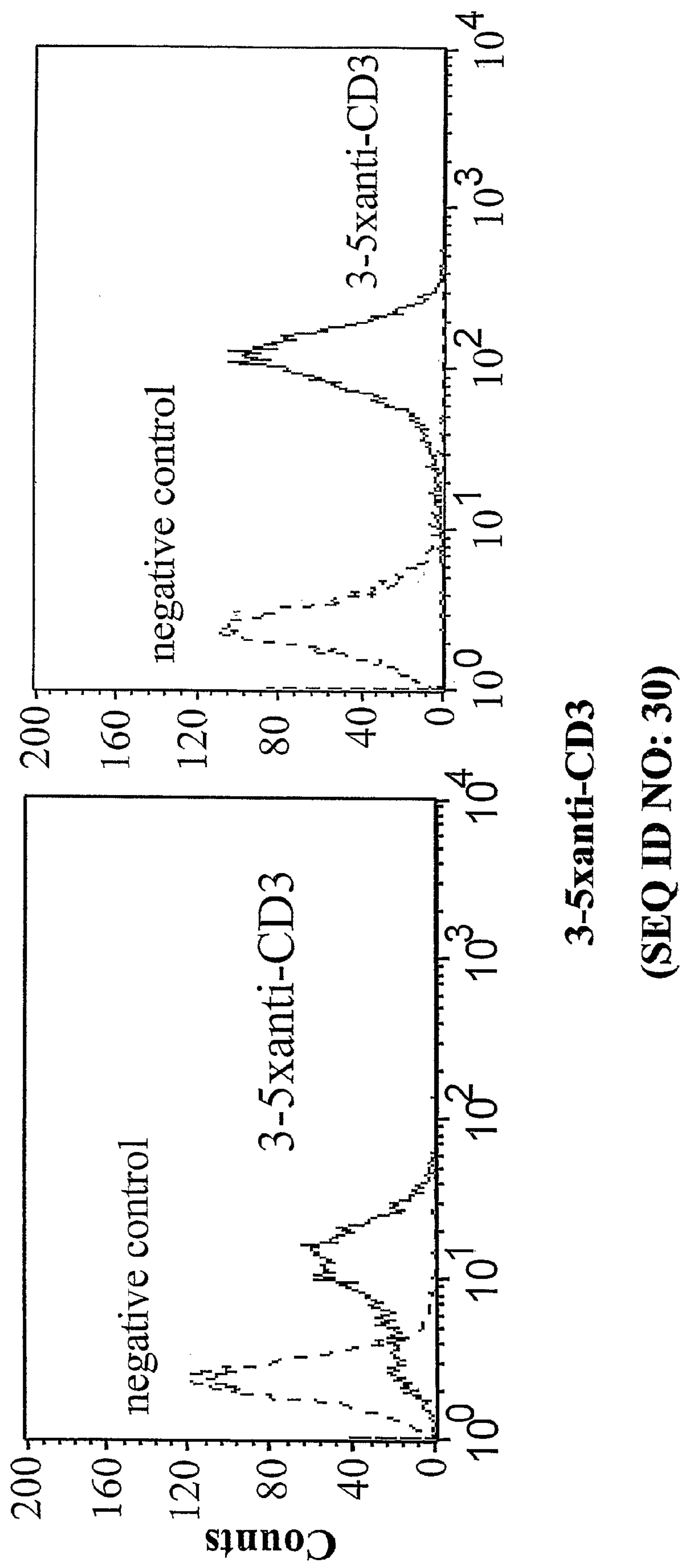
Figure 4C:
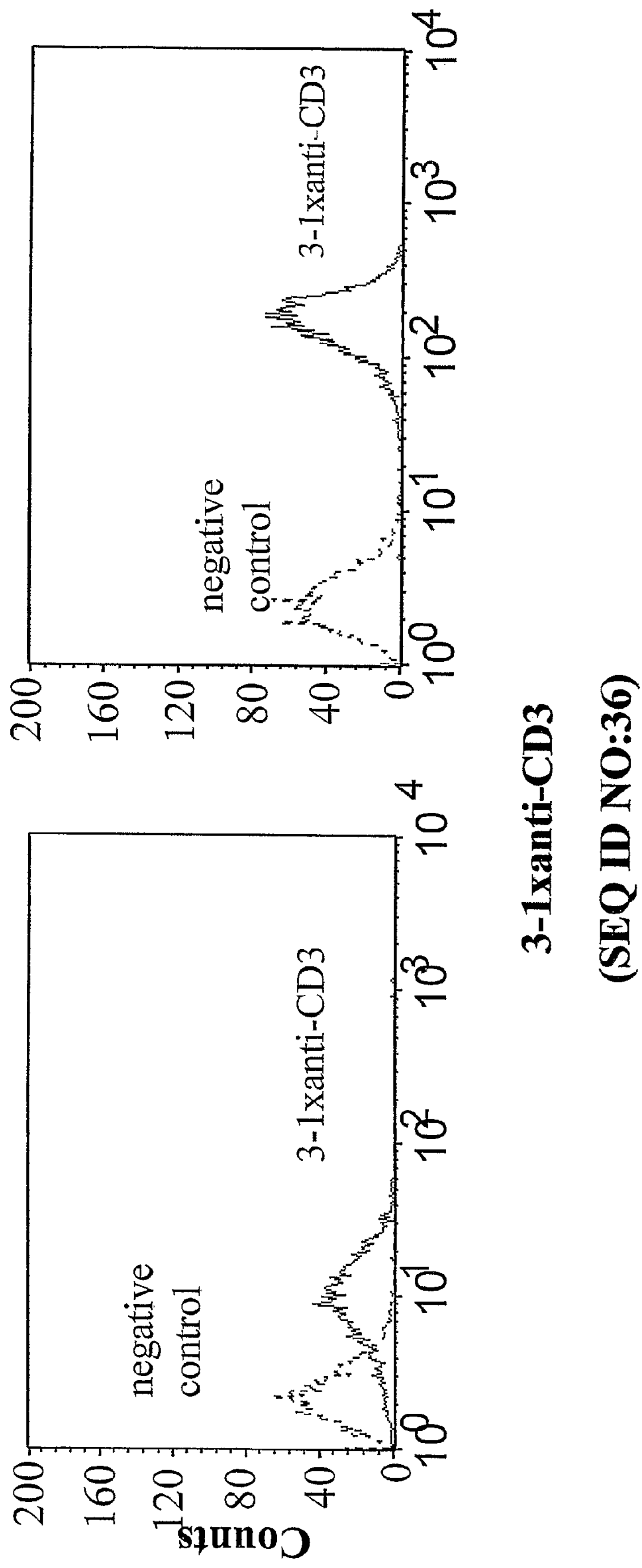
Figure 4D:
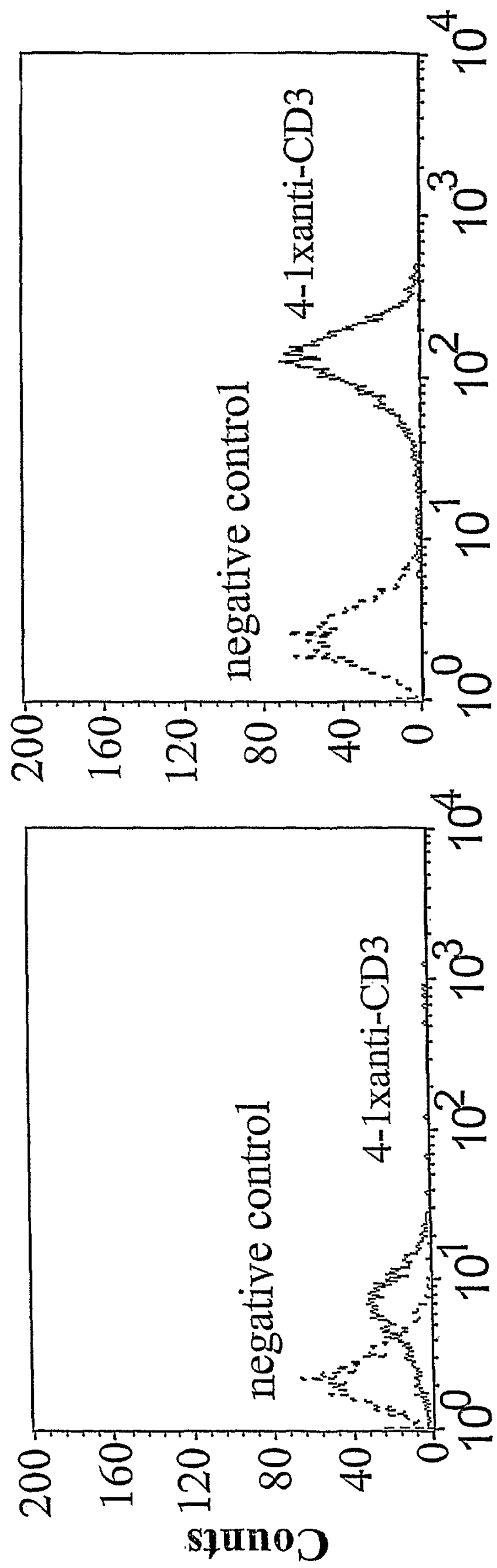
Figure 4E:
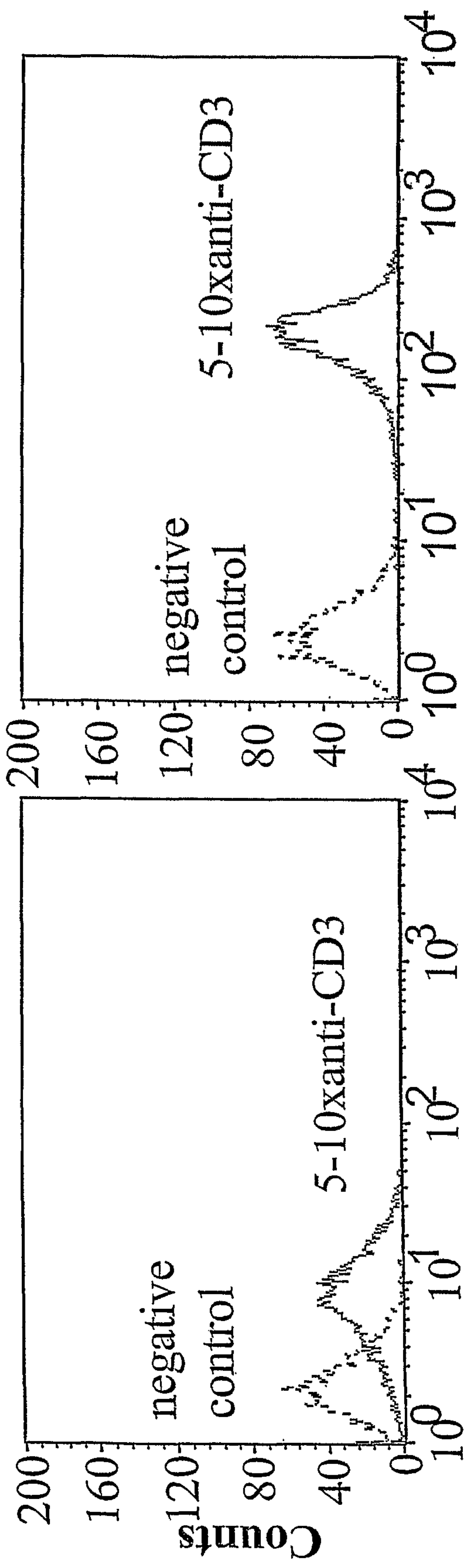
Figure 5:
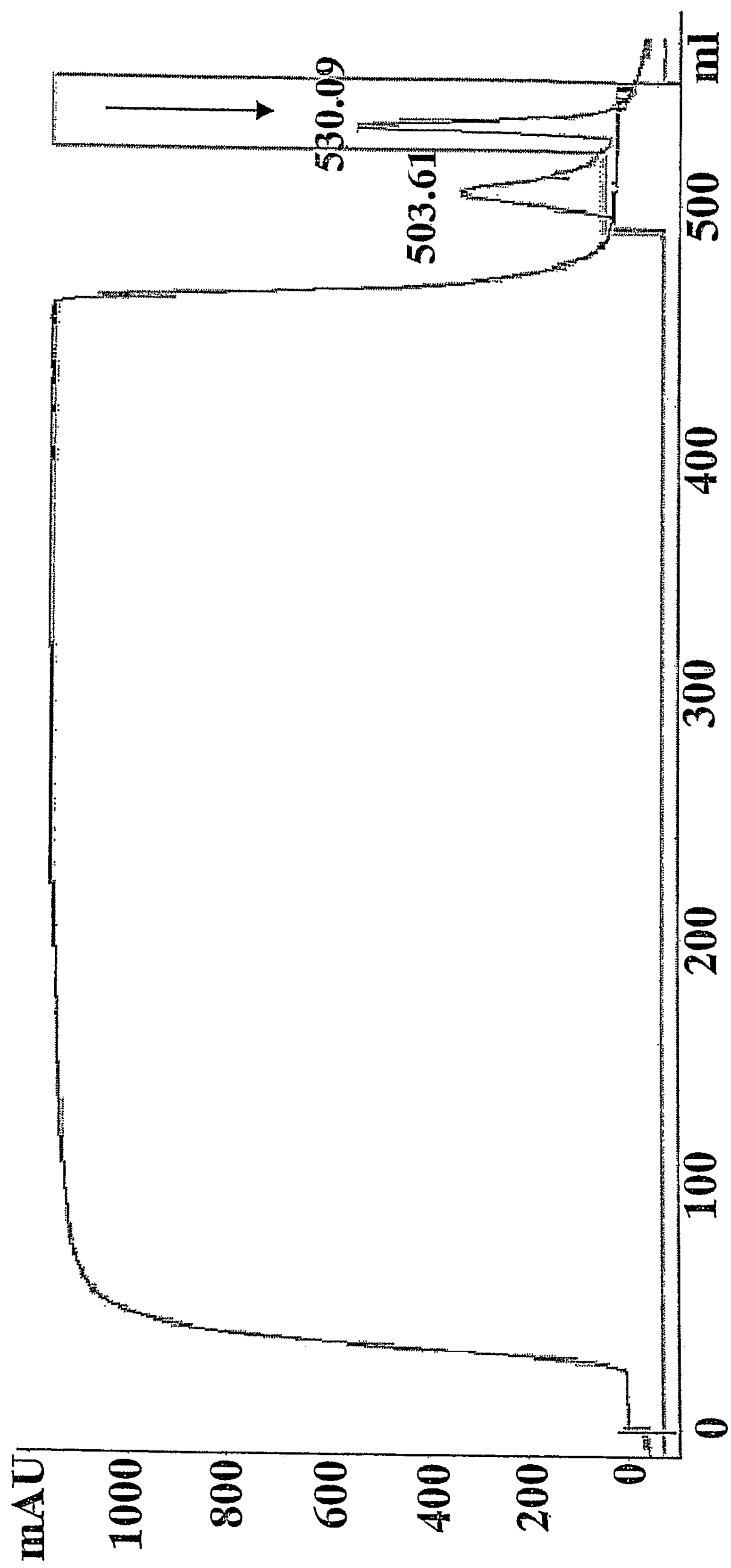

Gottlinger et al., The epithelial cell surface antigen 17-1A, a target for antibody-mediated tumor therapy: its biochemical nature, tissue distribution and recognition by different monoclonal antibodies, *Int. J. Cancer*, 38: 47-53 (1986).
Helfrich et al., Construction and characterization of a bispecific diabody for retargeting T cells to human carcinomas, *Int. J. Cancer* 76: 232-9 (1998).
Johnson et al., Preferred CDRH3 lengths for antibodies with defined specificities, *Int. Immunol.* 10(12): 1801-5 (1998).
Johnson et al., Preferred CDRH3 lengths for antibodies with defined specificities, *Int Immunol.*, 10(12): 1801-5 (1998).
Klimka et al., Human anti-CD30 recombinant antibodies by guided phage antibody selection using cell panning. *Br. J. Cancer*, 83: 252-60 (2000).
Kroesen et al., Bispecific antibody-mediated target cell-specific costimulation of resting T cells via CD5 and CD28, *Cancer Res.* 55: 4409-15 (1995).
Kufer et al., Construction and biological activity of a recombinant bispecific single-chain antibody designed for therapy of minimal residual colorectal cancer, *Cancer Immunol. Immunother.* 45: 193-7 (1997).
Lamminmaki et al., Crystal structure of a recombinant anti-estradiol Fab fragment in complex with 17beta -estradiol. *J. Biol. Chem.* 276: 36687-94 (2001).
MacCallum et al., Antibody-antigen interactions: contact analysis and binding site topography. *J. Mol. Biol.* 262: 732-45 (1996).
Mack et al., Biologic properties of a bispecific single-chain antibody directed against 17-1A (EpCAM) and CD3, *J. Immunol.* 158: 3965-70 (1997).
Mack, et al., A small bispecific antibody construct expressed as a functional single-chain molecule with high tumor cell cytotoxicity, *Proc. Natl. Acad. Sci. USA*, 92: 7021-5 (1995).
Martin et al., Expression of the 17-1A antigen in gastric and gastro-oesophageal junction adenocarcinomas: A potential immunotherapeutic target? *J Clin Pathol.* 52: 701-4 (1999).
Moller et al., Bispecific-monoclonal-antibody-directed lysis of ovarian carcinoma cells by activated human T lymphocytes *Cancer Immunol. Immunother.* 33: 210-6 (1991).
Packeisen et al., Detection of surface antigen 17-1A in breast and colorectal cancer, *Hybridoma*, 18(1) 1999.
Padlan et al., Structure of an antibody-antigen complex: crystal structure of the HyHEL-10 Fab-lysozyme complex. *Proc. Natl. Acad. Sci. USA*, 86: 5938-42 (1989).
Passlick et al., The 17-1A antigen is expressed on primary, metastatic and disseminated non-small cell lung carcinoma cells, *Int. J. Cancer*, 87: 548-52 (2000).
Piyathilake et al., The expression of Ep-CAM (17-1A) in squamous cell cancers of the lung, *Hum. Pathol.*, 31(4): 482-7 (2000).
Poczatek et al., Ep-Cam levels in prostatic adenocarcinoma and prostatic intraepithelial neoplasia, *J. Urology*, 162: 1462-6 (1998).
Raum et al., Anti-self antibodies selected from a human IgD heavy chain repertoire: a novel approach to generate therapeutic human antibodies against tumor-associated differentiation antigens, *Cancer Immunol. Immunother.*, 50(3): 141-50 (2001).
Raum et al., Anti-self antibodies selected from a human IgD heavy chain repertoire: a novel approach to generate therapeutic human antibodies against tumor-associated differentiation antigens, *Cancer Immunol. Lmmunother.* 50: 141-50 (2001).
Riethmuller et al., Monoclonal antibody (Mab) adjuvant therapy of Dukes C colorectal carcinoma: 7-year update of a prospective randomized trial, *Proc. ASCO*, vol. 15, Mar. 1996.
Riethmuller et al., Monoclonal antibody therapy for resected Dukes' C colorectal cancer: Seven-year outcome of a multicenter randomized trial, *J. Clin. Oncol.* 16(5): 1788-94 (1998).
Riethmuller et al., Randomised trial of monoclonal antibody for adjuvant therapy of resected Dukes' C colorectal carcinoma, *Lancet*, 343 (8907): 1177-83 (1994).
Rudikoff et al., Single amino acid substitution altering antigen-binding specificity. *Proc. Natl. Acad. Sci. USA*, 79: 1979-83 (1982).
Simon et al., Epithelial glycoprotein is a member of a family of epithelial cell surface antigens homologous to nidogen, a matrix adhesion protein, *Proc. Nati. Acad. Sci. USA*, 87: 2755-9 (1990).
Skolnick et al., From genes to protein structure and function: novel applications of computational approaches in the genomic era. *Trends in Biotech.* 18: 34-9 (2000).
Traunecker et al., Bispecific single chain molecules (Janusins) target cytotoxic lymphocytes on HIV infected cells, *EMBO J.* 10(12): 3655-9 (1991).
Zeidler et al., Simultaneous activation of T cells and accessory cells by a new class of intact bispecific antibody results in efficient tumor cell killing, *J. Immunol.* 163: 1246-52 (1999).

* cited by examiner

Figure 1

A) anti-CD3 VHVL stL x 3-1 VHVL (SEQ ID NO: 11)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGGTGGTGGTGGTT
CTGGCGGCGGCGGCTCCGGTGGTGGTGGTTCTGACATTCAGCTGACCCAGTCTCCAGCAATCATGTCTGCATCT
CCAGGGGAGAAGGTCACCATGACCTGCAGAGCCAGTTCAAGTGTAAGTTACATGAACTGGTACCAGCAGAAGTC
AGGCACCTCCCCCAAAAGATGGATTTATGACACATCCAAAGTGGCTTCTGGAGTCCCTTATCGCTTCAGTGGCA
GTGGGTCTGGGACCTCATACTCTCTCACAATCAGCAGCATGGAGGCTGAAGATGCTGCCACTTATTACTGCCAA
CAGTGGAGTAGTAACCCGCTCACGTTCGGTGCTGGGACCAAGCTGGAGCTGAAATCCGGAGGTGGTGGATCCGA
GGTGCAGCTGCTCGAGCAGTCTGGAGCTGAGCTGGTGAAACCTGGGGCCTCAGTGAAGATATCCTGCAAGGCTT
CTGGATACGCCTTCACTAACTACTGGCTAGGTTGGGTAAAGCAGAGGCCTGGACATGGACTTGAGTGGATTGGA
GATCTTTTCCCTGGAAGTGGTAATACTCACTACAATGAGAGGTTCAGGGGCAAAGCCACACTGACTGCAGACAA
ATCCTCGAGCACAGCCTTTATGCAGCTCAGTAGCCTGACATCTGAGGACTCTGCTGTCTATTTCTGTGCAAGAT
TGAGGAACTGGGACGAGGCTATGGACTACTGGGGCCAAGGGACCACGGTCACCGTCTCCTCAGGTGGTGGTGGT
TCTGGCGGCGGCGGCTCCGGTGGTGGTGGTTCTGAGCTCGTCATGACCCAGTCTCCATCTTATCTTGCTGCATC
TCCTGGAGAAACCATTACTATTAATTGCAGGGCAAGTAAGAGCATTAGCAAATATTTAGCCTGGTATCAAGAGA
AACCTGGGAAAACTAATAAGCTTCTTATCTACTCTGGATCCACTTTGCAATCTGGAATTCCATCAAGGTTCAGT
GGCAGTGGATCTGGTACAGATTTCACTCTCACCATCAGTAGCCTGGAGCCTGAAG

Figure 1 A) continued

ATTTTGCAATGTATTACTGTCAACAGCATAATGAATATCCGTACACGTTCGGAGGGGGGACCAAGCTTGAGATC
AAACATCATCACCATCATCATTAG (SEQ ID NO: 12)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSGGGGSGGGGSGGGGSDIQLTQSPAIMSAS
PGEKVTMTCRASSSVSYMNWYQQKSGTSPKRWIYDTSKVASGVPYRFSGSGSGTSYSLTISSMEAEDAATYYCQ
QWSSNPLTFGAGTKLELKSGGGGSEVQLLEQSGAELVKPGASVKISCKASGYAFTNYWLGWVKQRPGHGLEWIG
DLFPGSGNTHYNERFRGKATLTADKSSSTAFMQLSSLTSEDSAVYFCARLRNWDEAMDYWGQGTTVTVSSGGGG
SGGGGSGGGGSELVMTQSPSYLAASPGETITINCRASKSISKYLAWYQEKPGKTNKLLIYSGSTLQSGIPSRFS
GSGSGTDFTLTISSLEPEDFAMYYCQQHNEYPYTFGGGTKLEIKHHHHHH

Figure 1

B) anti-CD3 VHVL aL x 4-7 VHVL (SEQ ID NO:1)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGTCGAAGGTGGAA
GTGGAGGTTCTGGTGGAAGTGGAGGTTCAGGTGGAGTCGACGACATTCAGCTGACCCAGTCTCCAGCAATCATG
TCTGCATCTCCAGGGGAGAAGGTCACCATGACCTGCAGAGCCAGTTCAAGTGTAAGTTACATGAACTGGTACCA
GCAGAAGTCAGGCACCTCCCCCAAAAGATGGATTTATGACACATCCAAAGTGGCTTCTGGAGTCCCTTATCGCT
TCAGTGGCAGTGGGTCTGGGACCTCATACTCTCTCACAATCAGCAGCATGGAGGCTGAAGATGCTGCCACTTAT
TACTGCCAACAGTGGAGTAGTAACCCGCTCACGTTCGGTGCTGGGACCAAGCTGGAGCTGAAATCCGGAGGTGG
TGGATCCGAGGTGCAGCTGCTCGAGCAGTCTGGAGCTGAGCTGGCGAGGCCTGGGGCTTCAGTGAAGCTGTCCT
GCAAGGCTTCTGGCTACACCTTCACAAACTATGGTTTAAGCTGGGTGAAGCAGAGGCCTGGACAGGTCCTTGAG
TGGATTGGAGAGGTTTATCCTAGAATTGGTAATGCTTACTACAATGAGAAGTTCAAGGGCAAGGCCACACTGAC
TGCAGACAAATCCTCCAGCACAGCGTCCATGGAGCTCCGCAGCCTGACCTCTGAGGACTCTGCGGTCTATTTCT
GTGCAAGACGGGGATCCTACGATACTAACTACGACTGGTACTTCGATGTCTGGGGCCAAGGGACCACGGTCACC
GTCTCCTCAGGTGGTGGTGGTTCTGGCGGCGGCGGCTCCGGTGGTGGTGGTTCTGAGCTCGTGATGACCCAGAC
TCCACTCTCCCTGCCTGTCAGTCTTGGAGATCAAGCCTCCATCTCTTGCAGATCTAGTCAGAGCCTTGTACACA
GTAATGGAAACACCTATTTACATTGGTACCTGCAGAAGCCAGGCCAGTCTCCAAAG

Figure 1 B) continued

CTCCTGATCTACAAAGTTTCCAACCGATTTTCTGGGGTCCCAGACAGGTTCAGTGGCAGTGGATCAGGGACAGA
TTTCACACTCAAGATCAGCAGAGTGGAGGCTGAGGATCTGGGAGTTTATTTCTGCTCTCAAAGTACACATGTTC
CGTACACGTTCGGAGGGGGGACCAAGCTTGAGATCAAACATCATCACCATCATCATTAG (SEQ ID NO: 2)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSVEGGSGGSGGSGGSGGVDDIQLTQSPAIM
SASPGEKVTMTCRASSSVSYMNWYQQKSGTSPKRWIYDTSKVASGVPYRFSGSGSGTSYSLTISSMEAEDAATY
YCQQWSSNPLTFGAGTKLELKSGGGGSEVQLLEQSGAELARPGASVKLSCKASGYTFTNYGLSWVKQRPGQVLE
WIGEVYPRIGNAYYNEKFKGKATLTADKSSSTASMELRSLTSEDSAVYFCARRGSYDTNYDWYFDVWGQGTTVT
VSSGGGGSGGGGSGGGGSELVMTQTPLSLPVSLGDQASISCRSSQSLVHSNGNTYLHWYLQKPGQSPKLLIYKV
SNRFSGVPDRFSGSGSGTDFTLKISRVEAEDLGVYFCSQSTHVPYTFGGGTKLEIKHHHHHH

Figure 1

C) anti-CD3 VHVL aL Ser x 4-7 VHVL (SEQ ID NO: 7)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTCCCTTGACTACTGGGGCCAAGGCACCACTCTCACAGTCTCCTCAGTCGAAGGTGGAA
GTGGAGGTTCTGGTGGAAGTGGAGGTTCAGGTGGAGTCGACGACATTCAGCTGACCCAGTCTCCAGCAATCATG
TCTGCATCTCCAGGGGAGAAGGTCACCATGACCTGCAGAGCCAGTTCAAGTGTAAGTTACATGAACTGGTACCA
GCAGAAGTCAGGCACCTCCCCCAAAAGATGGATTTATGACACATCCAAAGTGGCTTCTGGAGTCCCTTATCGCT
TCAGTGGCAGTGGGTCTGGGACCTCATACTCTCTCACAATCAGCAGCATGGAGGCTGAAGATGCTGCCACTTAT
TACTGCCAACAGTGGAGTAGTAACCCGCTCACGTTCGGTGCTGGGACCAAGCTGGAGCTGAAATCCGGAGGTGG
TGGATCCGAGGTGCAGCTGCTCGAGCAGTCTGGAGCTGAGCTGGCGAGGCCTGGGGCTTCAGTGAAGCTGTCCT
GCAAGGCTTCTGGCTACACCTTCACAAACTATGGTTTAAGCTGGGTGAAGCAGAGGCCTGGACAGGTCCTTGAG
TGGATTGGAGAGGTTTATCCTAGAATTGGTAATGCTTACTACAATGAGAAGTTCAAGGGCAAGGCCACACTGAC
TGCAGACAAATCCTCCAGCACAGCGTCCATGGAGCTCCGCAGCCTGACCTCTGAGGACTCTGCGGTCTATTTCT
GTGCAAGACGGGGATCCTACGATACTAACTACGACTGGTACTTCGATGTCTGGGGCCAAGGGACCACGGTCACC
GTCTCCTCAGGTGGTGGTGGTTCTGGCGGCGGCGGCTCCGGTGGTGGTGGTTCTGAGCTCGTGATGACCCAGAC
TCCACTCTCCCTGCCTGTCAGTCTTGGAGATCAAGCCTCCATCTCTTGCAGATCTAGTCAGAGCCTTGTACACA
GTAATGGAAACACCTATTTACATTGGTACCTGCAGAAGCCAGGCCAGTCTCCAAAGCTCCTGATCTACAAAGTT
TCCAACCGATTTTCTGGGGTCCCAGACAGGTTCAGTGGCAGTGGATCAGGGACAG

Figure 1 C) continued

ATTTCACACTCAAGATCAGCAGAGTGGAGGCTGAGGATCTGGGAGTTTATTTCTGCTCTCAAAGTACACATGTT
CCGTACACGTTCGGAGGGGGGACCAAGCTTGAGATCAAACATCATCACCATCATCATTAG (SEQ ID NO: 8)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYSLDYWGQGTTLTVSSVEGGSGGSGGSGGSGGVDDIQLTQSPAIM
SASPGEKVTMTCRASSSVSYMNWYQQKSGTSPKRWIYDTSKVASGVPYRFSGSGSGTSYSLTISSMEAEDAATY
YCQQWSSNPLTFGAGTKLELKSGGGGSEVQLLEQSGAELARPGASVKLSCKASGYTFTNYGLSWVKQRPGQVLE
WIGEVYPRIGNAYYNEKFKGKATLTADKSSSTASMELRSLTSEDSAVYFCARRGSYDTNYDWYFDVWGQGTTVT
VSSGGGGSGGGGSGGGGSELVMTQTPLSLPVSLGDQASISCRSSQSLVHSNGNTYLHWYLQKPGQSPKLLIYKV
SNRFSGVPDRFSGSGSGTDFTLKISRVEAEDLGVYFCSQSTHVPYTFGGGTKLEIKHHHHHH

Figure 1

D) anti-CD3 VHVL stL x 4-7 VHVL (SEQ ID NO: 13)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGGTGGTGGTGGTT
CTGGCGGCGGCGGCTCCGGTGGTGGTGGTTCTGACATTCAGCTGACCCAGTCTCCAGCAATCATGTCTGCATCT
CCAGGGGAGAAGGTCACCATGACCTGCAGAGCCAGTTCAAGTGTAAGTTACATGAACTGGTACCAGCAGAAGTC
AGGCACCTCCCCCAAAAGATGGATTTATGACACATCCAAAGTGGCTTCTGGAGTCCCTTATCGCTTCAGTGGCA
GTGGGTCTGGGACCTCATACTCTCTCACAATCAGCAGCATGGAGGCTGAAGATGCTGCCACTTATTACTGCCAA
CAGTGGAGTAGTAACCCGCTCACGTTCGGTGCTGGGACCAAGCTGGAGCTGAAATCCGGAGGTGGTGGATCCGA
GGTGCAGCTGCTCGAGCAGTCTGGAGCTGAGCTGGCGAGGCCTGGGGCTTCAGTGAAGCTGTCCTGCAAGGCTT
CTGGCTACACCTTCACAAACTATGGTTTAAGCTGGGTGAAGCAGAGGCCTGGACAGGTCCTTGAGTGGATTGGA
GAGGTTTATCCTAGAATTGGTAATGCTTACTACAATGAGAAGTTCAAGGGCAAGGCCACACTGACTGCAGACAA
ATCCTCCAGCACAGCGTCCATGGAGCTCCGCAGCCTGACCTCTGAGGACTCTGCGGTCTATTTCTGTGCAAGAC
GGGGATCCTACGATACTAACTACGACTGGTACTTCGATGTCTGGGGCCAAGGGACCACGGTCACCGTCTCCTCA
GGTGGTGGTGGTTCTGGCGGCGGCGGCTCCGGTGGTGGTGGTTCTGAGCTCGTGATGACCCAGACTCCACTCTC
CCTGCCTGTCAGTCTTGGAGATCAAGCCTCCATCTCTTGCAGATCTAGTCAGAGCCTTGTACACAGTAATGGAA
ACACCTATTTACATTGGTACCTGCAGAAGCCAGGCCAGTCTCCAAAGCTCCTGATCTACAAAGTTTCCAACCGA
TTTTCTGGGGTCCCAGACAGGTTCAGTGGCAGTGGATCAGGGACAGATTTCACAC

Figure 1 D) continued

TCAAGATCAGCAGAGTGGAGGCTGAGGATCTGGGAGTTTATTTCTGCTCTCAAAGTACACATGTTCCGTACACG
TTCGGAGGGGGGACCAAGCTTGAGATCAAACATCATCACCATCATCATTAG (SEQ ID NO: 14)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSGGGGSGGGGSGGGGSDIQLTQSPAIMSAS
PGEKVTMTCRASSSVSYMNWYQQKSGTSPKRWIYDTSKVASGVPYRFSGSGSGTSYSLTISSMEAEDAATYYCQ
QWSSNPLTFGAGTKLELKSGGGGSEVQLLEQSGAELARPGASVKLSCKASGYTFTNYGLSWVKQRPGQVLEWIG
EVYPRIGNAYYNEKFKGKATLTADKSSSTASMELRSLTSEDSAVYFCARRGSYDTNYDWYFDVWGQGTTVTVSS
GGGGSGGGGSGGGGSELVMTQTPLSLPVSLGDQASISCRSSQSLVHSNGNTYLHWYLQKPGQSPKLLIYKVSNR
FSGVPDRFSGSGSGTDFTLKISRVEAEDLGVYFCSQSTHVPYTFGGGTKLEIKHHHHHH

Figure 1

E) anti-CD3 VHVL stL x 4-7 VLVH (SEQ ID NO: 15)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGGTGGTGGTGGTT
CTGGCGGCGGCGGCTCCGGTGGTGGTGGTTCTGACATTCAGCTGACCCAGTCTCCAGCAATCATGTCTGCATCT
CCAGGGGAGAAGGTCACCATGACCTGCAGAGCCAGTTCAAGTGTAAGTTACATGAACTGGTACCAGCAGAAGTC
AGGCACCTCCCCCAAAAGATGGATTTATGACACATCCAAAGTGGCTTCTGGAGTCCCTTATCGCTTCAGTGGCA
GTGGGTCTGGGACCTCATACTCTCTCACAATCAGCAGCATGGAGGCTGAAGATGCTGCCACTTATTACTGCCAA
CAGTGGAGTAGTAACCCGCTCACGTTCGGTGCTGGGACCAAGCTGGAGCTGAAATCCGGAGGTGGTGGATCCGA
GCTCGTGATGACCCAGACTCCACTCTCCCTGCCTGTCAGTCTTGGAGATCAAGCCTCCATCTCTTGCAGATCTA
GTCAGAGCCTTGTACACAGTAATGGAAACACCTATTTACATTGGTACCTGCAGAAGCCAGGCCAGTCTCCAAAG
CTCCTGATCTACAAAGTTTCCAACCGATTTTCTGGGGTCCCAGACAGGTTCAGTGGCAGTGGATCAGGGACAGA
TTTCACACTCAAGATCAGCAGAGTGGAGGCTGAGGATCTGGGAGTTTATTTCTGCTCTCAAAGTACACATGTTC
CGTACACGTTCGGAGGGGGGACCAAGCTTGAGATCAAAGGTGGTGGTGGTTCTGGCGGCGGCGGCTCCGGTGGT
GGTGGTTCTGAGGTGCAGCTGCTCGAGCAGTCTGGAGCTGAGCTGGCGAGGCCTGGGGCTTCAGTGAAGCTGTC
CTGCAAGGCTTCTGGCTACACCTTCACAAACTATGGTTTAAGCTGGGTGAAGCAGAGGCCTGGACAGGTCCTTG
AGTGGATTGGAGAGGTTTATCCTAGAATTGGTAATGCTTACTACAATGAGAAGTTCAAGGGCAAGGCCACACTG
ACTGCAGACAAATCCTCCAGCACAGCGTCCATGGAGCTCCGCAGCCTGACCTCTG

Figure 1 E) continued

AGGACTCTGCGGTCTATTTCTGTGCAAGACGGGGATCCTACGATACTAACTACGACTGGTACTTCGATGTCTGG
GGCCAAGGGACCACGGTCACCGTCTCCTCACATCATCACCATCATCATTAG (SEQ ID NO: 16)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSGGGGSGGGGSGGGGSDIQLTQSPAIMSAS
PGEKVTMTCRASSSVSYMNWYQQKSGTSPKRWIYDTSKVASGVPYRFSGSGSGTSYSLTISSMEAEDAATYYCQ
QWSSNPLTFGAGTKLELKSGGGGSELVMTQTPLSLPVSLGDQASISCRSSQSLVHSNGNTYLHWYLQKPGQSPK
LLIYKVSNRFSGVPDRFSGSGSGTDFTLKISRVEAEDLGVYFCSQSTHVPYTFGGGTKLEIKGGGGSGGGGSGG
GGSEVQLLEQSGAELARPGASVKLSCKASGYTFTNYGLSWVKQRPGQVLEWIGEVYPRIGNAYYNEKFKGKATL
TADKSSSTASMELRSLTSEDSAVYFCARRGSYDTNYDWYFDVWGQGTTVTVSSHHHHHH

Figure 1

F) anti-CD3 VHVL aL x 5-10 VHVL (SEQ ID NO: 3)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGTCGAAGGTGGAA
GTGGAGGTTCTGGTGGAAGTGGAGGTTCAGGTGGAGTCGACGACATTCAGCTGACCCAGTCTCCAGCAATCATG
TCTGCATCTCCAGGGGAGAAGGTCACCATGACCTGCAGAGCCAGTTCAAGTGTAAGTTACATGAACTGGTACCA
GCAGAAGTCAGGCACCTCCCCCAAAAGATGGATTTATGACACATCCAAAGTGGCTTCTGGAGTCCCTTATCGCT
TCAGTGGCAGTGGGTCTGGGACCTCATACTCTCTCACAATCAGCAGCATGGAGGCTGAAGATGCTGCCACTTAT
TACTGCCAACAGTGGAGTAGTAACCCGCTCACGTTCGGTGCTGGGACCAAGCTGGAGCTGAAATCCGGAGGTGG
TGGATCCGAGGTGCAGCTGCTCGAGCAGTCTGGAGCTGAGCTGGTAAGGCCTGGGACTTCAGTGAAGATATCCT
GCAAGGCTTCTGGATACGCCTTCACTAACTACTGGCTAGGTTGGGTAAAGCAGAGGCCTGGACATGGACTTGAG
TGGATTGGAGATATTTTCCCTGGAAGTGGTAATATCCACTACAATGAGAAGTTCAAGGGCAAAGCCACACTGAC
TGCAGACAAATCTTCGAGCACAGCCTATATGCAGCTCAGTAGCCTGACATTTGAGGACTCTGCTGTCTATTTCT
GTGCAAGACTGAGGAACTGGGACGAGCCTATGGACTACTGGGGCCAAGGGACCACGGTCACCGTCTCCTCAGGT
GGTGGTGGTTCTGGCGGCGGCGGCTCCGGTGGTGGTGGTTCTGAGCTCGTGATGACACAGTCTCCATCCTCCCT
GACTGTGACAGCAGGAGAGAAGGTCACTATGAGCTGCAAGTCCAGTCAGAGTCTGTTAAACAGTGGAAATCAAA
AGAACTACTTGACCTGGTACCAGCAGAAACCAGGGCAGCCTCCTAAACTGTTGATCTACTGGGCATCCACTAGG
GAATCTGGGGTCCCTGATCGCTTCACAGGCAGTGGATCTGGAACAGATTTCACTC

Figure 1 F) continued

TCACCATCAGCAGTGTGCAGGCTGAAGACCTGGCAGTTTATTACTGTCAGAATGATTATAGTTATCCGCTCACG
TTCGGTGCTGGGACCAAGCTTGAGATCAAACATCATCACCATCATCATTAG (SEQ ID NO: 4)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSVEGGSGGSGGSGGSGGVDDIQLTQSPAIM
SASPGEKVTMTCRASSSVSYMNWYQQKSGTSPKRWIYDTSKVASGVPYRFSGSGSGTSYSLTISSMEAEDAATY
YCQQWSSNPLTFGAGTKLELKSGGGGSEVQLLEQSGAELVRPGTSVKISCKASGYAFTNYWLGWVKQRPGHGLE
WIGDIFPGSGNIHYNEKFKGKATLTADKSSSTAYMQLSSLTFEDSAVYFCARLRNWDEPMDYWGQGTTVTVSSG
GGGSGGGGSGGGGSELVMTQSPSSLTVTAGEKVTMSCKSSQSLLNSGNQKNYLTWYQQKPGQPPKLLIYWASTR
ESGVPDRFTGSGSGTDFTLTISSVQAEDLAVYYCQNDYSYPLTFGAGTKLEIKHHHHHH

Figure 1

G) anti-CD3 VHVL aL Ser x 5-10 VHVL (SEQ ID NO: 9)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTCCCTTGACTACTGGGGCCAAGGCACCACTCTCACAGTCTCCTCAGTCGAAGGTGGAA
GTGGAGGTTCTGGTGGAAGTGGAGGTTCAGGTGGAGTCGACGACATTCAGCTGACCCAGTCTCCAGCAATCATG
TCTGCATCTCCAGGGGAGAAGGTCACCATGACCTGCAGAGCCAGTTCAAGTGTAAGTTACATGAACTGGTACCA
GCAGAAGTCAGGCACCTCCCCCAAAAGATGGATTTATGACACATCCAAAGTGGCTTCTGGAGTCCCTTATCGCT
TCAGTGGCAGTGGGTCTGGGACCTCATACTCTCTCACAATCAGCAGCATGGAGGCTGAAGATGCTGCCACTTAT
TACTGCCAACAGTGGAGTAGTAACCCGCTCACGTTCGGTGCTGGGACCAAGCTGGAGCTGAAATCCGGAGGTGG
TGGATCCGAGGTGCAGCTGCTCGAGCAGTCTGGAGCTGAGCTGGTAAGGCCTGGGACTTCAGTGAAGATATCCT
GCAAGGCTTCTGGATACGCCTTCACTAACTACTGGCTAGGTTGGGTAAAGCAGAGGCCTGGACATGGACTTGAG
TGGATTGGAGATATTTTCCCTGGAAGTGGTAATATCCACTACAATGAGAAGTTCAAGGGCAAAGCCACACTGAC
TGCAGACAAATCTTCGAGCACAGCCTATATGCAGCTCAGTAGCCTGACATTTGAGGACTCTGCTGTCTATTTCT
GTGCAAGACTGAGGAACTGGGACGAGCCTATGGACTACTGGGGCCAAGGGACCACGGTCACCGTCTCCTCAGGT
GGTGGTGGTTCTGGCGGCGGCGGCTCCGGTGGTGGTGGTTCTGAGCTCGTGATGACACAGTCTCCATCCTCCCT
GACTGTGACAGCAGGAGAGAAGGTCACTATGAGCTGCAAGTCCAGTCAGAGTCTGTTAAACAGTGGAAATCAAA
AGAACTACTTGACCTGGTACCAGCAGAAACCAGGGCAGCCTCCTAAACTGTTGATC

Figure 1 G) continued

TACTGGGCATCCACTAGGGAATCTGGGGTCCCTGATCGCTTCACAGGCAGTGGATCTGGAACAGATTTCACTCT
CACCATCAGCAGTGTGCAGGCTGAAGACCTGGCAGTTTATTACTGTCAGAATGATTATAGTTATCCGCTCACGT
TCGGTGCTGGGACCAAGCTTGAGATCAAACATCATCACCATCATCATTAG (SEQ ID NO: 10)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYSLDYWGQGTTLTVSSVEGGSGGSGGSGGSGGVDDIQLTQSPAIM
SASPGEKVTMTCRASSSVSYMNWYQQKSGTSPKRWIYDTSKVASGVPYRFSGSGSGTSYSLTISSMEAEDAATY
YCQQWSSNPLTFGAGTKLELKSGGGGSEVQLLEQSGAELVRPGTSVKISCKASGYAFTNYWLGWVKQRPGHGLE
WIGDIFPGSGNIHYNEKFKGKATLTADKSSSTAYMQLSSLTFEDSAVYFCARLRNWDEPMDYWGQGTTVTVSSG
GGGSGGGGSGGGGSELVMTQSPSSLTVTAGEKVTMSCKSSQSLLNSGNQKNYLTWYQQKPGQPPKLLIYWASTR
ESGVPDRFTGSGSGTDFTLTISSVQAEDLAVYYCQNDYSYPLTFGAGTKLEIKHHHHHH

Figure 1

H) anti-CD3 VHVL stL x 5-10 VHVL (SEQ ID NO: 17)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGGTGGTGGTGGTT
CTGGCGGCGGCGGCTCCGGTGGTGGTGGTTCTGACATTCAGCTGACCCAGTCTCCAGCAATCATGTCTGCATCT
CCAGGGGAGAAGGTCACCATGACCTGCAGAGCCAGTTCAAGTGTAAGTTACATGAACTGGTACCAGCAGAAGTC
AGGCACCTCCCCCAAAAGATGGATTTATGACACATCCAAAGTGGCTTCTGGAGTCCCTTATCGCTTCAGTGGCA
GTGGGTCTGGGACCTCATACTCTCTCACAATCAGCAGCATGGAGGCTGAAGATGCTGCCACTTATTACTGCCAA
CAGTGGAGTAGTAACCCGCTCACGTTCGGTGCTGGGACCAAGCTGGAGCTGAAATCCGGAGGTGGTGGATCCGA
GGTGCAGCTGCTCGAGCAGTCTGGAGCTGAGCTGGTAAGGCCTGGGACTTCAGTGAAGATATCCTGCAAGGCTT
CTGGATACGCCTTCACTAACTACTGGCTAGGTTGGGTAAAGCAGAGGCCTGGACATGGACTTGAGTGGATTGGA
GATATTTTCCCTGGAAGTGGTAATATCCACTACAATGAGAAGTTCAAGGGCAAAGCCACACTGACTGCAGACAA
ATCTTCGAGCACAGCCTATATGCAGCTCAGTAGCCTGACATTTGAGGACTCTGCTGTCTATTTCTGTGCAAGAC
TGAGGAACTGGGACGAGCCTATGGACTACTGGGGCCAAGGGACCACGGTCACCGTCTCCTCAGGTGGTGGTGGT
TCTGGCGGCGGCGGCTCCGGTGGTGGTGGTTCTGAGCTCGTGATGACACAGTCTCCATCCTCCCTGACTGTGAC
AGCAGGAGAGAAGGTCACTATGAGCTGCAAGTCCAGTCAGAGTCTGTTAAACAGTGGAAATCAAAAGAACTACT
TGACCTGGTACCAGCAGAAACCAGGGCAGCCTCCTAAACTGTTGATCTACTGGGCATCCACTAGGGAATCTGGG
GTCCCTGATCGCTTCACAGGCAGTGGATCTGGAACAGATTTCACTCTCACCATCA

Figure 1 H) continued

GCAGTGTGCAGGCTGAAGACCTGGCAGTTTATTACTGTCAGAATGATTATAGTTATCCGCTCACGTTCGGTGCT
GGGACCAAGCTTGAGATCAAACATCATCACCATCATCATTAG (SEQ ID NO: 18)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSGGGGSGGGGSGGGGSDIQLTQSPAIMSAS
PGEKVTMTCRASSSVSYMNWYQQKSGTSPKRWIYDTSKVASGVPYRFSGSGSGTSYSLTISSMEAEDAATYYCQ
QWSSNPLTFGAGTKLELKSGGGGSEVQLLEQSGAELVRPGTSVKISCKASGYAFTNYWLGWVKQRPGHGLEWIG
DIFPGSGNIHYNEKFKGKATLTADKSSSTAYMQLSSLTFEDSAVYFCARLRNWDEPMDYWGQGTTVTVSSGGGG
SGGGGSGGGGSELVMTQSPSSLTVTAGEKVTMSCKSSQSLLNSGNQKNYLTWYQQKPGQPPKLLIYWASTRESG
VPDRFTGSGSGTDFTLTISSVQAEDLAVYYCQNDYSYPLTFGAGTKLEIKHHHHHH

Figure 1

I) anti-CD3 VHVL stL x 5-10 VLVH (SEQ ID NO: 19)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGGTGGTGGTGGTT
CTGGCGGCGGCGGCTCCGGTGGTGGTGGTTCTGACATTCAGCTGACCCAGTCTCCAGCAATCATGTCTGCATCT
CCAGGGGAGAAGGTCACCATGACCTGCAGAGCCAGTTCAAGTGTAAGTTACATGAACTGGTACCAGCAGAAGTC
AGGCACCTCCCCCAAAAGATGGATTTATGACACATCCAAAGTGGCTTCTGGAGTCCCTTATCGCTTCAGTGGCA
GTGGGTCTGGGACCTCATACTCTCTCACAATCAGCAGCATGGAGGCTGAAGATGCTGCCACTTATTACTGCCAA
CAGTGGAGTAGTAACCCGCTCACGTTCGGTGCTGGGACCAAGCTGGAGCTGAAATCCGGAGGTGGTGGATCCGA
GCTCGTGATGACACAGTCTCCATCCTCCCTGACTGTGACAGCAGGAGAGAAGGTCACTATGAGCTGCAAGTCCA
GTCAGAGTCTGTTAAACAGTGGAAATCAAAAGAACTACTTGACCTGGTACCAGCAGAAACCAGGGCAGCCTCCT
AAACTGTTGATCTACTGGGCATCCACTAGGGAATCTGGGGTCCCTGATCGCTTCACAGGCAGTGGATCTGGAAC
AGATTTCACTCTCACCATCAGCAGTGTGCAGGCTGAAGACCTGGCAGTTTATTACTGTCAGAATGATTATAGTT
ATCCGCTCACGTTCGGTGCTGGGACCAAGCTTGAGATCAAAGGTGGTGGTGGTTCTGGCGGCGGCGGCTCCGGT
GGTGGTGGTTCTGAGGTGCAGCTGCTCGAGCAGTCTGGAGCTGAGCTGGTAAGGCCTGGGACTTCAGTGAAGAT
ATCCTGCAAGGCTTCTGGATACGCCTTCACTAACTACTGGCTAGGTTGGGTAAAGCAGAGGCCTGGACATGGAC
TTGAGTGGATTGGAGATATTTTCCCTGGAAGTGGTAATATCCACTACAATGAGAAGTTCAAGGGCAAAGCCACA
CTGACTGCAGACAAATCTTCGAGCACAGCCTATATGCAGCTCAGTAGCCTGACAT

Figure 1 I) continued

TTGAGGACTCTGCTGTCTATTTCTGTGCAAGACTGAGGAACTGGGACGAGCCTATGGACTACTGGGGCCAAGGG
ACCACGGTCACCGTCTCCTCACATCATCACCATCATCATTAG (SEQ ID NO: 20)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSGGGGSGGGGSGGGGSDIQLTQSPAIMSAS
PGEKVTMTCRASSSVSYMNWYQQKSGTSPKRWIYDTSKVASGVPYRFSGSGSGTSYSLTISSMEAEDAATYYCQ
QWSSNPLTFGAGTKLELKSGGGGSELVMTQSPSSLTVTAGEKVTMSCKSSQSLLNSGNQKNYLTWYQQKPGQPP
KLLIYWASTRESGVPDRFTGSGSGTDFTLTISSVQAEDLAVYYCQNDYSYPLTFGAGTKLEIKGGGGSGGGGSG
GGGSEVQLLEQSGAELVRPGTSVKISCKASGYAFTNYWLGWVKQRPGHGLEWIGDIFPGSGNIHYNEKFKGKAT
LTADKSSSTAYMQLSSLTFEDSAVYFCARLRNWDEPMDYWGQGTTVTVSSHHHHHH

Figure 1

J) anti-CD3 VHVL aL x 3-1 VHVL (SEQ ID NO: 45)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGTCGAAGGTGGAA
GTGGAGGTTCTGGTGGAAGTGGAGGTTCAGGTGGAGTCGACGACATTCAGCTGACCCAGTCTCCAGCAATCATG
TCTGCATCTCCAGGGGAGAAGGTCACCATGACCTGCAGAGCCAGTTCAAGTGTAAGTTACATGAACTGGTACCA
GCAGAAGTCAGGCACCTCCCCCAAAAGATGGATTTATGACACATCCAAAGTGGCTTCTGGAGTCCCTTATCGCT
TCAGTGGCAGTGGGTCTGGGACCTCATACTCTCTCACAATCAGCAGCATGGAGGCTGAAGATGCTGCCACTTAT
TACTGCCAACAGTGGAGTAGTAACCCGCTCACGTTCGGTGCTGGGACCAAGCTGGAGCTGAAATCCGGAGGTGG
TGGATCCGAGGTGCAGCTGCTCGAGCAGTCTGGAGCTGAGCTGGTGAAACCTGGGGCCTCAGTGAAGATATCCT
GCAAGGCTTCTGGATACGCCTTCACTAACTACTGGCTAGGTTGGGTAAAGCAGAGGCCTGGACATGGACTTGAG
TGGATTGGAGATCTTTTCCCTGGAAGTGGTAATACTCACTACAATGAGAGGTTCAGGGGCAAAGCCACACTGAC
TGCAGACAAATCCTCGAGCACAGCCTTTATGCAGCTCAGTAGCCTGACATCTGAGGACTCTGCTGTCTATTTCT
GTGCAAGATTGAGGAACTGGGACGAGGCTATGGACTACTGGGGCCAAGGGACCACGGTCACCGTCTCCTCAGGT
GGTGGTGGTTCTGGCGGCGGCGGCTCCGGTGGTGGTGGTTCTGAGCTCGTCATGACCCAGTCTCCATCTTATCT
TGCTGCATCTCCTGGAGAAACCATTACTATTAATTGCAGGGCAAGTAAGAGCATTAGCAAATATTTAGCCTGGT
ATCAAGAGAAACCTGGGAAAACTAATAAGCTTCTTATCTACTCTGGATCCACTTTGCAATCTGGAATTCCATCA
AGGTTCAGTGGCAGTGGATCTGGTACAGATTTCACTCTCACCATCAGTAGCCTGG

Figure 1 J) continued

AGCCTGAAGATTTTGCAATGTATTACTGTCAACAGCATAATGAATATCCGTACACGTTCGGAGGGGGGACCAAG
CTTGAGATCAAACATCATCACCATCATCATTAG (SEQ ID NO: 46)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSVEGGSGGSGGSGGSGGVDDIQLTQSPAIM
SASPGEKVTMTCRASSSVSYMNWYQQKSGTSPKRWIYDTSKVASGVPYRFSGSGSGTSYSLTISSMEAEDAATY
YCQQWSSNPLTFGAGTKLELKSGGGGSEVQLLEQSGAELVKPGASVKISCKASGYAFTNYWLGWVKQRPGHGLE
WIGDLFPGSGNTHYNERFRGKATLTADKSSSTAFMQLSSLTSEDSAVYFCARLRNWDEAMDYWGQGTTVTVSSG
GGGSGGGGSGGGGSELVMTQSPSYLAASPGETITINCRASKSISKYLAWYQEKPGKTNKLLIYSGSTLQSGIPS
RFSGSGSGTDFTLTISSLEPEDFAMYYCQQHNEYPYTFGGGTKLEIKHHHHHH

Figure 1

K) anti-CD3 VHVL aL Ser x 3-1 VHVL (SEQ ID NO: 47)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTCCCTTGACTACTGGGGCCAAGGCACCACTCTCACAGTCTCCTCAGTCGAAGGTGGAA
GTGGAGGTTCTGGTGGAAGTGGAGGTTCAGGTGGAGTCGACGACATTCAGCTGACCCAGTCTCCAGCAATCATG
TCTGCATCTCCAGGGGAGAAGGTCACCATGACCTGCAGAGCCAGTTCAAGTGTAAGTTACATGAACTGGTACCA
GCAGAAGTCAGGCACCTCCCCCAAAAGATGGATTTATGACACATCCAAAGTGGCTTCTGGAGTCCCTTATCGCT
TCAGTGGCAGTGGGTCTGGGACCTCATACTCTCTCACAATCAGCAGCATGGAGGCTGAAGATGCTGCCACTTAT
TACTGCCAACAGTGGAGTAGTAACCCGCTCACGTTCGGTGCTGGGACCAAGCTGGAGCTGAAATCCGGAGGTGG
TGGATCCGAGGTGCAGCTGCTCGAGCAGTCTGGAGCTGAGCTGGTGAAACCTGGGGCCTCAGTGAAGATATCCT
GCAAGGCTTCTGGATACGCCTTCACTAACTACTGGCTAGGTTGGGTAAAGCAGAGGCCTGGACATGGACTTGAG
TGGATTGGAGATCTTTTCCCTGGAAGTGGTAATACTCACTACAATGAGAGGTTCAGGGGCAAAGCCACACTGAC
TGCAGACAAATCCTCGAGCACAGCCTTTATGCAGCTCAGTAGCCTGACATCTGAGGACTCTGCTGTCTATTTCT
GTGCAAGATTGAGGAACTGGGACGAGGCTATGGACTACTGGGGCCAAGGGACCACGGTCACCGTCTCCTCAGGT
GGTGGTGGTTCTGGCGGCGGCGGCTCCGGTGGTGGTGGTTCTGAGCTCGTCATGACCCAGTCTCCATCTTATCT
TGCTGCATCTCCTGGAGAAACCATTACTATTAATTGCAGGGCAAGTAAGAGCATTAGCAAATATTTAGCCTGGT
ATCAAGAGAAACCTGGGAAAACTAATAAGCTTCTTATCTACTCTGGATCCACTTTG

Figure 1 K) continued

CAATCTGGAATTCCATCAAGGTTCAGTGGCAGTGGATCTGGTACAGATTTCACTCTCACCATCAGTAGCCTGGA
GCCTGAAGATTTTGCAATGTATTACTGTCAACAGCATAATGAATATCCGTACACGTTCGGAGGGGGGACCAAGC
TTGAGATCAAACATCATCACCATCATCATTAG (SEQ ID NO: 48)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYSLDYWGQGTTLTVSSVEGGSGGSGGSGGSGGVDDIQLTQSPAIM
SASPGEKVTMTCRASSSVSYMNWYQQKSGTSPKRWIYDTSKVASGVPYRFSGSGSGTSYSLTISSMEAEDAATY
YCQQWSSNPLTFGAGTKLELKSGGGGSEVQLLEQSGAELVKPGASVKISCKASGYAFTNYWLGWVKQRPGHGLE
WIGDLFPGSGNTHYNERFRGKATLTADKSSSTAFMQLSSLTSEDSAVYFCARLRNWDEAMDYWGQGTTVTVSSG
GGGSGGGGSGGGGSELVMTQSPSYLAASPGETITINCRASKSISKYLAWYQEKPGKTNKLLIYSGSTLQSGIPS
RFSGSGSGTDFTLTISSLEPEDFAMYYCQQHNEYPYTFGGGTKLEIKHHHHHH

Figure 1

L) anti-CD3 VHVL aL x 3-5 VHVL (SEQ ID NO: 49)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGTCGAAGGTGGAA
GTGGAGGTTCTGGTGGAAGTGGAGGTTCAGGTGGAGTCGACGACATTCAGCTGACCCAGTCTCCAGCAATCATG
TCTGCATCTCCAGGGGAGAAGGTCACCATGACCTGCAGAGCCAGTTCAAGTGTAAGTTACATGAACTGGTACCA
GCAGAAGTCAGGCACCTCCCCCAAAAGATGGATTTATGACACATCCAAAGTGGCTTCTGGAGTCCCTTATCGCT
TCAGTGGCAGTGGGTCTGGGACCTCATACTCTCTCACAATCAGCAGCATGGAGGCTGAAGATGCTGCCACTTAT
TACTGCCAACAGTGGAGTAGTAACCCGCTCACGTTCGGTGCTGGGACCAAGCTGGAGCTGAAATCCGGAGGTGG
TGGATCCGAGGTGCAGCTGCTCGAGCAGTCTGGAGCTGAGCTGGTAAGGCCTGGGACTTCAGTGAAGCTGTCCT
GCAAGGCTTCTGGCTACACCTTCACAAGCTATGGTTTAAGCTGGGTGAAGCAGAGAACTGGACAGGGCCTTGAG
TGGATTGGAGAGGTTTATCCTAGAATTGGTAATGCTTACTACAATGAGAAGTTCAAGGGCAAGGCCACACTGAC
TGCAGACAAATCCTCCAGCACAGCGTCCATGGAGCTCCGCAGCCTGACATCTGAGGACTCTGCGGTCTATTTCT
GTGCAAGACGGGGATCCTACGGTAGTAACTACGACTGGTACTTCGATGTCTGGGGCCAAGGGACCACGGTCACC
GTCTCCTCAGGTGGTGGTGGTTCTGGCGGCGGCGGCTCCGGTGGTGGTGGTTCTGAGCTCGTGATGACCCAGAC
TCCACTCTCCCTGCCTGTCAGTCTTGGAGATCAAGCCTCCATCTCTTGCAGATCTAGTCAGAGCCTTGTACACA
GTAATGGAAACACCTATTTACATTGGTACCTGCAGAAGCCAGGCCAGTCTCCAAAGCTCCTGATCTACAAAGTT
TCCAACCGATTTTCTGGGGTCCCAGACAGGTTCAGTGGCAGTGGATCAGGGACAG

Figure 1 L) continued

ATTTCACACTCAAGATCAGCAGAGTGGAGGCTGAGGATCTGGGAGTTTATTTCTGCTCTCAAAGTACACATGTT
CCGTACACGTTCGGAGGGGGGACCAAGCTTGAGATCAAACATCATCACCATCATCATTAG (SEQ ID NO: 50)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSVEGGSGGSGGSGGSGGVDDIQLTQSPAIM
SASPGEKVTMTCRASSSVSYMNWYQQKSGTSPKRWIYDTSKVASGVPYRFSGSGSGTSYSLTISSMEAEDAATY
YCQQWSSNPLTFGAGTKLELKSGGGGSEVQLLEQSGAELVRPGTSVKLSCKASGYTFTSYGLSWVKQRTGQGLE
WIGEVYPRIGNAYYNEKFKGKATLTADKSSSTASMELRSLTSEDSAVYFCARRGSYGSNYDWYFDVWGQGTTVT
VSSGGGGSGGGGSGGGGSELVMTQTPLSLPVSLGDQASISCRSSQSLVHSNGNTYLHWYLQKPGQSPKLLIYKV
SNRFSGVPDRFSGSGSGTDFTLKISRVEAEDLGVYFCSQSTHVPYTFGGGTKLEIKHHHHHH

Figure 1

M) anti-CD3 VHVL aL Ser x 3-5 VHVL (SEQ ID NO: 51)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTCCCTTGACTACTGGGGCCAAGGCACCACTCTCACAGTCTCCTCAGTCGAAGGTGGAA
GTGGAGGTTCTGGTGGAAGTGGAGGTTCAGGTGGAGTCGACGACATTCAGCTGACCCAGTCTCCAGCAATCATG
TCTGCATCTCCAGGGGAGAAGGTCACCATGACCTGCAGAGCCAGTTCAAGTGTAAGTTACATGAACTGGTACCA
GCAGAAGTCAGGCACCTCCCCCAAAAGATGGATTTATGACACATCCAAAGTGGCTTCTGGAGTCCCTTATCGCT
TCAGTGGCAGTGGGTCTGGGACCTCATACTCTCTCACAATCAGCAGCATGGAGGCTGAAGATGCTGCCACTTAT
TACTGCCAACAGTGGAGTAGTAACCCGCTCACGTTCGGTGCTGGGACCAAGCTGGAGCTGAAATCCGGAGGTGG
TGGATCCGAGGTGCAGCTGCTCGAGCAGTCTGGAGCTGAGCTGGTAAGGCCTGGGACTTCAGTGAAGCTGTCCT
GCAAGGCTTCTGGCTACACCTTCACAAGCTATGGTTTAAGCTGGGTGAAGCAGAGAACTGGACAGGGCCTTGAG
TGGATTGGAGAGGTTTATCCTAGAATTGGTAATGCTTACTACAATGAGAAGTTCAAGGGCAAGGCCACACTGAC
TGCAGACAAATCCTCCAGCACAGCGTCCATGGAGCTCCGCAGCCTGACATCTGAGGACTCTGCGGTCTATTTCT
GTGCAAGACGGGGATCCTACGGTAGTAACTACGACTGGTACTTCGATGTCTGGGGCCAAGGGACCACGGTCACC
GTCTCCTCAGGTGGTGGTGGTTCTGGCGGCGGCGGCTCCGGTGGTGGTGGTTCTGAGCTCGTGATGACCCAGAC
TCCACTCTCCCTGCCTGTCAGTCTTGGAGATCAAGCCTCCATCTCTTGCAGATCTAGTCAGAGCCTTGTACACA
GTAATGGAAACACCTATTTACATTGGTACCTGCAGAAGCCAGGCCAGTCTCCAAAGCTCCTGATCTACAAAGTT
TCCAACCGATTTTCTGGGGTCCCAGACAGGTTCAGTGGCAGTGGATCAGGGACAG

Figure 1 M) continued

ATTTCACACTCAAGATCAGCAGAGTGGAGGCTGAGGATCTGGGAGTTTATTTCTGCTCTCAAAGTACACATGTT
CCGTACACGTTCGGAGGGGGGACCAAGCTTGAGATCAAACATCATCACCATCATCATTAG (SEQ ID NO: 52)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYSLDYWGQGTTLTVSSVEGGSGGSGGSGGSGGVDDIQLTQSPAIM
SASPGEKVTMTCRASSSVSYMNWYQQKSGTSPKRWIYDTSKVASGVPYRFSGSGSGTSYSLTISSMEAEDAATY
YCQQWSSNPLTFGAGTKLELKSGGGGSEVQLLEQSGAELVRPGTSVKLSCKASGYTFTSYGLSWVKQRTGQGLE
WIGEVYPRIGNAYYNEKFKGKATLTADKSSSTASMELRSLTSEDSAVYFCARRGSYGSNYDWYFDVWGQGTTVT
VSSGGGGSGGGGSGGGGSELVMTQTPLSLPVSLGDQASISCRSSQSLVHSNGNTYLHWYLQKPGQSPKLLIYKV
SNRFSGVPDRFSGSGSGTDFTLKISRVEAEDLGVYFCSQSTHVPYTFGGGTKLEIKHHHHHH

Figure 1

N) anti-CD3 VHVL stL x 3-5 VHVL (SEQ ID NO: 53)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGGTGGTGGTGGTT
CTGGCGGCGGCGGCTCCGGTGGTGGTGGTTCTGACATTCAGCTGACCCAGTCTCCAGCAATCATGTCTGCATCT
CCAGGGGAGAAGGTCACCATGACCTGCAGAGCCAGTTCAAGTGTAAGTTACATGAACTGGTACCAGCAGAAGTC
AGGCACCTCCCCCAAAAGATGGATTTATGACACATCCAAAGTGGCTTCTGGAGTCCCTTATCGCTTCAGTGGCA
GTGGGTCTGGGACCTCATACTCTCTCACAATCAGCAGCATGGAGGCTGAAGATGCTGCCACTTATTACTGCCAA
CAGTGGAGTAGTAACCCGCTCACGTTCGGTGCTGGGACCAAGCTGGAGCTGAAATCCGGAGGTGGTGGATCCGA
GGTGCAGCTGCTCGAGCAGTCTGGAGCTGAGCTGGTAAGGCCTGGGACTTCAGTGAAGCTGTCCTGCAAGGCTT
CTGGCTACACCTTCACAAGCTATGGTTTAAGCTGGGTGAAGCAGAGAACTGGACAGGGCCTTGAGTGGATTGGA
GAGGTTTATCCTAGAATTGGTAATGCTTACTACAATGAGAAGTTCAAGGGCAAGGCCACACTGACTGCAGACAA
ATCCTCCAGCACAGCGTCCATGGAGCTCCGCAGCCTGACATCTGAGGACTCTGCGGTCTATTTCTGTGCAAGAC
GGGGATCCTACGGTAGTAACTACGACTGGTACTTCGATGTCTGGGGCCAAGGGACCACGGTCACCGTCTCCTCA
GGTGGTGGTGGTTCTGGCGGCGGCGGCTCCGGTGGTGGTGGTTCTGAGCTCGTGATGACCCAGACTCCACTCTC
CCTGCCTGTCAGTCTTGGAGATCAAGCCTCCATCTCTTGCAGATCTAGTCAGAGCCTTGTACACAGTAATGGAA
ACACCTATTTACATTGGTACCTGCAGAAGCCAGGCCAGTCTCCAAAGCTCCTGATCTACAAAGTTTCCAACCGA
TTTTCTGGGGTCCCAGACAGGTTCAGTGGCAGTGGATCAGGGACAGATTTCACAC

Figure 1 N) continued

TCAAGATCAGCAGAGTGGAGGCTGAGGATCTGGGAGTTTATTTCTGCTCTCAAAGTACACATGTTCCGTACACG
TTCGGAGGGGGGACCAAGCTTGAGATCAAACATCATCACCATCATCATTAG (SEQ ID NO: 54)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSGGGGSGGGGSGGGGSDIQLTQSPAIMSAS
PGEKVTMTCRASSSVSYMNWYQQKSGTSPKRWIYDTSKVASGVPYRFSGSGSGTSYSLTISSMEAEDAATYYCQ
QWSSNPLTFGAGTKLELKSGGGGSEVQLLEQSGAELVRPGTSVKLSCKASGYTFTSYGLSWVKQRTGQGLEWIG
EVYPRIGNAYYNEKFKGKATLTADKSSSTASMELRSLTSEDSAVYFCARRGSYGSNYDWYFDVWGQGTTVTVSS
GGGGSGGGGSGGGGSELVMTQTPLSLPVSLGDQASISCRSSQSLVHSNGNTYLHWYLQKPGQSPKLLIYKVSNR
FSGVPDRFSGSGSGTDFTLKISRVEAEDLGVYFCSQSTHVPYTFGGGTKLEIKHHHHHH

Figure 1

O) anti-CD3 VHVL aL x 4-1 VHVL (SEQ ID NO: 55)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGTCGAAGGTGGAA
GTGGAGGTTCTGGTGGAAGTGGAGGTTCAGGTGGAGTCGACGACATTCAGCTGACCCAGTCTCCAGCAATCATG
TCTGCATCTCCAGGGGAGAAGGTCACCATGACCTGCAGAGCCAGTTCAAGTGTAAGTTACATGAACTGGTACCA
GCAGAAGTCAGGCACCTCCCCCAAAAGATGGATTTATGACACATCCAAAGTGGCTTCTGGAGTCCCTTATCGCT
TCAGTGGCAGTGGGTCTGGGACCTCATACTCTCTCACAATCAGCAGCATGGAGGCTGAAGATGCTGCCACTTAT
TACTGCCAACAGTGGAGTAGTAACCCGCTCACGTTCGGTGCTGGGACCAAGCTGGAGCTGAAATCCGGAGGTGG
TGGATCCGAGGTGCAGCTGCTCGAGCAGTCTGGAGCTGAGCTGGTAAGGCCTGGGACTTCAGTGAAGATATCCT
GCAAGGCTTCTGGATACGCCTTCACTAACTACTGGCTAGGTTGGGTTAAGCAGAGGCCTGGACATGGACTTGAA
TGGGTTGGAGATATTTTCCCTGGAAGTGGTAATGCTCACTACAATGAGAAGTTCAAGGGCAAAGCCACACTGAC
TGCAGACAAGTCCTCGTACACAGCCTATATGCAGCTCAGTAGCCTGACATCTGAGGACTCTGCTGTCTATTTCT
GTGCAAGATTGCGGAACTGGGACGAGGCTATGGACTACTGGGGCCAAGGGACCACGGTCACCGTCTCCTCAGGT
GGTGGTGGTTCTGGCGGCGGCGGCTCCGGTGGTGGTGGTTCTGAGCTCGTGATGACACAGTCTCCATCCTCCCT
GAGTGTGTCAGCAGGAGAGAAGGTCACTATGAGCTGCAAGTCCAGTCAGAGTCTGTTAAACAGTGGAAATCAAA
AGAACTACTTGGCCTGGTACCAGCAGAAACCAGGGCAGCCTCCTAAACTGTTGATCTACGGGGCATCCACTAGG
GAATCTGGGGTCCCTGATCGCTTCACAGGCAGTGGATCTGGAACAGATTTCACTC

Figure 1 O) continued

TCACCATCAGCAGTGTGCAGGCTGAAGACCTGGCAGTTTATTACTGTCAGAATGATTATAGTTATCCGTACACG
TTCGGAGGGGGGACCAAGCTTGAGATCAAACATCATCACCATCATCATTAG (SEQ ID NO: 56)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSVEGGSGGSGGSGGSGGVDDIQLTQSPAIM
SASPGEKVTMTCRASSSVSYMNWYQQKSGTSPKRWIYDTSKVASGVPYRFSGSGSGTSYSLTISSMEAEDAATY
YCQQWSSNPLTFGAGTKLELKSGGGGSEVQLLEQSGAELVRPGTSVKISCKASGYAFTNYWLGWVKQRPGHGLE
WVGDIFPGSGNAHYNEKFKGKATLTADKSSYTAYMQLSSLTSEDSAVYFCARLRNWDEAMDYWGQGTTVTVSSG
GGGSGGGGSGGGGSELVMTQSPSSLSVSAGEKVTMSCKSSQSLLNSGNQKNYLAWYQQKPGQPPKLLIYGASTR
ESGVPDRFTGSGSGTDFTLTISSVQAEDLAVYYCQNDYSYPYTFGGGTKLEIKHHHHHH

Figure 1

P) anti-CD3 VHVL aL Ser x 4-1 VHVL (SEQ ID NO: 57)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTCCCTTGACTACTGGGGCCAAGGCACCACTCTCACAGTCTCCTCAGTCGAAGGTGGAA
GTGGAGGTTCTGGTGGAAGTGGAGGTTCAGGTGGAGTCGACGACATTCAGCTGACCCAGTCTCCAGCAATCATG
TCTGCATCTCCAGGGGAGAAGGTCACCATGACCTGCAGAGCCAGTTCAAGTGTAAGTTACATGAACTGGTACCA
GCAGAAGTCAGGCACCTCCCCCAAAAGATGGATTTATGACACATCCAAAGTGGCTTCTGGAGTCCCTTATCGCT
TCAGTGGCAGTGGGTCTGGGACCTCATACTCTCTCACAATCAGCAGCATGGAGGCTGAAGATGCTGCCACTTAT
TACTGCCAACAGTGGAGTAGTAACCCGCTCACGTTCGGTGCTGGGACCAAGCTGGAGCTGAAATCCGGAGGTGG
TGGATCCGAGGTGCAGCTGCTCGAGCAGTCTGGAGCTGAGCTGGTAAGGCCTGGGACTTCAGTGAAGATATCCT
GCAAGGCTTCTGGATACGCCTTCACTAACTACTGGCTAGGTTGGGTTAAGCAGAGGCCTGGACATGGACTTGAA
TGGGTTGGAGATATTTTCCCTGGAAGTGGTAATGCTCACTACAATGAGAAGTTCAAGGGCAAAGCCACACTGAC
TGCAGACAAGTCCTCGTACACAGCCTATATGCAGCTCAGTAGCCTGACATCTGAGGACTCTGCTGTCTATTTCT
GTGCAAGATTGCGGAACTGGGACGAGGCTATGGACTACTGGGGCCAAGGGACCACGGTCACCGTCTCCTCAGGT
GGTGGTGGTTCTGGCGGCGGCGGCTCCGGTGGTGGTGGTTCTGAGCTCGTGATGACACAGTCTCCATCCTCCCT
GAGTGTGTCAGCAGGAGAGAAGGTCACTATGAGCTGCAAGTCCAGTCAGAGTCTGTTAAACAGTGGAAATCAAA
AGAACTACTTGGCCTGGTACCAGCAGAAACCAGGGCAGCCTCCTAAACTGTTGATCTACGGGGCATCCACTAGG
GAATCTGGGGTCCCTGATCGCTTCACAGGCAGTGGATCTGGAACAGATTTCACTC

Figure 1 P) continued

TCACCATCAGCAGTGTGCAGGCTGAAGACCTGGCAGTTTATTACTGTCAGAATGATTATAGTTATCCGTACACG
TTCGGAGGGGGGACCAAGCTTGAGATCAAACATCATCACCATCATCATTAG (SEQ ID NO: 58)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYSLDYWGQGTTLTVSSVEGGSGGSGGSGGSGGVDDIQLTQSPAIM
SASPGEKVTMTCRASSSVSYMNWYQQKSGTSPKRWIYDTSKVASGVPYRFSGSGSGTSYSLTISSMEAEDAATY
YCQQWSSNPLTFGAGTKLELKSGGGGSEVQLLEQSGAELVRPGTSVKISCKASGYAFTNYWLGWVKQRPGHGLE
WVGDIFPGSGNAHYNEKFKGKATLTADKSSYTAYMQLSSLTSEDSAVYFCARLRNWDEAMDYWGQGTTVTVSSG
GGGSGGGGSGGGGSELVMTQSPSSLSVSAGEKVTMSCKSSQSLLNSGNQKNYLAWYQQKPGQPPKLLIYGASTR
ESGVPDRFTGSGSGTDFTLTISSVQAEDLAVYYCQNDYSYPYTFGGGTKLEIKHHHHHH

Figure 1

Q) anti-CD3 VHVL stL x 4-1 VHVL (SEQ ID NO: 59)

GATATCAAACTGCAGCAGTCAGGGGCTGAACTGGCAAGACCTGGGGCCTCAGTGAAGATGTCCTGCAAGACTTC
TGGCTACACCTTTACTAGGTACACGATGCACTGGGTAAAACAGAGGCCTGGACAGGGTCTGGAATGGATTGGAT
ACATTAATCCTAGCCGTGGTTATACTAATTACAATCAGAAGTTCAAGGACAAGGCCACATTGACTACAGACAAA
TCCTCCAGCACAGCCTACATGCAACTGAGCAGCCTGACATCTGAGGACTCTGCAGTCTATTACTGTGCAAGATA
TTATGATGATCATTACTGCCTTGACTACTGGGGCCAAGGCACCACTCTCACAGTCTCCTCAGGTGGTGGTGGTT
CTGGCGGCGGCGGCTCCGGTGGTGGTGGTTCTGACATTCAGCTGACCCAGTCTCCAGCAATCATGTCTGCATCT
CCAGGGGAGAAGGTCACCATGACCTGCAGAGCCAGTTCAAGTGTAAGTTACATGAACTGGTACCAGCAGAAGTC
AGGCACCTCCCCCAAAAGATGGATTTATGACACATCCAAAGTGGCTTCTGGAGTCCCTTATCGCTTCAGTGGCA
GTGGGTCTGGGACCTCATACTCTCTCACAATCAGCAGCATGGAGGCTGAAGATGCTGCCACTTATTACTGCCAA
CAGTGGAGTAGTAACCCGCTCACGTTCGGTGCTGGGACCAAGCTGGAGCTGAAATCCGGAGGTGGTGGATCCGA
GGTGCAGCTGCTCGAGCAGTCTGGAGCTGAGCTGGTAAGGCCTGGGACTTCAGTGAAGATATCCTGCAAGGCTT
CTGGATACGCCTTCACTAACTACTGGCTAGGTTGGGTTAAGCAGAGGCCTGGACATGGACTTGAATGGGTTGGA
GATATTTTCCCTGGAAGTGGTAATGCTCACTACAATGAGAAGTTCAAGGGCAAAGCCACACTGACTGCAGACAA
GTCCTCGTACACAGCCTATATGCAGCTCAGTAGCCTGACATCTGAGGACTCTGCTGTCTATTTCTGTGCAAGAT
TGCGGAACTGGGACGAGGCTATGGACTACTGGGGCCAAGGGACCACGGTCACCGTCTCCTCAGGTGGTGGTGGT
TCTGGCGGCGGCGGCTCCGGTGGTGGTGGTTCTGAGCTCGTGATGACACAGTCTCCATCCTCCCTGAGTGTGTC
AGCAGGAGAGAAGGTCACTATGAGCTGCAAGTCCAGTCAGAGTCTGTTAAACAGTGGAAATCAAAAGAACTACT
TGGCCTGGTACCAGCAGAAACCAGGGCAGCCTCCTAAACTGTTGATCTACGGGGCATCCACTAGGGAATCTGGG
GTCCCTGATCGCTTCACAGGCAGTGGATCTGGAACAGATTTCACTCTCACCATCA

Figure 1 Q) continued

GCAGTGTGCAGGCTGAAGACCTGGCAGTTTATTACTGTCAGAATGATTATAGTTATCCGTACACGTTCGGAGGG
GGGACCAAGCTTGAGATCAAACATCATCACCATCATCATTAG (SEQ ID NO: 60)

DIKLQQSGAELARPGASVKMSCKTSGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSGGGGSGGGGSGGGGSDIQLTQSPAIMSAS
PGEKVTMTCRASSSVSYMNWYQQKSGTSPKRWIYDTSKVASGVPYRFSGSGSGTSYSLTISSMEAEDAATYYCQ
QWSSNPLTFGAGTKLELKSGGGGSEVQLLEQSGAELVRPGTSVKISCKASGYAFTNYWLGWVKQRPGHGLEWVG
DIFPGSGNAHYNEKFKGKATLTADKSSYTAYMQLSSLTSEDSAVYFCARLRNWDEAMDYWGQGTTVTVSSGGGG
SGGGGSGGGGSELVMTQSPSSLSVSAGEKVTMSCKSSQSLLNSGNQKNYLAWYQQKPGQPPKLLIYGASTRESG
VPDRFTGSGSGTDFTLTISSVQAEDLAVYYCQNDYSYPYTFGGGTKLEIKHHHHHH

Figure 2 A
anti-CD3 VHVL stL x 5-10 (SEQ ID NO:18)
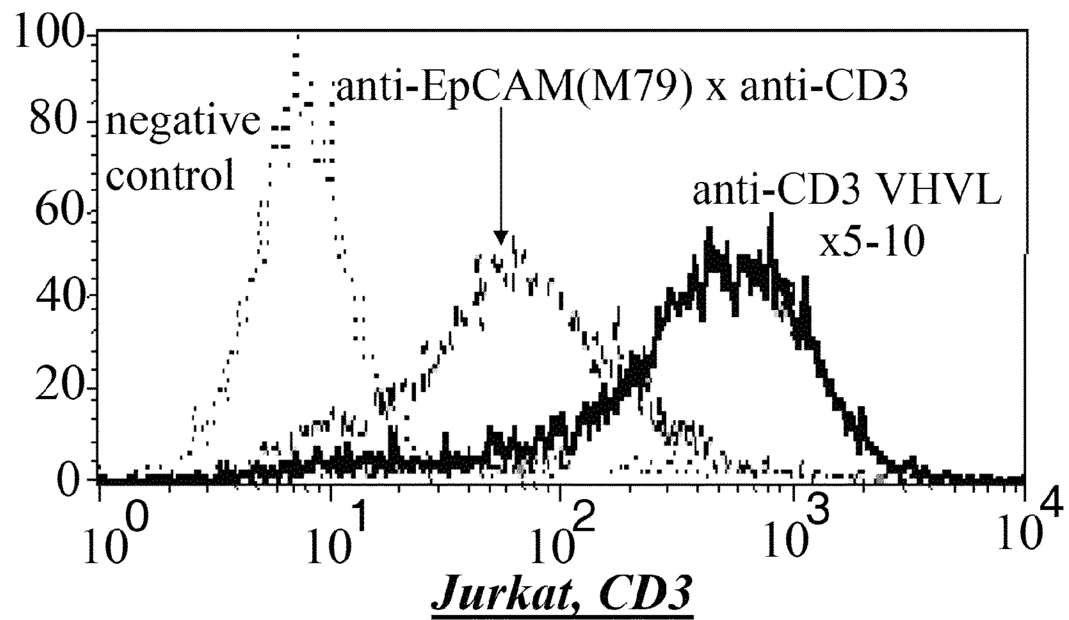
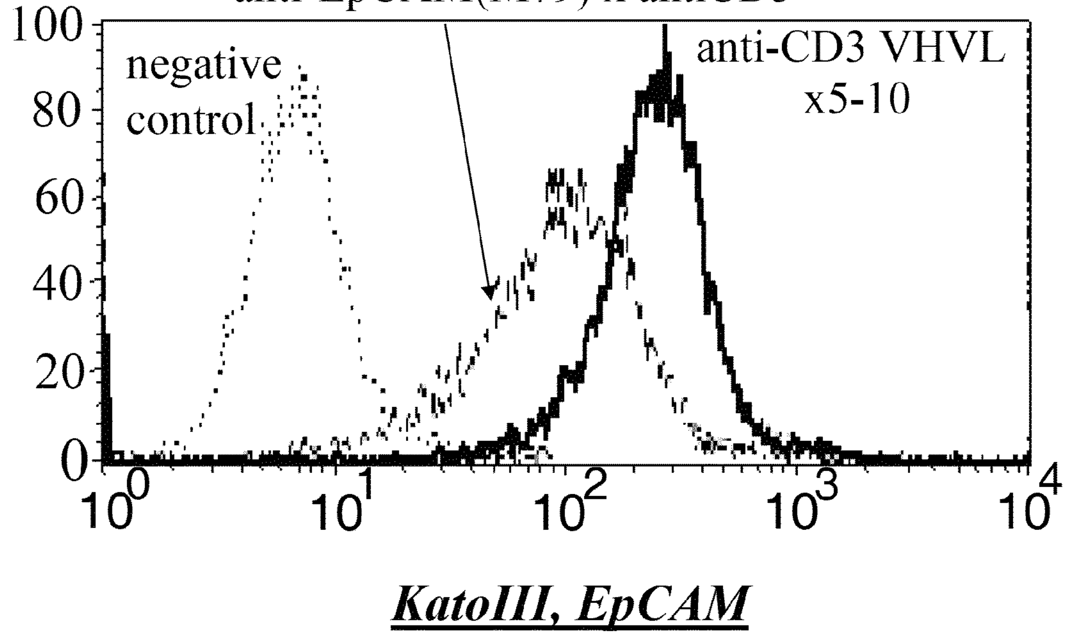

Figure 2 B
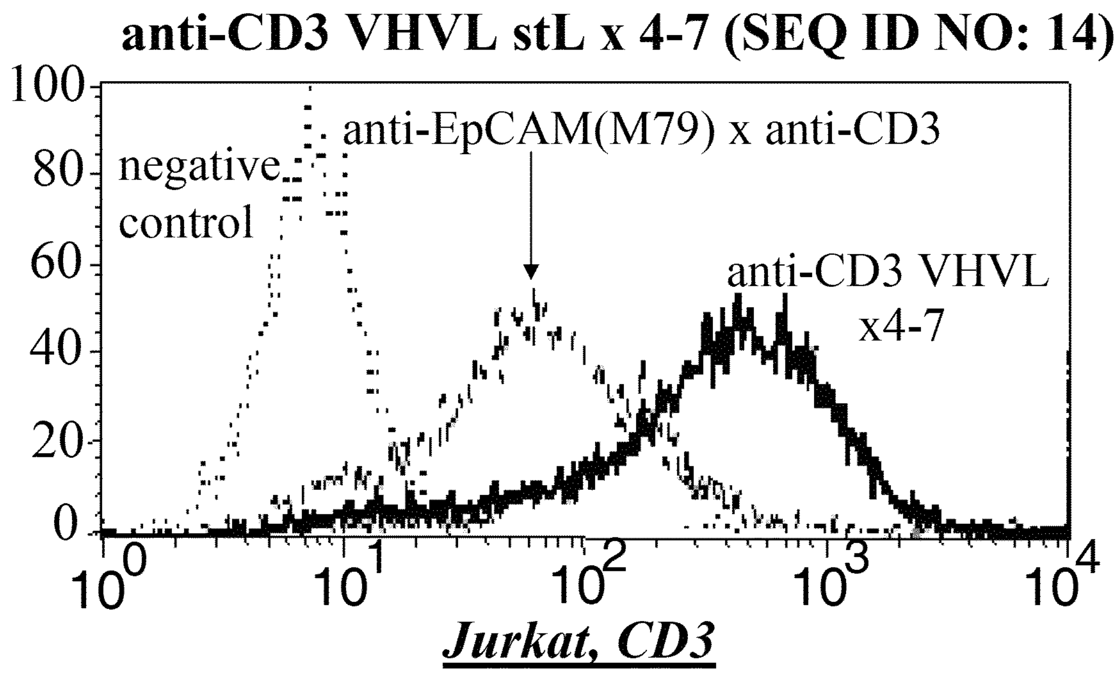
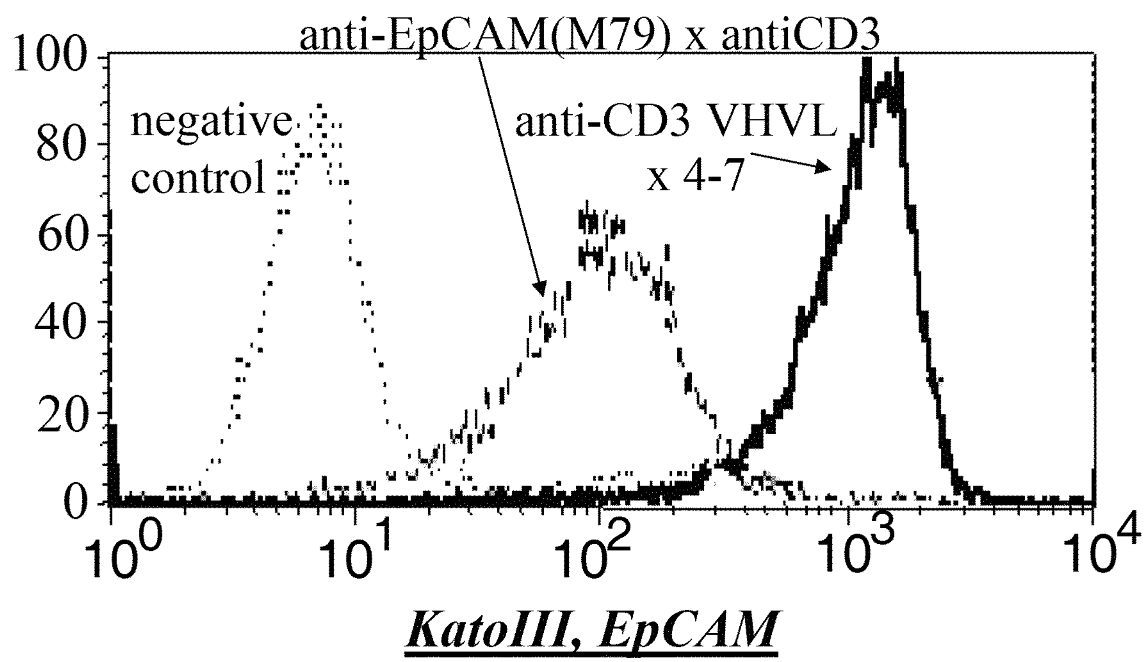

Figure 2D
anti-CD3 VHVL aL x 4-7 (SEQ ID NO: 2)
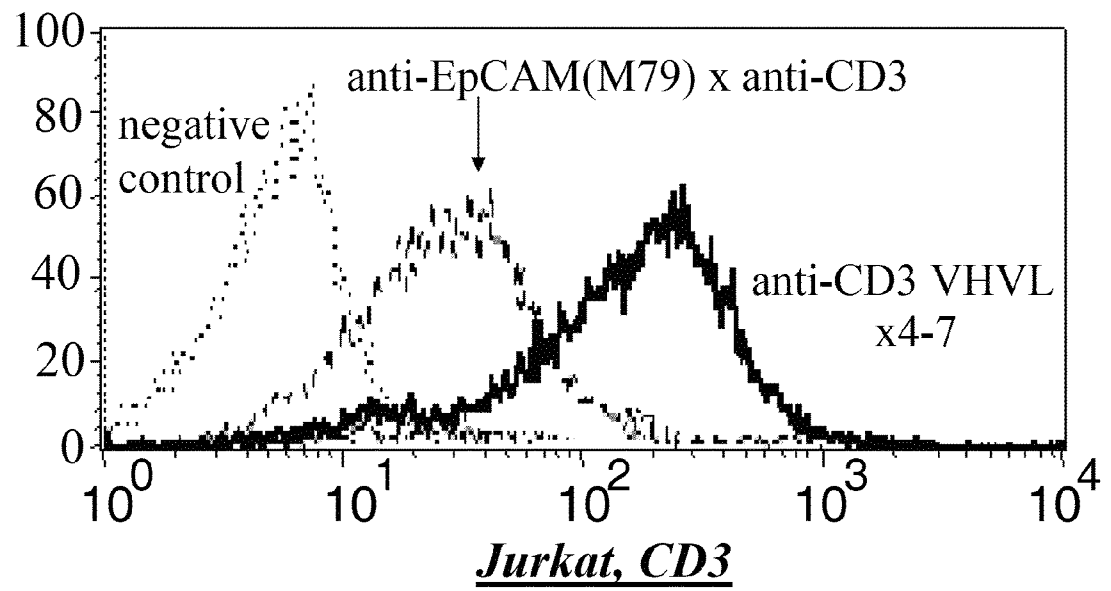
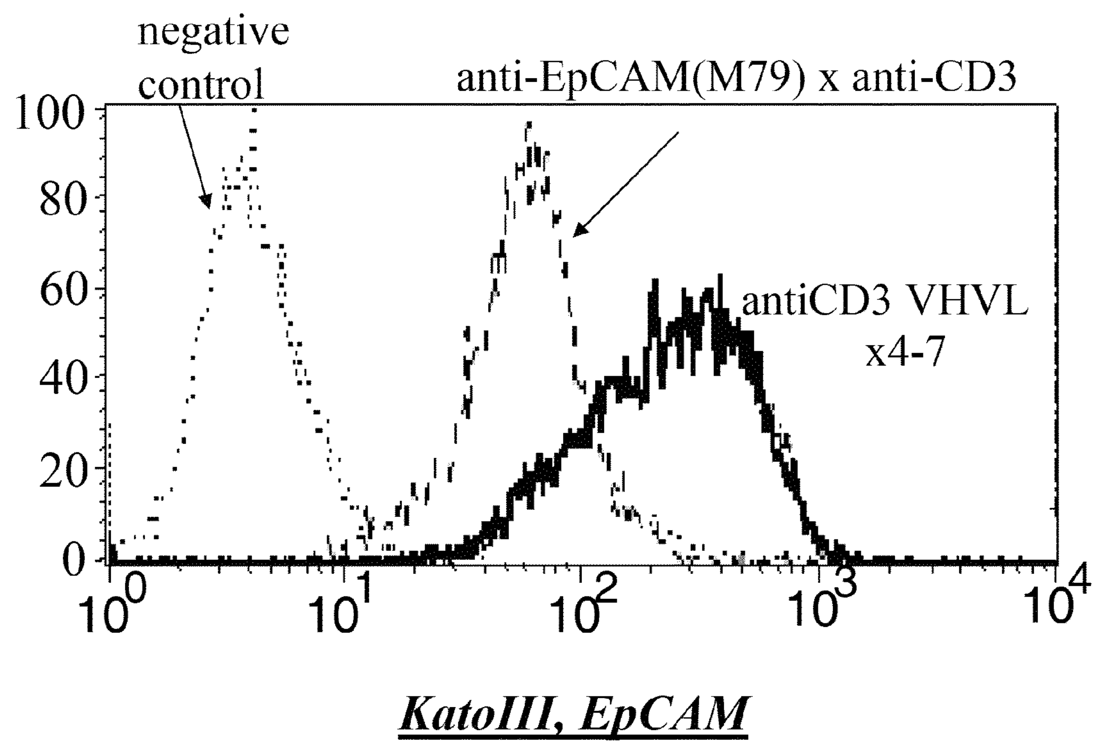

Figure 2E
anti-CD3VHVL aL Ser x 5-10 (SEQ ID NO: 10)
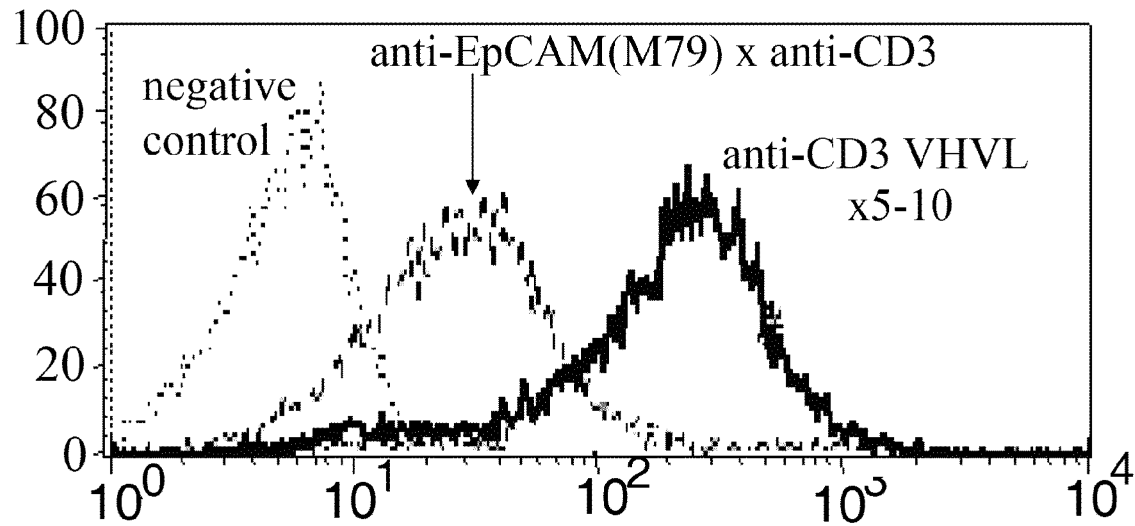
*Jurkat, CD3*
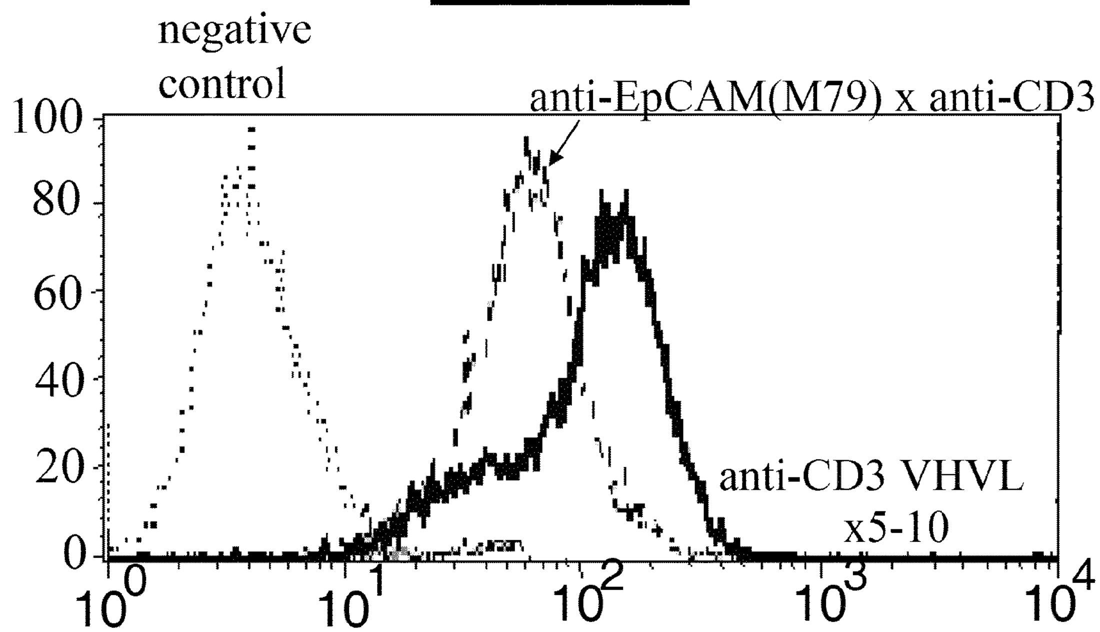
*KatoIII, EpCAM*

Figure 2F
anti-CD3 VHVL aL Ser x 4-7 (SEQ ID NO: 8)
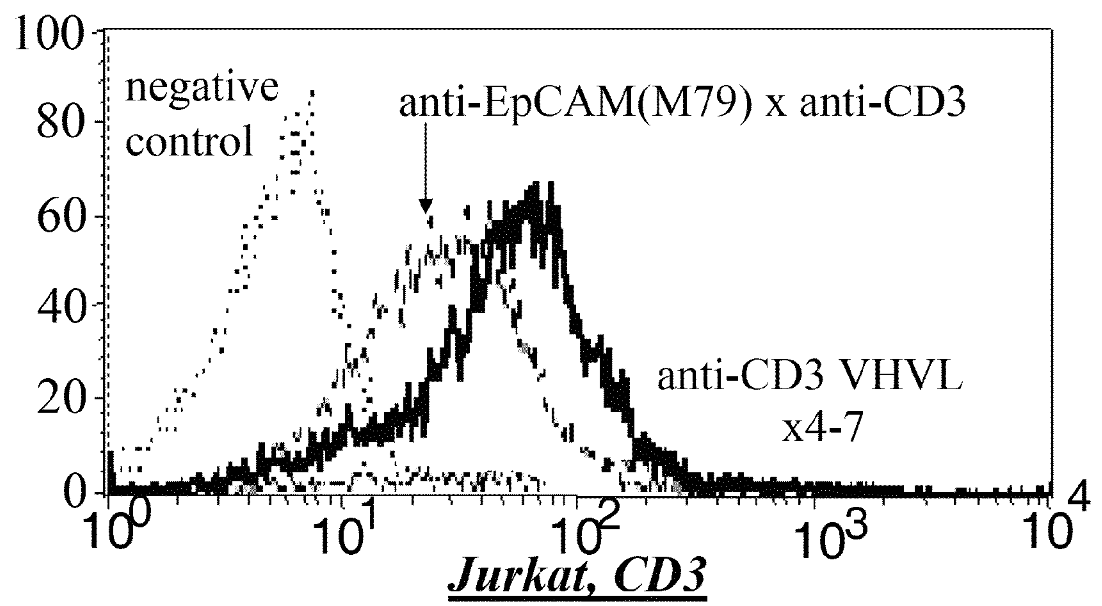
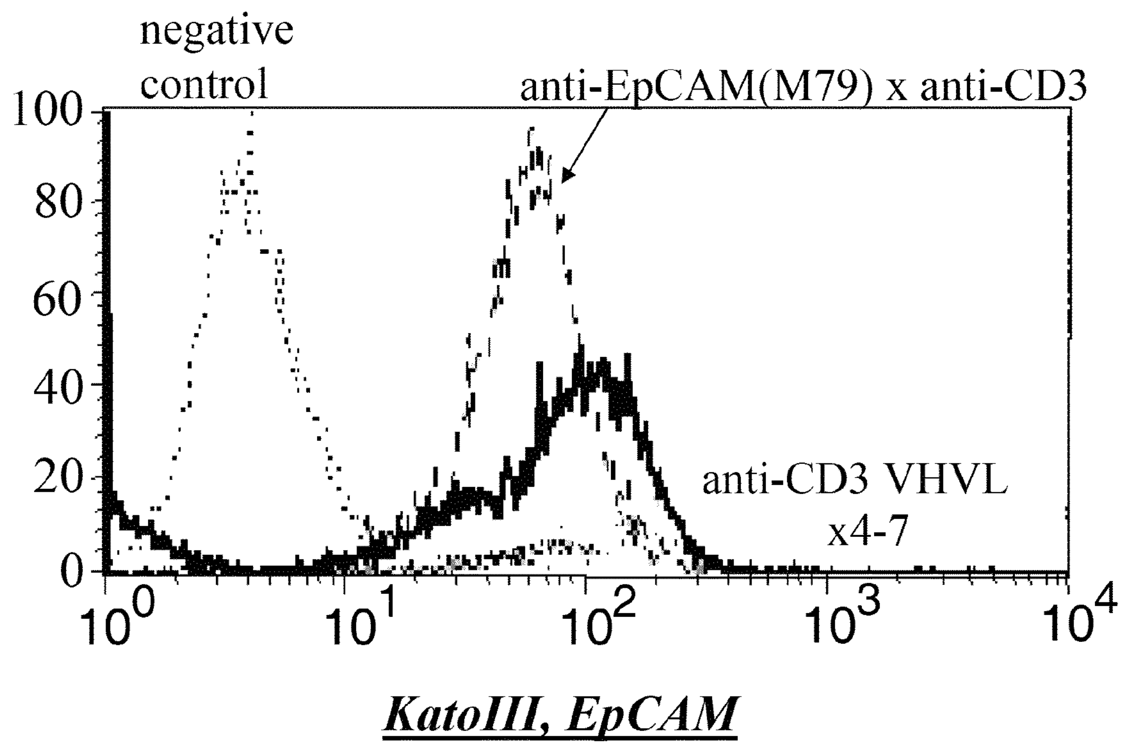

Figure 2G
anti-CD3 VHVL stL x 3-1 (SEQ ID NO: 12)
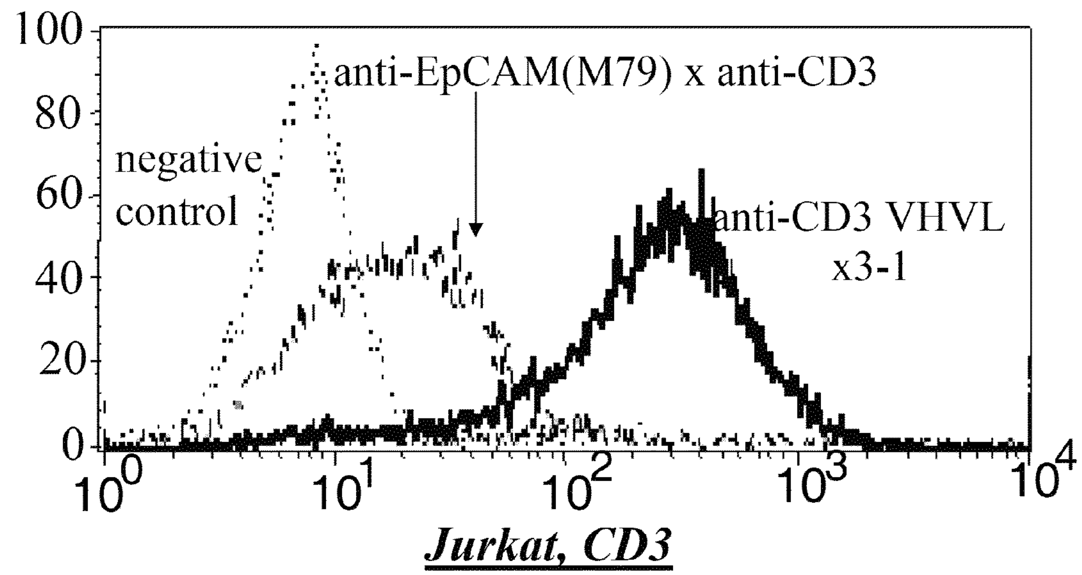
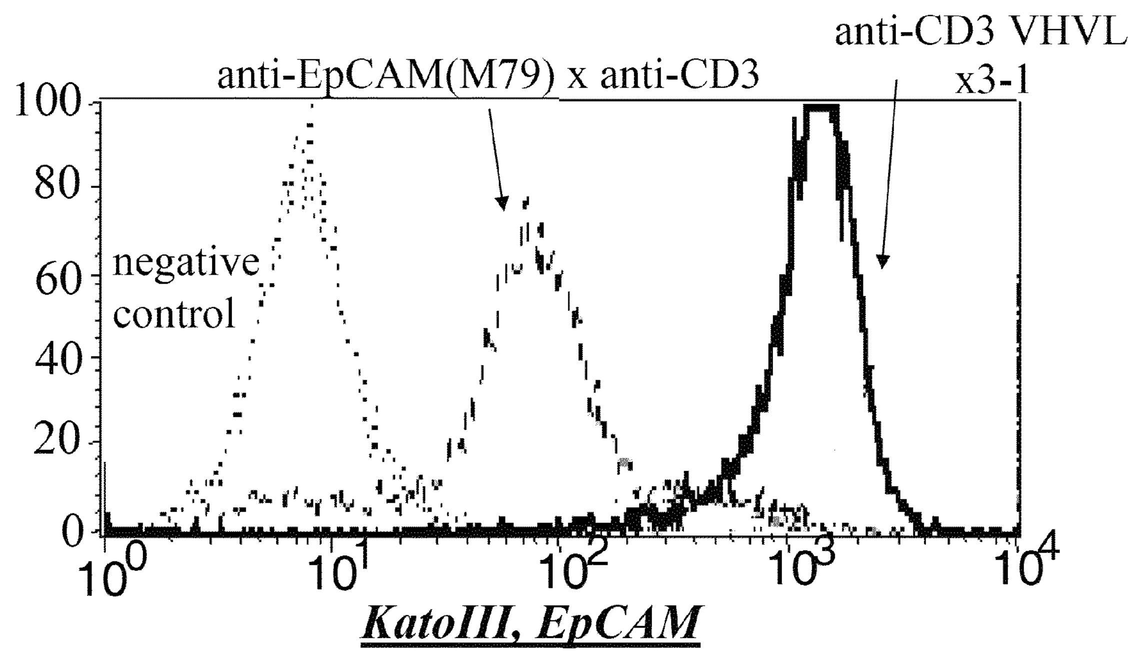

Figure 2H
anti-CD3 VHVL stL x 5-10 VLVH (SEQ ID NO: 20)
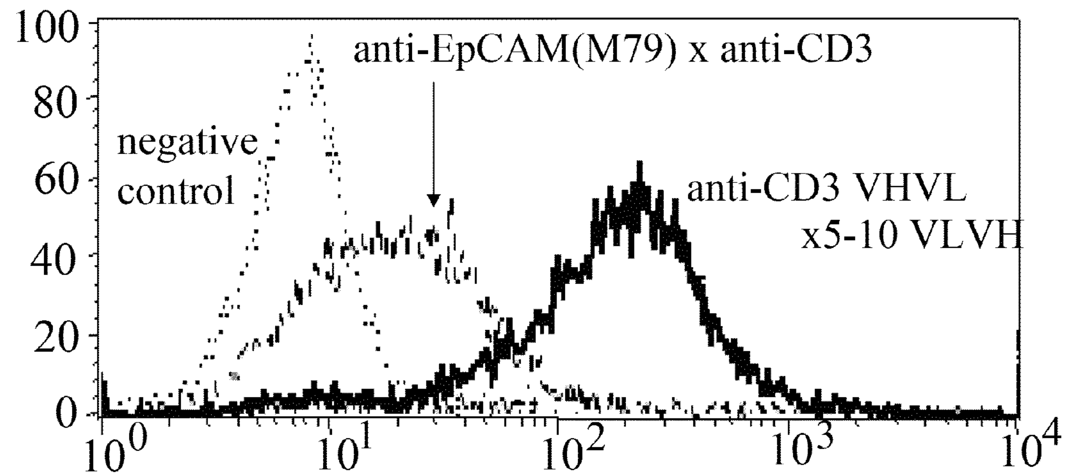
*Jurkat, CD3*
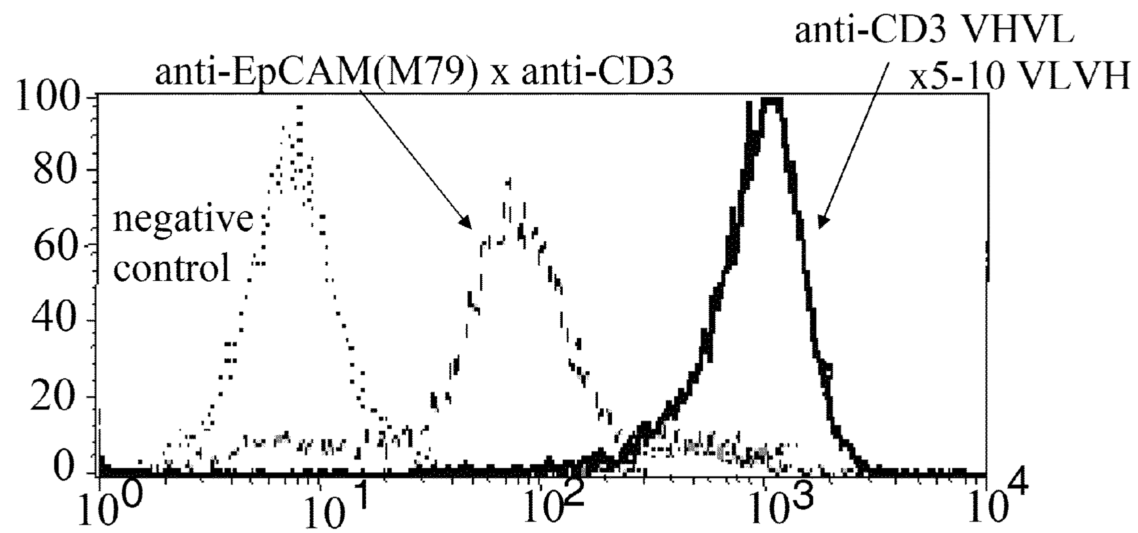
*KatoIII, EpCAM*

Figure 2I
anti-CD3 VHVL stL x 4-7 VLVH (SEQ ID NO: 16)
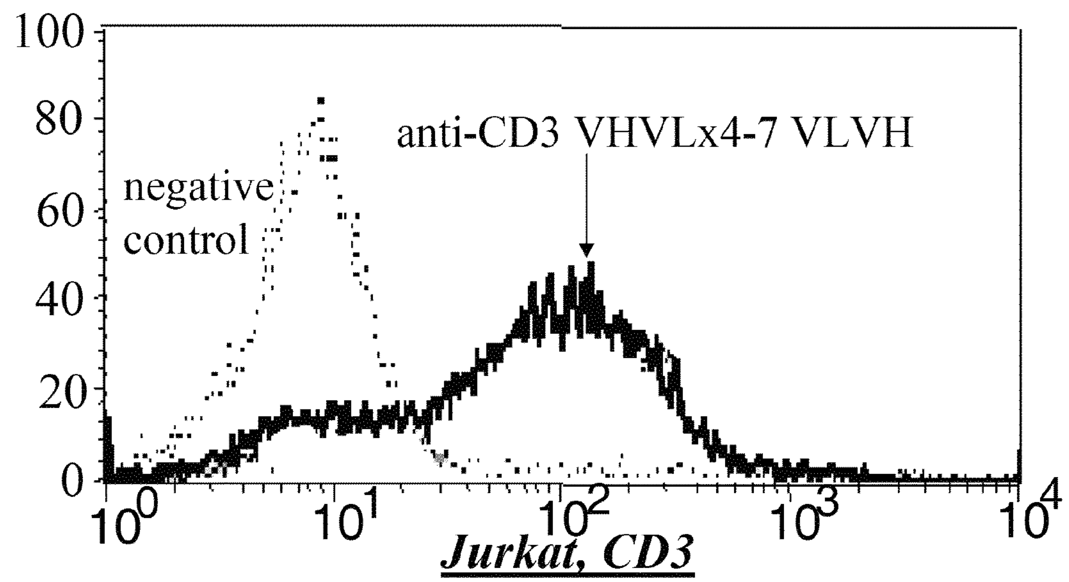
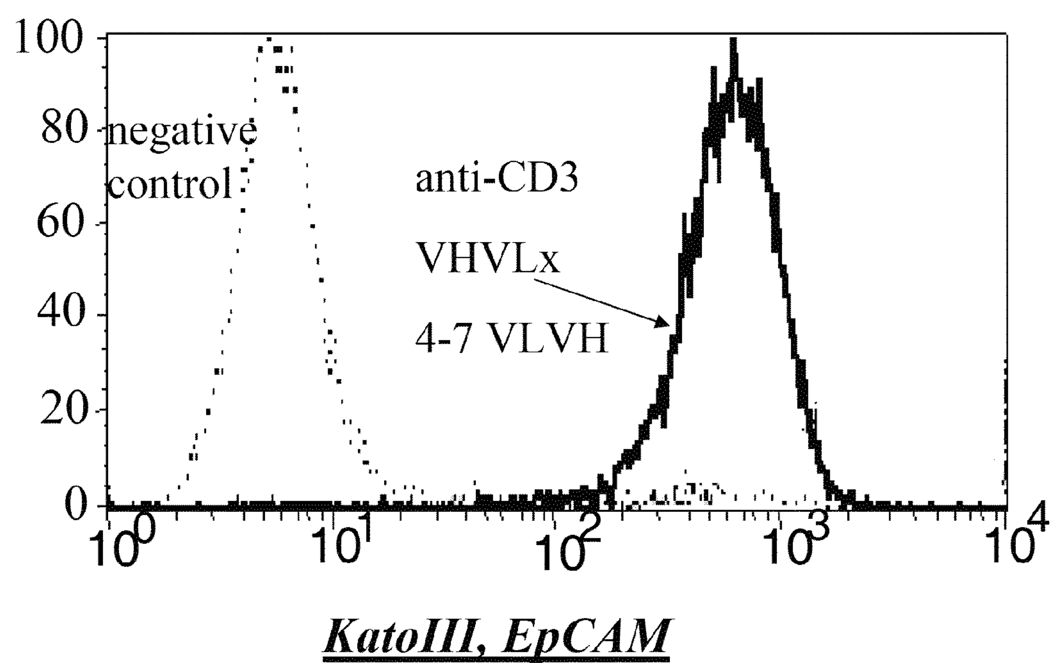

Figure 3A 4-7(vLvH) x anti-CD3 (SEQ ID NO: 42)

```
  1 MGWSCIILFL VATATGVHSA RELVMTQTPL SLPVSLGDQA SISCRSSQSL
 51 VHSNGNTYLH WYLQKPGQSP KLLIYKVSNR FSGVPDRFSG SGSGTDFTLK
101 ISRVEAEDLG VYFCSQSTHV PYTFGGGTKL EIKGGGGSGG GGSGGGGSEV
151 QLLEQSGAEL ARPGASVKLS CKASGYTFTN YGLSWVKQRP GQVLEWIGEV
201 YPRIGNAYYN EKFKGKATLT ADKSSSTASM ELRSLTSEDS AVYFCARRGS
251 YDTNYDWYFD VWGQGTTVTV SSGGGGSDIK LQQSGAELAR PGASVKMSCK
301 TSGYTFTRYT MHWVKQRPGQ GLEWIGYINP SRGYTNYNQK FKDKATLTTD
351 KSSSTAYMQL SSLTSEDSAV YYCARYYDDH YCLDYWGQGT TLTVSSVEGG
401 SGGSGGSGGS GGVDDIQLTQ SPAIMSASPG EKVTMTCRAS SSVSYMNWYQ
451 QKSGTSPKRW IYDTSKVASG VPYRFSGSGS GTSYSLTISS MEAEDAATYY
501 CQQWSSNPLT FGAGTKLELK HHHHHH*
```

Figure 3A (continued)

SEQ ID NO: 41

```
  1 ATGGGATGGA GCTGTATCAT CCTCTTCTTG GTAGCAACAG CTACAGGTGT
 51 ACACTCCGCG CGCGAGCTCG TGATGACCCA GACTCCACTC TCCCTGCCTG
101 TCAGTCTTGG AGATCAAGCC TCCATCTCTT GCAGATCTAG TCAGAGCCTT
151 GTACACAGTA ATGGAAACAC CTATTTACAT TGGTACCTGC AGAAGCCAGG
201 CCAGTCTCCA AAGCTCCTGA TCTACAAAGT TTCCAACCGA TTTTCTGGGG
251 TCCCAGACAG GTTCAGTGGC AGTGGATCAG GGACAGATTT CACACTCAAG
301 ATCAGCAGAG TGGAGGCTGA GGATCTGGGA GTTTATTTCT GCTCTCAAAG
351 TACACATGTT CCGTACACGT TCGGAGGGGG GACCAAGCTT GAGATCAAAG
401 GTGGTGGTGG TTCTGGCGGC GGCGGCTCCG GTGGTGGTGG TTCTGAGGTG
451 CAGCTGCTCG AGCAGTCTGG AGCTGAGCTG GCGAGGCCTG GGGCTTCAGT
501 GAAGCTGTCC TGCAAGGCTT CTGGCTACAC CTTCACAAAC TATGGTTTAA
551 GCTGGGTGAA GCAGAGGCCT GGACAGGTCC TTGAGTGGAT TGGAGAGGTT
601 TATCCTAGAA TTGGTAATGC TTACTACAAT GAGAAGTTCA AGGGCAAGGC
651 CACACTGACT GCAGACAAAT CCTCCAGCAC AGCGTCCATG GAGCTCCGCA
701 GCCTGACCTC TGAGGACTCT GCGGTCTATT TCTGTGCAAG ACGGGGATCC
751 TACGATACTA ACTACGACTG GTACTTCGAT GTCTGGGGCC AAGGGACCAC
801 GGTCACCGTC TCCTCCGGAG GTGGTGGATC CGATATCAAA CTGCAGCAGT
851 CAGGGGCTGA ACTGGCAAGA CCTGGGGCCT CAGTGAAGAT GTCCTGCAAG
```

Figure 3A (continued)

```
 901 ACTTCTGGCT ACACCTTTAC TAGGTACACG ATGCACTGGG TAAAACAGAG
 951 GCCTGGACAG GGTCTGGAAT GGATTGGATA CATTAATCCT AGCCGTGGTT
1001 ATACTAATTA CAATCAGAAG TTCAAGGACA AGGCCACATT GACTACAGAC
1051 AAATCCTCCA GCACAGCCTA CATGCAACTG AGCAGCCTGA CATCTGAGGA
1101 CTCTGCAGTC TATTACTGTG CAAGATATTA TGATGATCAT TACTGCCTTG
1151 ACTACTGGGG CCAAGGCACC ACTCTCACAG TCTCCTCAGT CGAAGGTGGA
1201 AGTGGAGGTT CTGGTGGAAG TGGAGGTTCA GGTGGAGTCG ACGACATTCA
1251 GCTGACCCAG TCTCCAGCAA TCATGTCTGC ATCTCCAGGG GAGAAGGTCA
1301 CCATGACCTG CAGAGCCAGT TCAAGTGTAA GTTACATGAA CTGGTACCAG
1351 CAGAAGTCAG GCACCTCCCC CAAAAGATGG ATTTATGACA CATCCAAAGT
1401 GGCTTCTGGA GTCCCTTATC GCTTCAGTGG CAGTGGGTCT GGGACCTCAT
1451 ACTCTCTCAC AATCAGCAGC ATGGAGGCTG AAGATGCTGC CACTTATTAC
1501 TGCCAACAGT GGAGTAGTAA CCCGCTCACG TTCGGTGCTG GGACCAAGCT
1551 GGAGCTGAAA CATCATCACC ATCATCATTA G
```

Figure 3B 3-5(vLvH) x anti-CD3 (SEQ ID NO: 30)

```
  1 MGWSCIILFL VATATGVHSA RELVMTQTPL SLPVSLGDQA SISCRSSQSL
 51 VHSNGNTYLH WYLQKPGQSP KLLIYKVSNR FSGVPDRFSG SGSGTDFTLK
101 ISRVEAEDLG VYFCSQSTHV PYTFGGGTKL EIKGGGGSGG GGSGGGGSEV
151 QLLEQSGAEL VRPGTSVKLS CKASGYTFTS YGLSWVKQRT GQGLEWIGEV
201 YPRIGNAYYN EKFKGKATLT ADKSSSTASM ELRSLTSEDS AVYFCARRGS
251 YGSNYDWYFD VWGQGTTVTV SSGGGGSDIK LQQSGAELAR PGASVKMSCK
301 TSGYTFTRYT MHWVKQRPGQ GLEWIGYINP SRGYTNYNQK FKDKATLTTD
351 KSSSTAYMQL SSLTSEDSAV YYCARYYDDH YCLDYWGQGT TLTVSSVEGG
401 SGGSGGSGGS GGVDDIQLTQ SPAIMSASPG EKVTMTCRAS SSVSYMNWYQ
451 QKSGTSPKRW IYDTSKVASG VPYRFSGSGS GTSYSLTISS MEAEDAATYY
501 CQQWSSNPLT FGAGTKLELK HHHHHH*
```

Figure 3B (continued)

SEQ ID NO:29:

```
  1 ATGGGATGGA GCTGTATCAT CCTCTTCTTG GTAGCAACAG CTACAGGTGT
 51 ACACTCCGCG CGCGAGCTCG TGATGACCCA GACTCCACTC TCCCTGCCTG
101 TCAGTCTTGG AGATCAAGCC TCCATCTCTT GCAGATCTAG TCAGAGCCTT
151 GTACACAGTA ATGGAAACAC CTATTTACAT TGGTACCTGC AGAAGCCAGG
201 CCAGTCTCCA AAGCTCCTGA TCTACAAAGT TTCCAACCGA TTTTCTGGGG
251 TCCCAGACAG GTTCAGTGGC AGTGGATCAG GGACAGATTT CACACTCAAG
301 ATCAGCAGAG TGGAGGCTGA GGATCTGGGA GTTTATTTCT GCTCTCAAAG
351 TACACATGTT CCGTACACGT TCGGAGGGGG GACCAAGCTT GAGATCAAAG
401 GTGGTGGTGG TTCTGGCGGC GGCGGCTCCG GTGGTGGTGG TTCTGAGGTG
451 CAGCTGCTCG AGCAGTCTGG AGCTGAGCTG GTAAGGCCTG GGACTTCAGT
501 GAAGCTGTCC TGCAAGGCTT CTGGCTACAC CTTCACAAGC TATGGTTTAA
551 GCTGGGTGAA GCAGAGAACT GGACAGGGCC TTGAGTGGAT TGGAGAGGTT
601 TATCCTAGAA TTGGTAATGC TTACTACAAT GAGAAGTTCA AGGGCAAGGC
651 CACACTGACT GCAGACAAAT CCTCCAGCAC AGCGTCCATG GAGCTCCGCA
701 GCCTGACATC TGAGGACTCT GCGGTCTATT TCTGTGCAAG ACGGGGATCC
751 TACGGTAGTA ACTACGACTG GTACTTCGAT GTCTGGGGCC AAGGGACCAC
801 GGTCACCGTC TCCTCCGGAG GTGGTGGATC CGATATCAAA CTGCAGCAGT
851 CAGGGGCTGA ACTGGCAAGA CCTGGGGCCT CAGTGAAGAT GTCCTGCAAG
901 ACTTCTGGCT ACACCTTTAC TAGGTACACG ATGCACTGGG TAAAACAGAG
```

Figure 3B (continued)

```
 951 GCCTGGACAG GGTCTGGAAT GGATTGGATA CATTAATCCT AGCCGTGGTT
1001 ATACTAATTA CAATCAGAAG TTCAAGGACA AGGCCACATT GACTACAGAC
1051 AAATCCTCCA GCACAGCCTA CATGCAACTG AGCAGCCTGA CATCTGAGGA
1101 CTCTGCAGTC TATTACTGTG CAAGATATTA TGATGATCAT TACTGCCTTG
1151 ACTACTGGGG CCAAGGCACC ACTCTCACAG TCTCCTCAGT CGAAGGTGGA
1201 AGTGGAGGTT CTGGTGGAAG TGGAGGTTCA GGTGGAGTCG ACGACATTCA
1251 GCTGACCCAG TCTCCAGCAA TCATGTCTGC ATCTCCAGGG GAGAAGGTCA
1301 CCATGACCTG CAGAGCCAGT TCAAGTGTAA GTTACATGAA CTGGTACCAG
1351 CAGAAGTCAG GCACCTCCCC CAAAAGATGG ATTTATGACA CATCCAAAGT
1401 GGCTTCTGGA GTCCCTTATC GCTTCAGTGG CAGTGGGTCT GGGACCTCAT
1451 ACTCTCTCAC AATCAGCAGC ATGGAGGCTG AAGATGCTGC CACTTATTAC
1501 TGCCAACAGT GGAGTAGTAA CCCGCTCACG TTCGGTGCTG GGACCAAGCT
1551 GGAGCTGAAA CATCATCACC ATCACATTA G
```

Figure 3C 3-1(vLvH) x anti-CD3 (SEQ ID NO: 36)

```
  1 MGWSCIILFL VATATGVHSE LVMTQSPSYL AASPGETITI NCRASKSISK
 51 YLAWYQEKPG KTNKLLIYSG STLQSGIPSR FSGSGSGTDF TLTISSLEPE
101 DFAMYYCQQH NEYPYTFGGG TKLEIKGGGG SGGGGSGGGG SEVQLLEQSG
151 AELVKPGASV KISCKASGYA FTNYWLGWVK QRPGHGLEWI GDLFPGSGNT
201 HYNERFRGKA TLTADKSSST AFMQLSSLTS EDSAVYFCAR LRNWDEAMDY
251 WGQGTTVTVS SGGGGSDIKL QQSGAELARP GASVKMSCKT SGYTFTRYTM
301 HWVKQRPGQG LEWIGYINPS RGYTNYNQKF KDKATLTTDK SSSTAYMQLS
351 SLTSEDSAVY YCARYYDDHY CLDYWGQGTT LTVSSVEGGS GGSGGSGGSG
401 GVDDIQLTQS PAIMSASPGE KVTMTCRASS SVSYMNWYQQ KSGTSPKRWI
451 YDTSKVASGV PYRFSGSGSG TSYSLTISSM EAEDAATYYC QQWSSNPLTF
501 GAGTKLELKH HHHHH*
```

Figure 3C (continued)

SEQ ID NO: 35

```
  1 ATGGGATGGA GCTGTATCAT CCTCTTCTTG GTAGCAACAG CTACAGGTGT
 51 ACACTCCGAG CTCGTCATGA CCCAGTCTCC ATCTTATCTT GCTGCATCTC
101 CTGGAGAAAC CATTACTATT AATTGCAGGG CAAGTAAGAG CATTAGCAAA
151 TATTTAGCCT GGTATCAAGA GAAACCTGGG AAAACTAATA AGCTTCTTAT
201 CTACTCTGGA TCCACTTTGC AATCTGGAAT TCCATCAAGG TTCAGTGGCA
251 GTGGATCTGG TACAGATTTC ACTCTCACCA TCAGTAGCCT GGAGCCTGAA
301 GATTTTGCAA TGTATTACTG TCAACAGCAT AATGAATATC CGTACACGTT
351 CGGAGGGGGG ACCAAGCTTG AGATCAAAGG TGGTGGTGGT TCTGGCGGCG
401 GCGGCTCCGG TGGTGGTGGT TCTGAGGTGC AGCTGCTCGA GCAGTCTGGA
451 GCTGAGCTGG TGAAACCTGG GGCCTCAGTG AAGATATCCT GCAAGGCTTC
501 TGGATACGCC TTCACTAACT ACTGGCTAGG TTGGGTAAAG CAGAGGCCTG
551 GACATGGACT TGAGTGGATT GGAGATCTTT TCCCTGGAAG TGGTAATACT
601 CACTACAATG AGAGGTTCAG GGGCAAAGCC ACACTGACTG CAGACAAATC
651 CTCGAGCACA GCCTTTATGC AGCTCAGTAG CCTGACATCT GAGGACTCTG
701 CTGTCTATTT CTGTGCAAGA TTGAGGAACT GGGACGAGGC TATGGACTAC
751 TGGGGCCAAG GGACCACGGT CACCGTCTCC TCCGGAGGTG GTGGATCCGA
801 TATCAAACTG CAGCAGTCAG GGGCTGAACT GGCAAGACCT GGGGCCTCAG
851 TGAAGATGTC CTGCAAGACT TCTGGCTACA CCTTTACTAG GTACACGATG
901 CACTGGGTAA AACAGAGGCC TGGACAGGGT CTGGAATGGA TTGGATACAT
```

Figure 3C (continued)

```
 951 TAATCCTAGC CGTGGTTATA CTAATTACAA TCAGAAGTTC AAGGACAAGG
1001 CCACATTGAC TACAGACAAA TCCTCCAGCA CAGCCTACAT GCAACTGAGC
1051 AGCCTGACAT CTGAGGACTC TGCAGTCTAT TACTGTGCAA GATATTATGA
1101 TGATCATTAC TGCCTTGACT ACTGGGGCCA AGGCACCACT CTCACAGTCT
1151 CCTCAGTCGA AGGTGGAAGT GGAGGTTCTG GTGGAAGTGG AGGTTCAGGT
1201 GGAGTCGACG ACATTCAGCT GACCCAGTCT CCAGCAATCA TGTCTGCATC
1251 TCCAGGGGAG AAGGTCACCA TGACCTGCAG AGCCAGTTCA AGTGTAAGTT
1301 ACATGAACTG GTACCAGCAG AAGTCAGGCA CCTCCCCCAA AAGATGGATT
1351 TATGACACAT CCAAAGTGGC TTCTGGAGTC CCTTATCGCT TCAGTGGCAG
1401 TGGGTCTGGG ACCTCATACT CTCTCACAAT CAGCAGCATG GAGGCTGAAG
1451 ATGCTGCCAC TTATTACTGC CAACAGTGGA GTAGTAACCC GCTCACGTTC
1501 GGTGCTGGGA CCAAGCTGGA GCTGAAACAT CATCACCATC ATCATTAG
```

Figure 3D 4-1(vLvH) x anti-CD3 (SEQ ID NO: 39)

```
  1 MGWSCIILFL VATATGVHSE LVMTQSPSSL SVSAGEKVTM SCKSSQSLLN
 51 SGNQKNYLAW YQQKPGQPPK LLIYGASTRE SGVPDRFTGS GSGTDFTLTI
101 SSVQAEDLAV YYCQNDYSYP YTFGGGTKLE IKGGGGSGGG GSGGGGSEVQ
151 LLEQSGAELV RPGTSVKISC KASGYAFTNY WLGWVKQRPG HGLEWVGDIF
201 PGSGNAHYNE KFKGKATLTA DKSSYTAYMQ LSSLTSEDSA VYFCARLRNW
251 DEAMDYWGQG TTVTVSSGGG GSDIKLQQSG AELARPGASV KMSCKTSGYT
301 FTRYTMHWVK QRPGQGLEWI GYINPSRGYT NYNQKFKDKA TLTTDKSSST
351 AYMQLSSLTS EDSAVYYCAR YYDDHYCLDY WGQGTTLTVS SVEGGSGGSG
401 GSGGSGGVDD IQLTQSPAIM SASPGEKVTM TCRASSSVSY MNWYQQKSGT
451 SPKRWIYDTS KVASGVPYRF SGSGSGTSYS LTISSMEAED AATYYCQQWS
501 SNPLTFGAGT KLELKHHHHH H*
```

Figure 3D (continued)

SEQ ID NO: 38:

```
  1 ATGGGATGGA GCTGTATCAT CCTCTTCTTG GTAGCAACAG CTACAGGTGT
 51 ACACTCCGAG CTCGTGATGA CACAGTCTCC ATCCTCCCTG AGTGTGTCAG
101 CAGGAGAGAA GGTCACTATG AGCTGCAAGT CCAGTCAGAG TCTGTTAAAC
151 AGTGGAAATC AAAAGAACTA CTTGGCCTGG TACCAGCAGA AACCAGGGCA
201 GCCTCCTAAA CTGTTGATCT ACGGGGCATC CACTAGGGAA TCTGGGGTCC
251 CTGATCGCTT CACAGGCAGT GGATCTGGAA CAGATTTCAC TCTCACCATC
301 AGCAGTGTGC AGGCTGAAGA CCTGGCAGTT TATTACTGTC AGAATGATTA
351 TAGTTATCCG TACACGTTCG GAGGGGGGAC CAAGCTTGAG ATCAAAGGTG
401 GTGGTGGTTC TGGCGGCGGC GGCTCCGGTG GTGGTGGTTC TGAGGTGCAG
451 CTGCTCGAGC AGTCTGGAGC TGAGCTGGTA AGGCCTGGGA CTTCAGTGAA
501 GATATCCTGC AAGGCTTCTG GATACGCCTT CACTAACTAC TGGCTAGGTT
551 GGGTTAAGCA GAGGCCTGGA CATGGACTTG AATGGGTTGG AGATATTTTC
601 CCTGGAAGTG GTAATGCTCA CTACAATGAG AAGTTCAAGG GCAAAGCCAC
651 ACTGACTGCA GACAAGTCCT CGTACACAGC CTATATGCAG CTCAGTAGCC
701 TGACATCTGA GGACTCTGCT GTCTATTTCT GTGCAAGATT GCGGAACTGG
751 GACGAGGCTA TGGACTACTG GGGCCAAGGG ACCACGGTCA CCGTCTCCTC
801 CGGAGGTGGT GGATCCGATA TCAAACTGCA GCAGTCAGGG GCTGAACTGG
851 CAAGACCTGG GGCCTCAGTG AAGATGTCCT GCAAGACTTC TGGCTACACC
901 TTTACTAGGT ACACGATGCA CTGGGTAAAA CAGAGGCCTG GACAGGGTCT
```

Figure 3D (continued)

```
 951 GGAATGGATT GGATACATTA ATCCTAGCCG TGGTTATACT AATTACAATC
1001 AGAAGTTCAA GGACAAGGCC ACATTGACTA CAGACAAATC CTCCAGCACA
1051 GCCTACATGC AACTGAGCAG CCTGACATCT GAGGACTCTG CAGTCTATTA
1101 CTGTGCAAGA TATTATGATG ATCATTACTG CCTTGACTAC TGGGGCCAAG
1151 GCACCACTCT CACAGTCTCC TCAGTCGAAG GTGGAAGTGG AGGTTCTGGT
1201 GGAAGTGGAG GTTCAGGTGG AGTCGACGAC ATTCAGCTGA CCCAGTCTCC
1251 AGCAATCATG TCTGCATCTC CAGGGGAGAA GGTCACCATG ACCTGCAGAG
1301 CCAGTTCAAG TGTAAGTTAC ATGAACTGGT ACCAGCAGAA GTCAGGCACC
1351 TCCCCCAAAA GATGGATTTA TGACACATCC AAAGTGGCTT CTGGAGTCCC
1401 TTATCGCTTC AGTGGCAGTG GGTCTGGGAC CTCATACTCT CTCACAATCA
1451 GCAGCATGGA GGCTGAAGAT GCTGCCACTT ATTACTGCCA ACAGTGGAGT
1501 AGTAACCCGC TCACGTTCGG TGCTGGGACC AAGCTGGAGC TGAAACATCA
1551 TCACCATCAT CATTAG
```

Figure 3E 5-10(vLvH) x anti-CD3 (SEQ ID NO: 44)

```
  1 MGWSCIILFL VATATGVHSE LVMTQSPSSL TVTAGEKVTM SCKSSQSLLN
 51 SGNQKNYLTW YQQKPGQPPK LLIYWASTRE SGVPDRFTGS GSGTDFTLTI
101 SSVQAEDLAV YYCQNDYSYP LTFGAGTKLE IKGGGGSGGG GSGGGGSEVQ
151 LLEQSGAELV RPGTSVKISC KASGYAFTNY WLGWVKQRPG HGLEWIGDIF
201 PGSGNIHYNE KFKGKATLTA DKSSSTAYMQ LSSLTFEDSA VYFCARLRNW
251 DEPMDYWGQG TTVTVSSGGG GSDIKLQQSG AELARPGASV KMSCKTSGYT
301 FTRYTMHWVK QRPGQGLEWI GYINPSRGYT NYNQKFKDKA TLTTDKSSST
351 AYMQLSSLTS EDSAVYYCAR YYDDHYCLDY WGQGTTLTVS SVEGGSGGSG
401 GSGGSGGVDD IQLTQSPAIM SASPGEKVTM TCRASSSVSY MNWYQQKSGT
451 SPKRWIYDTS KVASGVPYRF SGSGSGTSYS LTISSMEAED AATYYCQQWS
501 SNPLTFGAGT KLELKHHHHH H*
```

Figure 3E (continued)

SEQ ID NO: 43

```
  1 ATGGGATGGA GCTGTATCAT CCTCTTCTTG GTAGCAACAG CTACAGGTGT
 51 ACACTCCGAG CTCGTGATGA CACAGTCTCC ATCCTCCCTG ACTGTGACAG
101 CAGGAGAGAA GGTCACTATG AGCTGCAAGT CCAGTCAGAG TCTGTTAAAC
151 AGTGGAAATC AAAAGAACTA CTTGACCTGG TACCAGCAGA AACCAGGGCA
201 GCCTCCTAAA CTGTTGATCT ACTGGGCATC CACTAGGGAA TCTGGGGTCC
251 CTGATCGCTT CACAGGCAGT GGATCTGGAA CAGATTTCAC TCTCACCATC
301 AGCAGTGTGC AGGCTGAAGA CCTGGCAGTT TATTACTGTC AGAATGATTA
351 TAGTTATCCG CTCACGTTCG GTGCTGGGAC CAAGCTTGAG ATCAAAGGTG
401 GTGGTGGTTC TGGCGGCGGC GGCTCCGGTG GTGGTGGTTC TGAGGTGCAG
451 CTGCTCGAGC AGTCTGGAGC TGAGCTGGTA AGGCCTGGGA CTTCAGTGAA
501 GATATCCTGC AAGGCTTCTG GATACGCCTT CACTAACTAC TGGCTAGGTT
551 GGGTAAAGCA GAGGCCTGGA CATGGACTTG AGTGGATTGG AGATATTTTC
601 CCTGGAAGTG GTAATATCCA CTACAATGAG AAGTTCAAGG GCAAAGCCAC
651 ACTGACTGCA GACAAATCTT CGAGCACAGC CTATATGCAG CTCAGTAGCC
701 TGACATTTGA GGACTCTGCT GTCTATTTCT GTGCAAGACT GAGGAACTGG
751 GACGAGCCTA TGGACTACTG GGGCCAAGGG ACCACGGTCA CCGTCTCCTC
801 CGGAGGTGGT GGATCCGATA TCAAACTGCA GCAGTCAGGG GCTGAACTGG
851 CAAGACCTGG GGCCTCAGTG AAGATGTCCT GCAAGACTTC TGGCTACACC
901 TTTACTAGGT ACACGATGCA CTGGGTAAAA CAGAGGCCTG GACAGGGTCT
```

Figure 3E (continued)

```
 951 GGAATGGATT GGATACATTA ATCCTAGCCG TGGTTATACT AATTACAATC
1001 AGAAGTTCAA GGACAAGGCC ACATTGACTA CAGACAAATC CTCCAGCACA
1051 GCCTACATGC AACTGAGCAG CCTGACATCT GAGGACTCTG CAGTCTATTA
1101 CTGTGCAAGA TATTATGATG ATCATTACTG CCTTGACTAC TGGGGCCAAG
1151 GCACCACTCT CACAGTCTCC TCAGTCGAAG GTGGAAGTGG AGGTTCTGGT
1201 GGAAGTGGAG GTTCAGGTGG AGTCGACGAC ATTCAGCTGA CCCAGTCTCC
1251 AGCAATCATG TCTGCATCTC CAGGGGAGAA GGTCACCATG ACCTGCAGAG
1301 CCAGTTCAAG TGTAAGTTAC ATGAACTGGT ACCAGCAGAA GTCAGGCACC
1351 TCCCCCAAAA GATGGATTTA TGACACATCC AAAGTGGCTT CTGGAGTCCC
1401 TTATCGCTTC AGTGGCAGTG GGTCTGGGAC CTCATACTCT CTCACAATCA
1451 GCAGCATGGA GGCTGAAGAT GCTGCCACTT ATTACTGCCA ACAGTGGAGT
1501 AGTAACCCGC TCACGTTCGG TGCTGGGACC AAGCTGGAGC TGAAACATCA
1551 TCACCATCAT CATTAG
```

4-7xanti-CD3
(SEQ ID NO:42)

CD3 Binding (Jurkat cells)
EpCAM Binding (Kato cells)
Counts
200
160
120
80
40
0
$10^0$
$10^1$
$10^2$
$10^3$
$10^4$
negative control
3-5xanti-CD3
3-5xanti-CD3
(SEQ ID NO: 30)

CD3 Binding (Jurkat cells)
EpCAM Binding (Kato cells)
negative control
4-1xanti-CD3
negative control
4-1xanti-CD3
Counts
4-1xanti-CD3
(SEQ ID NO: 39)

5-10xanti-CD3
(SEQ ID NO: 44)

3-1x anti-CD3
23.58
56.37
58.99
Waste
ml
%B
100
80
60
40
20
0
0
10
20
30
40
50

Figure 8
A)
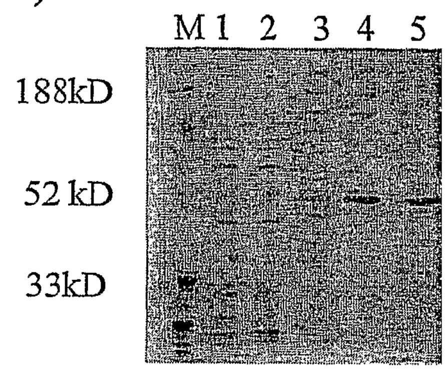
B)
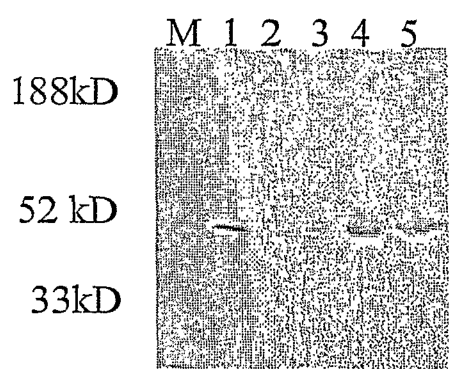

Figure 11A

| | |
|---|---|
| 3-1 | LR**NWD**EAMDY |
| 4-1 | LR**NWD**EAMDY |
| 5-10 | LR**NWD**EPMDY |
| 3-5 | RGSYGS**NYD**WYFDV |
| 4-7 | RGSYDT**NYD**WYFDV |
| M79 | MENWSFAY |
| HD70 | DMGWGSGWRPYYYYGMDV |
| 3B10 | FTSPDY |

PHARMACEUTICAL COMPOSITION COMPRISING A BISPECIFIC ANTIBODY FOR EPCAM

This application is a Continuation of U.S. patent application Ser. No. 10/554,851, filed Apr. 3, 2006, which is a National Stage application of PCT/EP2004/005687, filed May 26, 2004, which claims priority from European patent applications EP 03 01 2134.7, filed May 31, 2003, and EP 03 01 2133.9, filed May 31, 2003. The entire contents of each of the aforementioned applications are incorporated herein by reference.

The invention relates to a pharmaceutical composition comprising a bispecific single chain antibody construct. Said bispecific single chain antibody construct is characterized to comprise or consist of at least two domains, whereby one of said at least two domains specifically binds to human EpCAM antigen and comprises at least one CDR-H3 region comprising the amino acid sequence NXD and a second domain binds to human CD3 antigen. The invention further provides a process for the production of the pharmaceutical composition of the invention, a method for the prevention, treatment or amelioration of a tumorous disease and the use of the disclosed bispecific single chain antibody construct and corresponding means in the prevention, treatment or amelioration of a tumorous disease.

A variety of documents is cited throughout this specification. The disclosure content of said documents is herewith incorporated by reference.

Epithelial cell adhesion molecule (EpCAM, also called 17-1A antigen, KSA, EGP40, GA733-2, ks1-4 or esa) is a 40-kDa membrane-integrated glycoprotein of 314 amino acids with specific expression in certain epithelia and on many human carcinomas (reviewed in Baizar, J. Mol. Med. 1999, 77, 699-712). EpCAM was discovered and subsequently cloned through its recognition by the murine monoclonal antibody 17-1A/edrecolomab (Goettlinger, Int J Cancer. 1986; 38, 47-53 and Simon, Proc. Natl. Acad. Sci. USA. 1990; 87, 2755-2759). Monoclonal antibody 17-1A was generated by immunization of mice with human colon carcinoma cells (Koprowski, Somatic Cell Genet. 1979, 5, 957-971).

The EGF-like repeats of EpCAM were shown to mediate lateral and reciprocal interactions in homophilic cell adhesion (Balzar, Mol. Cell. Biol. 2001, 21, 2570-2580) and, for that reason, is predominantly located between epithelial cells (Litvinov, J Cell Biol. 1997, 139, 1337-1348, Balzar, J Mol Med. 1999, 77, 699-712 and Trebak, J Biol Chem. 2001, 276, 2299-2309). EpCAM serves to adhere epithelial cells in an oriented and highly ordered fashion (Litvinov, J Cell Biol. 1997, 139, 1337-1348). Data from experiments with transgenic mice and rats expressing human EpCAM on their epithelia suggest that EpCAM on normal tissue may however not be accessible to systemically administered antibody (McLaughlin, Cancer Immunol. Immunother., 1999, 48, 303-311). Upon malignant transformation of epithelial cells the rapidly growing tumor cells are abandoning the high cellular order of epithelia. Consequently, the surface distribution of EpCAM becomes less restricted and the molecule better exposed on tumor cells. Due to their epithelial cell origin, tumor cells from most carcinomas still express EpCAM on their surface.

In vivo, expression of EpCAM is related to increased epithelial proliferation and negatively correlates with cell differentiation (for review see Balzar, 1999, J. Mol. Med. 77, 699-712). Expression of EpCAM, as detected by immunohistochemistry using anti-EpCAM monoclonal antibodies, is essentially seen with all major carcinomas (reviewed in Balzar, J Mol Med. 1999, 77, 699-712). Best EpCAM expression was observed with non-small cell lung cancer (De Bree, Nucl Med Commun. 1994, 15, 613-27) and prostate cancer (Zhang, Clin Cancer Res. 1998, 4, 295-302) where 100% of tumor patient samples showed positive EpCAM staining. In these studies, EpCAM is also reported to homogeneously stained tumor tissues indicating that the antigen is expressed on a large proportion of cells of a' given tumor. Because of its widespread expression, EpCAM is referred to as a “pan-carcinoma” antigen.

EpCAM has been shown in various studies to be beneficial in diagnosis and therapy of various carcinomas. Furthermore, in many cases, tumor cells were observed to express EpCAM to a much higher degree than their parental epithelium or less aggressive forms of said cancers. For example, EpCAM expression was shown to be significantly higher on neoplastic tissue and in adenocarcinoma than on normal prostate epithelium ($n=76$; $p<0.0001$), suggesting that increased EpCAM expression represents an early event in the development of prostate cancer (Poczatek, J Urol., 1999, 162, 1462-1644). In addition, in the majority of both squamous and adenocarcinomas of the cervix a strong EpCAM expression correlates with an increased proliferation and the disappearance of markers for terminal differentiation (Litvinov, Am. J. Pathol. 1996, 148, 865-75). One example is breast cancer where overexpression of EpCAM on tumor cells is a predictor of survival (Gastl, Lancet. 2000, 356, 1981-1982). Furthermore, EpCAM has been described as a marker for the detection of disseminated tumor cells in patients suffering from squamous cell carcinoma of the head, neck and lung (Chaubal, Anticancer Res 1999, 19, 2237-2242, Piyathilake, Hum Pathol. 2000, 31, 482-487). Normal squamous epithelium, as found in epidermis, oral cavity, epiglottis, pharynx, larynx and esophagus did not significantly express. EpCAM (Quak, Hybridoma, 1990, 9, 377-387).

In addition to the above-mentioned carcinomas, EpCAM has been shown to be expressed on the majority of primary, metastatic, and disseminated NSCLC (non small cell lung cancer cells) (Passlick, Int J Cancer, 2000, 87, 548-552), on gastric and gastro-oesophageal junction adenocarcinomas (Martin, J Clin Pathol 1999, 52, 701-4) and in cell lines derived from colorectal, pancreatic carcinomas and breast carcinomas (Szala, Proc Natl Acad Sci USA 1990, 87, 3542-6, Packeisen, Hybridoma, 1999, 18, 37-40).

Clinical trials have shown that the use of antibodies directed against 17-1A (EpCAM) for treatment of patients with surgically completely resected colorectal carcinoma leads to a significant benefit concerning the overall survival and the frequency of distant metastasis (Riethmüller, Lancet, 1994, 343, 1177-1183). Murine monoclonal antibody against EpCAM was found to reduce the 5-year mortality (Riethmüller, Lancet, 1994, 343, 1177-1183) and also the 7-year mortality (Riethmüller, Proceedings of the American Society of Clinical Oncology, 1996, 15, 444) of patients with minimal residual disease. Example of murine monoclonal antibody recognizing EpCAM is Edrecolomab (Panorex) (Koprowski, Somatic Cell Genet. 1979, 5, 957-971 and Herlyn, Cancer Res., 1980, 40, 717-721). However, the first administration of Panorex during adjuvant immunotherapy of colon cancer led to the development and exacerbation of Wegener's granulomatosis suggesting that mAb 17-1A should be applied cautiously in a patient with autoimmune disease (Franz, Onkologie, 2000, 23, 472-474). The limitations of Panorex are the rapid formation of human anti-mouse antibodies (HAMA), the limited ability to interact by its murine IgG2a Fc-portion with human immune effector mechanisms and the short half-life in circulation (Frodin, Cancer Res., 1990, 50, 4866-

4871). Furthermore, the murine antibody caused immediate-type allergic reactions and anaphylaxis upon repeated injection in patients (Riethmüller, Lancet. 1994, 343, 1177-1183, Riethmüller, J Clin Oncol., 1998, 16, 1788-1794 and Mellstedt, Annals New York Academy of Sciences. 2000, 910, 254-261).

Humanized anti-EpCAM antibody called 3622W94 resulted in pancreatitis and increased serum levels of amylase, as being indicative for damage of pancreas epithelium, which were a dose-limiting toxicity of this high-affinity anti-EpCAM monoclonal antibody (LoBuglio, Proceedings of the American Society of Clinical Oncology (Abstract). 1997, 1562 and Khor, Proceedings of the American Society of Clinical Oncology (Abstract), 1997, 847).

Bispecific antibodies comprising a region directed against EpCAM and a region directed against CD3 have also been described. The authors of Möller & Reisfeld 1991 Cancer Immunol. Immunother. 33:210-216 describe the construction of two different bispecific antibodies by fusing a hybridoma producing monoclonal antibody against EpCAM with either of the two hybridomas OKT3 and 9.3. Furthermore, Kroesen, Cancer Research, 1995, 55:4409-4415 describe a quadroma bispecific monoclonal antibodies against CD3 (BIS-1) and EpCAM.

Other examples of bispecific antibodies against EpCAM comprise the bispecific antibody, BiUII, (anti-CD3 (rat IgG2b) x anti-EpCAM (mouse IgG2a)) a complete Ig molecule which also binds and activates Fc-receptor positive accessory cells (like monocytes/macrophages, NK cells and dendritic cells) through its Fc-region (Zeidler, J. Immunol., 1999, 163:1247-1252) and an anti-EpCAMxanti-CD3 bispecific antibody in the arrangement $V_{L17\text{-}1A}$-$V_{H17\text{-}1A}$-$V_{Hanti\text{-}CD3}$-$V_{Lanti\text{-}CD3}$ (Mack, Proc. Natl. Acad. Sci., 1995, 92:7021-7025).

In addition, other formats of antibody constructs comprising EpCAM have been described; e.g. a bispecific diabody having the structure $V_{H\ anti\text{-}CD3}$-$V_{L\ anti\text{-}EpCAM}$-$V_{H\text{-}anti\text{-}EpCAM}$-$V_{Lanti\text{-}CD3}$ (Helfrich, Int. J. Cancer, 1998, 76:232-239) and a trispecific antibody having two different tumour antigen specificities (two antigen binding regions which bind two different antigens on a tumour cell) and which may have a further specificity for an antigen localized on an effector cell (DE 195 31 348).

There exist various descriptions in the prior art of using phage display technology to identify antibodies or fragments thereof, which specifically bind to the human EpCAM antigen (De Kruif JMB, 1995, 248:97-105, WO 99/25818). However, it has been extremely difficult to identify antibodies against EpCAM, which show cytotoxic activity sufficient for therapeutic applications in a bispecific format.

It is therefore an aim of the present invention to provide a bispecific single chain molecule with a binding domain specific for EpCAM with strong cytotoxic activity mediated by target specific activation of T cells.

Thus, the technical problem underlying the present invention was to provide means and methods for the generation of well tolerated and convenient medicaments for the treatment and or amelioration of tumorous diseases.

The solution to said technical problem is achieved by providing the embodiments characterized in the claims.

Accordingly, the present invention relates to a composition, preferably a pharmaceutical composition, comprising a bispecific single chain antibody construct, whereby said construct comprises or consists of at least two binding domains, whereby one of said domains binds to human EpCAM antigen and a second domain binds to human CD3 antigen, wherein said binding domain specific for EpCAM comprises at least one CDR-H3 region comprising the amino acid sequence NXD preferably in position 102 to 104 of SEQ ID NOs: 80, 88 and 96, or preferably in position 106 to 108 of SEQ ID NOs: 84 and 92, wherein X is an aromatic amino acid.

Preferably or alternatively, the present invention relates to a composition, preferably a pharmaceutical composition, comprising a bispecific single chain antibody construct, whereby said construct comprises or consists of at least two domains, whereby one of said at least two domains specifically binds to human EpCAM antigen and a second domain binds to human CD3 antigen, wherein said binding domain specific for EpCAM comprises at least one CDR-H3 region of least 9 amino acid residues and wherein said binding domain specific for EpCAM has a $K_D$ value of more than $5\times10^{-9}$ M.

In accordance with this invention, the term "pharmaceutical composition" relates to a composition for administration to a patient, preferably a human patient. In a preferred embodiment, the pharmaceutical composition comprises a composition for parenteral, transdermal, intraluminal, intra-arterial, intrathecal or intravenous administration or for direct injection into the tumor. It is in particular envisaged that said pharmaceutical composition is administered to a patient via infusion or injection. Administration of the suitable compositions may be effected by different ways, e.g., by intravenous, subcutaneous, intraperitoneal, intramuscular, topical or intradermal administration. The pharmaceutical composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A preferred dosage for administration might be in the range of 0.24 μg to 48 mg, preferably 0.24 μg to 24 mg, more preferably 0.24 μg to 2.4 mg, even more preferably 0.24 μg to 1.2 mg and most preferably 0.24 μg to 240 μg units per kilogram of body weight per day. Particularly preferred dosages are recited herein below. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systematically. Administration will generally be parenteral, e.g., intravenous; DNA may also be administered directly to the target site, e.g., by biolistic delivery to an internal or external target site or by catheter to a site in an artery. In an preferred embodiment, the pharmaceutical composition is administered subcutaneously and in an even more preferred embodiment intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention might comprise proteinaceous carriers, like, e.g., serum albumine or immunoglobuline, preferably of human origin. It is envisaged that the pharmaceutical composition of the invention might comprise, in addition to the proteinaceous bispecific single chain antibody constructs or nucleic acid molecules or vectors encoding the same (as described in this invention), further biologically active agents, depending on the intended use of the pharmaceutical composition. Such agents might be drugs acting on the gastro-intestinal system, drugs acting as cytostatica, drugs preventing hyperurikemia, agents such as T-cell co-stimulatory molecules or cytokines, drugs inhibiting immune reactions (e.g. corticosteroids) and/or drugs acting on the circulatory system, e.g. on the blood pressure, known in the art.

Possible indications for administration of the composition(s) of the invention are tumorous diseases especially epithelial cancers/carcinomas such as breast cancer, colon cancer, prostate cancer, head and neck cancer, skin cancer, cancers of the genito-urinary tract, e.g. ovarial cancer, endometrial cancer, cervix cancer and kidney cancer, lung cancer, gastric cancer, cancer of the small intestine, liver cancer, pancreas cancer, gall bladder cancer, cancers of the bile duct, esophagus cancer, cancer of the salivatory glands and cancer of the thyroid gland. The administration of the composition(s) of the invention is especially indicated for minimal residual disease preferably early solid tumor, advanced solid tumor or metastatic solid tumor, which is characterized by the local and non-local reoccurrence of the tumor caused by the survival of single cells.

The invention further envisages the co-administration protocols with other compounds, e.g. bispecific antibody constructs, targeted toxins or other compounds, which act via T cells. The clinical regimen for co-administration of the inventive compound(s) may encompass co-administration at the same time, before or after the administration of the other component.

A possible approach to demonstrate the efficacy/activity of the inventive constructs is an in vivo model like mouse. Suitable models may be transgenic and chimeric mouse models. Mouse models expressing human CD3 and human EpCAM, a chimeric mouse model expressing murine CD3 and into which tumour cells expressing human EpCAM can be transfected and chimeric mouse models comprising nude mice into which human tumours expressing EpCAM can be transplanted or tumour cells expressing human EpCAM can be injected and, additionally, human PBMCs are injected. The term "bispecific single chain antibody construct" relates to a construct comprising two antibody derived binding domains. One of said binding domains consists of variable regions (or parts thereof) of an antibody, antibody fragment or derivative thereof, capable of specifically binding to/interacting with human EpCAM antigen (target molecule 1). The second binding domain consists of variable regions (or parts thereof) of an antibody, antibody fragment or derivative thereof, capable of specifically binding to/interacting with human CD3 antigen (target molecule 2). As will be detailed below, a part of a variable region may be at least one CDR ("Complementary determining region"), most preferably at least the CDR3 region. Said two domains/regions in the single chain antibody construct are preferably covalently connected to one another as a single chain. This connection can be effected either directly (domain 1 [specific for the CD3 antigen]-domain 2 [specific for the EpCAM antigen] or domain 1 [specific for the EpCAM antigen]-domain 2 [specific for the CD3 antigen]) or through an additional polypeptide linker sequence (domain1-linker sequence-domain2). In the event that a linker is used, this linker is preferably of a length and sequence sufficient to ensure that each of the first and second domains can, independently from one another, retain their differential binding specificities. Most preferably and as documented in the appended examples, the "bispecific single chain antibody construct" to be employed in the pharmaceutical composition of the invention is a bispecific single chain Fv (scFv). Bispecific single chain molecules are known in the art and are described in WO 99/54440, Mack, J. Immunol. (1997), 158, 3965-3970, Mack, PNAS, (1995), 92, 7021-7025, Kufer, Cancer Immunol. Immunother., (1997), 45, 193-197, Löffler, Blood, (2000), 95, 6, 2098-2103 and Brühl, J. Immunol., (2001), 166, 2420-2426. A particularly preferred molecular format of the invention provides a polypeptide construct wherein the antibody-derived region comprises one $V_H$ and one $V_L$ region. The intramolecular orientation of the $V_H$-domain and the $V_L$-domain, which are linked to each other by a linker-domain, in the scFv format is not decisive for the recited bispecific single chain constructs. Thus, scFvs with both possible arrangements ($V_H$-domain-linker domain-$V_L$-domain; $V_L$-domain-linker domain-$V_H$-domain) are particular embodiments of the recited bispecific single chain construct.

The antibody construct may also comprise additional domains, e.g. for the isolation and/or preparation of recombinantly produced constructs.

A corresponding format for a bispecific single chain antibody construct is described in the appended example 1.

The term "single-chain" as used in accordance with the present invention means that said first and second domain of the bispecific single chain construct are covalently linked, preferably in the form of a co-linear amino acid sequence encodable by a single nucleic acid molecule.

The term "binding to/interacting with" as used in the context with the present invention defines a binding/interaction of at least two "antigen-interaction-sites" with each other. The term "antigen-interaction-site" defines, in accordance with the present invention, a motif of a polypeptide which shows the capacity of specific interaction with a specific antigen or a specific group of antigens. Said binding/interaction is also understood to define a "specific recognition". The term "specifically recognizing" means in accordance with this invention that the antibody molecule is capable of specifically interacting with and/or binding to at least two amino acids of each of the human target molecule as defined herein. Said term relates to the specificity of the antibody molecule, i.e. to its ability to discriminate between the specific regions of the human target molecule as defined herein. The specific interaction of the antigen-interaction-site with its specific antigen may result in an initiation of a signal, e.g. due to the induction of a change of the conformation of the antigen, an oligomerization of the antigen, etc. Further, said binding may be exemplified by the specificity of a "key-lock-principle". Thus, specific motifs in the amino acid sequence of the antigen-interaction-site and the antigen bind to each other as a result of their primary, secondary or tertiary structure as well as the result of secondary modifications of said structure. The specific interaction of the antigen-interaction-site with its specific antigen may result as well in a simple binding of said site to the antigen.

The term "specific interaction" as used in accordance with the present invention means that the bispecific single chain construct does not or essentially does not cross-react with (poly)peptides of similar structures. Cross-reactivity of a panel of bispecific single chain construct under investigation may be tested, for example, by assessing binding of said panel of bispecific single chain construct under conventional conditions (see, e.g., Harlow and Lane, Antibodies: A Laboratory Manual, Cold Spring Harbor Laboratory Press, 1988 and Using Antibodies: A Laboratory Manual, Cold Spring Harbor Laboratory Press, 1999) to the (poly)peptide of interest as well as to a number of more or less (structurally and/or functionally) closely related (poly)peptides. Only those antibodies that bind to the (poly)peptide/protein of interest but do not or do not essentially bind to any of the other (poly)peptides are considered specific for the (poly)peptide/protein of interest. Examples for the specific interaction of an antigen-interaction-site with a specific antigen comprise the specificity of a ligand for its receptor. Said definition particularly comprises the interaction of ligands which induce a signal upon binding to its specific receptor. Examples for corresponding ligands comprise cytokines which interact/bind with/to its specific cytokine-receptors. Also particularly comprised by said definition is the binding of an antigen-interaction-site to antigens like antigens of the selectin family, integrins and of the family of growth factors like EGF. An other example for said interaction, which is also particularly comprised by said definition, is the interaction of an antigenic determinant (epitope) with the antigenic binding site of an antibody.

The term "binding to/interacting with" may also relate to a conformational epitope, a structural epitope or a discontinuous epitope consisting of two regions of the human target molecules or parts thereof. In context of this invention, a conformational epitope is defined by two or more discrete amino acid sequences separated in the primary sequence which come together on the surface of the molecule when the polypeptide folds to the native protein (Sela, (1969) Science 166, 1365 and Layer, (1990) Cell 61, 553-6).

The term "discontinuous epitope" means in context of the invention non-linear epitopes that are assembled from residues from distant portions of the polypeptide chain. These residues come together on the surface of the molecule when the polypeptide chain folds into a three-dimensional structure to constitute a conformational/structural epitope.

The constructs of the present invention are also envisaged to specifically bind to/interact with a conformational/structural epitope(s) composed of and/or comprising the two regions of the human CD3 complex described herein or parts thereof as disclosed herein below.

Accordingly, specificity can be determined experimentally by methods known in the art and methods as disclosed and described herein. Such methods comprise, but are not limited to Western blots, ELISA-, RIA-, ECL-, IRMA-, EIA-tests and peptide scans.

The term "antibody fragment or derivative thereof" relates to single chain antibodies, or fragments thereof, synthetic antibodies, antibody fragments, such as Fab, a $F(ab_2)'$, Fv or scFv fragments etc., or a chemically modified derivative of any of these. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) (e.g. posttranslational and chemical modifications, such as glycosylation and phosphorylation) known in the art either alone or in combination. Methods for introducing such modifications in the DNA sequence underlying the amino acid sequence of an immunoglobulin chain are well known to the person skilled in the art; see, e.g., Sambrook (1989), loc. cit.

The term "(poly)peptide" as used herein describes a group of molecules which comprise the group of peptides, as well as the group of polypeptides. The group of peptides is consisting of molecules with up to 30 amino acids, the group of polypeptides is consisting of molecules with more than 30 amino acids.

The term "antibody fragment or derivative thereof" particularly relates to (poly)peptide constructs comprising at least one CDR.

Fragments or derivatives of the recited antibody molecules define (poly)peptides which are parts of the above antibody molecules and/or which are modified by chemical/biochemical or molecular biological methods. Corresponding methods are known in the art and described inter alia in laboratory manuals (see Sambrook et al.; Molecular Cloning: A Laboratory Manual; Cold Spring Harbor Laboratory Press, 2nd edition 1989 and 3rd edition 2001; Gerhardt et al.; Methods for General and Molecular Bacteriology; ASM Press, 1994; Lefkovits; Immunology Methods Manual: The Comprehensive Sourcebook of Techniques; Academic Press, 1997; Golemis; Protein-Protein Interactions: A Molecular Cloning Manual; Cold Spring Harbor Laboratory Press, 2002).

Bispecific antibodies that specifically recognize the EpCAM antigen and the CD3 antigen are described in the prior art, e.g., in Mack (Proc. Natl. Acad. Sci., 1995, 92:7021-7025).

As mentioned above, the said variable domains comprised in the herein described bispecific single chain constructs are connected by additional linker sequences. The term "peptide linker" defines in accordance with the present invention an amino acid sequence by which the amino acid sequences of the first domain and the second domain of the defined construct are linked with each other. An essential technical feature of such peptide linker is that said peptide linker does not comprise any polymerization activity. A particularly preferred peptide linker is characterized by the amino acid sequence Gly-Gly-Gly-Gly-Ser, i.e. (Gly)4Ser, or polymers thereof, i.e. ((Gly)4Ser)x. The characteristics of said peptide linker, which comprise the absence of the promotion of secondary structures are known in the art and described e.g. in Dall'Acqua et al. (Biochem. (1998) 37, 9266-9273), Cheadle et al. (Mol Immunol (1992) 29, 21-30) and Raag and Whitlow (FASEB (1995) 9(1), 73-80). Also particularly preferred are peptide linkers which comprise less amino acid residues. An envisaged peptide linker with less than 5 amino acids can comprise 4, 3, 2 or one amino acids. A particularly preferred "single" amino acid in context of said "peptide linker" is Gly. Accordingly, said peptide linker may consist of the single amino acid Gly. Furthermore, peptide linkers which also do not promote any secondary structures are preferred. The linkage of said domains to each other can be provided by, e.g. genetic engineering, as described in the examples. Methods for preparing fused and operatively linked bispecific single chain constructs and expressing them in mammalian cells or bacteria are well-known in the art (e.g. WO 99/54440, Ausubel, Current Protocols in Molecular Biology, Green Publishing Associates and Wiley Interscience, N.Y. 1989 and 1994 or Sambrook et al., Molecular Cloning: A Laboratory Manual, Cold Spring Harbor Laboratory Press, Cold Spring Harbor, N.Y., 2001).

The bispecific single chain antibody constructs described herein above and below may be humanized or deimmunized antibody constructs. Methods for the humanization and/or deimmunization of (poly))peptides and, in particular, antibody constructs are known to the person skilled in the art.

Here it was surprisingly found that domains with specificity for the EpCAM antigen, comprising at least one CDR-H3 region comprising the amino acid sequence NXD (asparagine-X-aspartic acid) preferably in position 102 to 104 of SEQ ID NOs: 80, 88 and 96, or in position 106 to 108 of SEQ ID NOs: 84 and 92, wherein X is an aromatic amino acid are particularly useful in the specific format of a bispecific single chain antibody construct. These bispecific single chain antibody constructs are particularly useful as pharmaceutical compositions since these constructs are advantageous over constructs which do not comprise said amino acids.

Furthermore, it was surprisingly found that domains with specificity for the EpCAM antigen, comprising at least one CDR-H3 region of at least 9 amino acid residues and having a $K_D$ value of more than $5\times10^{-9}$ M are particularly useful in the specific format of a bispecific single chain antibody construct. These bispecific single chain antibody construct are particularly useful as pharmaceutical compositions since these constructs are advantageous over constructs of less than 9 amino acid residues and wherein said binding domain specific for EpCAM has a $K_D$ value of less than $5\times10^{-9}$ M.

Figure 11B:
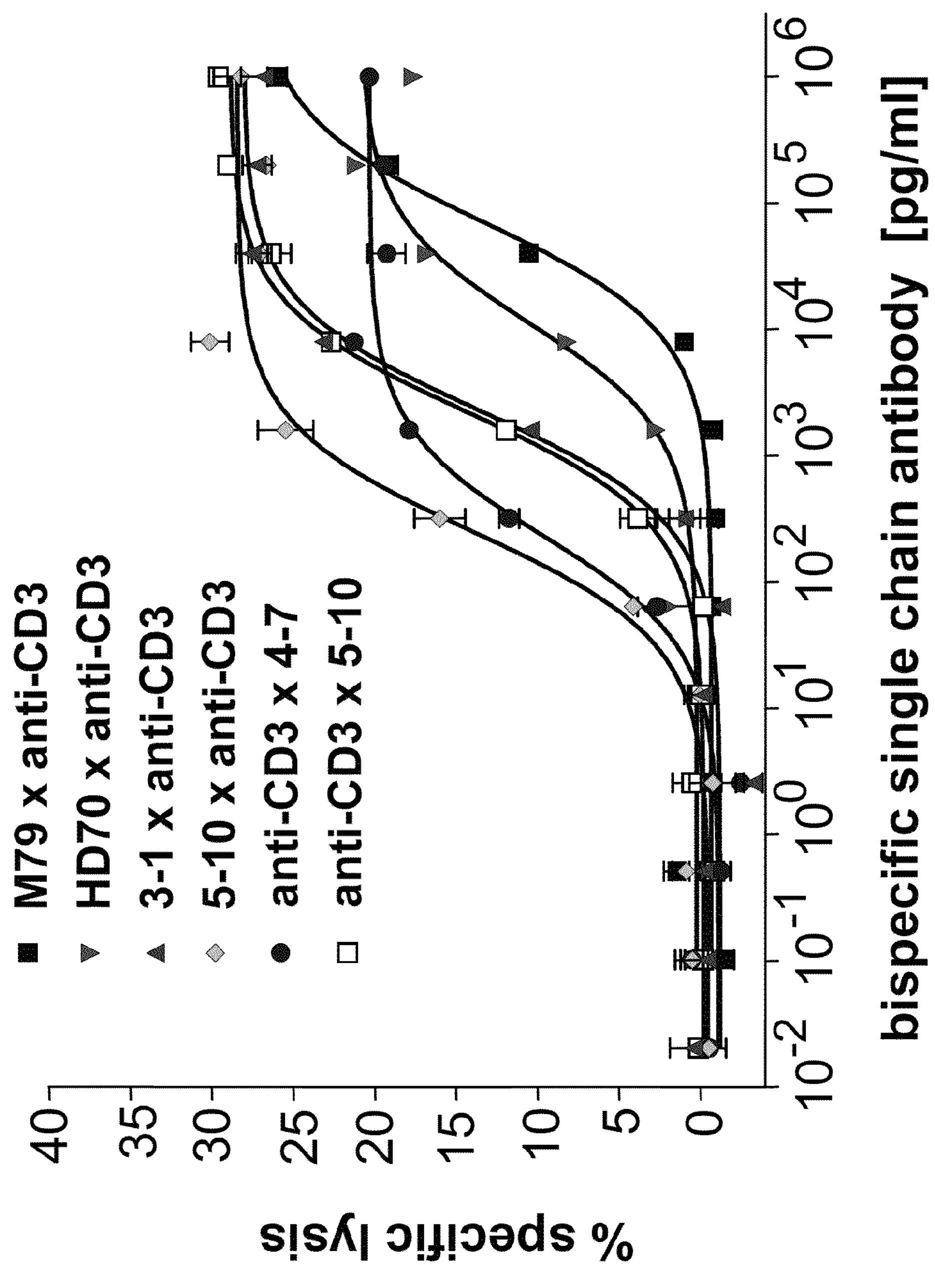

The prior art constructs are characterized by less advantageous $EC_{50}$ values and/or less efficient or complete purifications as shown in the appended examples. It was in particular surprising that the domain of the single chain constructs with specificity for the CD3 antigen to be employed in accordance with the invention are highly bioactive in N- as well as C-terminal position, wherein in particular arrangements in $V_{H(anti\text{-}CD3)}$-$V_{L(anti\text{-}CD3)}$ are preferred. The constructs to be employed in the pharmaceutical composition of the invention are characterized by advantageous production and purification properties as well as by their high bioactivity, i.e. their desired cytotoxic activity. In particular, when the cytotoxic activity of the constructs of the invention were compared with cytotoxic activity of conventional M79xanti-CD3 and HD70xanti-CD3 constructs, the constructs of the invention showed clearly higher bioactivity (FIG. 11B). The corresponding high bioactivity is reflected by low to very low $EC_{50}$ values as determined in cytotoxicity tests. The lower the $EC_{50}$ value of the molecule is, the higher cytotoxicity, i.e. the effectivity in the cell lysis, of the construct is higher. On the other hand, the higher the $EC_{50}$ value, the less effective the molecule is in inducing cell lysis. The term "$EC_{50}$" corresponds, in context of this invention, to $EC_{50}$ values as determined according to the methods known in the art and as illustrated in the appended examples: A standard dose-response curve is defined by four parameters: the baseline response (Bottom), the maximum response (Top), the slope, and the drug concentration that provokes a response halfway between baseline and maximum ($EC_{50}$). $EC_{50}$ is defined as the concentration of a drug or molecule that provokes a response half way between the baseline (Bottom) and maximum response (Top). A lower $K_D$ value of the constructs of the invention depicts higher binding affinity. E.g. a low $K_D$ of $10^{-9}$ M shows high binding affinity of the binding construct. On the other hand a high $K_D$ value of e.g. $10^{-6}$ M relates to lower binding affinity of the binding domain of the construct.

The percentage of cell lysis (i.e. cytotoxic activity) may be determined by, inter alia, release assays disclosed herein above, for example, $^{51}$Cr release assays, LDH-release assays and the like. Most preferably, in context of this invention fluorochrome release assays is employed as illustrated in the appended examples. Here, strong cytotoxic activity against EpCAM-positive cells (see CHO-EpCAM cells in appended example 3) of the bispecific single chain constructs described herein relates to a molecule comprising $EC_{50}$ values preferably ≤500 pg/ml, more preferably ≤400 pg/ml, even more preferably ≤300 pg/ml, even more preferably ≤250 pg/ml, most preferably ≤200 pg/ml, ≤100 pg/ml, 50 pg/ml.

The bispecific constructs comprised in the pharmaceutical compositions of the present invention show a surprisingly high cytotoxic activity (preferably in the range of about 10 pg/ml to 170 pg/ml) compared to the prior art M79xanti-CD3 construct ($VL_{17\text{-}1A}$-$VH_{17\text{-}1A}$-$VH_{CD3}$-$VL_{CD3}$; 8628 pg/ml). A skilled person is aware that EC50 values may vary depending to the bioactivity assay. Factors affecting EC50 value may comprise type of effector cells, activity of effector cells, type of target cells, E:T ratio, incubation time, incubation temperature and other external circumstances. Different EC50 values of same constructs in different experiments may be compared with the EC50 values of controls. A construct having high cytotoxic activity according to the invention has at least 2.5 time lower EC50 value than the control (at least 2.5 times higher cytotoxicity than the control), preferably at least three times lower EC50 value and more preferably at least five times lower EC50 value.

Furthermore, the constructs of the invention bind EpCAM with a surprisingly high affinity measured by surface plasmon resonance)(BIAcore°. The prior art EpCAM and CD3 binding construct M79xanti-CD3 has a $K_D$ of $4\times10^{-6}$ M and the constructs of the invention a $K_D$ of $2.3\times10^{-7}$-$2.5\times10^{-7}$ M.

Preferably, the X in said NXD motif is W (tryptophan) or Y (tyrosine).

It is further envisaged that the pharmaceutical composition of the invention comprises a bispecific single chain antibody construct, wherein the CDR-H3 of the EpCAM specific domain comprises at least 9 amino acid residues, preferably at least 14 amino acids. Preferably the CDR-H3 comprises less than 18 amino acids, more preferably less than 15 amino acids. Thus, preferably the CDR-H3 comprises 9 to 17 amino acids, more preferably 9 to 15 amino acids and most preferably 10 or 14 amino acids.

Bispecific single chain antibody construct comprising a corresponding EpCAM specific domain have been surprisingly found to be advantagous in the format of the above described construct over other EpCAM specific domain known in the art. Such effect is demonstrated in appended examples 3, 4 and 5. The prior art EpCAM binding antibody M79 comprises eight amino acids in its CDR-H3 region and does not comprise the sequence NXD (FIG. 11A).

The pharmaceutical composition according to the invention may also comprise constructs, wherein said binding domain specific for EpCAM has a $K_D$ value of more than $5\times10^{-9}$ M.

The pharmaceutical composition may additionally be characterized by the feature that said binding domain specific for the CD3 antigen has a $K_D$ value of more than $10^{-7}$ M.

The $K_D$ value is a physical value defining the tendency of a complex to dissociate. For the binding equilibrium A+B$\leftrightarrow$AB, the dissociation constant is given as the ratio of the two kinetic rate constants $k_{off}$ and $k_{on}$: [A][B] (kon)/[AB] (koff). The smaller the dissociation constant the tighter A and B bind to each other. In biological systems a good, specific binder has a dissociation constant in the range of $10^{-9}$-$10^{-7}$ M. $K_D$ can be measured with a number of methods known to the person skilled in the art, e.g. surface plasmon resonance (SPR, e.g. with BIAcore®), analytical ultracentrifugation, isothermal titration calorimetry, fluorescence anisotropy, fluorescence spectroscopy or by radiolabeled ligand binding assays.

The $K_D$s of the constructs of the invention have been measured using the surface plasmon resonance (SPR) spectroscopy. The ligand is injected over the immobilized antigen chip surface and the change in optical density on the chip surface upon binding is measured. The change in optical density, monitored by a change in reflection angle, correlates directly to the amount of ligand binding to the chip surface—the biophysical phenomenon used is called surface plasmon resonance.

One of the interaction partners has to be immobilized on the surface of the sensor chip of the apparatus based on surface plasmon resonance (e.g. BIAcore®). The kinetics of association and dissociation of ligand with the immobilized antigen on the chip surface are observed in real time. The binding curves are fitted for kinetic rate constants $k_{on}$ and $k_{off}$, resulting in an apparent equilibrium dissociation constant (KD).

It is particularly preferred, that said binding domain specific for EpCAM has a $K_D$ value in a range between $1\times10^{-7}$ and $5\times10^{-9}$ M and said binding domain specific for CD3 has a $K_D$ value in a range between $1\times10^{-6}$ and $5\times10^{-9}$ M.

In a particularly preferred embodiment, the pharmaceutical composition may additionally be characterized by the feature that said binding domain specific for the CD3 antigen has a $K_D$ value of >(more than) $1\times10^{-7}$ M.

The constructs of the invention have the advantage that they may be used a number of times for killing tumour cells since the EpCAM binding part has an affinity with a $K_D$ value of more than $5\times10^{-9}$ M. If the affinity of a bispecific construct for binding an EpCAM-expressing tumour cell is too high, the construct binds one EpCAM expressing tumour cell and remains on its surface even when it has been killed and cannot continue to another tumour cell to be killed. A further advantage of the construct of the invention is that the binding domain specific for EpCAM binds with a high affinity (corresponds to lower $K_D$ value), thus leading the circulating T-cells to the tumour cells marked with the bispecific construct. Therefore, the $K_D$ of the binding domain specific for EpCAM of the bispecific construct is preferably in the range of $10^{-7}$-$5\times10^{-9}$ M and the $K_D$ of the binding domain specific for CD3 is preferably in the range of $10^{-6}$-$5\times10^{-9}$ M. In a preferred embodiment, the KD value of the EpCAM binding domain is lower than the KD value of the CD3 binding domain corresponding to a higher affinity of the EpCAM binding domain compared to the CD3 binding domain.

Further it is envisaged that the pharmaceutical composition of the invention comprises a bispecific single chain antibody construct, wherein the CDR-H3 of the EpCAM specific domain comprises at least 9 amino acids, preferably at least 14 amino acids. Preferably the CDR-H3 comprises less than 18 amino acids, more preferably less than 15 amino acids. Thus, preferably the CDR-H3 comprises 9 to 17 amino acids, more preferably 9 to 15 amino acids and most preferably 10 or 14 amino acids.

In a preferred embodiment of the pharmaceutical composition of the invention the $V_H$ chain of the domain specific for human EpCAM antigen is selected from the group consisting of:

(a) an amino acid sequence as shown in any of SEQ ID NO: 80, SEQ ID NO: 84, SEQ ID NO: 88, SEQ ID NO: 92 and SEQ ID NO:96;
(b) an amino acid sequence encoded by a nucleic acid sequence as shown in SEQ ID NO: 79, SEQ ID NO: 83, SEQ ID NO: 87, SEQ ID NO: 91 and SEQ ID NO: 95;
(c) an amino acid sequence encoded by a nucleic acid sequence hybridizing with the complementary strand of a nucleic acid sequence as defined in (b) under stringent hybridization conditions;
(d) an amino acid sequence encoded by a nucleic acid sequence which is degenerate as a result of the genetic code to a nucleotide sequence of any one of (b) and (c).

The term "hybridizing" as used herein refers to polynucleotides/nucleic acid sequences which are capable of hybridizing to the polynucleotides encoding bispecific single chain constructs as defined herein or parts thereof. Therefore, said polynucleotides may be useful as probes in Northern or Southern Blot analysis of RNA or DNA preparations, respectively, or can be used as oligonucleotide primers in PCR analysis dependent on their respective size. Preferably, said hybridizing polynucleotides comprise at least 10, more preferably at least 15 nucleotides in length while a hybridizing polynucleotide of the present invention to be used as a probe preferably comprises at least 100, more preferably at least 200, or most preferably at least 500 nucleotides in length.

It is well known in the art how to perform hybridization experiments with nucleic acid molecules, i.e. the person skilled in the art knows what hybridization conditions s/he has to use in accordance with the present invention. Such hybridization conditions are referred to in standard text books such as Molecular Cloning A Laboratory Manual, Cold Spring Harbor Laboratory (2001) N.Y. Preferred in accordance with the present inventions are polynucleotides which are capable of hybridizing to the polynucleotides of the invention or parts thereof, under stringent hybridization conditions.

"Stringent hybridization conditions" refer, e.g. to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Also contemplated are nucleic acid molecules that hybridize to the polynucleotides of the invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). It is of note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The recited nucleic acid molecules may be, e.g., DNA, cDNA, RNA or synthetically produced DNA or RNA or a recombinantly produced chimeric nucleic acid molecule comprising any of those polynucleotides either alone or in combination.

Preferably said pharmaceutical composition of the invention may comprise a bispecific single chain construct, wherein the $V_L$ chain domains specific for human EpCAM antigen is selected from the group consisting of:

(a) an amino acid sequence as shown in any of SEQ ID NO: 82, SEQ ID NO: 86, SEQ ID NO: 90, SEQ ID NO: 94 and SEQ ID NO: 98;

(b) an amino acid sequence encoded by a nucleic acid sequence as shown in SEQ ID NO: 81, SEQ ID NO: 85, SEQ ID NO: 89, SEQ ID NO: 93 and SEQ ID NO: 97;

(c) an amino acid sequence encoded by a nucleic acid sequence hybridizing with the complementary strand of a nucleic acid sequence as defined in (b) under stringent hybridization conditions;

(d) an amino acid sequence encoded by a nucleic acid sequence which is degenerate as a result of the genetic code to a nucleotide sequence of any one of (b) and (c).

In a preferred embodiment of the pharmaceutical composition of this invention, the $V_H$ and $V_L$ regions of said human CD3 specific domain are derived from an CD3 specific antibody selected from the group consisting of X35-3, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, WT31 and F101.01. These CD3-specific antibodies are well known in the art and, inter alia, described in Tunnacliffe (1989), Int. Immunol. 1, 546-550. In a more preferred embodiment, said $V_H$ and $V_L$ regions of said CD3 specific domain are derived from OKT-3 (as defined and described above). Even more preferred. (and as illustrated in the appended examples) said $V_H$ and $V_L$ regions are or are derived from an antibody/antibody derivative with specificity for the CD3 molecule described by Traunecker (1991), EMBO J. 10, 3655-3659. In accordance with this invention, said $V_H$ and $V_L$ regions are derived from antibodies/antibody derivatives and the like which are capable of specifically recognizing the human CD3-ϵ chain in the context of other TCR subunits, e.g. in mouse cells transgenic for human CD3-ϵ chain. These transgenic mouse cells express human CD3-ϵ chain in a native or near native conformation. Accordingly, the $V_H$ and $V_L$ regions derived from an CD3-ϵ chain specific antibody is most preferred in accordance with this invention and said (parental) antibodies should be capable of specifically binding epitopes reflecting the native or near native structure or a conformational epitope of human CD3 presented in context of the TCR complex. Such antibodies have been classified by Tunnacliffe (1989) as “group II” antibodies. Further classifications in Tunnacliffe (1989) comprise the definition of “group I” and “group III” antibodies directed against CD3. “Group I” antibodies, like UCHT1, recognize CD3-ϵ chain expressed as recombinant protein and as part of the TCR on the cell surface. Therefore, “group I” antibodies are highly specific for CD3-ϵ chain. In contrast, the herein preferred “group II antibodies” recognize CD3-ϵ chain only in the native TCR complex in association with other TCR subunits. Without being bound by theory, it is speculated in context of this invention that in “group II” antibodies, the TCR context is required for recognition of CD3-ϵ chain. CD3-γ chain and δ chain, being associated with ϵ chain, are also involved in binding of “group II antibodies”. All three subunits express immunoreceptor-tyrosine activation motifs (ITAMs) which can be tyrosine phosphorylated by protein tyrosine-based kinases. For this reason group II antibodies induce T cell signaling via CD3-ϵ chain, γ chain and δ chain, leading to a stronger signal compared to group I antibodies selectively inducing T cell signaling via CD3-ϵ chain. Yet, since for therapeutic applications induction of a strong T cell signaling is desired, the $V_{H\,(anti\text{-}CD3)}$/$V_{L\,(anti\text{-}CD3)}$-regions (or parts thereof) to be employed in the bispecific single chain constructs comprised in the inventive pharmaceutical composition, are preferably derived from antibodies directed against human CD3 and classified in “group II” by Tunnacliffe (1989), loc.cit.

In one embodiment the present invention relates to a pharmaceutical composition wherein said bispecific single chain antibody construct comprises an amino acid sequence selected from the group of:

(a) an amino acid sequence as shown in any of SEQ ID NOs: 2, 4, 8, 10, 12, 14, 16, 18, 20, 30, 36, 39, 42, 44, 46, 48, 50, 52, 54, 56, 58 and 60;

(b) an amino acid sequence encoded by a nucleic acid sequence as shown in any of SEQ ID NOs: 1, 3, 7, 9, 11, 13, 15, 17, 19, 29, 35, 38, 41, 43, 45, 47, 49, 51, 53, 55, 57 and 59;

(c) an amino acid sequence encoded by a nucleic acid sequence hybridizing with the complementary strand of a nucleic acid sequence as defined in (b) under stringent hybridization conditions;

(d) an amino acid sequence encoded by a nucleic acid sequence which is degenerate as a result of the genetic code to a nucleotide sequence of any one of (b) and (c).

The present invention also provides for a pharmaceutical composition comprising a nucleic acid sequence encoding a bispecific single chain antibody construct as defined above.

Said nucleic acid molecule may be a natural nucleic acid molecule as well as a recombinant nucleic acid molecule. The nucleic acid molecule may, therefore, be of natural origin, synthetic or semi-synthetic. It may comprise DNA, RNA as well as PNA (peptide nucleic acid) and it may be a hybrid thereof.

Thus, the present invention relates to a pharmaceutical composition comprising a nucleic acid molecule comprising a nucleotide sequence selected from the group consisting of:

(a) a nucleotide sequence encoding the mature form of a protein comprising the amino acid sequence of the bispecific single chain antibody constructs defined herein, preferably as given in SEQ ID Nos: 2, 4, 8, 10, 12, 14, 16, 18, 20, 30, 36, 39, 42, 44, 46, 48, 50, 52, 54, 56, 58 and 60;

(b) a nucleotide sequence comprising or consisting of the DNA sequence as given in SEQ ID Nos: 1, 3, 7, 9, 11, 13, 15, 17, 19, 29, 35, 38, 41, 43, 45, 47, 49, 51, 53, 55, 57 and 59;

(c) a nucleotide sequence hybridizing with the complementary strand of a nucleotide sequence as defined in (b) under stringent hybridization conditions;

(d) a nucleotide sequence encoding a protein derived from the protein encoded by a nucleotide sequence of (a) or (b) by way of substitution, deletion and/or addition of one or several amino acids of the amino acid sequence encoded by the nucleotide sequence of (a) or (b);

(e) a nucleotide sequence encoding a protein having an amino acid sequence at least 60% identical to the amino acid sequence encoded by the nucleotide sequence of (a) or (b);

(f) a nucleotide sequence which is degenerate as a result of the genetic code to a nucleotide sequence of any one of (a) to (e);

The term “mature form of the protein” defines in context with the present invention a protein translated from its corresponding mRNA and optional subsequently modified.

The term “hybridizing” has been defined in the context of the present invention herein above.

It is evident to the person skilled in the art that regulatory sequences may be added to the nucleic acid molecule comprised in the pharmaceutical composition of the invention. For example, promoters, transcriptional enhancers and/or sequences which allow for induced expression of the polynucleotide of the invention may be employed. A suitable inducible system is for example tetracycline-regulated gene expression as described, e.g., by Gossen and Bujard (Proc. Natl. Acad. Sci. USA 89 (1992), 5547-5551) and Gossen et al.

(Trends Biotech. 12 (1994), 58-62), or a dexamethasone-inducible gene expression system as described, e.g. by Crook (1989) EMBO J. 8, 513-519.

Furthermore, it is envisaged for further purposes that nucleic acid molecules may contain, for example, thioester bonds and/or nucleotide analogues. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell. In this respect, it is also to be understood that such polynucleotide can be used for "gene targeting" or "gene therapeutic" approaches. In another embodiment said nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches.

Said nucleic acid molecule(s) may be a recombinantly produced chimeric nucleic acid molecule comprising any of the aforementioned nucleic acid molecules either alone or in combination. Preferably, the nucleic acid molecule is part of a vector.

The present invention therefore also relates to a pharmaceutical composition comprising a vector comprising the nucleic acid molecule described in the present invention.

Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

Preferably said vector comprises a nucleic acid sequence which is a regulatory sequence operably linked to said nucleic acid sequence encoding a bispecific single chain antibody constructs defined herein.

Such regulatory sequences (control elements) are known to the artisan and may include a promoter, a splice cassette, translation initiation codon, translation and insertion site for introducing an insert into the vector. Preferably, said nucleic acid molecule is operatively linked to said expression control sequences allowing expression in eukaryotic or prokaryotic cells.

It is envisaged that said vector is an expression vector comprising the nucleic acid molecule encoding a bispecific single chain antibody constructs defined herein.

The term "regulatory sequence" refers to DNA sequences which are necessary to effect the expression of coding sequences to which they are ligated. The nature of such control sequences differs depending upon the host organism. In prokaryotes, control sequences generally include promoters, ribosomal binding sites, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Thus, the recited vector is preferably an expression vector. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the $P_L$, lac, trp or tac promoter in *E. coli*, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art; see also, e.g., the appended examples. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pEF-Neo, pCDM8, pRc/CMV, pcDNA1, pcDNA3 (Invitrogene), pEF-DHFR and pEF-ADA, (Raum et al. Cancer Immunol Immunother (2001) 50(3), 141-150) or pSPORT1 (GIBCO BRL).

Preferably, the expression control sequences will be eukaryotic promoter systems in vectors capable of transforming of transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the invention may follow; see, e.g., the appended examples.

An alternative expression system which could be used to express a cell cycle interacting protein is an insect system. In one such system, *Autographa californica* nuclear polyhedrosis virus (AcNPV) is used as a vector to express foreign genes in *Spodoptera frugiperda* cells or in *Trichoplusia* larvae. The coding sequence of a recited nucleic acid molecule may be cloned into a nonessential region of the virus, such as the polyhedrin gene, and placed under control of the polyhedrin promoter. Successful insertion of said coding sequence will render the polyhedrin gene inactive and produce recombinant virus lacking coat protein coat. The recombinant viruses are then used to infect *S. frugiperda* cells or *Trichoplusia* larvae in which the protein of the invention is expressed (Smith, J. Virol. 46 (1983), 584; Engelhard, Proc. Nat. Acad. Sci. USA 91 (1994), 3224-3227).

Additional regulatory elements may include transcriptional as well as translational enhancers. Advantageously, the above-described vectors of the invention comprises a selectable and/or scorable marker.

Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, P I. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule can be used alone or as part of a vector to express the encoded polypeptide in cells, for, e.g., gene therapy. The nucleic acid molecules or vectors containing the DNA sequence(s) encoding any one of the above described bispecific single chain antibody constructs is introduced into the cells which in turn produce the polypeptide of interest. Gene therapy, which is based on introducing therapeutic genes into cells by ex-vivo or in-vivo techniques is one of the most important applications of gene transfer. Suitable vectors, methods or gene-delivery systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91 (1998), 30-36; Verma, Gene Ther. 5 (1998), 692-699; Nabel, Ann. N.Y. Acad. Sci. 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. No. 5,580,859; U.S. Pat. No. 5,589,466; or Schaper, Current Opinion in Biotechnology 7 (1996), 635-640. The recited nucleic acid molecules and vectors may be designed for direct introduction or for introduction via liposomes, or viral vectors (e.g., adenoviral, retroviral) into the cell. Preferably, said cell is a germ line cell, embryonic cell, or egg cell or derived therefrom, most preferably said cell is a stem cell. An example for an embryonic stem cell can be, inter alia, a stem cell as described in, Nagy, Proc. Natl. Acad. Sci. USA 90 (1993), 8424-8428.

In accordance with the above, the present invention relates to methods to derive vectors, particularly plasmids, cosmids, viruses and bacteriophages used conventionally in genetic engineering that comprise a nucleic acid molecule encoding the polypeptide sequence of a bispecific single chain antibody constructs defined herein. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the recited polynucleotides or vector into targeted cell populations. Methods which are well known to those skilled in the art can be used to construct recombinant vectors; see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

The recited vector may be the pEF-DHFR, pEF-ADA or pEF-neo.

The vectors pEF-DHFR and pEF-ADA have been described in the art, e.g. in Mack et al. (PNAS (1995) 92, 7021-7025) and Ram et al. (Cancer Immunol Immunother (2001) 50(3), 141-150).

It is further envisaged that the pharmaceutical composition of the invention comprises a host transformed or transfected with a vector defined herein above.

Said host may be produced by introducing said at least one of the above described vector or at least one of the above described nucleic acid molecules into the host. The presence of said at least one vector or at least one nucleic acid molecule in the host may mediate the expression of a gene encoding the above described bespecific single chan antibody constructs.

The described nucleic acid molecule or vector which is introduced in the host may either integrate into the genome of the host or it may be maintained extrachromosomally.

The host can be any prokaryote or eukaryotic cell.

The term "prokaryote" is meant to include all bacteria which can be transformed or transfected with a DNA or RNA molecules for the expression of a protein of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells. Depending upon the host employed in a recombinant production procedure, the protein encoded by the polynucleotide of the present invention may be glycosylated or may be non-glycosylated. Especially preferred is the use of a plasmid or a virus containing the coding sequence of the polypeptide of the invention and genetically fused thereto an N-terminal FLAG-tag and/or C-terminal His-tag. Preferably, the length of said FLAG-tag is about 4 to 8 amino acids, most preferably 8 amino acids. An above described polynucleotide can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, loc cit.).

Preferably, said the host is a bacteria, an insect, fungal, plant or animal cell.

It is particularly envisaged that the recited host may be a mammalian cell, more preferably a human cell or human cell line.

Particularly preferred host cells comprise CHO cells, COS cells, myeloma cell lines like SP2/0 or NS/0.

The pharmaceutical composition of the invention may also comprise a proteinaceous compound capable of providing an activation signal for immune effector cells useful for cell proliferation or cell stimulation.

The proteinaceous compound is not understood as an additional domain of the above defined bispecific single chain antibody construct, but at least one additional component of the pharmaceutical composition of the invention.

In the light of the present invention, said "proteinaceous compounds" providing an activation signal for immune effector cells" may be, e.g. a further activation signal for T cells (e.g. a further costimulatory molecule: molecules of the B7-family, Ox40 L, 4.1 BBL), or a further cytokine: interleukin (e.g. IL-2), or an NKG-2D engaging compound. Preferred formats of proteinaceous compounds comprise additional bispecific antibodies and fragments or derivatives thereof, e.g. bispecific scFv. Proteinaceous compounds can comprise, but are not limited to scFv fragments specific for the T cell receptor or superantigens. Superantigens directly bind to certain subfamilies of T cell receptor variable regions in an MHC-independent manner thus mediating the primary T cell activation signal. The proteinaceous compound may also provide an activation signal for immune effector cell which is a non-T cell. Examples for immune effector cells which are non-T cells comprise, inter alia, NK cells.

An additional technical feature of the pharmaceutical composition of the invention is that said pharmaceutical composition is thermostable at ≥37° C.

An alternative embodiment of the invention relates to a process for the production of a pharmaceutical composition of the invention, said process comprising culturing a host defined herein above under conditions allowing the expression of the construct and recovering the produced bispecific single chain antibody construct from the culture.

The transformed hosts can be grown in fermentors and cultured according to techniques known in the art to achieve optimal cell growth. The polypeptide of the invention can then be isolated from the growth medium, cellular lysates, or cellular membrane fractions. The isolation and purification of the, e.g., microbially expressed polypeptides of the invention may be by any conventional means such as, for example, preparative chromatographic separations and immunological separations such as those involving the use of monoclonal or polyclonal antibodies directed, e.g., against a tag of the polypeptide of the invention or as described in the appended examples.

The conditions for the culturing of a host which allow the expression are known in the art and discussed herein above. The same holds true for procedures for the purification/recovery of said constructs.

A further alternative embodiment of the invention relates to the use of a bispecific single chain antibody construct as defined above, a nucleic acid sequence as defined above, a vector as defined above, a host as defined above and/or produced by a process as defined above for the preparation of a pharmaceutical composition for the prevention, treatment or amelioration of a tumorous disease.

In particular, the pharmaceutical composition of the present invention may be particularly useful in preventing, ameliorating and/or treating cancer.

Preferably said tumorous disease is epithelial cancer or a minimal residual cancer.

It is envisaged by the present invention that the above defined bispecific single chain antibody construct, nucleic acid molecules and vectors are administered either alone or in any combination using standard vectors and/or gene delivery systems, and optionally together with a pharmaceutically acceptable carrier or excipient. Subsequent to administration, said nucleic acid molecules or vectors may be stably integrated into the genome of the subject.

On the other hand, viral vectors may be used which are specific for certain cells or tissues and persist in said cells. Suitable pharmaceutical carriers and excipients are well known in the art. The pharmaceutical compositions prepared according to the invention can be used for the prevention or treatment or delaying the above identified diseases.

Furthermore, it is possible to use a pharmaceutical composition of the invention which comprises described nucleic acid molecules or vectors in gene therapy. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (Proc. Natl. Acad. Sci. USA 88 (1991), 2726-2729). Further methods for the delivery of nucleic acids comprise particle-mediated gene transfer as, e.g., described in Verma, Gene Ther. 15 (1998), 692-699.

Furthermore the invention relates to a method for the prevention, treatment or amelioration of a tumorous disease comprising the step of administering to a subject in the need thereof an effective amount a bispecific single chain antibody construct as defined above, a nucleic acid sequence as defined above, a vector as defined as defined above, a host as defined above and/or produced in by a process as defined above.

Preferably said subject is a human.

The method for the prevention, treatment or amelioration of the invention may comprise the co-administration of an above defined proteinaceous compound capable of an activation signal for immune effector cells to the subject. The co-administration may be a simultaneous co-administration or a non-simultaneous co-administration.

It is particularly preferred for the use and the method of the invention that said tumorous disease is epithelial cancer, preferably adenocarcinomas, or a minimal residual cancer, preferably early solid tumor, advanced solid tumor or metastatic solid tumor.

Finally, the present invention relates to a kit comprising a bispecific single chain antibody construct as defined above, a nucleic acid sequence as defined above, a vector as defined above and/or a host as defined above. It is also envisaged that the kit of this invention comprises a pharmaceutical composition as described herein above, either alone or in combination with further medicaments to be administered to a patient in need of medical treatment or intervention.

The Figures show:

FIG. 1:

DNA and amino acid sequence of the anti-CD3-anti-EpCAM constructs A) anti-CD3 VHVL stL x 3-1 VHVL (SEQ ID NO.:11,12), B) anti-CD3 VHVL aL x 4-7 VHVL (SEQ ID NO.:1,2), C) anti-CD3 VHVL aL Ser x 4-7 VHVL (SEQ ID NO.:7, 8), D) anti-CD3 VHVL stL x 4-7 VHVL (SEQ ID NO.:13,14), E) anti-CD3 VHVL stL x 4-7 VLVH (SEQ ID NO.:15,16), F) anti-CD3 VHVL aL x 5-10 VHVL (SEQ ID NO.:3,4), G) anti-CD3 VHVL aL Ser x 5-10 VHVL (SEQ ID NO.:9, 10), H) anti-CD3 VHVL stL x 5-10 VHVL (SEQ ID NO.:17,18), I) anti-CD3 VHVL stL x 5-10 VLVH (SEQ ID NO.:19,20), J) anti-CD3 VHVL aL x 3-1 VHVL (SEQ ID NO.:45, 46), K) anti-CD3 VHVL aL Ser x 3-1 VHVL (SEQ ID NO.:47,48), L) anti-CD3 VHVL aL x 3-5 VHVL (SEQ ID NO.:49,50), M) anti-CD3 VHVL aL Ser x 3-5 VHVL (SEQ ID NO.:51,52), N) anti-CD3 VHVL stL x 3-5 VHVL (SEQ ID NO.:53,54), O) anti-CD3 VHVL aL x 4-1 VHVL (SEQ ID NO.:55,56), P) anti-CD3 VHVL aL Ser x 4-1 VHVL (SEQ ID NO.:57,58) and Q) anti-CD3 VHVL stL x 4-1 VHVL (SEQ ID NO.:59,60).

FIG. 2:

FACS analysis of the constructs A) anti-CD3 VHVL stL x 5-10 VHVL (SEQ ID NO.:18), B) anti-CD3 VHVL stL x 4-7 VHVL (SEQ ID NO.:14), C) anti-CD3 VHVL aL x 5-10 VHVL (SEQ ID NO.:4), D) anti-CD3 VHVL aL x 4-7 VHVL (SEQ ID NO.:2), E) anti-CD3 VHVL aL Ser x 5-10 VHVL (SEQ ID NO.:10), F) anti-CD3 VHVL aL Ser x 4-7 VHVL (SEQ ID NO.:8), G) anti-CD3 VHVL stL x 3-1 VHVL (SEQ ID NO.:12), H) anti-CD3 VHVL stL x 5-10 VLVH (SEQ ID NO.:20) and I) anti-CD3 VHVL stL x 4-7 VLVH (SEQ ID NO.:16) in CD3 positive Jurkat and EpCAM-positive Kato III cells. A shift to the right shows binding. In Jurkat and KatoIII cells the dotted line indicates the shift of the negative control (only secondary antibody), dashed line shows the binding of an anti-EpCAM-anti-CD3 control antibody and the bold line shows the bispecific construct of interest.

FIG. 3:

DNA and amino acid sequence of the anti-EpCAM-anti-CD3-constructs A) 4-7 VLVHx anti-CD3 VHVL (SEQ ID NO.:41,42), B) 3-5 VLVHx anti-CD3 VHVL (SEQ ID NO.: 29,30), C) 3-1 VLVHx anti-CD3 VHVL (SEQ ID NO.:35, 36), D) 4-1 VLVHx anti-CD3 VHVL (SEQ ID NO.:38,39) and E) 5-10 VLVHx anti-CD3 VHVL (SEQ ID NO.:43,44).

FIG. 4: FACS analysis of the constructs A) 4-7 VLVHx anti-CD3 VHVL (SEQ ID NO.:42), B) 3-5 VLVHx anti-CD3 VHVL (SEQ ID NO.:30), C) 3-1 VLVHx anti-CD3 VHVL (SEQ ID NO.:36), D) 4-1 VLVHx anti-CD3 VHVL (SEQ ID NO.:39) and E) 5-10 VLVHx anti-CD3 VHVL (SEQ ID NO.: 44) constructs in CD3 positive Jurkat and EpCAM-positive Kato III cells. A shift to the right shows binding.

FIG. 5:

A representative elution pattern of an EpCAM bispecific antibody containing protein fractions from a Zn-Chelating Fractogel® column at 280 nm. High adsorption at 280 nm from 50-450 ml retention time was due to non-bound protein in the column flow through. The arrow at the peak at 530.09 ml indicates the EpCAM bispecific construct containing protein fraction that was used or further purification.

FIG. 6:

A representative protein elution pattern from a Sephadex® S200 gelfiltration column at 280 nm. The protein peak at 82.66 ml containing bispecific antibodies against CD3 and EpCAM corresponds to a molecular weight of ca. 52 kD. Fractions were collected from 40-140 ml retention time.

FIG. 7

A) Cation exchange chromatogram of 3-1 x anti-CD3 (SEQ ID NO.:36) shows the overall charge isoforms of the protein. Cation exchange chromatography was performed on a MiniS® (Amersham) column. After washing with 20 mM MES buffer pH 5.5, the protein was eluted with a gradient of elution buffer containing 1 M NaCl: 0-30% in 60 column volumes. The bispecific construct was eluted at 23.58 ml. Unspecific protein was eluted with 1 M NaCl starting at 50 ml.

B) Cation exchange chromatogram of 5-10 x anti-CD3 (SEQ ID NO.:44) shows the overall charge isoforms of the protein. Cation exchange chromatography was performed as in FIG. 7A. The bispecific construct was eluted at a shoulder at 35.77 ml. Unspecific protein was eluted with 1 M NaCl starting at 50 ml.

FIG. 8:

A) Representative SDS-PAGE analysis of EpCAM bispecific single chain antibody protein fractions. Lane M: Molecular weight marker Lane 1: cell culture supernatant; lane 2: IMAC flow through; lane 3: IMAC wash; lane 4: IMAC eluate; lane 5: purified antibody against EpCAM and CD3 obtained from gel filtration.

B) Representative Western blot analysis of purified EpCAM bispecific single chain antibody protein fractions Lane 1: cell culture supernatant; lane 2: IMAC flow through; lane 3: IMAC wash; lane 4: IMAC eluate; lane 5: purified antibody against EpCAM and CD3 obtained from gel filtration.

FIG. 9:

Cytotoxicity assay of C-terminal EpCAM binders anti-CD3×3-1 (SEQ ID NO.:46), anti-CD3 x-5-10 (SEQ ID NO.: 4), and anti-CD3×4-7 (SEQ ID NO.:2). CB15 T cell clone and CHO-EpCAM cells were used in an E:T ratio of 5:1. CHO-EpCAM cells were stained with PKH26 dye and the cells were counted after bispecific single chain antibody incubation with FACS analysis.

FIG. 10:

Cytotoxicity assay of N-terminal EpCAM binders 3-1xanti-CD3 (SEQ ID NO.:36), and 5-10xanti-CD3 (SEQ ID NO.:44). CB15 T cell clone and CHO-EpCAM cells were used in an E:T ration of 5:1. CHO-EpCAM cells were stained with PKH26 dye and the cells were counted after bispecific single chain antibody incubation with FACS analysis.

FIG. 11:

A) Sequence alignment of the CDR3 of the VH chains of EpCAM 3-1 (SEQ ID NO.: 80), EpCAM 4-1 (SEQ ID NO.: 88), EpCAM 5-10 (SEQ ID NO.: 96), EpCAM 3-5 (SEQ ID NO.: 84), EpCAM 4-7 (SEQ ID NO.:92), compared with CDR3 of the VH chain of EpCAM M79, HD70 and 3B10. The NXD motif is depicted as bold.

B) Comparison of the cytotoxic activity of 3-1xanti-CD3 (SEQ ID NO.: 36), 5-10xanti-CD3 (SEQ ID NO.:44), anti-CD3×4-7 (SEQ ID NO.:2) and anti-CD3×5-10 (SEQ ID NO.: 18) with M79Xanti-CD3 and HD70xanti-CD3 controls. PBMC cells and Kato III cells were used in a E:T ratio of 10:1. KatoIII cells were stained with propidium iodide and the cells were counted after bispecific single chain antibody incubation with FACS analysis.

The invention will now be described by reference to the following biological examples which are merely illustrative and are not to be construed as a limitation of scope of the present invention.

EXAMPLE 1

Cloning and Expression of the EpCAM Constructs

A number of constructs comprising anti-CD3 and anti-EpCAM in various structures) and domain arrangements were generated. Anti-EpCAM VH and VL variable domains of the antibodies 3-1 are shown in SEQ ID NO.:79, 80, 81, 82, 3-5 in SEQ ID NO.:83, 84, 85, 86, 4-1 in SEQ ID NO.:87, 88, 89, 90, 4-7 SEQ ID NO.:91, 92, 93, 94 and 5-10 in SEQ ID NO.:95, 96, 97, 98. The constructs are summarized in Table 1.

TABLE 1 anti-CD3-anti-EpCAM and anti-EpCAM-anti-CD3 constructs

| SEQ ID NO.: Construct No. | Construct | Domain arrangement | Distinctive feature |
|---|---|---|---|
| anti-CD3xanti-EpCAM constructs | | | |
| SEQ ID NO.: 1, 2 | anti-CD3x4-7 | VH-VLXVH-VL | |
| SEQ ID NO.: 3, 4 | anti-CD3x5-10 | VH-VLXVH-VL | |
| SEQ ID NO.: 45, 46 | anti-CD3x3-1 | VH-VLXVH-VL | |
| SEQ ID NO.: 49, 50 | anti-CD3x3-5 | VH-VLXVH-VL | |
| SEQ ID NO.: 55, 56 | anti-CD3x4-1 | VH-VLXVH-VL | |
| SEQ ID NO.: 7, 8 | anti-CD3x 4-7Cys-Ser | VH-VLXVH-VL | Cys-Ser mutation |
| SEQ ID NO.: 9, 10 | anti-CD3x 5-10Cys-Ser | VH-VLXVH-VL | Cys-Ser mutation |
| SEQ ID NO.: 47, 48 | anti-CD3x3-1 | VH-VLXVH-VL | Cys-Ser mutation |
| SEQ ID NO.: 51, 52 | anti-CD3x3-5 | VH-VLXVH-VL | Cys-Ser mutation |
| SEQ ID NO.: 57, 58 | anti-CD3x4-1 | VH-VLXVH-VL | Cys-Ser mutation |
| SEQ ID NO.: 11, 12 | anti-CD3x3-1 | VH-VLXVH-VL | $(G_4S)_3$ -linker |
| SEQ ID NO.: 13, 14 | anti-CD3x4-7 | VH-VLXVH-VL | $(G_4S)_3$ -linker |
| SEQ ID NO.: 15, 16 | anti-CD3x4-7 | VH-VLXVL-VH | $(G_4S)_3$ -linker |
| SEQ ID NO.: 17, 18 1 | anti-CD3x5-10 | VH-VLXVH-VL | $(G_4S)_3$ -linker |
| SEQ ID NO.: 19, 20 | anti-CD3x5-10 | VH-VLXVL-VH | $(G_4S)_3$ -linker |
| SEQ ID NO.: 53, 54 | anti-CD3x3-5 | VH-VLXVH-VL | $(G_4S)_3$ -linker |
| SEQ ID NO.: 59, 60 | anti-CD3x4-1 | VH-VLXVH-VL | $(G_4S)_3$ -linker |
| anti-EpCAM- anti-CD3 constructs | | | |
| SEQ ID NO.: 29, 30 | 3-5xanti-CD3 | VL-VHxVH-VL | |
| SEQ ID NO.: 35, 36 | 3-1xanti-CD3 | VL-VHxVH-VL | |
| SEQ ID NO.: 38, 39 | 4-1xanti-CD3 | VL-VHxVH-VL | |
| SEQ ID NO.: 41, 42 | 4-7xanti-CD3 | VL-VHxVH-VL | |
| SEQ ID NO.: 43, 44 | 5-10xanti-CD3 | VL-VHxVH-VL | |

1.1 Cloning of C-Terminal EpCAM-Binders 1.1.1 Preparation of Anti-CD3 PCR Products a) Anti-CD3 Constructs with Original 18 Amino Acid Linker (SEQ ID NOs.:1, 2, 3 and 4)

The N-terminal original anti-CD3 containing the 18 amino acid linker (SEQ ID NO.:70) was obtained by PCR using the CD19xCD3 construct (Löffler A et al., Blood 2000 95:2098-103) as template and the following primers (CD3 VH BsrGI: AGGTGTACACTCCGATATCAAACTGCAGCAG (SEQ ID NO.:5), CD3 VL BspEI: AATCCGGATTTCAGCTCCAGCTTGG (SEQ ID NO.:6)).

b) Anti-CD3 Constructs with Original 18 Amino Acid Linker and Cys to Ser Mutation in CDRH3 (SEQ ID Nos. 7,8, 9 and 10)

The N-terminal original anti-CD3 containing the 18 amino acid linker (Seq ID NO.:70) and the Cys to Ser mutation was obtained by PCR using a CD19xanti-CD3 (C→S mutation) construct as template and the primers CD3 VH BsrGI and CD3 VL BspEI (Seq ID Nos. 5 and 6). The CDRH3 sequence with the Cys-Ser mutation is shown in SEQ ID NO.:78.

c) Anti-CD3-Anti-EpCAM Constructs with (G4S)3 Linker (Seq ID Nos. 11, 12, 13, 14, 15, 16, 17, 18, 19 and 20)

The N-terminal anti-CD3 containing the 15 amino acid standard $(G_4S)_3$ linker, (SEQ ID NO.:99) was obtained by PCR using the CD19xCD3 (Löffler A et al., Blood 2000 95:2098-103) as template. The anti-CD3 VH region and the anti-CD3 VL region were separately amplified by the following primers (CD3 VH: CD3 VH BsrG1 AGGTGTACACTCCGATATCAAACTGCAGCAG (SEQ ID NO.:5), 3"CD3 VH GS15 GGAGCCGCCGCCGCCAGAACCACCACCACCTGAGGAGACTGTGAGAGTGGTGCCTTG (SEQ ID NO.:21); CD3 VL: 5"CD3 VL GS15 GGCGGCGGCGGCTCCGGTGGTGGTGGTTCTGACATTCAGCTGACCCAGTCTCC (SEQ ID NO.:22), CD3 VL BspEI AATCCGGATTTCAGCTCCAGCTTGG (SEQ ID NO.:6)). Overlapping complementary sequences introduced into the PCR products were used to form the coding sequence of a 15-amino acid $(G_4S)_3$ (single-letter amino acid code) (SEQ ID NO.:99) linker during the subsequent fusion PCR. This amplification step was performed with the primer pair CD3 VH BsrGI (SEQ ID NO.:5) and CD3 VL BspEI (SEQ ID NO.:6).

1.1.2 Cloning of the Anti-CD3xanti EpCAM Constructs in $VH_{anti\text{-}CD3}$-$VL_{anti\text{-}CD3}$ x $VH_{anti\text{-}EpCAM}$-$VL_{anti\text{-}EpCAM}$ Orientation (SEQ ID NO.:1,2, SEQ ID NO.:3,4, SEQ ID NO.:7,8, SEQ ID NO.:9,10, SEQ ID NO.:11,12, SEQ ID NO.:13,14 and SEQ ID NO.:17,18)

The N-terminal original anti-CD3 containing the 18 amino acid linker (SEQ ID NO.:70) or the N-terminal original anti-CD3 containing the 15 amino acid standard $(G_4S)_3$ linker (SEQ ID NO.:99) was cleaved with the restriction enzymes BsrGI and BspEI and subsequently cloned into the bluescript KS vector (Stratagene, La Jolla, Calif.), containing the amino acid sequence of an eukaryotic secretory signal (leader peptide) as a EcoRI/BsrGI-Fragment. After cleavage of this construct with EcoRI and BspEI the resulting DNA fragment comprising the respective anti-CD3 scFv with the leader peptide was cloned into a EcoRI/BspEI cleaved plasmid containing the c-terminal EpCAM binders 3-1 (SEQ ID NO.:79-82), 4-7 (SEQ ID NO.:91-94), or 5-10 (SEQ ID NO.:95-98) in pEFDHFR. pEFDHFR was described in Mack et al. Proc. Natl. Acad. Sci. USA 92 (1995) 7021-7025).

1.1.3. Cloning of the Anti-CD3xanti EpCAM Constructs in $VH_{anti\text{-}CD3}$-$VL_{anti\text{-}CD3}$ x $VL_{anti\text{-}EpCAM}$-$VH_{anti\text{-}EpCAM}$ Orientation (SEQ ID Nos.: 15, 16, 19 and 20)

The C-terminal anti-EpCAM antibody 4-7 (SEQ ID NO.: 91-94) in VLVH orientation containing the 15 amino acid standard linker (SEQ ID NO.:99) was obtained by PCR. The 4-7 VH region and the 4-7 VL region were separately amplified by the following primers (4-7 VL: 4-7. VL BspEI FOR CTGAAATCCGGAGGTGGTGGATCCGAGCTCGTGATGACCCAGACTCC (SEQ ID NO.:100), 4-7 VL GS15 REV GGAGCCGCCGCCGCCAGAACCACCACCACCTTTGATCTCAAGCTTGGTCCCC (SEQ ID NO.:101); 4-7 VH: 4-7 VH GS15 FOR GGCGGCGGCGGCTCCGGTGGTGGTGGTTCTGAGGTGCAGCTGCTCGAGCAG (SEQ ID NO.:23), 4-7 VH SalI REV TTTTAAGTCGACCTAATGATGATGATGATGATGTGAGGAGACGGTGACCGTGG (SEQ ID NO.:24)). Overlapping complementary sequences introduced into the PCR products were used to form the coding sequence of a 15-amino acid $(G_4S)_3$ (single-letter amino acid code) linker (SEQ ID NO.:99) during the subsequent fusion PCR. This amplification step was performed with the primer pair 4-7 VL BspEI FOR and 4-7 VH SalI REV (SEQ ID NO.100, SEQ ID NO.:24).

The C-terminal anti-EpCAM antibody 5-10 (SEQ ID NO.: 95-98) in VLVH orientation containing the 15 amino acid standard linker (SEQ ID NO.:99) was obtained by PCR. The 5-10 VH region and the 5-10 VL region were separately amplified by the following primers (5-10 VL: 5-10 VL BspEI FOR CTGAAATCCGGAGGTGGTGGATC-CGAGCTCGTGATGACACAGTCTCCAT (SEQ ID NO.:25), 5-10 VL GS15 REV GGAGCCGCCGCCGCCA-GAACCACCACCACCTTTGATCTCAAGCT-TGGTCCCAG (SEQ ID NO.: 26); 5-10 VH: 5-10 VH GS15 FOR GGCGGCGGCGGCTCCGGTGGTGGTGGT-TCTGAGGTGCAGCTGCTCGAGC (SEQ ID NO.:27), 5-10 VH SalI REV TTTTAAGTCGACCTAATGATGAT-GATGATGATGTGAGGAGACGGTGACCGTGG (SEQ ID NO.:28)). Overlapping complementary sequences introduced into the PCR products were used to form the coding sequence of a 15-amino acid $(G_4S)_3$ linker (SEQ ID NO.:99) during the subsequent fusion PCR. This amplification step was performed with the primer pair 5-10 VL BspEI FOR and 5-10 VH SalI REV (SEQ ID NO.:25, SEQ ID NO:28).

These PCR products (5-10 VLVH and 4-7 VLVH) were cleaved with BspEI and Sa/I and ligated in the BspEI/SalI cleaved anti-CD3 VHVL stLx5-10 VHVL (SEQ ID NO.:17, 18) or anti-CD3 VHVL stL x 4-7 (SEQ ID NO.:13, 14) VHVL in pEFDHFR replacing the 5-10 VHVL DNA fragment.

1.1.4. Expression and Binding of the Anti-CD3-EpCAM Constructs

After confirmation of the sequence coding for the bispecific single chain by sequencing the plasmid was transfected into DHFR deficient CHO cells for eukaryotic expression. Eukaryotic protein expression in DHFR deficient CHO cells was performed as described in Kaufmann R. J. (1990) Methods Enzymol. 185, 537-566). The transfected cells were then expanded and 1 liter of supernatant produced. Expression and binding of the bispecific single chain molecules were confirmed by FACS analyses. For that purpose the EpCAM positive human gastric cancer cell line Kato III (obtained from American Type Culture Collection (ATCC) Manassas, Va. 20108 USA, ATCC number: HTB-103) was used. Binding of the anti-CD3 part was demonstrated on Jurkat cells (ATCC TIB 152).

Cells were cultured according to the recommendations of the supplier and ca. 200000 cells were incubated with 10 μg/ml of the construct in 50 μl PBS with 2% FCS. The binding of the construct was detected with an anti-His antibody (Penta-His Antibody, BSA free, obtained from Quiagen GmbH, Hilden, FRG) at 2 μg/ml in 50 μl PBS with 2% FCS. As a second step reagent a R-Phycoerythrin-conjugated affinity purified $F(ab')_2$ fragment, goat anti-mouse IgG, Fc-gamma fragment specific antibody, diluted 1:100 in 50 μl PBS with 2% FCS (obtained from Dianova, Hamburg, FRG) was used. The samples were measured on a FACSscan (BD biosciences, Heidelberg, FRG). All the constructs comprising anti-CD3 and anti-EpCAM showed stronger binding affinity to CD3 and to EpCAM than the prior art anti-EpCAM (M79) xanti-CD3 bispecific antibody (FIG. 2).

1.2 N-Terminal EpCAM Binders 1.2.1 Cloning of the Anti-EpCAMxanti-CD3 Constructs Cloning of the Construct 3-5xanti-CD3 (SEQ ID NOs.29, 30):

The C-terminal 3-5 in VH-VL orientation was obtained by PCR for the construction of 3-5 xanti-CD3 (SEQ ID NO.:29) molecule. Fragments I and II were amplified by PCR using primer pairs me 81 (SEQ ID NO.:31)/me 90 (SEQ ID NO.:34) and me 83 (SEQ ID NO.:32)/me 84 (SEQ ID NO.:33), respectively. Hot Start PCR was done using the Expand High Fidelity System of Roche Diagnostics. 20 cycles (94° C./30 sec; 60° C./1 min; 72° C./1 min) were used for amplification followed by one cycle of 3 min at 72° C.

PCR fragments I and II were subjected to electrophoresis on a 1.5% agarose gel. Fragments were mixed (1 ng of each) and used as a template for the next PCR reaction performed with primer pair me 81 (SEQ ID NO.:31) and me 84 (SEQ ID NO:33) for amplification of fragment III. PCR was performed as described above. Fragment III was purified on an agarose gel and digested with BssHII and BspEI (Biolabs), purified and subsequently cloned into the corresponding sites of the pEF-dHFR-signal peptide (77/78)-anti-CD3 cloning vector, which facilitates cloning of anti-target variable regions in front of the anti-CD3 region. The vector has a unique BssHII site just after the signal peptide followed by BspEI site, linker $(G_4S)$ and anti-CD3 region. The cloned region was verified by restriction digests and by DNA-sequencing.

Sequences of the Primers Used:

```
Me 81:
                                        (SEQ ID NO.: 31)
5'-GGA TGC GCG CGA GCT CGT GAT GAC CCA GAC TCCA
CTC TCC-3'

Me 83:
                                        (SEQ ID NO.: 32)
5'-GGT TCT GGC GGC GGC GGC TCC GGT GGT GGT GGT
TCT GAG GTG CAG CTG CTC GA CAG TCT G-3'

Me 84:
                                        (SEQ ID NO.: 33)
5'-GTG CTC CGG AGG AGA CGG TGA CCG TGG TCC CTT
GGC CCC AG-3'

Me 90:
                                        (SEQ ID NO.: 34)
5'-CCG GAG CCG CCG CCG CCA GAA CCA CCA CCA CCT
TTG ATC TCA AGC TTG GTC CC-3'
```

Cloning of the Construct 3-1xanti-CD3 (SEQ ID NO.:35, 36),

The C-terminal 3-1 in VH-VL orientation was obtained by PCR for the construction of 3-1 xanti-CD3 (SEQ ID NO.:35) molecule. Fragments I and II were amplified by PCR using primer pairs me 91a (SEQ ID NO.:37)/me 90 (SEQ ID NO.: 34) and me 83 (SEQ ID NO.:32)/me 84 (SEQ ID NO.:33), respectively. PCR was performed as above.

Agarose gel fragments comprising PCR fragments I and II were used as a template for the next PCR reaction performed with primer pair me 91a (SEQ ID NO.:37) and me 84 (SEQ ID NO.:33) for amplification of fragment III. PCR was performed as described above except, annealing was performed at 68° C. instead of at 60° C. Fragment III was purified on an agarose gel and digested with BsrGI and BspEI (Biolabs), purified and subsequently cloned into the corresponding sites of the pEF-dHFR-M79 X anti-CD3 cloning vector. The cloned region was verified by restriction digests and by DNA-sequencing.

```
Me 91a:
                                        (SEQ ID NO.: 37)
5'-GGA TTG TAC A CTCC GA GCT CGT CAT GAC CCA GTC

TCC ATC TTA TCT TGC TGC-3'
```

Cloning of the Construct 4-1 xanti-CD3 (SEQ ID NO.:38, 39):

The C-terminal 4-1 in VH-VL orientation was obtained by PCR for the construction of 4-1 xanti-CD3 (SEQ ID NO.:38, 39) molecule. Fragments I and II were amplified by PCR using primer pairs me 92a (SEQ ID NO.:40)/me 90 (SEQ ID NO.:34) and me 83 (SEQ ID NO.:32)/me 84 (SEQ ID NO.: 33), respectively. PCR was performed as above in annealing temperature of 60° C.

Agarose gel fragments comprising PCR fragments I and II were used as a template for the next PCR reaction performed with primer pair me 92a (SEQ ID NO.:40) and me 84 (SEQ ID NO.:33) for amplification of fragment III. PCR was performed as described above except, annealing was performed at 68° C. instead of at 60° C. Fragment III was purified on an agarose gel and digested with BsrGI and BspEI (Biolabs), purified and subsequently cloned into the corresponding sites of the pEF-dHFR-M79 X anti-CD3 is cloning vector. The cloned region was verified by restriction digests and by DNA-sequencing.

```
Me 92a:
                                   (SEQ ID NO.: 40)
5'-GGA TTG TAC A CTCC GA GCT CGT GAT GAC ACA

GTCTCC ATC CTC C-3'
```

Cloning of the Construct 4-7xanti-CD3 (SEQ ID NO.:41,42)

The C-terminal 4-7 in VH-VL orientation was obtained by PCR for the construction of 4-7 xanti-CD3 (SEQ ID NO.:41, 42) molecule. Fragments I and II were amplified by PCR using primer pairs me 81 (SEQ ID NO.:31)/me 90 (SEQ ID NO.:34) and me 83 (SEQ ID NO.:32)/me 84 SEQ ID NO.: 33), respectively. PCR was performed as above with an annealing temperature of 60° C.

Agarose gel fragments comprising PCR fragments I and II were used as a template for the next PCR reaction performed with primer pair me 81 (SEQ ID NO.:31) and me 84 (SEQ ID NO.:33) for amplification of fragment III. PCR was performed as described above. Fragment III was purified on an agarose gel and digested with BssHII and BspEI (Biolabs), purified and subsequently cloned into the corresponding sites of the pEF-dhfr-signal peptide (77/78)-anti-CD3 cloning vector. The cloned region was verified by restriction digests and by DNA-sequencing.

Cloning of the Construct 5-10xanti-CD3 (SEQ ID NO.:43, 44)

The C-terminal 5-10 in VH-VL orientation was obtained by PCR for the construction of 5-10xanti-CD3 (SEQ ID NO.: 43, 44) molecule. Fragments I and II were amplified by PCR using primer pairs me 92a (SEQ ID NO.:40)/me 90 (SEQ ID NO.:34) and me 83 (SEQ ID NO.:32)/me 84 (SEQ ID NO.: 33), respectively. PCR was performed as above with an annealing temperature of 60° C.

Agarose gel fragments comprising PCR fragments I and II were used as a template for PCR with primer pair me 92a (SEQ ID NO.:40) and me 84 (SEQ ID NO.:33) for amplification of fragment III. PCR was performed as described above except, annealing was performed at 68° C. instead of at 60° C. Fragment III was purified on an agarose gel and digested with BsrGI and BspEI (Biolabs), purified and subsequently cloned into the corresponding sites of the pEF-dhfr-M79 X anti-CD3 cloning vector. The cloned region was verified by restriction digests and by DNA-sequencing.

1.2.2 Expression of Anti-EpCAMxanti-CD3 Bispecific Molecules

CHO-cells lacking DHFR gene were maintained in alpha MEM medium (Life Technologies, cat. no: 32561) supplemented with 10% fetal Calf Serum (Life Technologies, heat inactivated at 65° C. for 30 minutes) and with HT (Hypoxanthin and Thymidine; Life Technologies, cat. no: 41065-012). The cells were transfected with pEF-dHFR-3-1xanti-CD3 (SEQ ID NO.:35, 36), pEF-dHFR-3-5xanti-CD3 (SEQ ID NO.:29, 30), pEF-dHFR-4-1xanti-CD3 (SEQ ID NO.:38, 39), pEF-dHFR-4-7xanti-CD3 (SEQ ID NO.:41, 42) and pEF-dHFR-5-10xanti-CD3 (SEQ ID NO.:43, 44) using Lipofectamine 2000 kit (Invitrogen; cat. no:11668-019) according to the instructions provided by the Manufacturer. After 48 hrs, the cells were subjected to selection by transferring the transfected cells into the selection medium (alpha MEM medium (cat. no:32561) containing heat inactivated 10% dialysed fetal Calf Serum (Life Technologies). After 2-3 weeks of selection, the cells were grown for 8 to 9 days (in 500 ml of selection medium) for production of bispecific molecules in 2 liter Tissue culture Roller Bottles (Falcon (cat. no: 353068; Becton Dickinson Labware). The tissue culture medium was centrifuged at 4° C. for 10 minutes at 300 g (1300 rpm) to remove the cells and cell debris. The supernatant containing the secreated bispecific molecules was stored at −20° C. until further analysis.

1.2.3 Binding Assays of Bispecific Anti EpCAMxanti CD3 Variants

In order to analyze the binding strength of the bispecific anti-EpCAMxanti-CD3 single chain constructs of the invention, the following binding assay was carried out.

250000 Jurkat cells (for CD3 binding) and Kato cells (for EpCAM binding) were independently incubated with crude supernatants (50 μl) containing bispecific construct for 45 min. at 4° C. Thereafter, the cells were washed twice in FACS buffer (phosphate-buffered saline containing 1% fetal calf serum (FCS) and 0.05% sodium azide) and incubated with mouse anti-His antibody (Dianova, DIA910) for 60 min. at 4° C. Washing steps were performed as above.

The cells were finally incubated either with goat anti-mouse-FITC-conjugated antibody (BD 550003) or with anti-mouse-PE conjugated antibody (IgG) (Sigma, P8547). After washing steps, 10,000 events were analysed using FACS Calibur (B&D). All the EpCAM constructs showed strong binding (FIG. 4).

EXAMPLE 2

Purification of the EpCAM Constructs

In order to purify the bispecific single chain constructs comprising anti-EpCAM and anti-CD3 the CHO-EpCAM cells were grown in roller bottles with HiClone® CHO modified DMEM medium (HiQ) for 7 days before harvest. The cells were removed by centrifugation and the supernatant containing the expressed protein was stored at −20° C.

Äkta FPLC System® (Pharmacia) and Unicorn Software® were used for chromatography. All chemicals were of research grade and purchased from Sigma (Deisenhofen) or Merck (Darmstadt).

IMAC was performed, using a Fractogel® column (Pharmacia) that was loaded with $ZnCl_2$ according to the manufacturers protocol. The column was equilibrated with buffer A2 (20 mM NaPP pH 7.5, 0.4 M NaCl) and the cell culture supernatant (500 ml) was applied to the column (10 ml) with a flow rate of 3 ml/min. The column was washed with buffer A2 to remove unbound sample. Bound protein was eluted using a 2-step gradient of buffer B2 (20 mM NaPP pH 7.5, 0.4 M NaCl, 0.5 M Imidazol). In Step 1 20% buffer B2 in 10 column volumes was used and in Step 2 100% buffer B2 in 10 column volumes was used. Eluted protein fractions from the 100% step were pooled for further purification.

Gel filtration chromatography was performed on a Sephadex S200 HiPrep® column (Pharmacia) equilibrated with PBS (Gibco). Eluted protein samples (flow rate 1 ml/min) were subjected to SDS-Page and Western Blot for detection.

The column was previously calibrated for molecular weight determination (molecular weight marker kit, Sigma MW GF-200).

Protein concentrations were determined using protein assay dye (MicroBCA, Pierce) and IgG (Biorad) as standard protein. The yields of the protein are shown in Table 2. All constructs were producible.

TABLE 2

Yields of the single-chain bispecific constructs comprising anti-EpCAM and anti-CD3

| Construct | Yield [μg purified protein per liter culture] |
|---|---|
| 4-1 x anti-CD3 (SEQ ID NO.: 39) | 172.5 |
| 3-5 x anti-CD3 (SEQ ID NO.: 30) | 265 |
| 4-7 x anti-CD3 (SEQ ID NO.: 42) | 37 |
| anti-CD3 x 4-7. (SEQ ID NO.: 2) | 112.5 |
| anti-CD3 Cys-Ser x 4-7 (SEQ ID NO.: 8) | 140 |
| 3-1 x anti-CD3 (SEQ ID NO.: 36) | 265 |
| 5-10 x anti-CD3 (SEQ ID NO.: 44) | 400 |
| anti-CD3 x 5-10 (SEQ ID NO.: 4) | 195 |

Figure 7A:
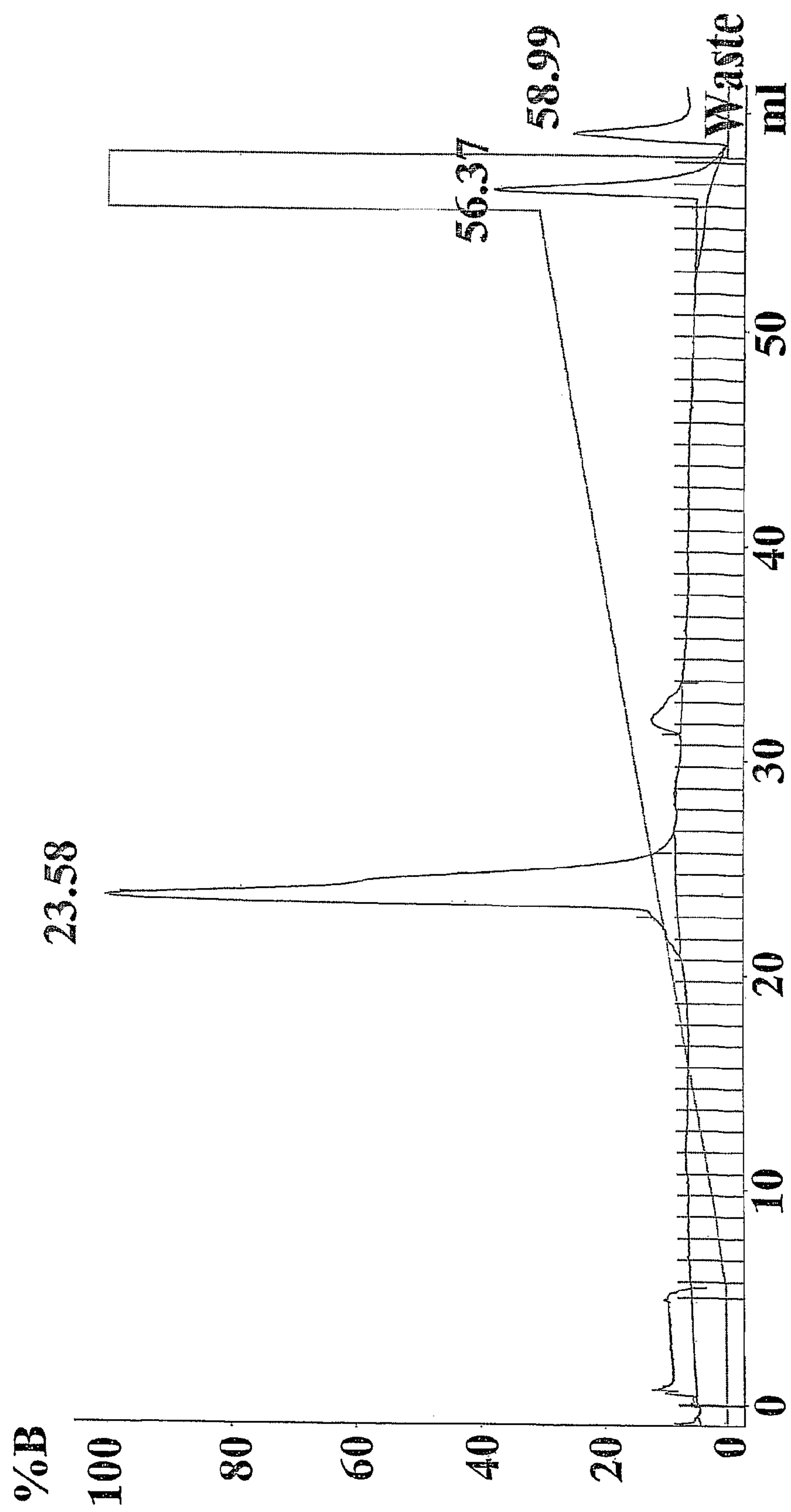
Figure 7B:
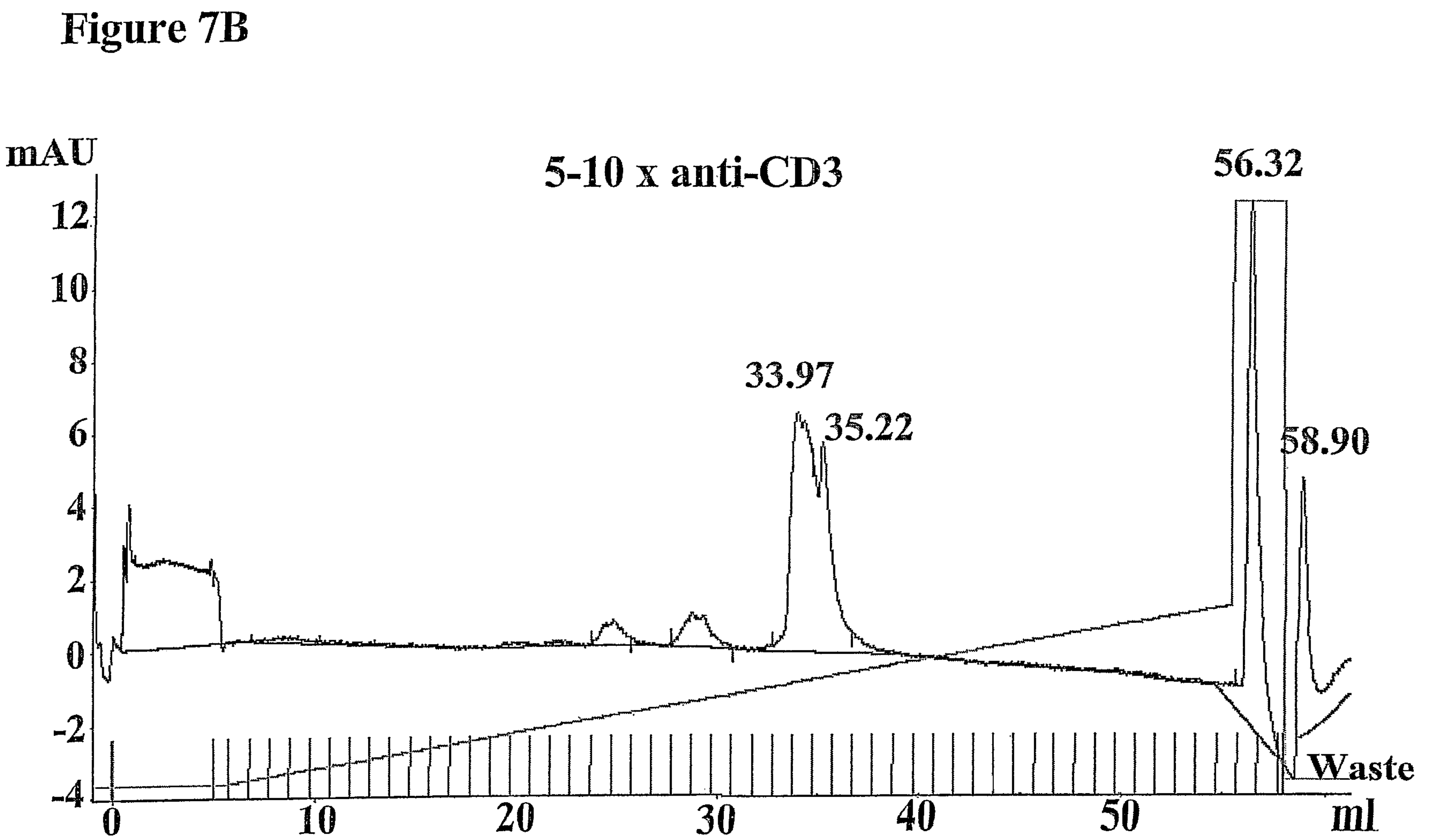

A further high resolution cation exchange chromatography was performed on a MiniS® column (Amersham), equilibrated with 20 mM MES buffer pH 5.5. The sample was diluted 1:3 with the same buffer before loading to the column. Bound protein was eluted with a gradient of equilibration buffer containing 1M NaCl: 0-30% in 60 column volumes. Remaining protein was eluted in 3 column volumes of 1M NaCl (FIG. 7).

Figure 6:
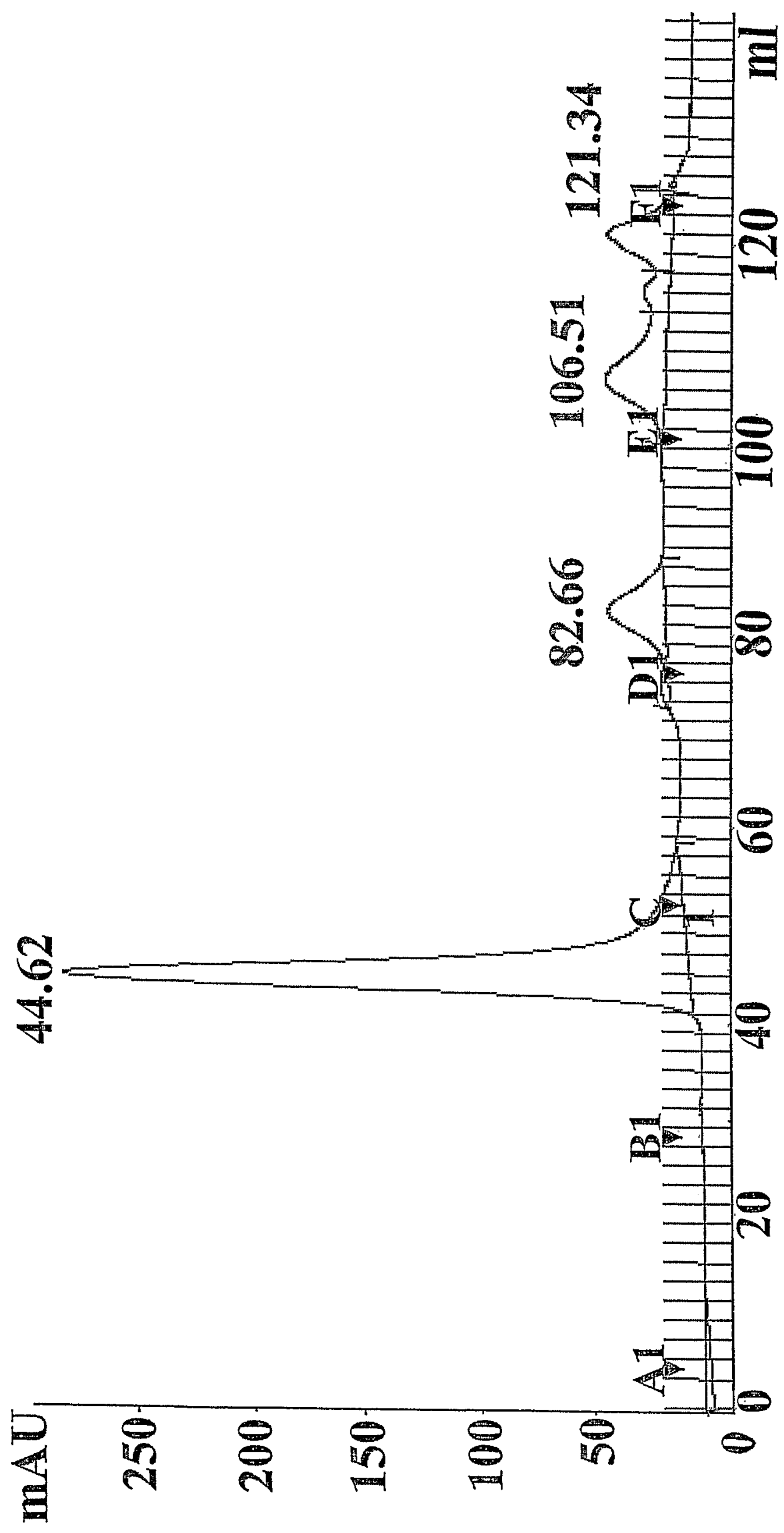

The EpCAM bispecific single chain construct proteins were isolated in a two-step purification process including immobilized metal affinity chromatography (IMAC) (FIG. 5) and gel filtration (FIG. 6). The main product had a molecular weight of 52 kDa under native conditions as determined by gelfiltration in PBS.

Purified bispecific protein was analyzed in SDS PAGE under reducing conditions performed with precast 4-12% Bis Tris gels (Invitrogen). Sample preparation and application were according to the manufacturers protocol. The molecular weight was determined with MultiMark® protein standard (Invitrogen). The gel was stained with colloidal Coomassie (Invitrogen protocol). The purity of the isolated protein was shown to be >95% (FIG. 8A). Western Blot was performed with an Optitran BA-S83® membrane and the Invitrogen Blot Module according to the manufacturers protocol. The antibodies used were Penta H is (Qiagen) and Goat-anti-Mouse-Ig labeled with alkaline phosphatase (AP) (Sigma), the chromogenic substrate solution was BCIP/NBT liquid (Sigma). The EpCAM bispecific protein could be specifically detected by Western Blot (FIG. 8B). The main signal corresponds to the main band in the SDS PAGE at 52 kD corresponding to the purified bispecific molecule.

EXAMPLE 3

Cytotoxicity Assays of the Constructs Comprising Anti-CD3 and Anti-EpCAM

In order to test the bioactivity of the constructs comprising anti-EpCAM and anti-CD3 a FACS based cytotoxicity test was performed.

For the cytotoxicity test, CHO cells from the American Type Cell Culture Collection (ATCC, Manassas, USA) were transfected with epithelial cell adhesion molecule (EpCAM). A cell clone derived from this transfection, referred to as CHO-EpCAM cells, was used for the experiments. CHO-EpCAM ($1.5\times10^7$) cells were washed free of serum two times with PBS and incubated with PKH26 dye (Sigma-Aldrich Co.) according to the manufacturers instructions. After staining cells were washed two times with RPMI/10% FCS.

Cells were counted and mixed with CB15 effector cells. The CD4-positive T cell clone CB15 was provided by Dr. Fickenscher, University of Erlangen/Nuernberg, Germany. Cells were cultured as recommended by the suppliers. The resulting cell suspension contained 400.000 target and $2\times10^6$ effector cells per ml. 50 μl of the mixture was used per well in a 96 well round bottom plate.

Figure 9:
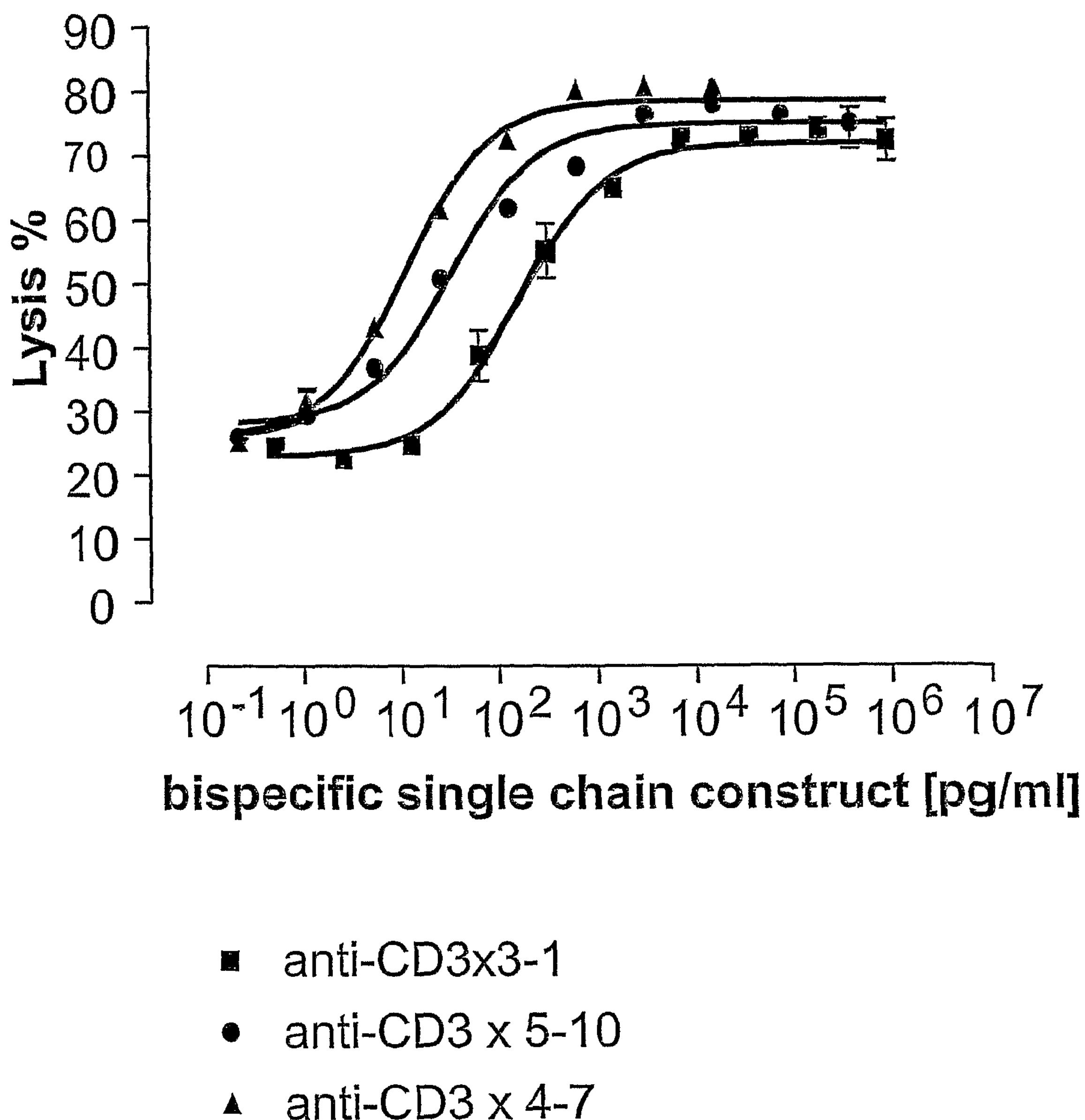
Figure 10:
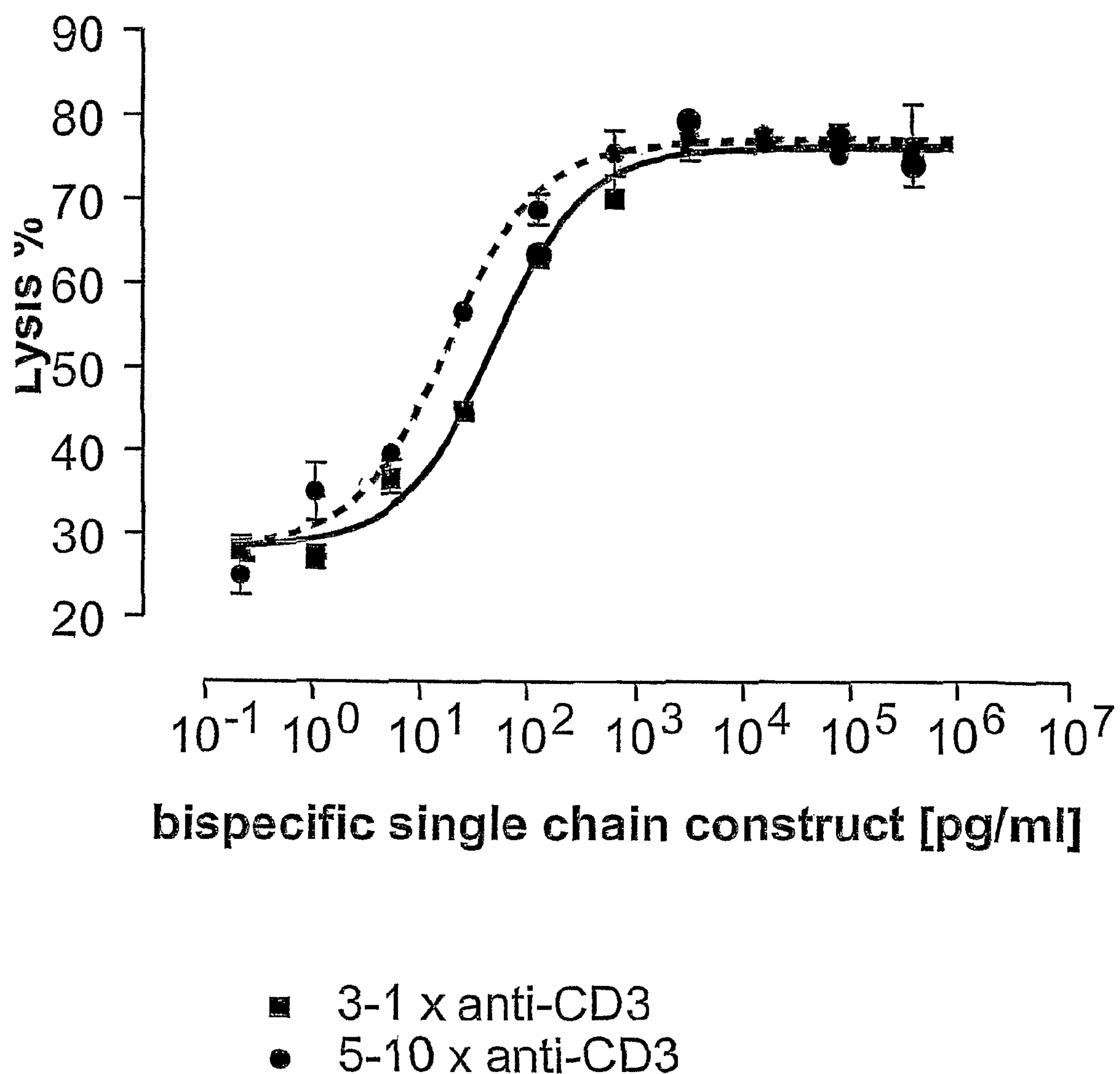

Antibodies were diluted in RPMI/10% FCS to the required concentration and 50 μl of this solution was added to the cell suspension. A standard reaction was incubated for 16 h at 37° C./5% $CO_2$. Propidium iodide was added to a final concentration of 1 μg/ml. After 10 min of incubation at room temperature cells were analysed by FACS. PKH26 fluorescence was used for positive identification of target cells. Cytotoxicity was measured as ratio of PI positive over all target cells. Sigmoidal dose response curves typically had $R^2$ values >0.97 as determined by Prism Software (GraphPad Software Inc., San Diego, USA) (FIGS. 9 and 10). $EC_{50}$ values calculated by the analysis program were used for comparison of bioactivity. All the constructs of the invention show at least 50 times better cytotoxicity (maximum EC50-value 169 pg/ml) than the prior art construct M79xanti-CD3 (8628 pg/ml).

EXAMPLE 4

Determination of the Binding Affinity by BIAcore™ 2000 of the Constructs Comprising Anti-EpCAM and Anti-CD3 to EpCAM In order to show the superior binding affinity of the constructs of the invention, the KD values of the constructs and of the prior art anti-EpCAM construct (M79)xanti-CD3 were determined.

Kinetic binding experiments were performed using surface plasmon resonance on the BIAcore™ 2000, Biacore AB (Uppsala, Sweden) with a flow rate of 5 μL/min and HBS-EP (0.01 M HEPES, pH 7.4, 0.15 M NaCl, 3 mM EDTA, 0.005% surfactant P20) as running buffer at 25° C. The extracellular domain of the EpCAM antigen (residues 17-265) was immobilized onto flow cells 2-4 on a CM5 sensor chip. The chip surface was activated injecting 80 μL of 0.1 M sodium-hydroxysuccinimid, 0.4 M N-ethyl-N'(3-dimethylaminepropyl)-carbodiimid (NHS/EDC). The antigen was coupled by manual injection of 60 μg/mL EpCAM in 0.01 M sodium-acetate, pH 4.7. Different densities of antigen were immobilized on flow cells 2-4 adjusting the amount of manual injection times. Flow cell 1 was left empty while flow cell 2 was coated with the highest density of EpCAM (4100 RU). Flow cell 3 was coated with ¼ of the amount of antigen immobilized on flow cell 2 (974 RU) and flow cell 4 was coated with lowest density of Ep-CAM antigen (265 RU). The activated surface of the sensor chip was blocked injecting 85 μL of 1 M ethanolamine and the chip was left to equilibrate over night at a constant flow of 5 μL/min of HBS-EP.

Binding kinetics of the bispecific constructs were measured injecting 10 μL of protein solution at concentrations ranging from 4 μM-0.07 μM and monitoring the dissociation for 100 sec. Protein was buffered in HBS-EP. The data were fitted using BIAevalution™ software determining the rate constant for dissociation and association kinetics with a 1:1 Langmuir binding equation (1, 2). Where A is the concentration of injected analyte and B[0] is Rmax.

$$dB/dt=-(ka*[A]*[B]-kd*[AB]) \quad (1)$$

$$dAB/dt=-(ka*[A]*[B]-kd*[AB]) \quad (2)$$

Kinetic binding curves were determined in four concentrations of each bispecific construct analysed. The independent fitting of the raw data resulted in dissociation and association rate constants that were used to calculate the equilibrium dissociation constant (KD). The calculated KD values were unbiased for concentration indicating reliable data analysis. The average of the independently determined dissociation constants as well as the standard deviation are summarized in table 3.

The analysed bispecific constructs bind to the Ep-CAM antigen immobilized on the chip surface within a well defined affinity range. The standard deviation for the calculated average dissociation constant is as expected.

TABLE 3

Dissociation constants for the bispecific constructs binding to EpCAM.

| | KD (M) |
|---|---|
| M79 x anti-CD3 (control) | $4.0 \times 10^{-6}$ |
| 4-1 x anti-CD3 (SEQ ID NO.: 39) | $2.5 \times 10^{-7}$ |
| 3-5 x anti-CD3 (SEQ ID NO.: 30) | $2.3 \times 10^{-7}$ |

The prior art anti-EpCAM x anti-CD3 construct M79xCD3 had a KD of $4.0\times10^{-6}$ M while surprisingly the constructs of the invention have a KD in the range of $2.3\times10^{-7}$-$2.5\times10^{-7}$ M. Thus, the constructs of the invention have more than 15 times stronger binding affinity than the prior art construct.

EXAMPLE 5

Comparison of the Cytotoxic Activity of the Constructs of the Invention with Prior Art Constructs In order to compare the bioactivity of constructs having the NXD motif with conventional M79xCD3 and HD70xCD3 constructs the following cytotoxic assay was carried out.

KatoIII cells (ATCC HTB-103) were used as target cells and grown in RPMI supplemented with 10% fetal calf serum at 37° C. in a 5% $CO_2$ humidified incubator. Subconfluent cultures were treated with 0.25% trypsin, counted in a Neubauer chamber slide and checked for vitality by trypan-blue exclusion. Only cultures with >95% vitality were used for cytotoxicity assays. Target cells were stained with PKH26 fluorescent membrane dye according to the manufacturers manual (Sigma-Aldrich GmbH, Germany, PKH26-GL). Cell number was adjusted to $8\times10^5$ cells/ml in RPMI complete medium.

Human peripheral blood mononuclear cells (PBMCs) were used as effector cells and isolated from healthy donors using ficoll density gradient centrifugation with subsequent 100×g centrifugation to remove thrombocytes. The pellet was resuspended in 10 vol. erythrocyte lysing buffer and incubated at room temperature for 10 min. Lysing reaction was stopped by addition PBS. PBMCs were resuspended in RPMI 1640 complete medium and cell number adjusted to $8\times10^6$ cells/ml.

Equal volumes of target and effector cell suspension were mixed and 50 μl of this suspension transferred to each well of a 96 well round bottom plate, 50 μl of EpCAM bispecific antibody serial dilution or RPMI complete medium as a negative control was added. Plates were incubated for 16 to 20 hrs at 37° C., 5% $CO_2$ in a humidified incubator. 50 μl propidium iodide was added to a final concentration of 1 μg/ml and incubated 15 min at room temperature. Samples were analysed by flow cytometry (FACSCalibur, Becton Dickinson). $2\times10^4$ events were counted.

Target cells were identified by their PKH26 fluorescent label and cytotoxicity within this population was subsequently determined. Viable cells were separated from dead cells by propidium iodide staining and the percentage of dead target cells was used as a measure for cytotoxicity. Mean values were plotted against the concentration of the bispecific antibody on a logarithmic scale, resulting in a dose response curve (FIG. 11B). The corresponding $EC_{50}$ values were obtained after nonlinear fitting of data with the GraphPad Prism software.

The cytotoxic activity of constructs having the NXD motif (SEQ ID NO.:36, 44, 2 and 18) was compared with conventional constructs M79xanti-CD3 and HD70-xanti-CD3 (FIG. 11B). A sequence alignment of the CDR3 regions of the VH chains of 3-1, 5-10, 4-7, 3-5 and 4-1 with M79, HD70 and 3B10 is shown in FIG. 11A. Only 3-1, 5-10, 4-7, 3-5 and 4-1 have the NXD motif and furthermore, the lengths of the CDR3 regions differ. As can be seen from FIG. 11A, 3-1, 4-1 and 5-10 have a CDR-H3 region of 10 amino acids, 3-5 and 4-7 have 14 amino acids whereas the prior art M79 has 8 amino acids, 3B10 has 6 amino acids and HD70 has 18 amino acids.

SEQ ID NO.: 36, 44, 2 and 18 showed a clearly better bioactivity compared to the conventional M79 and HD70 constructs (2250 pg/ml and less compared to 71460 and 11327 pg/ml of the prior art constructs, respectively) demonstrating the advantageous effects of the constructs of the invention.

The invention claimed is:

1. A bispecific single chain antibody construct, whereby said construct comprises at least two domains, whereby one of said domains binds to human EpCAM antigen and a second domain binds to human CD3 antigen, wherein said binding domain specific for EpCAM comprises at least one CDR-H3 region comprising the amino acid sequence NXD preferably in position 102 to 104 of SEQ ID NOs: 80, 88 and 96, or preferably in position 106 to 108 of SEQ ID NOS: 84 and 92, wherein X is an aromatic amino acid and wherein the $V_H$ chain domain specific for human EpCAM antigen is selected from the group consisting of:

(a) an amino acid sequence as shown in any of SEQ ID NO: 80, SEQ ID NO: 84,

SEQ ID NO: 88, SEQ ID NO: 92 and SEQ ID NO: 96;

(b) an amino acid sequence encoded by a nucleic acid sequence as shown in SEQ ID NO: 79, SEQ ID NO: 83, SEQ ID NO: 87, SEQ ID NO: 91 and SEQ ID NO: 95; and (c) an amino acid sequence encoded by a nucleic acid sequence which is degenerate as a result of the genetic code to a nucleotide sequence of (b); and wherein the $V_L$ chain domain specific for human EpCAM antigen is selected from the group consisting of:

(a) an amino acid sequence as shown in any of SEQ ID NO: 82, SEQ ID NO: 86, SEQ ID NO: 90, SEQ ID NO: 94 and SEQ ID NO: 98;

(b) an amino acid sequence encoded by a nucleic acid sequence as shown in SEQ ID NO: 81, SEQ ID NO: 85, SEQ ID NO: 89, SEQ ID NO: 93 and SEQ ID NO: 97; and (c) an amino acid sequence encoded by a nucleic acid sequence which is degenerate as a result of the genetic code to a nucleotide sequence of (b).

2. The bispecific single chain antibody construct of claim 1, wherein X is W or Y.

3. The bispecific single chain antibody construct of claim 1, wherein the CDR-H3 comprises at least 9 amino acid residues.

4. The bispecific single chain antibody construct of claim 1, wherein said binding domain specific for EpCAM has a KD value of more than $5\times10^{-9}$ M.

5. The bispecific single chain antibody construct of claim 1, wherein said binding domain specific for EpCAM has a KD value in a range between $I\times10^{-7}$ and $5\times10^{-9}$ M and said binding domain specific for CD3 has a KD value in a range between $1\times10^{-6}$ and 5×10−9 M.

6. The bispecific single chain antibody construct of claim 1, wherein said binding domain specific for CD3 has a KD value of more than $10^{-7}$ M.

7. The bispecific single chain antibody construct of claim 1, wherein the CDR-H3 region comprises at least 14 amino acids.

8. The bispecific single chain antibody construct of claim 1, wherein the binding domain specific for the CD3 antigen is derived from the OKT3D antibody.

9. The bispecific single chain antibody construct of claim 1, wherein said bispecific single chain antibody construct comprises an amino add sequence selected from the group consisting of (a) an amino acid sequence as shown in any of SEQ ID NOs: 2,4, 8,10, 12,14, 16,18, 20,30, 36, 39, 42, 46, 48, 50,52, 54,56, 58 and 60:

(b) an amino acid sequence encoded by a nucleic acid sequence as shown in any of SEQ ID NOs: 1,3, 7,9, 11,13, 15,17, 19,29, 35, 38,41, 43, 45, 47,49, 51,53, 55,57 and 59; and (c) an amino acid sequence encoded by a nucleic acid sequence which is degenerate as a result of the genetic code to a nucleotide sequence of (b).

10. A pharmaceutical composition comprising the bispecific single chain antibody construct of claim 1.

11. A pharmaceutical composition of claim 10, further comprising a proteinaceous compound capable of providing an activation signal for immune effector cells.

12. The pharmaceutical composition of claim 11, wherein the pharmaceutical composition is thermostable at 237° C.

13. A kit comprising a bispecific single chain antibody construct of claim 1.

* * * * *

SEQUENCE LISTING

```
<160> NUMBER OF SEQ ID NOS: 105

<210> SEQ ID NO 1
<211> LENGTH: 1521
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
```

```
gatatcaaac tgcagcagtc aggggctgaa ctggcaagac ctggggcctc agtgaagatg     60

tcctgcaaga cttctggcta cacctttact aggtacacga tgcactgggt aaaacagagg    120

cctggacagg gtctggaatg gattggatac attaatccta gccgtggtta tactaattac    180

aatcagaagt tcaaggacaa ggccacattg actacagaca aatcctccag cacagcctac    240

atgcaactga gcagcctgac atctgaggac tctgcagtct attactgtgc aagatattat    300

gatgatcatt actgccttga ctactggggc caaggcacca ctctcacagt ctcctcagtc    360

gaaggtggaa gtggaggttc tggtggaagt ggaggttcag gtggagtcga cgacattcag    420

ctgacccagt ctccagcaat catgtctgca tctccagggg agaaggtcac catgacctgc    480

agagccagtt caagtgtaag ttacatgaac tggtaccagc agaagtcagg cacctccccc    540

aaaagatgga tttatgacac atccaaagtg gcttctggag tcccttatcg cttcagtggc    600

agtgggtctg ggacctcata ctctctcaca atcagcagca tggaggctga agatgctgcc    660

acttattact gccaacagtg gagtagtaac ccgctcacgt tcggtgctgg gaccaagctg    720

gagctgaaat ccggaggtgg tggatccgag gtgcagctgc tcgagcagtc tggagctgag    780

ctggcgaggc ctggggcttc agtgaagctg tcctgcaagg cttctggcta caccttcaca    840

aactatggtt taagctgggt gaagcagagg cctggacagg tccttgagtg gattggagag    900

gtttatccta gaattggtaa tgcttactac aatgagaagt tcaagggcaa ggccacactg    960

actgcagaca aatcctccag cacagcgtcc atggagctcc gcagcctgac ctctgaggac   1020

tctgcggtct atttctgtgc aagacgggga tcctacgata ctaactacga ctggtacttc   1080

gatgtctggg gccaagggac cacggtcacc gtctcctcag gtggtggtgg ttctggcggc   1140

ggcggctccg gtggtggtgg ttctgagctc gtgatgaccc agactccact ctccctgcct   1200

gtcagtcttg gagatcaagc ctccatctct tgcagatcta gtcagagcct tgtacacagt   1260

aatggaaaca cctatttaca ttggtacctg cagaagccag gccagtctcc aaagctcctg   1320

atctacaaag tttccaaccg attttctggg gtcccagaca ggttcagtgg cagtggatca   1380

gggacagatt tcacactcaa gatcagcaga gtggaggctg aggatctggg agtttatttc   1440

tgctctcaaa gtacacatgt tccgtacacg ttcggagggg ggaccaagct tgagatcaaa   1500

catcatcacc atcatcatta g                                             1521
```

```
<210> SEQ ID NO 2
<211> LENGTH: 506
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ser Gly Gly Gly Gly Ser Glu Val Gln Leu Leu Glu Gln
                245                 250                 255

Ser Gly Ala Glu Leu Ala Arg Pro Gly Ala Ser Val Lys Leu Ser Cys
            260                 265                 270

Lys Ala Ser Gly Tyr Thr Phe Thr Asn Tyr Gly Leu Ser Trp Val Lys
        275                 280                 285

Gln Arg Pro Gly Gln Val Leu Glu Trp Ile Gly Glu Val Tyr Pro Arg
    290                 295                 300

Ile Gly Asn Ala Tyr Tyr Asn Glu Lys Phe Lys Gly Lys Ala Thr Leu
305                 310                 315                 320

Thr Ala Asp Lys Ser Ser Ser Thr Ala Ser Met Glu Leu Arg Ser Leu
                325                 330                 335

Thr Ser Glu Asp Ser Ala Val Tyr Phe Cys Ala Arg Arg Gly Ser Tyr
            340                 345                 350

Asp Thr Asn Tyr Asp Trp Tyr Phe Asp Val Trp Gly Gln Gly Thr Thr
        355                 360                 365

Val Thr Val Ser Ser Gly Gly Gly Gly Ser Gly Gly Gly Gly Ser Gly
    370                 375                 380

Gly Gly Gly Ser Glu Leu Val Met Thr Gln Thr Pro Leu Ser Leu Pro
385                 390                 395                 400

Val Ser Leu Gly Asp Gln Ala Ser Ile Ser Cys Arg Ser Ser Gln Ser
                405                 410                 415

Leu Val His Ser Asn Gly Asn Thr Tyr Leu His Trp Tyr Leu Gln Lys
            420                 425                 430

Pro Gly Gln Ser Pro Lys Leu Leu Ile Tyr Lys Val Ser Asn Arg Phe
        435                 440                 445

Ser Gly Val Pro Asp Arg Phe Ser Gly Ser Gly Ser Gly Thr Asp Phe
    450                 455                 460

Thr Leu Lys Ile Ser Arg Val Glu Ala Glu Asp Leu Gly Val Tyr Phe
465                 470                 475                 480

Cys Ser Gln Ser Thr His Val Pro Tyr Thr Phe Gly Gly Gly Thr Lys
                485                 490                 495

Leu Glu Ile Lys His His His His His His
```

500 505

<210> SEQ ID NO 3
<211> LENGTH: 1512
<212> TYPE: DNA
<213> ORGANISM: Artificial Sequence
<220> FEATURE:
<223> OTHER INFORMATION: Description of Artificial Sequence: Synthetic
construct

<400> SEQUENCE: 3
gatatcaaac tgcagcagtc aggggctgaa ctggcaagac ctggggcctc agtgaagatg 60
tcctgcaaga cttctggcta cacctttact aggtacacga tgcactgggt aaaacagagg 120
cctggacagg gtctggaatg gattggatac attaatccta gccgtggtta tactaattac 180
aatcagaagt tcaaggacaa ggccacattg actacagaca aatcctccag cacagcctac 240
atgcaactga gcagcctgac atctgaggac tctgcagtct attactgtgc aagatattat 300
gatgatcatt actgccttga ctactggggc caaggcacca ctctcacagt ctcctcagtc 360
gaaggtggaa gtggaggttc tggtggaagt ggaggttcag gtggagtcga cgacattcag 420
ctgacccagt ctccagcaat catgtctgca tctccagggg agaaggtcac catgacctgc 480
agagccagtt caagtgtaag ttacatgaac tggtaccagc agaagtcagg cacctccccc 540
aaaagatgga tttatgacac atccaaagtg gcttctggag tcccttatcg cttcagtggc 600
agtgggtctg ggacctcata ctctctcaca atcagcagca tggaggctga agatgctgcc 660
acttattact gccaacagtg gagtagtaac ccgctcacgt tcggtgctgg gaccaagctg 720
gagctgaaat ccggaggtgg tggatccgag gtgcagctgc tcgagcagtc tggagctgag 780
ctggtaaggc ctgggacttc agtgaagata tcctgcaagg cttctggata cgccttcact 840
aactactggc taggttgggt aaagcagagg cctggacatg gacttgagtg gattggagat 900
attttccctg gaagtggtaa tatccactac aatgagaagt tcaagggcaa agccacactg 960
actgcagaca aatcttcgag cacagcctat atgcagctca gtagcctgac atttgaggac 1020
tctgctgtct atttctgtgc aagactgagg aactgggacg agcctatgga ctactggggc 1080
caagggacca cggtcaccgt ctcctcaggt ggtggtggtt ctggcggcgg cggctccggt 1140
ggtggtggtt ctgagctcgt gatgacacag tctccatcct ccctgactgt gacagcagga 1200
gagaaggtca ctatgagctg caagtccagt cagagtctgt taaacagtgg aaatcaaaag 1260
aactacttga cctggtacca gcagaaacca gggcagcctc ctaaactgtt gatctactgg 1320
gcatccacta gggaatctgg ggtccctgat cgcttcacag gcagtggatc tggaacagat 1380
ttcactctca ccatcagcag tgtgcaggct gaagacctgg cagtttatta ctgtcagaat 1440
gattatagtt atccgctcac gttcggtgct gggaccaagc ttgagatcaa acatcatcac 1500
catcatcatt ag 1512

<210> SEQ ID NO 4
<211> LENGTH: 503
<212> TYPE: PRT
<213> ORGANISM: Artificial Sequence
<220> FEATURE:
<223> OTHER INFORMATION: Description of Artificial Sequence: Synthetic
construct

<400> SEQUENCE: 4

Asp Ile Lys Leu Gln Gln Ser Gly Ala Glu Leu Ala Arg Pro Gly Ala
1 5 10 15

```
Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ser Gly Gly Gly Gly Ser Glu Val Gln Leu Leu Glu Gln
                245                 250                 255

Ser Gly Ala Glu Leu Val Arg Pro Gly Thr Ser Val Lys Ile Ser Cys
            260                 265                 270

Lys Ala Ser Gly Tyr Ala Phe Thr Asn Tyr Trp Leu Gly Trp Val Lys
        275                 280                 285

Gln Arg Pro Gly His Gly Leu Glu Trp Ile Gly Asp Ile Phe Pro Gly
    290                 295                 300

Ser Gly Asn Ile His Tyr Asn Glu Lys Phe Lys Gly Lys Ala Thr Leu
305                 310                 315                 320

Thr Ala Asp Lys Ser Ser Ser Thr Ala Tyr Met Gln Leu Ser Ser Leu
                325                 330                 335

Thr Phe Glu Asp Ser Ala Val Tyr Phe Cys Ala Arg Leu Arg Asn Trp
            340                 345                 350

Asp Glu Pro Met Asp Tyr Trp Gly Gln Gly Thr Thr Val Thr Val Ser
        355                 360                 365

Ser Gly Gly Gly Gly Ser Gly Gly Gly Gly Ser Gly Gly Gly Gly Ser
    370                 375                 380

Glu Leu Val Met Thr Gln Ser Pro Ser Ser Leu Thr Val Thr Ala Gly
385                 390                 395                 400

Glu Lys Val Thr Met Ser Cys Lys Ser Ser Gln Ser Leu Leu Asn Ser
                405                 410                 415

Gly Asn Gln Lys Asn Tyr Leu Thr Trp Tyr Gln Gln Lys Pro Gly Gln
            420                 425                 430

Pro Pro Lys Leu Leu Ile Tyr Trp Ala Ser Thr Arg Glu Ser Gly Val
```

```
        435                 440                 445

Pro Asp Arg Phe Thr Gly Ser Gly Ser Gly Thr Asp Phe Thr Leu Thr
    450                 455                 460

Ile Ser Ser Val Gln Ala Glu Asp Leu Ala Val Tyr Tyr Cys Gln Asn
465                 470                 475                 480

Asp Tyr Ser Tyr Pro Leu Thr Phe Gly Ala Gly Thr Lys Leu Glu Ile
                485                 490                 495

Lys His His His His His His
            500


<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

aggtgtacac tccgatatca aactgcagca g                                  31


<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

aatccggatt tcagctccag cttgg                                         25


<210> SEQ ID NO 7
<211> LENGTH: 1521
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7

gatatcaaac tgcagcagtc aggggctgaa ctggcaagac ctggggcctc agtgaagatg     60

tcctgcaaga cttctggcta cacctttact aggtacacga tgcactgggt aaaacagagg    120

cctggacagg gtctggaatg gattggatac attaatccta gccgtggtta tactaattac    180

aatcagaagt tcaaggacaa ggccacattg actacagaca aatcctccag cacagcctac    240

atgcaactga gcagcctgac atctgaggac tctgcagtct attactgtgc aagatattat    300

gatgatcatt actcccttga ctactggggc caaggcacca ctctcacagt ctcctcagtc    360

gaaggtggaa gtggaggttc tggtggaagt ggaggttcag gtggagtcga cgacattcag    420

ctgacccagt ctccagcaat catgtctgca tctccagggg agaaggtcac catgacctgc    480

agagccagtt caagtgtaag ttacatgaac tggtaccagc agaagtcagg cacctccccc    540

aaaagatgga tttatgacac atccaaagtg gcttctggag tcccttatcg cttcagtggc    600

agtgggtctg ggacctcata ctctctcaca atcagcagca tggaggctga agatgctgcc    660

acttattact gccaacagtg gagtagtaac ccgctcacgt tcggtgctgg gaccaagctg    720

gagctgaaat ccggaggtgg tggatccgag gtgcagctgc tcgagcagtc tggagctgag    780

ctggcgaggc ctggggcttc agtgaagctg tcctgcaagg cttctggcta caccttcaca    840
```

```
aactatggtt taagctgggt gaagcagagg cctggacagg tccttgagtg gattggagag    900

gtttatccta gaattggtaa tgcttactac aatgagaagt tcaagggcaa ggccacactg    960

actgcagaca aatcctccag cacagcgtcc atggagctcc gcagcctgac ctctgaggac   1020

tctgcggtct atttctgtgc aagacgggga tcctacgata ctaactacga ctggtacttc   1080

gatgtctggg gccaagggac cacggtcacc gtctcctcag gtggtggtgg ttctggcggc   1140

ggcggctccg gtggtggtgg ttctgagctc gtgatgaccc agactccact ctccctgcct   1200

gtcagtcttg gagatcaagc ctccatctct tgcagatcta gtcagagcct tgtacacagt   1260

aatggaaaca cctatttaca ttggtacctg cagaagccag gccagtctcc aaagctcctg   1320

atctacaaag tttccaaccg attttctggg gtcccagaca ggttcagtgg cagtggatca   1380

gggacagatt tcacactcaa gatcagcaga gtggaggctg aggatctggg agtttatttc   1440

tgctctcaaa gtacacatgt tccgtacacg ttcggagggg ggaccaagct tgagatcaaa   1500

catcatcacc atcatcatta g                                              1521


<210> SEQ ID NO 8
<211> LENGTH: 506
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240
```

```
Glu Leu Lys Ser Gly Gly Gly Gly Ser Glu Val Gln Leu Leu Glu Gln
                245                 250                 255

Ser Gly Ala Glu Leu Ala Arg Pro Gly Ala Ser Val Lys Leu Ser Cys
            260                 265                 270

Lys Ala Ser Gly Tyr Thr Phe Thr Asn Tyr Gly Leu Ser Trp Val Lys
        275                 280                 285

Gln Arg Pro Gly Gln Val Leu Glu Trp Ile Gly Glu Val Tyr Pro Arg
    290                 295                 300

Ile Gly Asn Ala Tyr Tyr Asn Glu Lys Phe Lys Gly Lys Ala Thr Leu
305                 310                 315                 320

Thr Ala Asp Lys Ser Ser Ser Thr Ala Ser Met Glu Leu Arg Ser Leu
                325                 330                 335

Thr Ser Glu Asp Ser Ala Val Tyr Phe Cys Ala Arg Arg Gly Ser Tyr
            340                 345                 350

Asp Thr Asn Tyr Asp Trp Tyr Phe Asp Val Trp Gly Gln Gly Thr Thr
        355                 360                 365

Val Thr Val Ser Ser Gly Gly Gly Gly Ser Gly Gly Gly Gly Ser Gly
    370                 375                 380

Gly Gly Gly Ser Glu Leu Val Met Thr Gln Thr Pro Leu Ser Leu Pro
385                 390                 395                 400

Val Ser Leu Gly Asp Gln Ala Ser Ile Ser Cys Arg Ser Ser Gln Ser
                405                 410                 415

Leu Val His Ser Asn Gly Asn Thr Tyr Leu His Trp Tyr Leu Gln Lys
            420                 425                 430

Pro Gly Gln Ser Pro Lys Leu Leu Ile Tyr Lys Val Ser Asn Arg Phe
        435                 440                 445

Ser Gly Val Pro Asp Arg Phe Ser Gly Ser Gly Ser Gly Thr Asp Phe
    450                 455                 460

Thr Leu Lys Ile Ser Arg Val Glu Ala Glu Asp Leu Gly Val Tyr Phe
465                 470                 475                 480

Cys Ser Gln Ser Thr His Val Pro Tyr Thr Phe Gly Gly Gly Thr Lys
                485                 490                 495

Leu Glu Ile Lys His His His His His His
            500                 505
```

```
<210> SEQ ID NO 9
<211> LENGTH: 1512
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 9

gatatcaaac tgcagcagtc aggggctgaa ctggcaagac ctggggcctc agtgaagatg      60

tcctgcaaga cttctggcta cacctttact aggtacacga tgcactgggt aaaacagagg     120

cctggacagg gtctggaatg gattggatac attaatccta gccgtggtta tactaattac     180

aatcagaagt tcaaggacaa ggccacattg actacagaca aatcctccag cacagcctac     240

atgcaactga gcagcctgac atctgaggac tctgcagtct attactgtgc aagatattat     300

gatgatcatt actcccttga ctactggggc caaggcacca ctctcacagt ctcctcagtc     360

gaaggtggaa gtggaggttc tggtggaagt ggaggttcag gtggagtcga cgacattcag     420

ctgacccagt ctccagcaat catgtctgca tctccagggg agaaggtcac catgacctgc     480
```

```
agagccagtt caagtgtaag ttacatgaac tggtaccagc agaagtcagg cacctccccc    540

aaaagatgga tttatgacac atccaaagtg gcttctggag tcccttatcg cttcagtggc    600

agtgggtctg ggacctcata ctctctcaca atcagcagca tggaggctga agatgctgcc    660

acttattact gccaacagtg gagtagtaac ccgctcacgt tcggtgctgg gaccaagctg    720

gagctgaaat ccggaggtgg tggatccgag gtgcagctgc tcgagcagtc tggagctgag    780

ctggtaaggc ctgggacttc agtgaagata tcctgcaagg cttctggata cgccttcact    840

aactactggc taggttgggt aaagcagagg cctggacatg gacttgagtg gattggagat    900

attttccctg gaagtggtaa tatccactac aatgagaagt tcaagggcaa agccacactg    960

actgcagaca aatcttcgag cacagcctat atgcagctca gtagcctgac atttgaggac   1020

tctgctgtct atttctgtgc aagactgagg aactgggacg agcctatgga ctactggggc   1080

caagggacca cggtcaccgt ctcctcaggt ggtggtggtt ctggcggcgg cggctccggt   1140

ggtggtggtt ctgagctcgt gatgacacag tctccatcct ccctgactgt gacagcagga   1200

gagaaggtca ctatgagctg caagtccagt cagagtctgt taaacagtgg aaatcaaaag   1260

aactacttga cctggtacca gcagaaacca gggcagcctc ctaaactgtt gatctactgg   1320

gcatccacta gggaatctgg ggtccctgat cgcttcacag gcagtggatc tggaacagat   1380

ttcactctca ccatcagcag tgtgcaggct gaagacctgg cagtttatta ctgtcagaat   1440

gattatagtt atccgctcac gttcggtgct gggaccaagc ttgagatcaa acatcatcac   1500

catcatcatt ag                                                       1512
```

```
<210> SEQ ID NO 10
<211> LENGTH: 503
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175
```

```
Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ser Gly Gly Gly Gly Ser Glu Val Gln Leu Leu Glu Gln
                245                 250                 255

Ser Gly Ala Glu Leu Val Arg Pro Gly Thr Ser Val Lys Ile Ser Cys
            260                 265                 270

Lys Ala Ser Gly Tyr Ala Phe Thr Asn Tyr Trp Leu Gly Trp Val Lys
        275                 280                 285

Gln Arg Pro Gly His Gly Leu Glu Trp Ile Gly Asp Ile Phe Pro Gly
    290                 295                 300

Ser Gly Asn Ile His Tyr Asn Glu Lys Phe Lys Gly Lys Ala Thr Leu
305                 310                 315                 320

Thr Ala Asp Lys Ser Ser Ser Thr Ala Tyr Met Gln Leu Ser Ser Leu
                325                 330                 335

Thr Phe Glu Asp Ser Ala Val Tyr Phe Cys Ala Arg Leu Arg Asn Trp
            340                 345                 350

Asp Glu Pro Met Asp Tyr Trp Gly Gln Gly Thr Thr Val Thr Val Ser
        355                 360                 365

Ser Gly Gly Gly Gly Ser Gly Gly Gly Gly Ser Gly Gly Gly Gly Ser
    370                 375                 380

Glu Leu Val Met Thr Gln Ser Pro Ser Ser Leu Thr Val Thr Ala Gly
385                 390                 395                 400

Glu Lys Val Thr Met Ser Cys Lys Ser Ser Gln Ser Leu Leu Asn Ser
                405                 410                 415

Gly Asn Gln Lys Asn Tyr Leu Thr Trp Tyr Gln Gln Lys Pro Gly Gln
            420                 425                 430

Pro Pro Lys Leu Leu Ile Tyr Trp Ala Ser Thr Arg Glu Ser Gly Val
        435                 440                 445

Pro Asp Arg Phe Thr Gly Ser Gly Ser Gly Thr Asp Phe Thr Leu Thr
    450                 455                 460

Ile Ser Ser Val Gln Ala Glu Asp Leu Ala Val Tyr Tyr Cys Gln Asn
465                 470                 475                 480

Asp Tyr Ser Tyr Pro Leu Thr Phe Gly Ala Gly Thr Lys Leu Glu Ile
                485                 490                 495

Lys His His His His His His
            500
```

<210> SEQ ID NO 11
<211> LENGTH: 1485
<212> TYPE: DNA
<213> ORGANISM: Artificial Sequence
<220> FEATURE:
<223> OTHER INFORMATION: Description of Artificial Sequence: Synthetic construct

<400> SEQUENCE: 11

```
gatatcaaac tgcagcagtc aggggctgaa ctggcaagac ctggggcctc agtgaagatg     60

tcctgcaaga cttctggcta cacctttact aggtacacga tgcactgggt aaaacagagg    120
```

```
cctggacagg gtctggaatg gattggatac attaatccta gccgtggtta tactaattac    180

aatcagaagt tcaaggacaa ggccacattg actacagaca aatcctccag cacagcctac    240

atgcaactga gcagcctgac atctgaggac tctgcagtct attactgtgc aagatattat    300

gatgatcatt actgccttga ctactggggc caaggcacca ctctcacagt ctcctcaggt    360

ggtggtggtt ctggcggcgg cggctccggt ggtggtggtt ctgacattca gctgacccag    420

tctccagcaa tcatgtctgc atctccaggg gagaaggtca ccatgacctg cagagccagt    480

tcaagtgtaa gttacatgaa ctggtaccag cagaagtcag gcacctcccc caaaagatgg    540

atttatgaca catccaaagt ggcttctgga gtcccttatc gcttcagtgg cagtgggtct    600

gggacctcat actctctcac aatcagcagc atggaggctg aagatgctgc cacttattac    660

tgccaacagt ggagtagtaa cccgctcacg ttcggtgctg ggaccaagct ggagctgaaa    720

tccggaggtg gtggatccga ggtgcagctg ctcgagcagt ctggagctga gctggtgaaa    780

cctggggcct cagtgaagat atcctgcaag gcttctggat acgccttcac taactactgg    840

ctaggttggg taaagcagag gcctggacat ggacttgagt ggattggaga tcttttccct    900

ggaagtggta atactcacta caatgagagg ttcaggggca aagccacact gactgcagac    960

aaatcctcga gcacagcctt tatgcagctc agtagcctga catctgagga ctctgctgtc   1020

tatttctgtg caagattgag gaactgggac gaggctatgg actactgggg ccaagggacc   1080

acggtcaccg tctcctcagg tggtggtggt tctggcggcg gcggctccgg tggtggtggt   1140

tctgagctcg tcatgaccca gtctccatct tatcttgctg catctcctgg agaaaccatt   1200

actattaatt gcagggcaag taagagcatt agcaaatatt tagcctggta tcaagagaaa   1260

cctgggaaaa ctaataagct tcttatctac tctggatcca ctttgcaatc tggaattcca   1320

tcaaggttca gtggcagtgg atctggtaca gatttcactc tcaccatcag tagcctggag   1380

cctgaagatt ttgcaatgta ttactgtcaa cagcataatg aatatccgta cacgttcgga   1440

ggggggacca agcttgagat caaacatcat caccatcatc attag                   1485
```

```
<210> SEQ ID NO 12
<211> LENGTH: 494
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
```

```
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190

Tyr Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ser Gly Gly Gly Gly Ser Glu Val Gln Leu Leu Glu Gln Ser Gly Ala
                245                 250                 255

Glu Leu Val Lys Pro Gly Ala Ser Val Lys Ile Ser Cys Lys Ala Ser
            260                 265                 270

Gly Tyr Ala Phe Thr Asn Tyr Trp Leu Gly Trp Val Lys Gln Arg Pro
        275                 280                 285

Gly His Gly Leu Glu Trp Ile Gly Asp Leu Phe Pro Gly Ser Gly Asn
    290                 295                 300

Thr His Tyr Asn Glu Arg Phe Arg Gly Lys Ala Thr Leu Thr Ala Asp
305                 310                 315                 320

Lys Ser Ser Ser Thr Ala Phe Met Gln Leu Ser Ser Leu Thr Ser Glu
                325                 330                 335

Asp Ser Ala Val Tyr Phe Cys Ala Arg Leu Arg Asn Trp Asp Glu Ala
            340                 345                 350

Met Asp Tyr Trp Gly Gln Gly Thr Thr Val Thr Val Ser Ser Gly Gly
        355                 360                 365

Gly Gly Ser Gly Gly Gly Gly Ser Gly Gly Gly Gly Ser Glu Leu Val
    370                 375                 380

Met Thr Gln Ser Pro Ser Tyr Leu Ala Ala Ser Pro Gly Glu Thr Ile
385                 390                 395                 400

Thr Ile Asn Cys Arg Ala Ser Lys Ser Ile Ser Lys Tyr Leu Ala Trp
                405                 410                 415

Tyr Gln Glu Lys Pro Gly Lys Thr Asn Lys Leu Leu Ile Tyr Ser Gly
            420                 425                 430

Ser Thr Leu Gln Ser Gly Ile Pro Ser Arg Phe Ser Gly Ser Gly Ser
        435                 440                 445

Gly Thr Asp Phe Thr Leu Thr Ile Ser Ser Leu Glu Pro Glu Asp Phe
    450                 455                 460

Ala Met Tyr Tyr Cys Gln Gln His Asn Glu Tyr Pro Tyr Thr Phe Gly
465                 470                 475                 480

Gly Gly Thr Lys Leu Glu Ile Lys His His His His His His
                485                 490
```

<210> SEQ ID NO 13
<211> LENGTH: 1512
<212> TYPE: DNA
<213> ORGANISM: Artificial Sequence
<220> FEATURE:
<223> OTHER INFORMATION: Description of Artificial Sequence: Synthetic
construct

<400> SEQUENCE: 13

```
gatatcaaac tgcagcagtc aggggctgaa ctggcaagac ctggggcctc agtgaagatg     60

tcctgcaaga cttctggcta cacctttact aggtacacga tgcactgggt aaaacagagg    120

cctggacagg gtctggaatg gattggatac attaatccta gccgtggtta tactaattac    180

aatcagaagt tcaaggacaa ggccacattg actacagaca aatcctccag cacagcctac    240

atgcaactga gcagcctgac atctgaggac tctgcagtct attactgtgc aagatattat    300

gatgatcatt actgccttga ctactggggc caaggcacca ctctcacagt ctcctcaggt    360

ggtggtggtt ctggcggcgg cggctccggt ggtggtggtt ctgacattca gctgacccag    420

tctccagcaa tcatgtctgc atctccaggg gagaaggtca ccatgacctg cagagccagt    480

tcaagtgtaa gttacatgaa ctggtaccag cagaagtcag gcacctcccc caaaagatgg    540

atttatgaca catccaaagt ggcttctgga gtcccttatc gcttcagtgg cagtgggtct    600

gggacctcat actctctcac aatcagcagc atggaggctg aagatgctgc cacttattac    660

tgccaacagt ggagtagtaa cccgctcacg ttcggtgctg ggaccaagct ggagctgaaa    720

tccggaggtg gtggatccga ggtgcagctg ctcgagcagt ctggagctga gctggcgagg    780

cctggggctt cagtgaagct gtcctgcaag gcttctggct acaccttcac aaactatggt    840

ttaagctggg tgaagcagag gcctggacag gtccttgagt ggattggaga ggtttatcct    900

agaattggta atgcttacta caatgagaag ttcaagggca aggccacact gactgcagac    960

aaatcctcca gcacagcgtc catggagctc cgcagcctga cctctgagga ctctgcggtc   1020

tatttctgtg caagacgggg atcctacgat actaactacg actggtactt cgatgtctgg   1080

ggccaaggga ccacggtcac cgtctcctca ggtggtggtg gttctggcgg cggcggctcc   1140

ggtggtggtg gttctgagct cgtgatgacc cagactccac tctccctgcc tgtcagtctt   1200

ggagatcaag cctccatctc ttgcagatct agtcagagcc ttgtacacag taatggaaac   1260

acctatttac attggtacct gcagaagcca ggccagtctc caaagctcct gatctacaaa   1320

gtttccaacc gattttctgg ggtcccagac aggttcagtg gcagtggatc agggacagat   1380

ttcacactca agatcagcag agtggaggct gaggatctgg gagtttattt ctgctctcaa   1440

agtacacatg ttccgtacac gttcggaggg gggaccaagc ttgagatcaa acatcatcac   1500

catcatcatt ag                                                       1512
```

<210> SEQ ID NO 14
<211> LENGTH: 503
<212> TYPE: PRT
<213> ORGANISM: Artificial Sequence
<220> FEATURE:
<223> OTHER INFORMATION: Description of Artificial Sequence: Synthetic construct

<400> SEQUENCE: 14

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
```

```
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190

Tyr Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ser Gly Gly Gly Gly Ser Glu Val Gln Leu Leu Glu Gln Ser Gly Ala
                245                 250                 255

Glu Leu Ala Arg Pro Gly Ala Ser Val Lys Leu Ser Cys Lys Ala Ser
            260                 265                 270

Gly Tyr Thr Phe Thr Asn Tyr Gly Leu Ser Trp Val Lys Gln Arg Pro
        275                 280                 285

Gly Gln Val Leu Glu Trp Ile Gly Glu Val Tyr Pro Arg Ile Gly Asn
    290                 295                 300

Ala Tyr Tyr Asn Glu Lys Phe Lys Gly Lys Ala Thr Leu Thr Ala Asp
305                 310                 315                 320

Lys Ser Ser Ser Thr Ala Ser Met Glu Leu Arg Ser Leu Thr Ser Glu
                325                 330                 335

Asp Ser Ala Val Tyr Phe Cys Ala Arg Arg Gly Ser Tyr Asp Thr Asn
            340                 345                 350

Tyr Asp Trp Tyr Phe Asp Val Trp Gly Gln Gly Thr Thr Val Thr Val
        355                 360                 365

Ser Ser Gly Gly Gly Gly Ser Gly Gly Gly Gly Ser Gly Gly Gly Gly
    370                 375                 380

Ser Glu Leu Val Met Thr Gln Thr Pro Leu Ser Leu Pro Val Ser Leu
385                 390                 395                 400

Gly Asp Gln Ala Ser Ile Ser Cys Arg Ser Ser Gln Ser Leu Val His
                405                 410                 415

Ser Asn Gly Asn Thr Tyr Leu His Trp Tyr Leu Gln Lys Pro Gly Gln
            420                 425                 430

Ser Pro Lys Leu Leu Ile Tyr Lys Val Ser Asn Arg Phe Ser Gly Val
        435                 440                 445

Pro Asp Arg Phe Ser Gly Ser Gly Ser Gly Thr Asp Phe Thr Leu Lys
    450                 455                 460

Ile Ser Arg Val Glu Ala Glu Asp Leu Gly Val Tyr Phe Cys Ser Gln
465                 470                 475                 480

Ser Thr His Val Pro Tyr Thr Phe Gly Gly Gly Thr Lys Leu Glu Ile
                485                 490                 495
```

Lys His His His His His His
500

<210> SEQ ID NO 15
<211> LENGTH: 1512
<212> TYPE: DNA
<213> ORGANISM: Artificial Sequence
<220> FEATURE:
<223> OTHER INFORMATION: Description of Artificial Sequence: Synthetic construct

<400> SEQUENCE: 15
gatatcaaac tgcagcagtc aggggctgaa ctggcaagac ctggggcctc agtgaagatg 60
tcctgcaaga cttctggcta cacctttact aggtacacga tgcactgggt aaaacagagg 120
cctggacagg gtctggaatg gattggatac attaatccta gccgtggtta tactaattac 180
aatcagaagt tcaaggacaa ggccacattg actacagaca aatcctccag cacagcctac 240
atgcaactga gcagcctgac atctgaggac tctgcagtct attactgtgc aagatattat 300
gatgatcatt actgccttga ctactggggc caaggcacca ctctcacagt ctcctcaggt 360
ggtggtggtt ctggcggcgg cggctccggt ggtggtggtt ctgacattca gctgacccag 420
tctccagcaa tcatgtctgc atctccaggg gagaaggtca ccatgacctg cagagccagt 480
tcaagtgtaa gttacatgaa ctggtaccag cagaagtcag gcacctcccc caaaagatgg 540
atttatgaca catccaaagt ggcttctgga gtcccttatc gcttcagtgg cagtgggtct 600
gggacctcat actctctcac aatcagcagc atggaggctg aagatgctgc cacttattac 660
tgccaacagt ggagtagtaa cccgctcacg ttcggtgctg ggaccaagct ggagctgaaa 720
tccggaggtg gtggatccga gctcgtgatg acccagactc cactctccct gcctgtcagt 780
cttggagatc aagcctccat ctcttgcaga tctagtcaga gccttgtaca cagtaatgga 840
aacacctatt tacattggta cctgcagaag ccaggccagt ctccaaagct cctgatctac 900
aaagtttcca accgattttc tggggtccca gacaggttca gtggcagtgg atcagggaca 960
gatttcacac tcaagatcag cagagtggag gctgaggatc tgggagttta tttctgctct 1020
caaagtacac atgttccgta cacgttcgga ggggggacca agcttgagat caaaggtggt 1080
ggtggttctg gcggcggcgg ctccggtggt ggtggttctg aggtgcagct gctcgagcag 1140
tctggagctg agctggcgag gcctggggct tcagtgaagc tgtcctgcaa ggcttctggc 1200
tacaccttca caaactatgg tttaagctgg gtgaagcaga ggcctggaca ggtccttgag 1260
tggattggag aggtttatcc tagaattggt aatgcttact acaatgagaa gttcaagggc 1320
aaggccacac tgactgcaga caaatcctcc agcacagcgt ccatggagct ccgcagcctg 1380
acctctgagg actctgcggt ctatttctgt gcaagacggg gatcctacga tactaactac 1440
gactggtact tcgatgtctg gggccaaggg accacggtca ccgtctcctc acatcatcac 1500
catcatcatt ag 1512

<210> SEQ ID NO 16
<211> LENGTH: 503
<212> TYPE: PRT
<213> ORGANISM: Artificial Sequence
<220> FEATURE:
<223> OTHER INFORMATION: Description of Artificial Sequence: Synthetic construct

<400> SEQUENCE: 16

Asp Ile Lys Leu Gln Gln Ser Gly Ala Glu Leu Ala Arg Pro Gly Ala

-continued

```
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190

Tyr Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ser Gly Gly Gly Gly Ser Glu Leu Val Met Thr Gln Thr Pro Leu Ser
                245                 250                 255

Leu Pro Val Ser Leu Gly Asp Gln Ala Ser Ile Ser Cys Arg Ser Ser
            260                 265                 270

Gln Ser Leu Val His Ser Asn Gly Asn Thr Tyr Leu His Trp Tyr Leu
        275                 280                 285

Gln Lys Pro Gly Gln Ser Pro Lys Leu Leu Ile Tyr Lys Val Ser Asn
    290                 295                 300

Arg Phe Ser Gly Val Pro Asp Arg Phe Ser Gly Ser Gly Ser Gly Thr
305                 310                 315                 320

Asp Phe Thr Leu Lys Ile Ser Arg Val Glu Ala Glu Asp Leu Gly Val
                325                 330                 335

Tyr Phe Cys Ser Gln Ser Thr His Val Pro Tyr Thr Phe Gly Gly Gly
            340                 345                 350

Thr Lys Leu Glu Ile Lys Gly Gly Gly Gly Ser Gly Gly Gly Gly Ser
        355                 360                 365

Gly Gly Gly Gly Ser Glu Val Gln Leu Leu Glu Gln Ser Gly Ala Glu
    370                 375                 380

Leu Ala Arg Pro Gly Ala Ser Val Lys Leu Ser Cys Lys Ala Ser Gly
385                 390                 395                 400

Tyr Thr Phe Thr Asn Tyr Gly Leu Ser Trp Val Lys Gln Arg Pro Gly
                405                 410                 415

Gln Val Leu Glu Trp Ile Gly Glu Val Tyr Pro Arg Ile Gly Asn Ala
            420                 425                 430
```

```
Tyr Tyr Asn Glu Lys Phe Lys Gly Lys Ala Thr Leu Thr Ala Asp Lys
        435                 440                 445

Ser Ser Ser Thr Ala Ser Met Glu Leu Arg Ser Leu Thr Ser Glu Asp
    450                 455                 460

Ser Ala Val Tyr Phe Cys Ala Arg Arg Gly Ser Tyr Asp Thr Asn Tyr
465                 470                 475                 480

Asp Trp Tyr Phe Asp Val Trp Gly Gln Gly Thr Thr Val Thr Val Ser
                485                 490                 495

Ser His His His His His His
            500
```

```
<210> SEQ ID NO 17
<211> LENGTH: 1503
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 17

gatatcaaac tgcagcagtc aggggctgaa ctggcaagac ctggggcctc agtgaagatg     60

tcctgcaaga cttctggcta cacctttact aggtacacga tgcactgggt aaaacagagg    120

cctggacagg gtctggaatg gattggatac attaatccta gccgtggtta tactaattac    180

aatcagaagt tcaaggacaa ggccacattg actacagaca aatcctccag cacagcctac    240

atgcaactga gcagcctgac atctgaggac tctgcagtct attactgtgc aagatattat    300

gatgatcatt actgccttga ctactggggc caaggcacca ctctcacagt ctcctcaggt    360

ggtggtggtt ctggcggcgg cggctccggt ggtggtggtt ctgacattca gctgacccag    420

tctccagcaa tcatgtctgc atctccaggg gagaaggtca ccatgacctg cagagccagt    480

tcaagtgtaa gttacatgaa ctggtaccag cagaagtcag gcacctcccc caaaagatgg    540

atttatgaca catccaaagt ggcttctgga gtcccttatc gcttcagtgg cagtgggtct    600

gggacctcat actctctcac aatcagcagc atggaggctg aagatgctgc cacttattac    660

tgccaacagt ggagtagtaa cccgctcacg ttcggtgctg ggaccaagct ggagctgaaa    720

tccggaggtg gtggatccga ggtgcagctg ctcgagcagt ctggagctga gctggtaagg    780

cctgggactt cagtgaagat atcctgcaag gcttctggat acgccttcac taactactgg    840

ctaggttggg taaagcagag gcctggacat ggacttgagt ggattggaga tattttccct    900

ggaagtggta atatccacta caatgagaag ttcaagggca aagccacact gactgcagac    960

aaatcttcga gcacagccta tatgcagctc agtagcctga catttgagga ctctgctgtc   1020

tatttctgtg caagactgag gaactgggac gagcctatgg actactgggg ccaagggacc   1080

acggtcaccg tctcctcagg tggtggtggt tctggcggcg gcggctccgg tggtggtggt   1140

tctgagctcg tgatgacaca gtctccatcc tccctgactg tgacagcagg agagaaggtc   1200

actatgagct gcaagtccag tcagagtctg ttaaacagtg gaaatcaaaa gaactacttg   1260

acctggtacc agcagaaacc agggcagcct cctaaactgt tgatctactg ggcatccact   1320

agggaatctg gggtccctga tcgcttcaca ggcagtggat ctggaacaga tttcactctc   1380

accatcagca gtgtgcaggc tgaagacctg gcagtttatt actgtcagaa tgattatagt   1440

tatccgctca cgttcggtgc tgggaccaag cttgagatca aacatcatca ccatcatcat   1500

tag                                                                  1503
```

<210> SEQ ID NO 18
<211> LENGTH: 500
<212> TYPE: PRT
<213> ORGANISM: Artificial Sequence
<220> FEATURE:
<223> OTHER INFORMATION: Description of Artificial Sequence: Synthetic construct

<400> SEQUENCE: 18

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190

Tyr Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ser Gly Gly Gly Gly Ser Glu Val Gln Leu Leu Glu Gln Ser Gly Ala
                245                 250                 255

Glu Leu Val Arg Pro Gly Thr Ser Val Lys Ile Ser Cys Lys Ala Ser
            260                 265                 270

Gly Tyr Ala Phe Thr Asn Tyr Trp Leu Gly Trp Val Lys Gln Arg Pro
        275                 280                 285

Gly His Gly Leu Glu Trp Ile Gly Asp Ile Phe Pro Gly Ser Gly Asn
    290                 295                 300

Ile His Tyr Asn Glu Lys Phe Lys Gly Lys Ala Thr Leu Thr Ala Asp
305                 310                 315                 320

Lys Ser Ser Ser Thr Ala Tyr Met Gln Leu Ser Ser Leu Thr Phe Glu
                325                 330                 335

Asp Ser Ala Val Tyr Phe Cys Ala Arg Leu Arg Asn Trp Asp Glu Pro
            340                 345                 350

Met Asp Tyr Trp Gly Gln Gly Thr Thr Val Thr Val Ser Ser Gly Gly
        355                 360                 365
```

```
Gly Gly Ser Gly Gly Gly Gly Ser Gly Gly Gly Gly Ser Glu Leu Val
    370                 375                 380

Met Thr Gln Ser Pro Ser Ser Leu Thr Val Thr Ala Gly Glu Lys Val
385                 390                 395                 400

Thr Met Ser Cys Lys Ser Ser Gln Ser Leu Leu Asn Ser Gly Asn Gln
                405                 410                 415

Lys Asn Tyr Leu Thr Trp Tyr Gln Gln Lys Pro Gly Gln Pro Pro Lys
            420                 425                 430

Leu Leu Ile Tyr Trp Ala Ser Thr Arg Glu Ser Gly Val Pro Asp Arg
        435                 440                 445

Phe Thr Gly Ser Gly Ser Gly Thr Asp Phe Thr Leu Thr Ile Ser Ser
    450                 455                 460

Val Gln Ala Glu Asp Leu Ala Val Tyr Tyr Cys Gln Asn Asp Tyr Ser
465                 470                 475                 480

Tyr Pro Leu Thr Phe Gly Ala Gly Thr Lys Leu Glu Ile Lys His His
                485                 490                 495

His His His His
            500
```

<210> SEQ ID NO 19
<211> LENGTH: 1503
<212> TYPE: DNA
<213> ORGANISM: Artificial Sequence
<220> FEATURE:
<223> OTHER INFORMATION: Description of Artificial Sequence: Synthetic construct

<400> SEQUENCE: 19

```
gatatcaaac tgcagcagtc aggggctgaa ctggcaagac ctggggcctc agtgaagatg     60

tcctgcaaga cttctggcta cacctttact aggtacacga tgcactgggt aaaacagagg    120

cctggacagg gtctggaatg gattggatac attaatccta gccgtggtta tactaattac    180

aatcagaagt tcaaggacaa ggccacattg actacagaca aatcctccag cacagcctac    240

atgcaactga gcagcctgac atctgaggac tctgcagtct attactgtgc aagatattat    300

gatgatcatt actgccttga ctactggggc caaggcacca ctctcacagt ctcctcaggt    360

ggtggtggtt ctggcggcgg cggctccggt ggtggtggtt ctgacattca gctgacccag    420

tctccagcaa tcatgtctgc atctccaggg gagaaggtca ccatgacctg cagagccagt    480

tcaagtgtaa gttacatgaa ctggtaccag cagaagtcag gcacctcccc caaaagatgg    540

atttatgaca catccaaagt ggcttctgga gtcccttatc gcttcagtgg cagtgggtct    600

gggacctcat actctctcac aatcagcagc atggaggctg aagatgctgc cacttattac    660

tgccaacagt ggagtagtaa cccgctcacg ttcggtgctg ggaccaagct ggagctgaaa    720

tccggaggtg gtggatccga gctcgtgatg acacagtctc catcctccct gactgtgaca    780

gcaggagaga aggtcactat gagctgcaag tccagtcaga gtctgttaaa cagtggaaat    840

caaaagaact acttgacctg gtaccagcag aaaccagggc agcctcctaa actgttgatc    900

tactgggcat ccactaggga atctggggtc cctgatcgct tcacaggcag tggatctgga    960

acagatttca ctctcaccat cagcagtgtg caggctgaag acctggcagt ttattactgt   1020

cagaatgatt atagttatcc gctcacgttc ggtgctggga ccaagcttga gatcaaaggt   1080

ggtggtggtt ctggcggcgg cggctccggt ggtggtggtt ctgaggtgca gctgctcgag   1140

cagtctggag ctgagctggt aaggcctggg acttcagtga agatatcctg caaggcttct   1200
```

```
ggatacgcct tcactaacta ctggctaggt tgggtaaagc agaggcctgg acatggactt   1260

gagtggattg gagatatttt ccctggaagt ggtaatatcc actacaatga gaagttcaag   1320

ggcaaagcca cactgactgc agacaaatct tcgagcacag cctatatgca gctcagtagc   1380

ctgacatttg aggactctgc tgtctatttc tgtgcaagac tgaggaactg ggacgagcct   1440

atggactact ggggccaagg gaccacggtc accgtctcct cacatcatca ccatcatcat   1500

tag                                                                  1503


<210> SEQ ID NO 20
<211> LENGTH: 500
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 20

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190

Tyr Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ser Gly Gly Gly Gly Ser Glu Leu Val Met Thr Gln Ser Pro Ser Ser
                245                 250                 255

Leu Thr Val Thr Ala Gly Glu Lys Val Thr Met Ser Cys Lys Ser Ser
            260                 265                 270

Gln Ser Leu Leu Asn Ser Gly Asn Gln Lys Asn Tyr Leu Thr Trp Tyr
        275                 280                 285

Gln Gln Lys Pro Gly Gln Pro Pro Lys Leu Leu Ile Tyr Trp Ala Ser
    290                 295                 300
```

```
Thr Arg Glu Ser Gly Val Pro Asp Arg Phe Thr Gly Ser Gly Ser Gly
305                 310                 315                 320

Thr Asp Phe Thr Leu Thr Ile Ser Ser Val Gln Ala Glu Asp Leu Ala
                325                 330                 335

Val Tyr Tyr Cys Gln Asn Asp Tyr Ser Tyr Pro Leu Thr Phe Gly Ala
            340                 345                 350

Gly Thr Lys Leu Glu Ile Lys Gly Gly Gly Gly Ser Gly Gly Gly Gly
        355                 360                 365

Ser Gly Gly Gly Gly Ser Glu Val Gln Leu Leu Glu Gln Ser Gly Ala
    370                 375                 380

Glu Leu Val Arg Pro Gly Thr Ser Val Lys Ile Ser Cys Lys Ala Ser
385                 390                 395                 400

Gly Tyr Ala Phe Thr Asn Tyr Trp Leu Gly Trp Val Lys Gln Arg Pro
                405                 410                 415

Gly His Gly Leu Glu Trp Ile Gly Asp Ile Phe Pro Gly Ser Gly Asn
            420                 425                 430

Ile His Tyr Asn Glu Lys Phe Lys Gly Lys Ala Thr Leu Thr Ala Asp
        435                 440                 445

Lys Ser Ser Ser Thr Ala Tyr Met Gln Leu Ser Ser Leu Thr Phe Glu
    450                 455                 460

Asp Ser Ala Val Tyr Phe Cys Ala Arg Leu Arg Asn Trp Asp Glu Pro
465                 470                 475                 480

Met Asp Tyr Trp Gly Gln Gly Thr Thr Val Thr Val Ser Ser His His
                485                 490                 495

His His His His
            500


<210> SEQ ID NO 21
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

ggagccgccg ccgccagaac caccaccacc tgaggagact gtgagagtgg tgccttg        57


<210> SEQ ID NO 22
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

ggcggcggcg gctccggtgg tggtggttct gacattcagc tgacccagtc tcc            53


<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

ggcggcggcg gctccggtgg tggtggttct gaggtgcagc tgctcgagca g              51
```

<210> SEQ ID NO 24
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ttttaagtcg acctaatgat gatgatgatg atgtgaggag acggtgaccg tgg 53

<210> SEQ ID NO 25
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ctgaaatccg gaggtggtgg atccgagctc gtgatgacac agtctccat 49

<210> SEQ ID NO 26
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ggagccgccg ccgccagaac caccaccacc tttgatctca agcttggtcc cag 53

<210> SEQ ID NO 27
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ggcggcggcg gctccggtgg tggtggttct gaggtgcagc tgctcgagc 49

<210> SEQ ID NO 28
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ttttaagtcg acctaatgat gatgatgatg atgtgaggag acggtgaccg tgg 53

<210> SEQ ID NO 29
<211> LENGTH: 1581
<212> TYPE: DNA
<213> ORGANISM: Artificial Sequence
<220> FEATURE:
<223> OTHER INFORMATION: Description of Artificial Sequence: Synthetic construct

<400> SEQUENCE: 29
atgggatgga gctgtatcat cctcttcttg gtagcaacag ctacaggtgt acactccgcg 60
cgcgagctcg tgatgaccca gactccactc tccctgcctg tcagtcttgg agatcaagcc 120

```
tccatctctt gcagatctag tcagagcctt gtacacagta atggaaacac ctatttacat    180

tggtacctgc agaagccagg ccagtctcca aagctcctga tctacaaagt ttccaaccga    240

ttttctgggg tcccagacag gttcagtggc agtggatcag ggacagattt cacactcaag    300

atcagcagag tggaggctga ggatctggga gtttatttct gctctcaaag tacacatgtt    360

ccgtacacgt tcggaggggg gaccaagctt gagatcaaag gtggtggtgg ttctggcggc    420

ggcggctccg gtggtggtgg ttctgaggtg cagctgctcg agcagtctgg agctgagctg    480

gtaaggcctg ggacttcagt gaagctgtcc tgcaaggctt ctggctacac cttcacaagc    540

tatggtttaa gctgggtgaa gcagagaact ggacagggcc ttgagtggat tggagaggtt    600

tatcctagaa ttggtaatgc ttactacaat gagaagttca agggcaaggc cacactgact    660

gcagacaaat cctccagcac agcgtccatg gagctccgca gcctgacatc tgaggactct    720

gcggtctatt tctgtgcaag acggggatcc tacggtagta actacgactg gtacttcgat    780

gtctggggcc aagggaccac ggtcaccgtc tcctccggag gtggtggatc cgatatcaaa    840

ctgcagcagt caggggctga actggcaaga cctggggcct cagtgaagat gtcctgcaag    900

acttctggct acacctttac taggtacacg atgcactggg taaaacagag gcctggacag    960

ggtctggaat ggattggata cattaatcct agccgtggtt atactaatta caatcagaag   1020

ttcaaggaca aggccacatt gactacagac aaatcctcca gcacagccta catgcaactg   1080

agcagcctga catctgagga ctctgcagtc tattactgtg caagatatta tgatgatcat   1140

tactgccttg actactgggg ccaaggcacc actctcacag tctcctcagt cgaaggtgga   1200

agtggaggtt ctggtggaag tggaggttca ggtggagtcg acgacattca gctgacccag   1260

tctccagcaa tcatgtctgc atctccaggg gagaaggtca ccatgacctg cagagccagt   1320

tcaagtgtaa gttacatgaa ctggtaccag cagaagtcag gcacctcccc caaaagatgg   1380

atttatgaca catccaaagt ggcttctgga gtcccttatc gcttcagtgg cagtgggtct   1440

gggacctcat actctctcac aatcagcagc atggaggctg aagatgctgc cacttattac   1500

tgccaacagt ggagtagtaa cccgctcacg ttcggtgctg ggaccaagct ggagctgaaa   1560

catcatcacc atcatcatta g                                             1581
```

```
<210> SEQ ID NO 30
<211> LENGTH: 526
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 30

Met Gly Trp Ser Cys Ile Ile Leu Phe Leu Val Ala Thr Ala Thr Gly
1               5                   10                  15

Val His Ser Ala Arg Glu Leu Val Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Ser Asn Gly Asn Thr Tyr Leu His Trp Tyr Leu Gln
    50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95
```

```
Phe Thr Leu Lys Ile Ser Arg Val Glu Ala Glu Asp Leu Gly Val Tyr
            100                 105                 110

Phe Cys Ser Gln Ser Thr His Val Pro Tyr Thr Phe Gly Gly Gly Thr
        115                 120                 125

Lys Leu Glu Ile Lys Gly Gly Gly Gly Ser Gly Gly Gly Gly Ser Gly
    130                 135                 140

Gly Gly Gly Ser Glu Val Gln Leu Leu Glu Gln Ser Gly Ala Glu Leu
145                 150                 155                 160

Val Arg Pro Gly Thr Ser Val Lys Leu Ser Cys Lys Ala Ser Gly Tyr
                165                 170                 175

Thr Phe Thr Ser Tyr Gly Leu Ser Trp Val Lys Gln Arg Thr Gly Gln
            180                 185                 190

Gly Leu Glu Trp Ile Gly Glu Val Tyr Pro Arg Ile Gly Asn Ala Tyr
        195                 200                 205

Tyr Asn Glu Lys Phe Lys Gly Lys Ala Thr Leu Thr Ala Asp Lys Ser
    210                 215                 220

Ser Ser Thr Ala Ser Met Glu Leu Arg Ser Leu Thr Ser Glu Asp Ser
225                 230                 235                 240

Ala Val Tyr Phe Cys Ala Arg Arg Gly Ser Tyr Gly Ser Asn Tyr Asp
                245                 250                 255

Trp Tyr Phe Asp Val Trp Gly Gln Gly Thr Thr Val Thr Val Ser Ser
            260                 265                 270

Gly Gly Gly Gly Ser Asp Ile Lys Leu Gln Gln Ser Gly Ala Glu Leu
        275                 280                 285

Ala Arg Pro Gly Ala Ser Val Lys Met Ser Cys Lys Thr Ser Gly Tyr
    290                 295                 300

Thr Phe Thr Arg Tyr Thr Met His Trp Val Lys Gln Arg Pro Gly Gln
305                 310                 315                 320

Gly Leu Glu Trp Ile Gly Tyr Ile Asn Pro Ser Arg Gly Tyr Thr Asn
                325                 330                 335

Tyr Asn Gln Lys Phe Lys Asp Lys Ala Thr Leu Thr Thr Asp Lys Ser
            340                 345                 350

Ser Ser Thr Ala Tyr Met Gln Leu Ser Ser Leu Thr Ser Glu Asp Ser
        355                 360                 365

Ala Val Tyr Tyr Cys Ala Arg Tyr Tyr Asp Asp His Tyr Cys Leu Asp
    370                 375                 380

Tyr Trp Gly Gln Gly Thr Thr Leu Thr Val Ser Ser Val Glu Gly Gly
385                 390                 395                 400

Ser Gly Gly Ser Gly Gly Ser Gly Gly Ser Gly Gly Val Asp Asp Ile
                405                 410                 415

Gln Leu Thr Gln Ser Pro Ala Ile Met Ser Ala Ser Pro Gly Glu Lys
            420                 425                 430

Val Thr Met Thr Cys Arg Ala Ser Ser Ser Val Ser Tyr Met Asn Trp
        435                 440                 445

Tyr Gln Gln Lys Ser Gly Thr Ser Pro Lys Arg Trp Ile Tyr Asp Thr
    450                 455                 460

Ser Lys Val Ala Ser Gly Val Pro Tyr Arg Phe Ser Gly Ser Gly Ser
465                 470                 475                 480

Gly Thr Ser Tyr Ser Leu Thr Ile Ser Ser Met Glu Ala Glu Asp Ala
                485                 490                 495

Ala Thr Tyr Tyr Cys Gln Gln Trp Ser Ser Asn Pro Leu Thr Phe Gly
            500                 505                 510
```

```
Ala Gly Thr Lys Leu Glu Leu Lys His His His His His His
        515                 520                 525


<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

ggatgcgcgc gagctcgtga tgacccagac tccactctcc                          40


<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

ggttctggcg gcggcggctc cggtggtggt ggttctgagg tgcagctgct cgacagtctg     60


<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

gtgctccgga ggagacggtg accgtggtcc cttggcccca g                         41


<210> SEQ ID NO 34
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

ccggagccgc cgccgccaga accaccacca cctttgatct caagcttggt ccc            53


<210> SEQ ID NO 35
<211> LENGTH: 1548
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 35

atgggatgga gctgtatcat cctcttcttg gtagcaacag ctacaggtgt acactccgag     60

ctcgtcatga cccagtctcc atcttatctt gctgcatctc ctggagaaac cattactatt    120

aattgcaggg caagtaagag cattagcaaa tatttagcct ggtatcaaga gaaacctggg    180

aaaactaata agcttcttat ctactctgga tccactttgc aatctggaat tccatcaagg    240

ttcagtggca gtggatctgg tacagatttc actctcacca tcagtagcct ggagcctgaa    300

gattttgcaa tgtattactg tcaacagcat aatgaatatc cgtacacgtt cggagggggg    360

accaagcttg agatcaaagg tggtggtggt tctggcggcg gcggctccgg tggtggtggt    420
```

```
tctgaggtgc agctgctcga gcagtctgga gctgagctgg tgaaacctgg ggcctcagtg    480

aagatatcct gcaaggcttc tggatacgcc ttcactaact actggctagg ttgggtaaag    540

cagaggcctg gacatggact tgagtggatt ggagatcttt tccctggaag tggtaatact    600

cactacaatg agaggttcag gggcaaagcc acactgactg cagacaaatc ctcgagcaca    660

gcctttatgc agctcagtag cctgacatct gaggactctg ctgtctattt ctgtgcaaga    720

ttgaggaact gggacgaggc tatggactac tggggccaag ggaccacggt caccgtctcc    780

tccggaggtg gtggatccga tatcaaactg cagcagtcag ggctgaact ggcaagacct    840

ggggcctcag tgaagatgtc ctgcaagact tctggctaca cctttactag gtacacgatg    900

cactgggtaa aacagaggcc tggacagggt ctggaatgga ttggatacat taatcctagc    960

cgtggttata ctaattacaa tcagaagttc aaggacaagg ccacattgac tacagacaaa   1020

tcctccagca cagcctacat gcaactgagc agcctgacat ctgaggactc tgcagtctat   1080

tactgtgcaa gatattatga tgatcattac tgccttgact actggggcca aggcaccact   1140

ctcacagtct cctcagtcga aggtggaagt ggaggttctg gtggaagtgg aggttcaggt   1200

ggagtcgacg acattcagct gacccagtct ccagcaatca tgtctgcatc tccaggggag   1260

aaggtcacca tgacctgcag agccagttca agtgtaagtt acatgaactg gtaccagcag   1320

aagtcaggca cctcccccaa aagatggatt tatgacacat ccaaagtggc ttctggagtc   1380

ccttatcgct tcagtggcag tgggtctggg acctcatact ctctcacaat cagcagcatg   1440

gaggctgaag atgctgccac ttattactgc caacagtgga gtagtaaccc gctcacgttc   1500

ggtgctggga ccaagctgga gctgaaacat catcaccatc atcattag                1548
```

```
<210> SEQ ID NO 36
<211> LENGTH: 515
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 36

Met Gly Trp Ser Cys Ile Ile Leu Phe Leu Val Ala Thr Ala Thr Gly
1               5                   10                  15

Val His Ser Glu Leu Val Met Thr Gln Ser Pro Ser Tyr Leu Ala Ala
            20                  25                  30

Ser Pro Gly Glu Thr Ile Thr Ile Asn Cys Arg Ala Ser Lys Ser Ile
        35                  40                  45

Ser Lys Tyr Leu Ala Trp Tyr Gln Glu Lys Pro Gly Lys Thr Asn Lys
    50                  55                  60

Leu Leu Ile Tyr Ser Gly Ser Thr Leu Gln Ser Gly Ile Pro Ser Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Met Tyr Tyr Cys Gln Gln His Asn Glu
            100                 105                 110

Tyr Pro Tyr Thr Phe Gly Gly Gly Thr Lys Leu Glu Ile Lys Gly Gly
        115                 120                 125

Gly Gly Ser Gly Gly Gly Gly Ser Gly Gly Gly Gly Ser Glu Val Gln
    130                 135                 140

Leu Leu Glu Gln Ser Gly Ala Glu Leu Val Lys Pro Gly Ala Ser Val
145                 150                 155                 160
```

```
Lys Ile Ser Cys Lys Ala Ser Gly Tyr Ala Phe Thr Asn Tyr Trp Leu
                165                 170                 175

Gly Trp Val Lys Gln Arg Pro Gly His Gly Leu Glu Trp Ile Gly Asp
            180                 185                 190

Leu Phe Pro Gly Ser Gly Asn Thr His Tyr Asn Glu Arg Phe Arg Gly
        195                 200                 205

Lys Ala Thr Leu Thr Ala Asp Lys Ser Ser Ser Thr Ala Phe Met Gln
    210                 215                 220

Leu Ser Ser Leu Thr Ser Glu Asp Ser Ala Val Tyr Phe Cys Ala Arg
225                 230                 235                 240

Leu Arg Asn Trp Asp Glu Ala Met Asp Tyr Trp Gly Gln Gly Thr Thr
                245                 250                 255

Val Thr Val Ser Ser Gly Gly Gly Gly Ser Asp Ile Lys Leu Gln Gln
            260                 265                 270

Ser Gly Ala Glu Leu Ala Arg Pro Gly Ala Ser Val Lys Met Ser Cys
        275                 280                 285

Lys Thr Ser Gly Tyr Thr Phe Thr Arg Tyr Thr Met His Trp Val Lys
    290                 295                 300

Gln Arg Pro Gly Gln Gly Leu Glu Trp Ile Gly Tyr Ile Asn Pro Ser
305                 310                 315                 320

Arg Gly Tyr Thr Asn Tyr Asn Gln Lys Phe Lys Asp Lys Ala Thr Leu
                325                 330                 335

Thr Thr Asp Lys Ser Ser Ser Thr Ala Tyr Met Gln Leu Ser Ser Leu
            340                 345                 350

Thr Ser Glu Asp Ser Ala Val Tyr Tyr Cys Ala Arg Tyr Tyr Asp Asp
        355                 360                 365

His Tyr Cys Leu Asp Tyr Trp Gly Gln Gly Thr Thr Leu Thr Val Ser
    370                 375                 380

Ser Val Glu Gly Gly Ser Gly Gly Ser Gly Gly Ser Gly Gly Ser Gly
385                 390                 395                 400

Gly Val Asp Asp Ile Gln Leu Thr Gln Ser Pro Ala Ile Met Ser Ala
                405                 410                 415

Ser Pro Gly Glu Lys Val Thr Met Thr Cys Arg Ala Ser Ser Ser Val
            420                 425                 430

Ser Tyr Met Asn Trp Tyr Gln Gln Lys Ser Gly Thr Ser Pro Lys Arg
        435                 440                 445

Trp Ile Tyr Asp Thr Ser Lys Val Ala Ser Gly Val Pro Tyr Arg Phe
    450                 455                 460

Ser Gly Ser Gly Ser Gly Thr Ser Tyr Ser Leu Thr Ile Ser Ser Met
465                 470                 475                 480

Glu Ala Glu Asp Ala Ala Thr Tyr Tyr Cys Gln Gln Trp Ser Ser Asn
                485                 490                 495

Pro Leu Thr Phe Gly Ala Gly Thr Lys Leu Glu Leu Lys His His His
            500                 505                 510

His His His
        515


<210> SEQ ID NO 37
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 37
ggattgtaca ctccgagctc gtcatgaccc agtctccatc ttatcttgct gc 52

<210> SEQ ID NO 38
<211> LENGTH: 1566
<212> TYPE: DNA
<213> ORGANISM: Artificial Sequence
<220> FEATURE:
<223> OTHER INFORMATION: Description of Artificial Sequence: Synthetic construct

<400> SEQUENCE: 38
atgggatgga gctgtatcat cctcttcttg gtagcaacag ctacaggtgt acactccgag 60
ctcgtgatga cacagtctcc atcctccctg agtgtgtcag caggagagaa ggtcactatg 120
agctgcaagt ccagtcagag tctgttaaac agtggaaatc aaaagaacta cttggcctgg 180
taccagcaga aaccagggca gcctcctaaa ctgttgatct acggggcatc cactagggaa 240
tctggggtcc ctgatcgctt cacaggcagt ggatctggaa cagatttcac tctcaccatc 300
agcagtgtgc aggctgaaga cctggcagtt tattactgtc agaatgatta tagttatccg 360
tacacgttcg gaggggggac caagcttgag atcaaaggtg gtggtggttc tggcggcggc 420
ggctccggtg gtggtggttc tgaggtgcag ctgctcgagc agtctggagc tgagctggta 480
aggcctggga cttcagtgaa gatatcctgc aaggcttctg gatacgcctt cactaactac 540
tggctaggtt gggttaagca gaggcctgga catggacttg aatgggttgg agatattttc 600
cctggaagtg gtaatgctca ctacaatgag aagttcaagg gcaaagccac actgactgca 660
gacaagtcct cgtacacagc ctatatgcag ctcagtagcc tgacatctga ggactctgct 720
gtctatttct gtgcaagatt gcggaactgg gacgaggcta tggactactg gggccaaggg 780
accacggtca ccgtctcctc cggaggtggt ggatccgata tcaaactgca gcagtcaggg 840
gctgaactgg caagacctgg ggcctcagtg aagatgtcct gcaagacttc tggctacacc 900
tttactaggt acacgatgca ctgggtaaaa cagaggcctg gacagggtct ggaatggatt 960
ggatacatta atcctagccg tggttatact aattacaatc agaagttcaa ggacaaggcc 1020
acattgacta cagacaaatc ctccagcaca gcctacatgc aactgagcag cctgacatct 1080
gaggactctg cagtctatta ctgtgcaaga tattatgatg atcattactg ccttgactac 1140
tggggccaag gcaccactct cacagtctcc tcagtcgaag gtggaagtgg aggttctggt 1200
ggaagtggag gttcaggtgg agtcgacgac attcagctga cccagtctcc agcaatcatg 1260
tctgcatctc caggggagaa ggtcaccatg acctgcagag ccagttcaag tgtaagttac 1320
atgaactggt accagcagaa gtcaggcacc tcccccaaaa gatggattta tgacacatcc 1380
aaagtggctt ctggagtccc ttatcgcttc agtggcagtg ggtctgggac ctcatactct 1440
ctcacaatca gcagcatgga ggctgaagat gctgccactt attactgcca acagtggagt 1500
agtaacccgc tcacgttcgg tgctgggacc aagctggagc tgaaacatca tcaccatcat 1560
cattag 1566

<210> SEQ ID NO 39
<211> LENGTH: 521
<212> TYPE: PRT
<213> ORGANISM: Artificial Sequence
<220> FEATURE:
<223> OTHER INFORMATION: Description of Artificial Sequence: Synthetic construct

<400> SEQUENCE: 39

```
Met Gly Trp Ser Cys Ile Ile Leu Phe Leu Val Ala Thr Ala Thr Gly
1               5                   10                  15

Val His Ser Glu Leu Val Met Thr Gln Ser Pro Ser Ser Leu Ser Val
            20                  25                  30

Ser Ala Gly Glu Lys Val Thr Met Ser Cys Lys Ser Ser Gln Ser Leu
        35                  40                  45

Leu Asn Ser Gly Asn Gln Lys Asn Tyr Leu Ala Trp Tyr Gln Gln Lys
    50                  55                  60

Pro Gly Gln Pro Pro Lys Leu Leu Ile Tyr Gly Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Tyr Thr Phe Gly Gly Gly Thr Lys
        115                 120                 125

Leu Glu Ile Lys Gly Gly Gly Gly Ser Gly Gly Gly Gly Ser Gly Gly
    130                 135                 140

Gly Gly Ser Glu Val Gln Leu Leu Glu Gln Ser Gly Ala Glu Leu Val
145                 150                 155                 160

Arg Pro Gly Thr Ser Val Lys Ile Ser Cys Lys Ala Ser Gly Tyr Ala
                165                 170                 175

Phe Thr Asn Tyr Trp Leu Gly Trp Val Lys Gln Arg Pro Gly His Gly
            180                 185                 190

Leu Glu Trp Val Gly Asp Ile Phe Pro Gly Ser Gly Asn Ala His Tyr
        195                 200                 205

Asn Glu Lys Phe Lys Gly Lys Ala Thr Leu Thr Ala Asp Lys Ser Ser
    210                 215                 220

Tyr Thr Ala Tyr Met Gln Leu Ser Ser Leu Thr Ser Glu Asp Ser Ala
225                 230                 235                 240

Val Tyr Phe Cys Ala Arg Leu Arg Asn Trp Asp Glu Ala Met Asp Tyr
                245                 250                 255

Trp Gly Gln Gly Thr Thr Val Thr Val Ser Ser Gly Gly Gly Gly Ser
            260                 265                 270

Asp Ile Lys Leu Gln Gln Ser Gly Ala Glu Leu Ala Arg Pro Gly Ala
        275                 280                 285

Ser Val Lys Met Ser Cys Lys Thr Ser Gly Tyr Thr Phe Thr Arg Tyr
    290                 295                 300

Thr Met His Trp Val Lys Gln Arg Pro Gly Gln Gly Leu Glu Trp Ile
305                 310                 315                 320

Gly Tyr Ile Asn Pro Ser Arg Gly Tyr Thr Asn Tyr Asn Gln Lys Phe
                325                 330                 335

Lys Asp Lys Ala Thr Leu Thr Thr Asp Lys Ser Ser Ser Thr Ala Tyr
            340                 345                 350

Met Gln Leu Ser Ser Leu Thr Ser Glu Asp Ser Ala Val Tyr Tyr Cys
        355                 360                 365

Ala Arg Tyr Tyr Asp Asp His Tyr Cys Leu Asp Tyr Trp Gly Gln Gly
    370                 375                 380

Thr Thr Leu Thr Val Ser Ser Val Glu Gly Gly Ser Gly Gly Ser Gly
385                 390                 395                 400

Gly Ser Gly Gly Ser Gly Gly Val Asp Asp Ile Gln Leu Thr Gln Ser
                405                 410                 415
```

```
Pro Ala Ile Met Ser Ala Ser Pro Gly Glu Lys Val Thr Met Thr Cys
            420                 425                 430

Arg Ala Ser Ser Ser Val Ser Tyr Met Asn Trp Tyr Gln Gln Lys Ser
        435                 440                 445

Gly Thr Ser Pro Lys Arg Trp Ile Tyr Asp Thr Ser Lys Val Ala Ser
    450                 455                 460

Gly Val Pro Tyr Arg Phe Ser Gly Ser Gly Ser Gly Thr Ser Tyr Ser
465                 470                 475                 480

Leu Thr Ile Ser Ser Met Glu Ala Glu Asp Ala Ala Thr Tyr Tyr Cys
                485                 490                 495

Gln Gln Trp Ser Ser Asn Pro Leu Thr Phe Gly Ala Gly Thr Lys Leu
            500                 505                 510

Glu Leu Lys His His His His His His
        515                 520


<210> SEQ ID NO 40
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

ggattgtaca ctccgagctc gtgatgacac agtctccatc ctcc                  44


<210> SEQ ID NO 41
<211> LENGTH: 1581
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 41

atgggatgga gctgtatcat cctcttcttg gtagcaacag ctacaggtgt acactccgcg     60

cgcgagctcg tgatgaccca gactccactc tccctgcctg tcagtcttgg agatcaagcc    120

tccatctctt gcagatctag tcagagcctt gtacacagta atggaaacac ctatttacat    180

tggtacctgc agaagccagg ccagtctcca aagctcctga tctacaaagt ttccaaccga    240

ttttctgggg tcccagacag gttcagtggc agtggatcag ggacagattt cacactcaag    300

atcagcagag tggaggctga ggatctggga gtttatttct gctctcaaag tacacatgtt    360

ccgtacacgt tcggaggggg gaccaagctt gagatcaaag gtggtggtgg ttctggcggc    420

ggcggctccg gtggtggtgg ttctgaggtg cagctgctcg agcagtctgg agctgagctg    480

gcgaggcctg gggcttcagt gaagctgtcc tgcaaggctt ctggctacac cttcacaaac    540

tatggtttaa gctgggtgaa gcagaggcct ggacaggtcc ttgagtggat tggagaggtt    600

tatcctagaa ttggtaatgc ttactacaat gagaagttca agggcaaggc cacactgact    660

gcagacaaat cctccagcac agcgtccatg gagctccgca gcctgacctc tgaggactct    720

gcggtctatt tctgtgcaag acggggatcc tacgatacta actacgactg gtacttcgat    780

gtctggggcc aagggaccac ggtcaccgtc tcctccggag gtggtggatc cgatatcaaa    840

ctgcagcagt caggggctga actggcaaga cctggggcct cagtgaagat gtcctgcaag    900

acttctggct acacctttac taggtacacg atgcactggg taaaacagag gcctggacag    960

ggtctggaat ggattggata cattaatcct agccgtggtt atactaatta caatcagaag   1020
```

```
ttcaaggaca aggccacatt gactacagac aaatcctcca gcacagccta catgcaactg   1080

agcagcctga catctgagga ctctgcagtc tattactgtg caagatatta tgatgatcat   1140

tactgccttg actactgggg ccaaggcacc actctcacag tctcctcagt cgaaggtgga   1200

agtggaggtt ctggtggaag tggaggttca ggtggagtcg acgacattca gctgacccag   1260

tctccagcaa tcatgtctgc atctccaggg gagaaggtca ccatgacctg cagagccagt   1320

tcaagtgtaa gttacatgaa ctggtaccag cagaagtcag gcacctcccc caaaagatgg   1380

atttatgaca catccaaagt ggcttctgga gtcccttatc gcttcagtgg cagtgggtct   1440

gggacctcat actctctcac aatcagcagc atggaggctg aagatgctgc cacttattac   1500

tgccaacagt ggagtagtaa cccgctcacg ttcggtgctg ggaccaagct ggagctgaaa   1560

catcatcacc atcatcatta g                                             1581
```

```
<210> SEQ ID NO 42
<211> LENGTH: 526
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 42

Met Gly Trp Ser Cys Ile Ile Leu Phe Leu Val Ala Thr Ala Thr Gly
1               5                   10                  15

Val His Ser Ala Arg Glu Leu Val Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Ser Asn Gly Asn Thr Tyr Leu His Trp Tyr Leu Gln
    50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Ser Thr His Val Pro Tyr Thr Phe Gly Gly Gly Thr
        115                 120                 125

Lys Leu Glu Ile Lys Gly Gly Gly Gly Ser Gly Gly Gly Gly Ser Gly
    130                 135                 140

Gly Gly Gly Ser Glu Val Gln Leu Leu Glu Gln Ser Gly Ala Glu Leu
145                 150                 155                 160

Ala Arg Pro Gly Ala Ser Val Lys Leu Ser Cys Lys Ala Ser Gly Tyr
                165                 170                 175

Thr Phe Thr Asn Tyr Gly Leu Ser Trp Val Lys Gln Arg Pro Gly Gln
            180                 185                 190

Val Leu Glu Trp Ile Gly Glu Val Tyr Pro Arg Ile Gly Asn Ala Tyr
        195                 200                 205

Tyr Asn Glu Lys Phe Lys Gly Lys Ala Thr Leu Thr Ala Asp Lys Ser
    210                 215                 220

Ser Ser Thr Ala Ser Met Glu Leu Arg Ser Leu Thr Ser Glu Asp Ser
225                 230                 235                 240

Ala Val Tyr Phe Cys Ala Arg Arg Gly Ser Tyr Asp Thr Asn Tyr Asp
                245                 250                 255
```

```
Trp Tyr Phe Asp Val Trp Gly Gln Gly Thr Thr Val Thr Val Ser Ser
            260                 265                 270

Gly Gly Gly Gly Ser Asp Ile Lys Leu Gln Gln Ser Gly Ala Glu Leu
        275                 280                 285

Ala Arg Pro Gly Ala Ser Val Lys Met Ser Cys Lys Thr Ser Gly Tyr
    290                 295                 300

Thr Phe Thr Arg Tyr Thr Met His Trp Val Lys Gln Arg Pro Gly Gln
305                 310                 315                 320

Gly Leu Glu Trp Ile Gly Tyr Ile Asn Pro Ser Arg Gly Tyr Thr Asn
                325                 330                 335

Tyr Asn Gln Lys Phe Lys Asp Lys Ala Thr Leu Thr Thr Asp Lys Ser
            340                 345                 350

Ser Ser Thr Ala Tyr Met Gln Leu Ser Ser Leu Thr Ser Glu Asp Ser
        355                 360                 365

Ala Val Tyr Tyr Cys Ala Arg Tyr Tyr Asp Asp His Tyr Cys Leu Asp
    370                 375                 380

Tyr Trp Gly Gln Gly Thr Thr Leu Thr Val Ser Ser Val Glu Gly Gly
385                 390                 395                 400

Ser Gly Gly Ser Gly Gly Ser Gly Gly Ser Gly Gly Val Asp Asp Ile
                405                 410                 415

Gln Leu Thr Gln Ser Pro Ala Ile Met Ser Ala Ser Pro Gly Glu Lys
            420                 425                 430

Val Thr Met Thr Cys Arg Ala Ser Ser Ser Val Ser Tyr Met Asn Trp
        435                 440                 445

Tyr Gln Gln Lys Ser Gly Thr Ser Pro Lys Arg Trp Ile Tyr Asp Thr
    450                 455                 460

Ser Lys Val Ala Ser Gly Val Pro Tyr Arg Phe Ser Gly Ser Gly Ser
465                 470                 475                 480

Gly Thr Ser Tyr Ser Leu Thr Ile Ser Ser Met Glu Ala Glu Asp Ala
                485                 490                 495

Ala Thr Tyr Tyr Cys Gln Gln Trp Ser Ser Asn Pro Leu Thr Phe Gly
            500                 505                 510

Ala Gly Thr Lys Leu Glu Leu Lys His His His His His His
        515                 520                 525
```

<210> SEQ ID NO 43
<211> LENGTH: 1566
<212> TYPE: DNA
<213> ORGANISM: Artificial Sequence
<220> FEATURE:
<223> OTHER INFORMATION: Description of Artificial Sequence: Synthetic construct

<400> SEQUENCE: 43

```
atgggatgga gctgtatcat cctcttcttg gtagcaacag ctacaggtgt acactccgag      60

ctcgtgatga cacagtctcc atcctccctg actgtgacag caggagagaa ggtcactatg     120

agctgcaagt ccagtcagag tctgttaaac agtggaaatc aaaagaacta cttgacctgg     180

taccagcaga aaccagggca gcctcctaaa ctgttgatct actgggcatc cactagggaa     240

tctggggtcc ctgatcgctt cacaggcagt ggatctggaa cagatttcac tctcaccatc     300

agcagtgtgc aggctgaaga cctggcagtt tattactgtc agaatgatta tagttatccg     360

ctcacgttcg gtgctgggac caagcttgag atcaaaggtg gtggtggttc tggcggcggc     420

ggctccggtg gtggtggttc tgaggtgcag ctgctcgagc agtctggagc tgagctggta     480

aggcctggga cttcagtgaa gatatcctgc aaggcttctg gatacgcctt cactaactac     540
```

```
tggctaggtt gggtaaagca gaggcctgga catggacttg agtggattgg agatattttc    600

cctggaagtg gtaatatcca ctacaatgag aagttcaagg gcaaagccac actgactgca    660

gacaaatctt cgagcacagc ctatatgcag ctcagtagcc tgacatttga ggactctgct    720

gtctatttct gtgcaagact gaggaactgg gacgagccta tggactactg gggccaaggg    780

accacggtca ccgtctcctc cggaggtggt ggatccgata tcaaactgca gcagtcaggg    840

gctgaactgg caagacctgg ggcctcagtg aagatgtcct gcaagacttc tggctacacc    900

tttactaggt acacgatgca ctgggtaaaa cagaggcctg gacagggtct ggaatggatt    960

ggatacatta atcctagccg tggttatact aattacaatc agaagttcaa ggacaaggcc   1020

acattgacta cagacaaatc ctccagcaca gcctacatgc aactgagcag cctgacatct   1080

gaggactctg cagtctatta ctgtgcaaga tattatgatg atcattactg ccttgactac   1140

tggggccaag gcaccactct cacagtctcc tcagtcgaag gtggaagtgg aggttctggt   1200

ggaagtggag gttcaggtgg agtcgacgac attcagctga cccagtctcc agcaatcatg   1260

tctgcatctc caggggagaa ggtcaccatg acctgcagag ccagttcaag tgtaagttac   1320

atgaactggt accagcagaa gtcaggcacc tcccccaaaa gatggattta tgacacatcc   1380

aaagtggctt ctggagtccc ttatcgcttc agtggcagtg ggtctgggac ctcatactct   1440

ctcacaatca gcagcatgga ggctgaagat gctgccactt attactgcca acagtggagt   1500

agtaacccgc tcacgttcgg tgctgggacc aagctggagc tgaaacatca tcaccatcat   1560

cattag                                                              1566


<210> SEQ ID NO 44
<211> LENGTH: 521
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 44

Met Gly Trp Ser Cys Ile Ile Leu Phe Leu Val Ala Thr Ala Thr Gly
1               5                   10                  15

Val His Ser Glu Leu Val Met Thr Gln Ser Pro Ser Ser Leu Thr Val
            20                  25                  30

Thr Ala Gly Glu Lys Val Thr Met Ser Cys Lys Ser Ser Gln Ser Leu
        35                  40                  45

Leu Asn Ser Gly Asn Gln Lys Asn Tyr Leu Thr Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Leu Thr Phe Gly Ala Gly Thr Lys
        115                 120                 125

Leu Glu Ile Lys Gly Gly Gly Gly Ser Gly Gly Gly Gly Ser Gly Gly
    130                 135                 140

Gly Gly Ser Glu Val Gln Leu Leu Glu Gln Ser Gly Ala Glu Leu Val
145                 150                 155                 160

Arg Pro Gly Thr Ser Val Lys Ile Ser Cys Lys Ala Ser Gly Tyr Ala
```

```
                165                 170                 175

Phe Thr Asn Tyr Trp Leu Gly Trp Val Lys Gln Arg Pro Gly His Gly
            180                 185                 190

Leu Glu Trp Ile Gly Asp Ile Phe Pro Gly Ser Gly Asn Ile His Tyr
        195                 200                 205

Asn Glu Lys Phe Lys Gly Lys Ala Thr Leu Thr Ala Asp Lys Ser Ser
    210                 215                 220

Ser Thr Ala Tyr Met Gln Leu Ser Ser Leu Thr Phe Glu Asp Ser Ala
225                 230                 235                 240

Val Tyr Phe Cys Ala Arg Leu Arg Asn Trp Asp Glu Pro Met Asp Tyr
                245                 250                 255

Trp Gly Gln Gly Thr Thr Val Thr Val Ser Ser Gly Gly Gly Gly Ser
            260                 265                 270

Asp Ile Lys Leu Gln Gln Ser Gly Ala Glu Leu Ala Arg Pro Gly Ala
        275                 280                 285

Ser Val Lys Met Ser Cys Lys Thr Ser Gly Tyr Thr Phe Thr Arg Tyr
    290                 295                 300

Thr Met His Trp Val Lys Gln Arg Pro Gly Gln Gly Leu Glu Trp Ile
305                 310                 315                 320

Gly Tyr Ile Asn Pro Ser Arg Gly Tyr Thr Asn Tyr Asn Gln Lys Phe
                325                 330                 335

Lys Asp Lys Ala Thr Leu Thr Thr Asp Lys Ser Ser Ser Thr Ala Tyr
            340                 345                 350

Met Gln Leu Ser Ser Leu Thr Ser Glu Asp Ser Ala Val Tyr Tyr Cys
        355                 360                 365

Ala Arg Tyr Tyr Asp Asp His Tyr Cys Leu Asp Tyr Trp Gly Gln Gly
    370                 375                 380

Thr Thr Leu Thr Val Ser Ser Val Glu Gly Gly Ser Gly Gly Ser Gly
385                 390                 395                 400

Gly Ser Gly Gly Ser Gly Gly Val Asp Asp Ile Gln Leu Thr Gln Ser
                405                 410                 415

Pro Ala Ile Met Ser Ala Ser Pro Gly Glu Lys Val Thr Met Thr Cys
            420                 425                 430

Arg Ala Ser Ser Ser Val Ser Tyr Met Asn Trp Tyr Gln Gln Lys Ser
        435                 440                 445

Gly Thr Ser Pro Lys Arg Trp Ile Tyr Asp Thr Ser Lys Val Ala Ser
    450                 455                 460

Gly Val Pro Tyr Arg Phe Ser Gly Ser Gly Ser Gly Thr Ser Tyr Ser
465                 470                 475                 480

Leu Thr Ile Ser Ser Met Glu Ala Glu Asp Ala Ala Thr Tyr Tyr Cys
                485                 490                 495

Gln Gln Trp Ser Ser Asn Pro Leu Thr Phe Gly Ala Gly Thr Lys Leu
            500                 505                 510

Glu Leu Lys His His His His His His
        515                 520


<210> SEQ ID NO 45
<211> LENGTH: 1494
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 45
```

```
gatatcaaac tgcagcagtc aggggctgaa ctggcaagac ctggggcctc agtgaagatg     60

tcctgcaaga cttctggcta cacctttact aggtacacga tgcactgggt aaaacagagg    120

cctggacagg gtctggaatg gattggatac attaatccta gccgtggtta tactaattac    180

aatcagaagt tcaaggacaa ggccacattg actacagaca aatcctccag cacagcctac    240

atgcaactga gcagcctgac atctgaggac tctgcagtct attactgtgc aagatattat    300

gatgatcatt actgccttga ctactggggc caaggcacca ctctcacagt ctcctcagtc    360

gaaggtggaa gtggaggttc tggtggaagt ggaggttcag gtggagtcga cgacattcag    420

ctgacccagt ctccagcaat catgtctgca tctccagggg agaaggtcac catgacctgc    480

agagccagtt caagtgtaag ttacatgaac tggtaccagc agaagtcagg cacctccccc    540

aaaagatgga tttatgacac atccaaagtg gcttctggag tcccttatcg cttcagtggc    600

agtgggtctg ggacctcata ctctctcaca atcagcagca tggaggctga agatgctgcc    660

acttattact gccaacagtg gagtagtaac ccgctcacgt tcggtgctgg gaccaagctg    720

gagctgaaat ccggaggtgg tggatccgag gtgcagctgc tcgagcagtc tggagctgag    780

ctggtgaaac ctggggcctc agtgaagata tcctgcaagg cttctggata cgccttcact    840

aactactggc taggttgggt aaagcagagg cctggacatg gacttgagtg gattggagat    900

cttttccctg gaagtggtaa tactcactac aatgagaggt tcaggggcaa agccacactg    960

actgcagaca aatcctcgag cacagccttt atgcagctca gtagcctgac atctgaggac   1020

tctgctgtct atttctgtgc aagattgagg aactgggacg aggctatgga ctactggggc   1080

caagggacca cggtcaccgt ctcctcaggt ggtggtggtt ctggcggcgg cggctccggt   1140

ggtggtggtt ctgagctcgt catgacccag tctccatctt atcttgctgc atctcctgga   1200

gaaaccatta ctattaattg cagggcaagt aagagcatta gcaaatattt agcctggtat   1260

caagagaaac ctgggaaaac taataagctt cttatctact ctggatccac tttgcaatct   1320

ggaattccat caaggttcag tggcagtgga tctggtacag atttcactct caccatcagt   1380

agcctggagc ctgaagattt tgcaatgtat tactgtcaac agcataatga atatccgtac   1440

acgttcggag gggggaccaa gcttgagatc aaacatcatc accatcatca ttag         1494
```

```
<210> SEQ ID NO 46
<211> LENGTH: 497
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 46

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ser Gly Gly Gly Gly Ser Glu Val Gln Leu Leu Glu Gln
                245                 250                 255

Ser Gly Ala Glu Leu Val Lys Pro Gly Ala Ser Val Lys Ile Ser Cys
            260                 265                 270

Lys Ala Ser Gly Tyr Ala Phe Thr Asn Tyr Trp Leu Gly Trp Val Lys
        275                 280                 285

Gln Arg Pro Gly His Gly Leu Glu Trp Ile Gly Asp Leu Phe Pro Gly
    290                 295                 300

Ser Gly Asn Thr His Tyr Asn Glu Arg Phe Arg Gly Lys Ala Thr Leu
305                 310                 315                 320

Thr Ala Asp Lys Ser Ser Ser Thr Ala Phe Met Gln Leu Ser Ser Leu
                325                 330                 335

Thr Ser Glu Asp Ser Ala Val Tyr Phe Cys Ala Arg Leu Arg Asn Trp
            340                 345                 350

Asp Glu Ala Met Asp Tyr Trp Gly Gln Gly Thr Thr Val Thr Val Ser
        355                 360                 365

Ser Gly Gly Gly Gly Ser Gly Gly Gly Gly Ser Gly Gly Gly Gly Ser
    370                 375                 380

Glu Leu Val Met Thr Gln Ser Pro Ser Tyr Leu Ala Ala Ser Pro Gly
385                 390                 395                 400

Glu Thr Ile Thr Ile Asn Cys Arg Ala Ser Lys Ser Ile Ser Lys Tyr
                405                 410                 415

Leu Ala Trp Tyr Gln Glu Lys Pro Gly Lys Thr Asn Lys Leu Leu Ile
            420                 425                 430

Tyr Ser Gly Ser Thr Leu Gln Ser Gly Ile Pro Ser Arg Phe Ser Gly
        435                 440                 445

Ser Gly Ser Gly Thr Asp Phe Thr Leu Thr Ile Ser Ser Leu Glu Pro
    450                 455                 460

Glu Asp Phe Ala Met Tyr Tyr Cys Gln Gln His Asn Glu Tyr Pro Tyr
465                 470                 475                 480

Thr Phe Gly Gly Gly Thr Lys Leu Glu Ile Lys His His His His His
                485                 490                 495

His
```

<210> SEQ ID NO 47

<211> LENGTH: 1494
<212> TYPE: DNA
<213> ORGANISM: Artificial Sequence
<220> FEATURE:
<223> OTHER INFORMATION: Description of Artificial Sequence: Synthetic construct

<400> SEQUENCE: 47

```
gatatcaaac tgcagcagtc aggggctgaa ctggcaagac ctggggcctc agtgaagatg     60

tcctgcaaga cttctggcta cacctttact aggtacacga tgcactgggt aaaacagagg    120

cctggacagg gtctggaatg gattggatac attaatccta gccgtggtta tactaattac    180

aatcagaagt tcaaggacaa ggccacattg actacagaca aatcctccag cacagcctac    240

atgcaactga gcagcctgac atctgaggac tctgcagtct attactgtgc aagatattat    300

gatgatcatt actcccttga ctactggggc caaggcacca ctctcacagt ctcctcagtc    360

gaaggtggaa gtggaggttc tggtggaagt ggaggttcag gtggagtcga cgacattcag    420

ctgacccagt ctccagcaat catgtctgca tctccagggg agaaggtcac catgacctgc    480

agagccagtt caagtgtaag ttacatgaac tggtaccagc agaagtcagg cacctccccc    540

aaaagatgga tttatgacac atccaaagtg gcttctggag tcccttatcg cttcagtggc    600

agtgggtctg ggacctcata ctctctcaca atcagcagca tggaggctga agatgctgcc    660

acttattact gccaacagtg gagtagtaac ccgctcacgt tcggtgctgg gaccaagctg    720

gagctgaaat ccggaggtgg tggatccgag gtgcagctgc tcgagcagtc tggagctgag    780

ctggtgaaac ctggggcctc agtgaagata tcctgcaagg cttctggata cgccttcact    840

aactactggc taggttgggt aaagcagagg cctggacatg gacttgagtg gattggagat    900

cttttccctg gaagtggtaa tactcactac aatgagaggt tcaggggcaa agccacactg    960

actgcagaca aatcctcgag cacagccttt atgcagctca gtagcctgac atctgaggac   1020

tctgctgtct atttctgtgc aagattgagg aactgggacg aggctatgga ctactggggc   1080

caagggacca cggtcaccgt ctcctcaggt ggtggtggtt ctggcggcgg cggctccggt   1140

ggtggtggtt ctgagctcgt catgacccag tctccatctt atcttgctgc atctcctgga   1200

gaaaccatta ctattaattg cagggcaagt aagagcatta gcaaatattt agcctggtat   1260

caagagaaac ctgggaaaac taataagctt cttatctact ctggatccac tttgcaatct   1320

ggaattccat caaggttcag tggcagtgga tctggtacag atttcactct caccatcagt   1380

agcctggagc ctgaagattt tgcaatgtat tactgtcaac agcataatga atatccgtac   1440

acgttcggag gggggaccaa gcttgagatc aaacatcatc accatcatca ttag          1494
```

<210> SEQ ID NO 48
<211> LENGTH: 497
<212> TYPE: PRT
<213> ORGANISM: Artificial Sequence
<220> FEATURE:
<223> OTHER INFORMATION: Description of Artificial Sequence: Synthetic construct

<400> SEQUENCE: 48

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45
```

```
Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ser Gly Gly Gly Gly Ser Glu Val Gln Leu Leu Glu Gln
                245                 250                 255

Ser Gly Ala Glu Leu Val Lys Pro Gly Ala Ser Val Lys Ile Ser Cys
            260                 265                 270

Lys Ala Ser Gly Tyr Ala Phe Thr Asn Tyr Trp Leu Gly Trp Val Lys
        275                 280                 285

Gln Arg Pro Gly His Gly Leu Glu Trp Ile Gly Asp Leu Phe Pro Gly
    290                 295                 300

Ser Gly Asn Thr His Tyr Asn Glu Arg Phe Arg Gly Lys Ala Thr Leu
305                 310                 315                 320

Thr Ala Asp Lys Ser Ser Ser Thr Ala Phe Met Gln Leu Ser Ser Leu
                325                 330                 335

Thr Ser Glu Asp Ser Ala Val Tyr Phe Cys Ala Arg Leu Arg Asn Trp
            340                 345                 350

Asp Glu Ala Met Asp Tyr Trp Gly Gln Gly Thr Thr Val Thr Val Ser
        355                 360                 365

Ser Gly Gly Gly Gly Ser Gly Gly Gly Gly Ser Gly Gly Gly Gly Ser
    370                 375                 380

Glu Leu Val Met Thr Gln Ser Pro Ser Tyr Leu Ala Ala Ser Pro Gly
385                 390                 395                 400

Glu Thr Ile Thr Ile Asn Cys Arg Ala Ser Lys Ser Ile Ser Lys Tyr
                405                 410                 415

Leu Ala Trp Tyr Gln Glu Lys Pro Gly Lys Thr Asn Lys Leu Leu Ile
            420                 425                 430

Tyr Ser Gly Ser Thr Leu Gln Ser Gly Ile Pro Ser Arg Phe Ser Gly
        435                 440                 445

Ser Gly Ser Gly Thr Asp Phe Thr Leu Thr Ile Ser Ser Leu Glu Pro
    450                 455                 460

Glu Asp Phe Ala Met Tyr Tyr Cys Gln Gln His Asn Glu Tyr Pro Tyr
```

465 470 475 480

Thr Phe Gly Gly Gly Thr Lys Leu Glu Ile Lys His His His His His
485 490 495

His

<210> SEQ ID NO 49
<211> LENGTH: 1521
<212> TYPE: DNA
<213> ORGANISM: Artificial Sequence
<220> FEATURE:
<223> OTHER INFORMATION: Description of Artificial Sequence: Synthetic construct

<400> SEQUENCE: 49
gatatcaaac tgcagcagtc aggggctgaa ctggcaagac ctggggcctc agtgaagatg 60
tcctgcaaga cttctggcta cacctttact aggtacacga tgcactgggt aaaacagagg 120
cctggacagg gtctggaatg gattggatac attaatccta gccgtggtta tactaattac 180
aatcagaagt tcaaggacaa ggccacattg actacagaca aatcctccag cacagcctac 240
atgcaactga gcagcctgac atctgaggac tctgcagtct attactgtgc aagatattat 300
gatgatcatt actgccttga ctactggggc caaggcacca ctctcacagt ctcctcagtc 360
gaaggtggaa gtggaggttc tggtggaagt ggaggttcag gtggagtcga cgacattcag 420
ctgacccagt ctccagcaat catgtctgca tctccagggg agaaggtcac catgacctgc 480
agagccagtt caagtgtaag ttacatgaac tggtaccagc agaagtcagg cacctccccc 540
aaaagatgga tttatgacac atccaaagtg gcttctggag tcccttatcg cttcagtggc 600
agtgggtctg ggacctcata ctctctcaca atcagcagca tggaggctga agatgctgcc 660
acttattact gccaacagtg gagtagtaac ccgctcacgt tcggtgctgg gaccaagctg 720
gagctgaaat ccggaggtgg tggatccgag gtgcagctgc tcgagcagtc tggagctgag 780
ctggtaaggc ctgggacttc agtgaagctg tcctgcaagg cttctggcta caccttcaca 840
agctatggtt taagctgggt gaagcagaga actggacagg gccttgagtg gattggagag 900
gtttatccta gaattggtaa tgcttactac aatgagaagt tcaagggcaa ggccacactg 960
actgcagaca aatcctccag cacagcgtcc atggagctcc gcagcctgac atctgaggac 1020
tctgcggtct atttctgtgc aagacgggga tcctacggta gtaactacga ctggtacttc 1080
gatgtctggg gccaagggac cacggtcacc gtctcctcag gtggtggtgg ttctggcggc 1140
ggcggctccg gtggtggtgg ttctgagctc gtgatgaccc agactccact ctccctgcct 1200
gtcagtcttg gagatcaagc ctccatctct tgcagatcta gtcagagcct tgtacacagt 1260
aatggaaaca cctatttaca ttggtacctg cagaagccag gccagtctcc aaagctcctg 1320
atctacaaag tttccaaccg attttctggg gtcccagaca ggttcagtgg cagtggatca 1380
gggacagatt tcacactcaa gatcagcaga gtggaggctg aggatctggg agtttatttc 1440
tgctctcaaa gtacacatgt tccgtacacg ttcggagggg ggaccaagct tgagatcaaa 1500
catcatcacc atcatcatta g 1521

<210> SEQ ID NO 50
<211> LENGTH: 506
<212> TYPE: PRT
<213> ORGANISM: Artificial Sequence
<220> FEATURE:
<223> OTHER INFORMATION: Description of Artificial Sequence: Synthetic construct

<400> SEQUENCE: 50

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ser Gly Gly Gly Gly Ser Glu Val Gln Leu Leu Glu Gln
                245                 250                 255

Ser Gly Ala Glu Leu Val Arg Pro Gly Thr Ser Val Lys Leu Ser Cys
            260                 265                 270

Lys Ala Ser Gly Tyr Thr Phe Thr Ser Tyr Gly Leu Ser Trp Val Lys
        275                 280                 285

Gln Arg Thr Gly Gln Gly Leu Glu Trp Ile Gly Glu Val Tyr Pro Arg
    290                 295                 300

Ile Gly Asn Ala Tyr Tyr Asn Glu Lys Phe Lys Gly Lys Ala Thr Leu
305                 310                 315                 320

Thr Ala Asp Lys Ser Ser Ser Thr Ala Ser Met Glu Leu Arg Ser Leu
                325                 330                 335

Thr Ser Glu Asp Ser Ala Val Tyr Phe Cys Ala Arg Arg Gly Ser Tyr
            340                 345                 350

Gly Ser Asn Tyr Asp Trp Tyr Phe Asp Val Trp Gly Gln Gly Thr Thr
        355                 360                 365

Val Thr Val Ser Ser Gly Gly Gly Gly Ser Gly Gly Gly Gly Ser Gly
    370                 375                 380

Gly Gly Gly Ser Glu Leu Val Met Thr Gln Thr Pro Leu Ser Leu Pro
385                 390                 395                 400

Val Ser Leu Gly Asp Gln Ala Ser Ile Ser Cys Arg Ser Ser Gln Ser
                405                 410                 415
```

```
Leu Val His Ser Asn Gly Asn Thr Tyr Leu His Trp Tyr Leu Gln Lys
            420                 425                 430

Pro Gly Gln Ser Pro Lys Leu Leu Ile Tyr Lys Val Ser Asn Arg Phe
        435                 440                 445

Ser Gly Val Pro Asp Arg Phe Ser Gly Ser Gly Ser Gly Thr Asp Phe
    450                 455                 460

Thr Leu Lys Ile Ser Arg Val Glu Ala Glu Asp Leu Gly Val Tyr Phe
465                 470                 475                 480

Cys Ser Gln Ser Thr His Val Pro Tyr Thr Phe Gly Gly Gly Thr Lys
                485                 490                 495

Leu Glu Ile Lys His His His His His His
            500                 505
```

```
<210> SEQ ID NO 51
<211> LENGTH: 1521
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 51

gatatcaaac tgcagcagtc aggggctgaa ctggcaagac ctggggcctc agtgaagatg      60

tcctgcaaga cttctggcta cacctttact aggtacacga tgcactgggt aaaacagagg     120

cctggacagg gtctggaatg gattggatac attaatccta gccgtggtta tactaattac     180

aatcagaagt tcaaggacaa ggccacattg actacagaca aatcctccag cacagcctac     240

atgcaactga gcagcctgac atctgaggac tctgcagtct attactgtgc aagatattat     300

gatgatcatt actcccttga ctactggggc caaggcacca ctctcacagt ctcctcagtc     360

gaaggtggaa gtggaggttc tggtggaagt ggaggttcag gtggagtcga cgacattcag     420

ctgacccagt ctccagcaat catgtctgca tctccagggg agaaggtcac catgacctgc     480

agagccagtt caagtgtaag ttacatgaac tggtaccagc agaagtcagg cacctccccc     540

aaaagatgga tttatgacac atccaaagtg gcttctggag tcccttatcg cttcagtggc     600

agtgggtctg ggacctcata ctctctcaca atcagcagca tggaggctga agatgctgcc     660

acttattact gccaacagtg gagtagtaac ccgctcacgt tcggtgctgg gaccaagctg     720

gagctgaaat ccggaggtgg tggatccgag gtgcagctgc tcgagcagtc tggagctgag     780

ctggtaaggc ctgggacttc agtgaagctg tcctgcaagg cttctggcta caccttcaca     840

agctatggtt taagctgggt gaagcagaga actggacagg gccttgagtg gattggagag     900

gtttatccta gaattggtaa tgcttactac aatgagaagt tcaagggcaa ggccacactg     960

actgcagaca aatcctccag cacagcgtcc atggagctcc gcagcctgac atctgaggac    1020

tctgcggtct atttctgtgc aagacgggga tcctacggta gtaactacga ctggtacttc    1080

gatgtctggg gccaagggac cacggtcacc gtctcctcag gtggtggtgg ttctggcggc    1140

ggcggctccg gtggtggtgg ttctgagctc gtgatgaccc agactccact ctccctgcct    1200

gtcagtcttg gagatcaagc ctccatctct tgcagatcta gtcagagcct tgtacacagt    1260

aatggaaaca cctatttaca ttggtacctg cagaagccag gccagtctcc aaagctcctg    1320

atctacaaag tttccaaccg attttctggg gtcccagaca ggttcagtgg cagtggatca    1380

gggacagatt tcacactcaa gatcagcaga gtggaggctg aggatctggg agtttatttc    1440

tgctctcaaa gtacacatgt tccgtacacg ttcggagggg ggaccaagct tgagatcaaa    1500
```

catcatcacc atcatcatta g 1521

<210> SEQ ID NO 52
<211> LENGTH: 506
<212> TYPE: PRT
<213> ORGANISM: Artificial Sequence
<220> FEATURE:
<223> OTHER INFORMATION: Description of Artificial Sequence: Synthetic construct

<400> SEQUENCE: 52

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ser Gly Gly Gly Gly Ser Glu Val Gln Leu Leu Glu Gln
                245                 250                 255

Ser Gly Ala Glu Leu Val Arg Pro Gly Thr Ser Val Lys Leu Ser Cys
            260                 265                 270

Lys Ala Ser Gly Tyr Thr Phe Thr Ser Tyr Gly Leu Ser Trp Val Lys
        275                 280                 285

Gln Arg Thr Gly Gln Gly Leu Glu Trp Ile Gly Glu Val Tyr Pro Arg
    290                 295                 300

Ile Gly Asn Ala Tyr Tyr Asn Glu Lys Phe Lys Gly Lys Ala Thr Leu
305                 310                 315                 320

Thr Ala Asp Lys Ser Ser Ser Thr Ala Ser Met Glu Leu Arg Ser Leu
                325                 330                 335

Thr Ser Glu Asp Ser Ala Val Tyr Phe Cys Ala Arg Arg Gly Ser Tyr
            340                 345                 350
```

```
Gly Ser Asn Tyr Asp Trp Tyr Phe Asp Val Trp Gly Gln Gly Thr Thr
        355                 360                 365

Val Thr Val Ser Ser Gly Gly Gly Gly Ser Gly Gly Gly Gly Ser Gly
    370                 375                 380

Gly Gly Gly Ser Glu Leu Val Met Thr Gln Thr Pro Leu Ser Leu Pro
385                 390                 395                 400

Val Ser Leu Gly Asp Gln Ala Ser Ile Ser Cys Arg Ser Ser Gln Ser
                405                 410                 415

Leu Val His Ser Asn Gly Asn Thr Tyr Leu His Trp Tyr Leu Gln Lys
            420                 425                 430

Pro Gly Gln Ser Pro Lys Leu Leu Ile Tyr Lys Val Ser Asn Arg Phe
        435                 440                 445

Ser Gly Val Pro Asp Arg Phe Ser Gly Ser Gly Ser Gly Thr Asp Phe
    450                 455                 460

Thr Leu Lys Ile Ser Arg Val Glu Ala Glu Asp Leu Gly Val Tyr Phe
465                 470                 475                 480

Cys Ser Gln Ser Thr His Val Pro Tyr Thr Phe Gly Gly Gly Thr Lys
                485                 490                 495

Leu Glu Ile Lys His His His His His His
            500                 505
```

<210> SEQ ID NO 53
<211> LENGTH: 1512
<212> TYPE: DNA
<213> ORGANISM: Artificial Sequence
<220> FEATURE:
<223> OTHER INFORMATION: Description of Artificial Sequence: Synthetic construct

<400> SEQUENCE: 53

```
gatatcaaac tgcagcagtc aggggctgaa ctggcaagac ctggggcctc agtgaagatg      60

tcctgcaaga cttctggcta cacctttact aggtacacga tgcactgggt aaaacagagg     120

cctggacagg gtctggaatg gattggatac attaatccta gccgtggtta tactaattac     180

aatcagaagt tcaaggacaa ggccacattg actacagaca aatcctccag cacagcctac     240

atgcaactga gcagcctgac atctgaggac tctgcagtct attactgtgc aagatattat     300

gatgatcatt actgccttga ctactggggc caaggcacca ctctcacagt ctcctcaggt     360

ggtggtggtt ctggcggcgg cggctccggt ggtggtggtt ctgacattca gctgacccag     420

tctccagcaa tcatgtctgc atctccaggg gagaaggtca ccatgacctg cagagccagt     480

tcaagtgtaa gttacatgaa ctggtaccag cagaagtcag gcacctcccc caaaagatgg     540

atttatgaca catccaaagt ggcttctgga gtcccttatc gcttcagtgg cagtgggtct     600

gggacctcat actctctcac aatcagcagc atggaggctg aagatgctgc cacttattac     660

tgccaacagt ggagtagtaa cccgctcacg ttcggtgctg ggaccaagct ggagctgaaa     720

tccggaggtg gtggatccga ggtgcagctg ctcgagcagt ctggagctga gctggtaagg     780

cctgggactt cagtgaagct gtcctgcaag gcttctggct acaccttcac aagctatggt     840

ttaagctggg tgaagcagag aactggacag ggccttgagt ggattggaga ggtttatcct     900

agaattggta atgcttacta caatgagaag ttcaagggca aggccacact gactgcagac     960

aaatcctcca gcacagcgtc catggagctc cgcagcctga catctgagga ctctgcggtc    1020

tatttctgtg caagacgggg atcctacggt agtaactacg actggtactt cgatgtctgg    1080

ggccaaggga ccacggtcac cgtctcctca ggtggtggtg gttctggcgg cggcggctcc    1140
```

```
ggtggtggtg gttctgagct cgtgatgacc cagactccac tctccctgcc tgtcagtctt   1200

ggagatcaag cctccatctc ttgcagatct agtcagagcc ttgtacacag taatggaaac   1260

acctatttac attggtacct gcagaagcca ggccagtctc caaagctcct gatctacaaa   1320

gtttccaacc gattttctgg ggtcccagac aggttcagtg gcagtggatc agggacagat   1380

ttcacactca agatcagcag agtggaggct gaggatctgg gagtttattt ctgctctcaa   1440

agtacacatg ttccgtacac gttcggaggg gggaccaagc ttgagatcaa acatcatcac   1500

catcatcatt ag                                                       1512
```

```
<210> SEQ ID NO 54
<211> LENGTH: 503
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 54

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190

Tyr Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ser Gly Gly Gly Gly Ser Glu Val Gln Leu Leu Glu Gln Ser Gly Ala
                245                 250                 255

Glu Leu Val Arg Pro Gly Thr Ser Val Lys Leu Ser Cys Lys Ala Ser
            260                 265                 270

Gly Tyr Thr Phe Thr Ser Tyr Gly Leu Ser Trp Val Lys Gln Arg Thr
        275                 280                 285
```

```
Gly Gln Gly Leu Glu Trp Ile Gly Glu Val Tyr Pro Arg Ile Gly Asn
    290                 295                 300

Ala Tyr Tyr Asn Glu Lys Phe Lys Gly Lys Ala Thr Leu Thr Ala Asp
305                 310                 315                 320

Lys Ser Ser Ser Thr Ala Ser Met Glu Leu Arg Ser Leu Thr Ser Glu
                325                 330                 335

Asp Ser Ala Val Tyr Phe Cys Ala Arg Arg Gly Ser Tyr Gly Ser Asn
            340                 345                 350

Tyr Asp Trp Tyr Phe Asp Val Trp Gly Gln Gly Thr Thr Val Thr Val
        355                 360                 365

Ser Ser Gly Gly Gly Gly Ser Gly Gly Gly Gly Ser Gly Gly Gly Gly
    370                 375                 380

Ser Glu Leu Val Met Thr Gln Thr Pro Leu Ser Leu Pro Val Ser Leu
385                 390                 395                 400

Gly Asp Gln Ala Ser Ile Ser Cys Arg Ser Ser Gln Ser Leu Val His
                405                 410                 415

Ser Asn Gly Asn Thr Tyr Leu His Trp Tyr Leu Gln Lys Pro Gly Gln
            420                 425                 430

Ser Pro Lys Leu Leu Ile Tyr Lys Val Ser Asn Arg Phe Ser Gly Val
        435                 440                 445

Pro Asp Arg Phe Ser Gly Ser Gly Ser Gly Thr Asp Phe Thr Leu Lys
    450                 455                 460

Ile Ser Arg Val Glu Ala Glu Asp Leu Gly Val Tyr Phe Cys Ser Gln
465                 470                 475                 480

Ser Thr His Val Pro Tyr Thr Phe Gly Gly Gly Thr Lys Leu Glu Ile
                485                 490                 495

Lys His His His His His His
            500
```

<210> SEQ ID NO 55
<211> LENGTH: 1512
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 55

```
gatatcaaac tgcagcagtc aggggctgaa ctggcaagac ctggggcctc agtgaagatg     60

tcctgcaaga cttctggcta cacctttact aggtacacga tgcactgggt aaaacagagg    120

cctggacagg gtctggaatg gattggatac attaatccta gccgtggtta tactaattac    180

aatcagaagt tcaaggacaa ggccacattg actacagaca aatcctccag cacagcctac    240

atgcaactga gcagcctgac atctgaggac tctgcagtct attactgtgc aagatattat    300

gatgatcatt actgccttga ctactggggc caaggcacca ctctcacagt ctcctcagtc    360

gaaggtggaa gtggaggttc tggtggaagt ggaggttcag gtggagtcga cgacattcag    420

ctgacccagt ctccagcaat catgtctgca tctccagggg agaaggtcac catgacctgc    480

agagccagtt caagtgtaag ttacatgaac tggtaccagc agaagtcagg cacctccccc    540

aaaagatgga tttatgacac atccaaagtg gcttctggag tcccttatcg cttcagtggc    600

agtgggtctg ggacctcata ctctctcaca atcagcagca tggaggctga agatgctgcc    660

acttattact gccaacagtg gagtagtaac ccgctcacgt tcggtgctgg gaccaagctg    720

gagctgaaat ccggaggtgg tggatccgag gtgcagctgc tcgagcagtc tggagctgag    780
```

```
ctggtaaggc ctgggacttc agtgaagata tcctgcaagg cttctggata cgccttcact    840

aactactggc taggttgggt taagcagagg cctggacatg gacttgaatg ggttggagat    900

attttccctg gaagtggtaa tgctcactac aatgagaagt tcaagggcaa agccacactg    960

actgcagaca agtcctcgta cacagcctat atgcagctca gtagcctgac atctgaggac   1020

tctgctgtct atttctgtgc aagattgcgg aactgggacg aggctatgga ctactggggc   1080

caagggacca cggtcaccgt ctcctcaggt ggtggtggtt ctggcggcgg cggctccggt   1140

ggtggtggtt ctgagctcgt gatgacacag tctccatcct ccctgagtgt gtcagcagga   1200

gagaaggtca ctatgagctg caagtccagt cagagtctgt taaacagtgg aaatcaaaag   1260

aactacttgg cctggtacca gcagaaacca gggcagcctc ctaaactgtt gatctacggg   1320

gcatccacta gggaatctgg ggtccctgat cgcttcacag gcagtggatc tggaacagat   1380

ttcactctca ccatcagcag tgtgcaggct gaagacctgg cagtttatta ctgtcagaat   1440

gattatagtt atccgtacac gttcggaggg gggaccaagc ttgagatcaa acatcatcac   1500

catcatcatt ag                                                       1512
```

```
<210> SEQ ID NO 56
<211> LENGTH: 503
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 56

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220
```

```
Gln Gln Trp Ser Ser Asn Pro Leu Thr Phe Gly Ala Gly Thr Lys Leu
225                 230                 235                 240

Glu Leu Lys Ser Gly Gly Gly Gly Ser Glu Val Gln Leu Leu Glu Gln
                245                 250                 255

Ser Gly Ala Glu Leu Val Arg Pro Gly Thr Ser Val Lys Ile Ser Cys
            260                 265                 270

Lys Ala Ser Gly Tyr Ala Phe Thr Asn Tyr Trp Leu Gly Trp Val Lys
        275                 280                 285

Gln Arg Pro Gly His Gly Leu Glu Trp Val Gly Asp Ile Phe Pro Gly
    290                 295                 300

Ser Gly Asn Ala His Tyr Asn Glu Lys Phe Lys Gly Lys Ala Thr Leu
305                 310                 315                 320

Thr Ala Asp Lys Ser Ser Tyr Thr Ala Tyr Met Gln Leu Ser Ser Leu
                325                 330                 335

Thr Ser Glu Asp Ser Ala Val Tyr Phe Cys Ala Arg Leu Arg Asn Trp
            340                 345                 350

Asp Glu Ala Met Asp Tyr Trp Gly Gln Gly Thr Thr Val Thr Val Ser
        355                 360                 365

Ser Gly Gly Gly Gly Ser Gly Gly Gly Gly Ser Gly Gly Gly Gly Ser
    370                 375                 380

Glu Leu Val Met Thr Gln Ser Pro Ser Ser Leu Ser Val Ser Ala Gly
385                 390                 395                 400

Glu Lys Val Thr Met Ser Cys Lys Ser Ser Gln Ser Leu Leu Asn Ser
                405                 410                 415

Gly Asn Gln Lys Asn Tyr Leu Ala Trp Tyr Gln Gln Lys Pro Gly Gln
            420                 425                 430

Pro Pro Lys Leu Leu Ile Tyr Gly Ala Ser Thr Arg Glu Ser Gly Val
        435                 440                 445

Pro Asp Arg Phe Thr Gly Ser Gly Ser Gly Thr Asp Phe Thr Leu Thr
    450                 455                 460

Ile Ser Ser Val Gln Ala Glu Asp Leu Ala Val Tyr Tyr Cys Gln Asn
465                 470                 475                 480

Asp Tyr Ser Tyr Pro Tyr Thr Phe Gly Gly Gly Thr Lys Leu Glu Ile
                485                 490                 495

Lys His His His His His His
            500
```

<210> SEQ ID NO 57
<211> LENGTH: 1512
<212> TYPE: DNA
<213> ORGANISM: Artificial Sequence
<220> FEATURE:
<223> OTHER INFORMATION: Description of Artificial Sequence: Synthetic construct

<400> SEQUENCE: 57

```
gatatcaaac tgcagcagtc aggggctgaa ctggcaagac ctggggcctc agtgaagatg      60

tcctgcaaga cttctggcta cacctttact aggtacacga tgcactgggt aaaacagagg     120

cctggacagg gtctggaatg gattggatac attaatccta gccgtggtta tactaattac     180

aatcagaagt tcaaggacaa ggccacattg actacagaca aatcctccag cacagcctac     240

atgcaactga gcagcctgac atctgaggac tctgcagtct attactgtgc aagatattat     300

gatgatcatt actcccttga ctactggggc caaggcacca ctctcacagt ctcctcagtc     360

gaaggtggaa gtggaggttc tggtggaagt ggaggttcag gtggagtcga cgacattcag     420
```

```
ctgacccagt ctccagcaat catgtctgca tctccagggg agaaggtcac catgacctgc    480

agagccagtt caagtgtaag ttacatgaac tggtaccagc agaagtcagg cacctccccc    540

aaaagatgga tttatgacac atccaaagtg gcttctggag tcccttatcg cttcagtggc    600

agtgggtctg ggacctcata ctctctcaca atcagcagca tggaggctga agatgctgcc    660

acttattact gccaacagtg gagtagtaac ccgctcacgt tcggtgctgg gaccaagctg    720

gagctgaaat ccggaggtgg tggatccgag gtgcagctgc tcgagcagtc tggagctgag    780

ctggtaaggc ctgggacttc agtgaagata tcctgcaagg cttctggata cgccttcact    840

aactactggc taggttgggt taagcagagg cctggacatg gacttgaatg ggttggagat    900

attttccctg gaagtggtaa tgctcactac aatgagaagt tcaagggcaa agccacactg    960

actgcagaca agtcctcgta cacagcctat atgcagctca gtagcctgac atctgaggac   1020

tctgctgtct atttctgtgc aagattgcgg aactgggacg aggctatgga ctactggggc   1080

caagggacca cggtcaccgt ctcctcaggt ggtggtggtt ctggcggcgg cggctccggt   1140

ggtggtggtt ctgagctcgt gatgacacag tctccatcct ccctgagtgt gtcagcagga   1200

gagaaggtca ctatgagctg caagtccagt cagagtctgt taaacagtgg aaatcaaaag   1260

aactacttgg cctggtacca gcagaaacca gggcagcctc ctaaactgtt gatctacggg   1320

gcatccacta gggaatctgg ggtccctgat cgcttcacag gcagtggatc tggaacagat   1380

ttcactctca ccatcagcag tgtgcaggct gaagacctgg cagtttatta ctgtcagaat   1440

gattatagtt atccgtacac gttcggaggg gggaccaagc ttgagatcaa acatcatcac   1500

catcatcatt ag                                                       1512
```

```
<210> SEQ ID NO 58
<211> LENGTH: 503
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 58

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160
```

```
Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ser Gly Gly Gly Gly Ser Glu Val Gln Leu Leu Glu Gln
                245                 250                 255

Ser Gly Ala Glu Leu Val Arg Pro Gly Thr Ser Val Lys Ile Ser Cys
            260                 265                 270

Lys Ala Ser Gly Tyr Ala Phe Thr Asn Tyr Trp Leu Gly Trp Val Lys
        275                 280                 285

Gln Arg Pro Gly His Gly Leu Glu Trp Val Gly Asp Ile Phe Pro Gly
    290                 295                 300

Ser Gly Asn Ala His Tyr Asn Glu Lys Phe Lys Gly Lys Ala Thr Leu
305                 310                 315                 320

Thr Ala Asp Lys Ser Ser Tyr Thr Ala Tyr Met Gln Leu Ser Ser Leu
                325                 330                 335

Thr Ser Glu Asp Ser Ala Val Tyr Phe Cys Ala Arg Leu Arg Asn Trp
            340                 345                 350

Asp Glu Ala Met Asp Tyr Trp Gly Gln Gly Thr Thr Val Thr Val Ser
        355                 360                 365

Ser Gly Gly Gly Gly Ser Gly Gly Gly Gly Ser Gly Gly Gly Gly Ser
    370                 375                 380

Glu Leu Val Met Thr Gln Ser Pro Ser Ser Leu Ser Val Ser Ala Gly
385                 390                 395                 400

Glu Lys Val Thr Met Ser Cys Lys Ser Ser Gln Ser Leu Leu Asn Ser
                405                 410                 415

Gly Asn Gln Lys Asn Tyr Leu Ala Trp Tyr Gln Gln Lys Pro Gly Gln
            420                 425                 430

Pro Pro Lys Leu Leu Ile Tyr Gly Ala Ser Thr Arg Glu Ser Gly Val
        435                 440                 445

Pro Asp Arg Phe Thr Gly Ser Gly Ser Gly Thr Asp Phe Thr Leu Thr
    450                 455                 460

Ile Ser Ser Val Gln Ala Glu Asp Leu Ala Val Tyr Tyr Cys Gln Asn
465                 470                 475                 480

Asp Tyr Ser Tyr Pro Tyr Thr Phe Gly Gly Gly Thr Lys Leu Glu Ile
                485                 490                 495

Lys His His His His His His
            500
```

<210> SEQ ID NO 59
<211> LENGTH: 1503
<212> TYPE: DNA
<213> ORGANISM: Artificial Sequence
<220> FEATURE:
<223> OTHER INFORMATION: Description of Artificial Sequence: Synthetic construct

<400> SEQUENCE: 59

```
gatatcaaac tgcagcagtc aggggctgaa ctggcaagac ctggggcctc agtgaagatg     60
```

```
tcctgcaaga cttctggcta cacctttact aggtacacga tgcactgggt aaaacagagg    120

cctggacagg gtctggaatg gattggatac attaatccta gccgtggtta tactaattac    180

aatcagaagt tcaaggacaa ggccacattg actacagaca aatcctccag cacagcctac    240

atgcaactga gcagcctgac atctgaggac tctgcagtct attactgtgc aagatattat    300

gatgatcatt actgccttga ctactggggc caaggcacca ctctcacagt ctcctcaggt    360

ggtggtggtt ctggcggcgg cggctccggt ggtggtggtt ctgacattca gctgacccag    420

tctccagcaa tcatgtctgc atctccaggg gagaaggtca ccatgacctg cagagccagt    480

tcaagtgtaa gttacatgaa ctggtaccag cagaagtcag gcacctcccc caaaagatgg    540

atttatgaca catccaaagt ggcttctgga gtcccttatc gcttcagtgg cagtgggtct    600

gggacctcat actctctcac aatcagcagc atggaggctg aagatgctgc cacttattac    660

tgccaacagt ggagtagtaa cccgctcacg ttcggtgctg ggaccaagct ggagctgaaa    720

tccggaggtg gtggatccga ggtgcagctg ctcgagcagt ctggagctga gctggtaagg    780

cctgggactt cagtgaagat atcctgcaag gcttctggat acgccttcac taactactgg    840

ctaggttggg ttaagcagag gcctggacat ggacttgaat gggttggaga tattttccct    900

ggaagtggta atgctcacta caatgagaag ttcaagggca aagccacact gactgcagac    960

aagtcctcgt acacagccta tatgcagctc agtagcctga catctgagga ctctgctgtc   1020

tatttctgtg caagattgcg gaactgggac gaggctatgg actactgggg ccaagggacc   1080

acggtcaccg tctcctcagg tggtggtggt tctggcggcg gcggctccgg tggtggtggt   1140

tctgagctcg tgatgacaca gtctccatcc tccctgagtg tgtcagcagg agagaaggtc   1200

actatgagct gcaagtccag tcagagtctg ttaaacagtg gaaatcaaaa gaactacttg   1260

gcctggtacc agcagaaacc agggcagcct cctaaactgt tgatctacgg ggcatccact   1320

agggaatctg gggtccctga tcgcttcaca ggcagtggat ctggaacaga tttcactctc   1380

accatcagca gtgtgcaggc tgaagacctg gcagtttatt actgtcagaa tgattatagt   1440

tatccgtaca cgttcggagg ggggaccaag cttgagatca aacatcatca ccatcatcat   1500

tag                                                                 1503
```

```
<210> SEQ ID NO 60
<211> LENGTH: 500
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 60

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190

Tyr Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ser Gly Gly Gly Gly Ser Glu Val Gln Leu Leu Glu Gln Ser Gly Ala
                245                 250                 255

Glu Leu Val Arg Pro Gly Thr Ser Val Lys Ile Ser Cys Lys Ala Ser
            260                 265                 270

Gly Tyr Ala Phe Thr Asn Tyr Trp Leu Gly Trp Val Lys Gln Arg Pro
        275                 280                 285

Gly His Gly Leu Glu Trp Val Gly Asp Ile Phe Pro Gly Ser Gly Asn
    290                 295                 300

Ala His Tyr Asn Glu Lys Phe Lys Gly Lys Ala Thr Leu Thr Ala Asp
305                 310                 315                 320

Lys Ser Ser Tyr Thr Ala Tyr Met Gln Leu Ser Ser Leu Thr Ser Glu
                325                 330                 335

Asp Ser Ala Val Tyr Phe Cys Ala Arg Leu Arg Asn Trp Asp Glu Ala
            340                 345                 350

Met Asp Tyr Trp Gly Gln Gly Thr Thr Val Thr Val Ser Ser Gly Gly
        355                 360                 365

Gly Gly Ser Gly Gly Gly Gly Ser Gly Gly Gly Gly Ser Glu Leu Val
    370                 375                 380

Met Thr Gln Ser Pro Ser Ser Leu Ser Val Ser Ala Gly Glu Lys Val
385                 390                 395                 400

Thr Met Ser Cys Lys Ser Ser Gln Ser Leu Leu Asn Ser Gly Asn Gln
                405                 410                 415

Lys Asn Tyr Leu Ala Trp Tyr Gln Gln Lys Pro Gly Gln Pro Pro Lys
            420                 425                 430

Leu Leu Ile Tyr Gly Ala Ser Thr Arg Glu Ser Gly Val Pro Asp Arg
        435                 440                 445

Phe Thr Gly Ser Gly Ser Gly Thr Asp Phe Thr Leu Thr Ile Ser Ser
    450                 455                 460

Val Gln Ala Glu Asp Leu Ala Val Tyr Tyr Cys Gln Asn Asp Tyr Ser
465                 470                 475                 480

Tyr Pro Tyr Thr Phe Gly Gly Gly Thr Lys Leu Glu Ile Lys His His
                485                 490                 495

His His His His
            500
```

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

His Tyr Asp Asp His Tyr Cys Leu Asp Tyr
1 5 10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Tyr Ser Asp Asp His Tyr Cys Leu Asp Tyr
1 5 10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Tyr Tyr Asp Ala His Tyr Cys Leu Asp Tyr
1 5 10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Tyr Tyr Asp Asp Gln Tyr Cys Leu Asp Tyr
1 5 10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Tyr Tyr Asp Asp Pro Tyr Cys Leu Asp Tyr
1 5 10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Tyr Phe Asn Asp His Tyr Cys Leu Asp Tyr
1 5 10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Tyr Tyr Asn Asp Gln Tyr Cys Leu Asp Tyr
1 5 10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Tyr His Asp Asp Pro Tyr Cys Leu Asp Tyr
1 5 10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Tyr Tyr Asp Asp Asn Tyr Cys Leu Asp Tyr
1 5 10

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Val Glu Gly Gly Ser Gly Gly Ser Gly Gly Ser Gly Gly Ser Gly Gly
1 5 10 15

Val Asp

<210> SEQ ID NO 71
<211> LENGTH: 357
<212> TYPE: DNA
<213> ORGANISM: Artificial Sequence
<220> FEATURE:
<223> OTHER INFORMATION: Description of Artificial Sequence: Synthetic construct

<400> SEQUENCE: 71
gatatcaaac tgcagcagtc aggggctgaa ctggcaagac ctggggcctc agtgaagatg 60
tcctgcaaga cttctggcta cacctttact aggtacacga tgcactgggt aaaacagagg 120
cctggacagg gtctggaatg gattggatac attaatccta gccgtggtta tactaattac 180

```
aatcagaagt tcaaggacaa ggccacattg actacagaca aatcctccag cacagcctac    240

atgcaactga gcagcctgac atctgaggac tctgcagtct attactgtgc aagatattat    300

gatgatcatt actgccttga ctactggggc caaggcacca ctctcacagt ctcctca       357


<210> SEQ ID NO 72
<211> LENGTH: 119
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 72

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115


<210> SEQ ID NO 73
<211> LENGTH: 318
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 73

gacattcagc tgacccagtc tccagcaatc atgtctgcat ctccagggga gaaggtcacc     60

atgacctgca gagccagttc aagtgtaagt tacatgaact ggtaccagca gaagtcaggc    120

acctccccca aaagatggat ttatgacaca tccaaagtgg cttctggagt cccttatcgc    180

ttcagtggca gtgggtctgg gacctcatac tctctcacaa tcagcagcat ggaggctgaa    240

gatgctgcca cttattactg ccaacagtgg agtagtaacc cgctcacgtt cggtgctggg    300

accaagctgg agctgaaa                                                  318


<210> SEQ ID NO 74
<211> LENGTH: 106
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 74

Asp Ile Gln Leu Thr Gln Ser Pro Ala Ile Met Ser Ala Ser Pro Gly
1               5                   10                  15
```

```
Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105


<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Tyr Thr Phe Thr Arg Tyr Thr Met His
1               5                   10


<210> SEQ ID NO 76
<211> LENGTH: 357
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 76

gatatcaaac tgcagcagtc aggggctgaa ctggcaagac ctggggcctc agtgaagatg      60

tcctgcaaga cttctggcta cacctttact aggtacacga tgcactgggt aaaacagagg     120

cctggacagg gtctggaatg gattggatac attaatccta gccgtggtta tactaattac     180

aatcagaagt tcaaggacaa ggccacattg actacagaca aatcctccag cacagcctac     240

atgcaactga gcagcctgac atctgaggac tctgcagtct attactgtgc aagatattat     300

gatgatcatt actcccttga ctactggggc caaggcacca ctctcacagt ctcctca        357


<210> SEQ ID NO 77
<211> LENGTH: 119
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 77

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
```

```
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser
        115


<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Tyr Asp Asp His Tyr Ser Leu Asp Tyr
1               5                   10


<210> SEQ ID NO 79
<211> LENGTH: 360
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 79

gaggtgcagc tgctcgagca gtctggagct gagctggtga aacctggggc ctcagtgaag     60

atatcctgca aggcttctgg atacgccttc actaactact ggctaggttg ggtaaagcag    120

aggcctggac atggacttga gtggattgga gatcttttcc ctggaagtgg taatactcac    180

tacaatgaga ggttcagggg caaagccaca ctgactgcag acaaatcctc gagcacagcc    240

tttatgcagc tcagtagcct gacatctgag gactctgctg tctatttctg tgcaagattg    300

aggaactggg acgaggctat ggactactgg ggccaaggga ccacggtcac cgtctcctca    360


<210> SEQ ID NO 80
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 80

Glu Val Gln Leu Leu Glu Gln Ser Gly Ala Glu Leu Val Lys Pro Gly
1               5                   10                  15

Ala Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Leu Phe Pro Gly Ser Gly Asn Thr His Tyr Asn Glu Arg
    50                  55                  60

Phe Arg Gly Lys Ala Thr Leu Thr Ala Asp Lys Ser Ser Ser Thr Ala
65                  70                  75                  80

Phe Met Gln Leu Ser Ser Leu Thr Ser Glu Asp Ser Ala Val Tyr Phe
                85                  90                  95

Cys Ala Arg Leu Arg Asn Trp Asp Glu Ala Met Asp Tyr Trp Gly Gln
            100                 105                 110
```

```
Gly Thr Thr Val Thr Val Ser Ser
        115                 120


<210> SEQ ID NO 81
<211> LENGTH: 321
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 81

gagctcgtca tgacccagtc tccatcttat cttgctgcat ctcctggaga aaccattact      60

attaattgca gggcaagtaa gagcattagc aaatatttag cctggtatca agagaaacct     120

gggaaaacta ataagcttct tatctactct ggatccactt tgcaatctgg aattccatca     180

aggttcagtg gcagtggatc tggtacagat ttcactctca ccatcagtag cctggagcct     240

gaagattttg caatgtatta ctgtcaacag cataatgaat atccgtacac gttcggaggg     300

gggaccaagc ttgagatcaa a                                               321


<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 82

Glu Leu Val Met Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys
            100                 105


<210> SEQ ID NO 83
<211> LENGTH: 372
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 83

gaggtgcagc tgctcgagca gtctggagct gagctggtaa ggcctgggac ttcagtgaag      60

ctgtcctgca aggcttctgg ctacaccttc acaagctatg gtttaagctg ggtgaagcag     120

agaactggac agggccttga gtggattgga gaggtttatc ctagaattgg taatgcttac     180

tacaatgaga agttcaaggg caaggccaca ctgactgcag acaaatcctc cagcacagcg     240

tccatggagc tccgcagcct gacatctgag gactctgcgg tctatttctg tgcaagacgg     300
```

ggatcctacg gtagtaacta cgactggtac ttcgatgtct ggggccaagg gaccacggtc 360
accgtctcct ca 372

<210> SEQ ID NO 84
<211> LENGTH: 124
<212> TYPE: PRT
<213> ORGANISM: Artificial Sequence
<220> FEATURE:
<223> OTHER INFORMATION: Description of Artificial Sequence: Synthetic construct

<400> SEQUENCE: 84

```
Glu Val Gln Leu Leu Glu Gln Ser Gly Ala Glu Leu Val Arg Pro Gly
1               5                   10                  15

Thr Ser Val Lys Leu Ser Cys Lys Ala Ser Gly Tyr Thr Phe Thr Ser
            20                  25                  30

Tyr Gly Leu Ser Trp Val Lys Gln Arg Thr Gly Gln Gly Leu Glu Trp
        35                  40                  45

Ile Gly Glu Val Tyr Pro Arg Ile Gly Asn Ala Tyr Tyr Asn Glu Lys
    50                  55                  60

Phe Lys Gly Lys Ala Thr Leu Thr Ala Asp Lys Ser Ser Ser Thr Ala
65                  70                  75                  80

Ser Met Glu Leu Arg Ser Leu Thr Ser Glu Asp Ser Ala Val Tyr Phe
                85                  90                  95

Cys Ala Arg Arg Gly Ser Tyr Gly Ser Asn Tyr Asp Trp Tyr Phe Asp
            100                 105                 110

Val Trp Gly Gln Gly Thr Thr Val Thr Val Ser Ser
        115                 120
```

<210> SEQ ID NO 85
<211> LENGTH: 336
<212> TYPE: DNA
<213> ORGANISM: Artificial Sequence
<220> FEATURE:
<223> OTHER INFORMATION: Description of Artificial Sequence: Synthetic construct

<400> SEQUENCE: 85
gagctcgtga tgacccagac tccactctcc ctgcctgtca gtcttggaga tcaagcctcc 60
atctcttgca gatctagtca gagccttgta cacagtaatg gaaacaccta tttacattgg 120
tacctgcaga agccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tatttctgct ctcaaagtac acatgttccg 300
tacacgttcg gaggggggac caagcttgag atcaaa 336

<210> SEQ ID NO 86
<211> LENGTH: 112
<212> TYPE: PRT
<213> ORGANISM: Artificial Sequence
<220> FEATURE:
<223> OTHER INFORMATION: Description of Artificial Sequence: Synthetic construct

<400> SEQUENCE: 86

```
Glu Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30
```

```
Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110


<210> SEQ ID NO 87
<211> LENGTH: 360
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 87

gaggtgcagc tgctcgagca gtctggagct gagctggtaa ggcctgggac ttcagtgaag      60

atatcctgca aggcttctgg atacgccttc actaactact ggctaggttg ggttaagcag     120

aggcctggac atggacttga atgggttgga gatattttcc ctggaagtgg taatgctcac     180

tacaatgaga agttcaaggg caaagccaca ctgactgcag acaagtcctc gtacacagcc     240

tatatgcagc tcagtagcct gacatctgag gactctgctg tctatttctg tgcaagattg     300

cggaactggg acgaggctat ggactactgg ggccaaggga ccacggtcac cgtctcctca     360


<210> SEQ ID NO 88
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 88

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Val Gly Asp Ile Phe Pro Gly Ser Gly Asn Ala His Tyr Asn Glu Lys
    50                  55                  60

Phe Lys Gly Lys Ala Thr Leu Thr Ala Asp Lys Ser Ser Tyr Thr Ala
65                  70                  75                  80

Tyr Met Gln Leu Ser Ser Leu Thr Ser Glu Asp Ser Ala Val Tyr Phe
                85                  90                  95

Cys Ala Arg Leu Arg Asn Trp Asp Glu Ala Met Asp Tyr Trp Gly Gln
            100                 105                 110

Gly Thr Thr Val Thr Val Ser Ser
        115                 120


<210> SEQ ID NO 89
<211> LENGTH: 339
<212> TYPE: DNA
<213> ORGANISM: Artificial Sequence
```

```
<220> FEATURE:
<223> OTHER INFORMATION: Description of Artificial Sequence: Synthetic
      construct

<400> SEQUENCE: 89

gagctcgtga tgacacagtc tccatcctcc ctgagtgtgt cagcaggaga gaaggtcact     60

atgagctgca agtccagtca gagtctgtta aacagtggaa atcaaaagaa ctacttggcc    120

tggtaccagc agaaaccagg gcagcctcct aaactgttga tctacggggc atccactagg    180

gaatctgggg tccctgatcg cttcacaggc agtggatctg gaacagattt cactctcacc    240

atcagcagtg tgcaggctga agacctggca gtttattact gtcagaatga ttatagttat    300

ccgtacacgt tcggaggggg gaccaagctt gagatcaaa                           339


<210> SEQ ID NO 90
<211> LENGTH: 113
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 90

Glu Leu Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile
            100                 105                 110

Lys


<210> SEQ ID NO 91
<211> LENGTH: 372
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 91

gaggtgcagc tgctcgagca gtctggagct gagctggcga ggcctggggc ttcagtgaag     60

ctgtcctgca aggcttctgg ctacaccttc acaaactatg gtttaagctg ggtgaagcag    120

aggcctggac aggtccttga gtggattgga gaggtttatc ctagaattgg taatgcttac    180

tacaatgaga agttcaaggg caaggccaca ctgactgcag acaaatcctc cagcacagcg    240

tccatggagc tccgcagcct gacctctgag gactctgcgg tctatttctg tgcaagacgg    300

ggatcctacg atactaacta cgactggtac ttcgatgtct ggggccaagg gaccacggtc    360

accgtctcct ca                                                        372


<210> SEQ ID NO 92
```

```
<211> LENGTH: 124
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 92

Glu Val Gln Leu Leu Glu Gln Ser Gly Ala Glu Leu Ala Arg Pro Gly
1               5                   10                  15

Ala Ser Val Lys Leu Ser Cys Lys Ala Ser Gly Tyr Thr Phe Thr Asn
            20                  25                  30

Tyr Gly Leu Ser Trp Val Lys Gln Arg Pro Gly Gln Val Leu Glu Trp
        35                  40                  45

Ile Gly Glu Val Tyr Pro Arg Ile Gly Asn Ala Tyr Tyr Asn Glu Lys
    50                  55                  60

Phe Lys Gly Lys Ala Thr Leu Thr Ala Asp Lys Ser Ser Ser Thr Ala
65                  70                  75                  80

Ser Met Glu Leu Arg Ser Leu Thr Ser Glu Asp Ser Ala Val Tyr Phe
                85                  90                  95

Cys Ala Arg Arg Gly Ser Tyr Asp Thr Asn Tyr Asp Trp Tyr Phe Asp
            100                 105                 110

Val Trp Gly Gln Gly Thr Thr Val Thr Val Ser Ser
        115                 120


<210> SEQ ID NO 93
<211> LENGTH: 336
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 93

gagctcgtga tgacccagac tccactctcc ctgcctgtca gtcttggaga tcaagcctcc      60

atctcttgca gatctagtca gagccttgta cacagtaatg gaaacaccta tttacattgg     120

tacctgcaga agccaggcca gtctccaaag ctcctgatct acaaagtttc caaccgattt     180

tctggggtcc cagacaggtt cagtggcagt ggatcaggga cagatttcac actcaagatc     240

agcagagtgg aggctgagga tctgggagtt tatttctgct ctcaaagtac acatgttccg     300

tacacgttcg gaggggggac caagcttgag atcaaa                               336


<210> SEQ ID NO 94
<211> LENGTH: 112
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 94

Glu Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110


<210> SEQ ID NO 95
<211> LENGTH: 360
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 95

gaggtgcagc tgctcgagca gtctggagct gagctggtaa ggcctgggac ttcagtgaag     60

atatcctgca aggcttctgg atacgccttc actaactact ggctaggttg ggtaaagcag    120

aggcctggac atggacttga gtggattgga gatattttcc ctggaagtgg taatatccac    180

tacaatgaga agttcaaggg caaagccaca ctgactgcag acaaatcttc gagcacagcc    240

tatatgcagc tcagtagcct gacatttgag gactctgctg tctatttctg tgcaagactg    300

aggaactggg acgagcctat ggactactgg ggccaaggga ccacggtcac cgtctcctca    360


<210> SEQ ID NO 96
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 96

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser
        115                 120


<210> SEQ ID NO 97
<211> LENGTH: 339
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 97

gagctcgtga tgacacagtc tccatcctcc ctgactgtga cagcaggaga gaaggtcact     60
```

```
atgagctgca agtccagtca gagtctgtta aacagtggaa atcaaaagaa ctacttgacc    120

tggtaccagc agaaaccagg gcagcctcct aaactgttga tctactgggc atccactagg    180

gaatctgggg tccctgatcg cttcacaggc agtggatctg gaacagattt cactctcacc    240

atcagcagtg tgcaggctga agacctggca gtttattact gtcagaatga ttatagttat    300

ccgctcacgt tcggtgctgg gaccaagctt gagatcaaa                           339
```

```
<210> SEQ ID NO 98
<211> LENGTH: 113
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 98

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys


<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Ser Gly Gly Gly Gly Ser Gly Gly Gly Gly Ser
1               5                   10                  15


<210> SEQ ID NO 100
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

ctgaaatccg gaggtggtgg atccgagctc gtgatgaccc agactcc                   47


<210> SEQ ID NO 101
<211> LENGTH: 52
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 101

ggagccgccg ccgccagaac caccaccacc tttgatctca agcttggtcc cc            52


<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Gly Gly Ser
1               5


<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Met Glu Asn Trp Ser Phe Ala Tyr
1               5


<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Met Gly Trp Gly Ser Gly Trp Arg Pro Tyr Tyr Tyr Tyr Gly Met
1               5                   10                  15

Asp Val


<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Phe Thr Ser Pro Asp Tyr
1               5
```